(12) United States Patent
Santoro et al.

(10) Patent No.: US 11,993,660 B2
(45) Date of Patent: May 28, 2024

(54) CHIMERIC POLYPEPTIDES AND METHODS OF ALTERING THE MEMBRANE LOCALIZATION OF THE SAME

(71) Applicant: Cell Design Labs, Inc., Emeryville, CA (US)

(72) Inventors: Stephen Santoro, Daly City, CA (US); Scott Coyle, San Francisco, CA (US); Levi Rupp, San Francisco, CA (US); Peter Emtage, Lafayette, CA (US)

(73) Assignee: CELL DESIGN LABS, INC., Emeryville, CA (US)

(*) Notice: Subject to any disclaimer, the term of this patent is extended or adjusted under 35 U.S.C. 154(b) by 168 days.

(21) Appl. No.: 17/402,009

(22) Filed: Aug. 13, 2021

(65) Prior Publication Data

US 2021/0395386 A1 Dec. 23, 2021

Related U.S. Application Data

(62) Division of application No. 15/938,600, filed on Mar. 28, 2018, now Pat. No. 11,111,310.

(60) Provisional application No. 62/587,262, filed on Nov. 16, 2017, provisional application No. 62/477,733, filed on Mar. 28, 2017.

(51) Int. Cl.
| | | |
|---|---|---|
| *C07K 16/30* | (2006.01) |
| *A61K 38/17* | (2006.01) |
| *A61K 39/00* | (2006.01) |
| *A61K 39/395* | (2006.01) |
| *A61K 48/00* | (2006.01) |
| *A61P 35/00* | (2006.01) |
| *C07K 14/705* | (2006.01) |
| *C07K 14/715* | (2006.01) |
| *C07K 14/72* | (2006.01) |
| *C07K 14/725* | (2006.01) |
| *C07K 16/28* | (2006.01) |
| *C07K 19/00* | (2006.01) |
| *C12N 5/0783* | (2010.01) |
| *C12N 15/62* | (2006.01) |
| *C12N 15/63* | (2006.01) |

(52) U.S. Cl.
CPC ............ *C07K 16/30* (2013.01); *A61K 38/177* (2013.01); *A61K 39/001112* (2018.08); *A61K 39/39558* (2013.01); *A61K 48/005* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 14/7153* (2013.01); *C07K 14/721* (2013.01); *C07K 16/2878* (2013.01); *C07K 19/00* (2013.01); *C12N 5/0637* (2013.01); *C12N 5/0646* (2013.01); *C12N 15/62* (2013.01); *C12N 15/63* (2013.01); *C07K 2319/02* (2013.01); *C07K 2319/03* (2013.01); *C07K 2319/035* (2013.01)

(58) Field of Classification Search
None
See application file for complete search history.

(56) References Cited

U.S. PATENT DOCUMENTS

| | | |
|---|---|---|
| 5,122,458 A | 6/1992 | Post et al. |
| 5,219,740 A | 6/1993 | Miller et al. |
| 6,207,453 B1 | 3/2001 | Maass et al. |
| 7,150,971 B2 | 12/2006 | Rothman et al. |
| 7,612,181 B2 | 11/2009 | Wu et al. |
| 8,258,268 B2 | 9/2012 | Wu et al. |
| 8,586,714 B2 | 11/2013 | Ghayur et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 2006/0040354 A1 | 2/2006 | O'Keefe |
| 2014/0286987 A1 | 9/2014 | Spencer et al. |
| 2016/0046700 A1 | 2/2016 | Foster et al. |

FOREIGN PATENT DOCUMENTS

| | | |
|---|---|---|
| EP | 1912069 A2 | 4/2008 |
| JP | H07-316200 A | 12/1995 |
| JP | 2002-153287 A | 5/2002 |
| WO | 2014127261 A1 | 8/2014 |
| WO | 2015017214 A1 | 2/2015 |
| WO | 2015142661 A1 | 9/2015 |
| WO | 2015150771 A1 | 10/2015 |
| WO | 2016073456 A1 | 5/2016 |
| WO | 2016138034 A1 | 9/2016 |
| WO | 2016160791 A1 | 10/2016 |
| WO | 2017120546 A1 | 7/2017 |

OTHER PUBLICATIONS

Katkitsuka Akira, translation provided by Espacenet for JPH07-316200A with Figures, published Dec. 5, 1995; 11 pages total (Year: 1995).*
Final Rejection issued in JP Application No. 2019-554395, dated Sep. 28, 2021.
Christopher DeRenzo and Stephen Gottschalk, Front. Immunol. 10: 218. doi: 10.3389/fimmu.2019.00218; 8 pages total (Year: 2019).
Bhattacharya et al., PLoS ONE 12(3): e0171355. https://doi.org/10.1371/journal.pone.0171355; 22 pages total (Year: 2017).
Alonso-Camino et al., "CARbodies: Human Antibodies Against Cell Surface Tumor Antigens Selected From Repertoires Displayed on T Cell Chimeric Antigen Receptors," Mol. Ther. Nucleic Acids 21(2):e93, May 2013.

(Continued)

*Primary Examiner* — Christina M Borgeest
(74) *Attorney, Agent, or Firm* — Barnes & Thornburg LLP

(57) ABSTRACT

Methods and compositions are provided for reversibly localizing proteins to the exterior part of the cell surface. Compositions provided herein can include nucleic acids that encode polypeptides of interest and the ligand binding domain (LBD) of a nuclear hormone receptor. Medical applications are provided, including controlling the toxicity of CAR T cells.

18 Claims, 19 Drawing Sheets

Specification includes a Sequence Listing.

(56) References Cited

OTHER PUBLICATIONS

Baeuerle et al., "BiTE: Teaching antibodies to engage T-cells for cancer therapy," Curr. Opin. Mol. Ther. 11(1):22-30, Feb. 2009.
Barrett et al., "Chimeric antigen receptor therapy for cancer," Ann. Rev. Med. 65:333-347, 2014.
Batt and Carmichael, "Characterization of the polyomavirus late polyadenylation signal," Mol. Cell Biol. 15(9):4783-4790, Sep. 1995.
Boris-Lawrie et al., "Recent advances in retrovirus vector technology," Curr. Opin. Genet. Develop. 3(1):102-109, Feb. 1993.
Burns et al., "Vesicular stomatitis vims G glycoprotein pseudotyped retroviral vectors: concentration to very high titer and efficient gene transfer into mammalian and nonmammalian cells," Proc. Natl. Acad. Sci. U.S.A. 90(17):8033-8037, Sep. 1993.
Carlens et al., "Ex vivo T lymphocyte expansion for retroviral transduction: influence of serum-free media on variations In cell expansion rates and lymphocyte subset distribution," Exp. Hematol. 28(10):1137-1146, Oct. 2000.
Cartellieri et al., "Chimeric antigen receptor-engineered T cells for immunotherapy of cancer," J Biomed. Biotechnol. vol. 2010, Article No. 956304, May 2010, 13 pages.
Cavalieri et al., "Human T lymphocytes transduced by lentiviral vectors in the absence of TCR activation maintain an Intact immune competence," Blood 102(2):497-505, Jul. 2003.
Cheadle et al., "CART cells: driving the road from the laboratory to the clinic," Immunol. Rev. 257(1):91-106, Jan. 2014.
Chen et al., "Molecular mechanisms of T cell co-stimulation and co-inhibition," Nature Reviews Immunol. 13(4):227-242, 2013.
Constantinescu et al., "Ligand-independent oligomerization of cell-surface erythropoietin receptor is medicated by the transmembrane domain," Proc. Natl. Acad. Sci. U.S.A. 98(8):4379-4384, Apr. 2001.
Cooper et al., "T-cell clones can be rendered specific for CD19: toward the selective augmentation of the graft-versus-B-lineage leukemia effect," Blood 101:1637-1644, Feb. 2003.
Cromie et al., "Nanobodies and their Use in GPCR Drug Discovery," Curr. Top. Med. Chem. 15(24):2543-2557, 2015.
De Genst et al., "Antibody repertoire development in camelids," Dev. Comp. Immunol. 30(1-2):187-198, 2006.
De Meyer et al., "Nanobody-based products as research and diagnostic tools," Trends Biotechnol. 32(5):263-270, May 2014.
DiGiammarino et al., "Design and generation of DVD-Ig™ molecules for dual-specific targeting," Methods Mol. Biol. 899:145-156, 2012.
Fedorov et al., "PD-1- and CTLA-4-based inhibitory chimeric antigen receptors (iCARs) divert off-target Immunotherapy responses," Sci. Transl. Med. 5(215):215ra172, Dec. 2013, 25 pages.
Garber, "Bispecific antibodies rise again," Nature Reviews Drug Discovery 13:799-801, Nov. 2014.
Glienke et al., "Advantages and applications of CAR-expressing natural killer cells," Front. Pharmacol. 6(21), Feb. 12, 2015, 7 pages.
Huehls et al., "Bispecific T-cell engagers for cancer immunotherapy," Immunol. Cell Biol. 93:290-296, Mar. 2015.
Jakob et al., "Structure reveals function of the dual variable domain immunoglobulin (DVD-Ig™) molecule, " MABs 5(3):358-363, May-Jun. 2013.
Kakarla and Gottschalk, "CART cells for solid tumors: armed and ready to go?" Cancer J 20(2):151-155, Mar.-Apr. 2014.
Kijanka et al., "Nanobody-based cancer therapy of solid tumors," Nanomedicine 10(1):161-174, Jan. 2015.

Kovaleva et al., "Shark variable new antigen receptor biologics—a novel technology platform for therapeutic drug development," Expert. Opin. Biol. Ther. 14:1527-1539, Oct. 2014.
Krah et al., "Single-domain antibodies for biomedical applications," Immunopharmacol. Immunotoxicol. 38(1):21-28, 2016.
Levitt el al., "Definition of an efficient synthetic poly(A) site," Genes Dev. 3(7):1019-1025, Jul. 1989.
Miller et al., "Improved retroviral vectors for gene transfer and expression," BioTechniques 7:980-990, Oct. 1989.
Miller, "Retrovirus packaging cells," Human Gene Therapy 1(1):5-14, Spring 1990.
Mujic-Delic et al., "GPCR-targeting nanobodies: attractive research tools, diagnostics, and therapeutics," Trends Pharmacol. Sci. 35:247-255, May 2014.
Muyldermans et al., "Recognition of antigens by single-domain antibody fragments: the superfluous luxury of paired domains," Trends Biochem. Sci. 26:230-235, Apr. 2001.
Muyldermans, "Nanobodies: natural single-domain antibodies," Ann. Rev. Biochem. 82:775-797, 2013.
Muyldermans, "Single domain camel antibodies: current status," Rev in Mol Biotechnol. 74:277-302, Jun. 2001.
Orkin et al., "Thalassemia due to a mutation in the cleavage-polyadenylation signal of the human beta-globin gene," EMBO J. 4(2):453-456, Feb. 1985.
Park et al., "Treating cancer with genetically engineered T cells," Trends Biotechnol. 29(11):550-557, Nov. 2011.
PCT International Search Report and Written Opinion in International Appln. No. PCT/US2018/024916, dated Jun. 14, 2018, 28 pages.
Pegram et al., "CD28z CARs and armored CARs," Cancer J 20(2):127-133, Mar.-Apr. 2014.
Pluckthun, "Antibodies from *Escherichia coli*," Pharmacol. Monoclonal Antibodies 269-315, 1994.
Rahbarizadeh et al., "Nanobody; an old concept and new vehicle for immunotargeting," Immunol. Invest. 40(3):299-338, 2011.
Riddell et al., "Adoptive therapy with chimeric antigen receptor-modified T cells of defined subset composition," Cancer J 20(2):141-144, Mar.-Apr. 2014.
Sadelain et al., "The basic principles of chimeric antigen receptor design," Cancer Discov. 3(4):388-398, Apr. 2013.
Sadelain, "Chimeric antigen receptors: driving immunology towards synthetic biology," Current Opin. Immunol. 41:68-76, Aug. 2016.
Scarpa et al., "Characterization of recombinant helper retroviruses from Moloney-based vectors in ecotropic and amphotropic packaging cell lines," Virology 180:849-852, Feb. 1991.
Schek et al., "Definition of the upstream efficiency element of the simian vims 40 late polyadenylation signal by using in vitro analyses," Mol. Cell Biol. 12(12):5386-5393, Dec. 1992.
Spiess et al., "Alternative molecular formats and therapeutic applications for bispecific antibodies," Mol. Immunol. 67(2 Pt A):95-106, Oct. 2015.
Szymanski et al., "Development and validation of a robust and versatile one-plasmid regulated gene expression system," Mol. Therapy 15(7):1340-1347, Jul. 2007.
Van Audenhove et al., "Nanobodies as Versatile Tools to Understand, Diagnose, Visualize and Treat Cancer," EBioMedicine 8:40-48, Jun. 2016.
Van Bockstaele et al., "The development of nanobodies for therapeutic applications," Curr. Opin. Invest. Drugs 10(11):1212-1224, Nov. 2009.
Final Rejection issued in KR Application No. 10-2019-7031800, dated Dec. 2, 2021.
Examiner Requisition, issued in CA Application No. 3058262, dated Aug. 19, 2021.
Second Examination Report, issued in GC Application No. 2018-35038, dated Aug. 1, 2021.

* cited by examiner

SEQUENCE LISTING

```
<160> NUMBER OF SEQ ID NOS: 119

<210> SEQ ID NO 1
<211> LENGTH: 220
<212> TYPE: PRT
<213> ORGANISM: Homo sapiens

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 2
<211> LENGTH: 164
<212> TYPE: PRT
<213> ORGANISM: Homo sapiens

<400> SEQUENCE: 2

Met Lys Trp Lys Ala Leu Phe Thr Ala Ala Ile Leu Gln Ala Gln Leu
```

```
                1               5                   10                  15
        Pro Ile Thr Glu Ala Gln Ser Phe Gly Leu Leu Asp Pro Lys Leu Cys
                        20                  25                  30

Tyr Leu Leu Asp Gly Ile Leu Phe Ile Tyr Gly Val Ile Leu Thr Ala
                        35                  40                  45

Leu Phe Leu Arg Val Lys Phe Ser Arg Ser Ala Asp Ala Pro Ala Tyr
                50                  55                  60

Gln Gln Gly Gln Asn Gln Leu Tyr Asn Glu Leu Asn Leu Gly Arg Arg
        65                      70                  75                  80

Glu Glu Tyr Asp Val Leu Asp Lys Arg Arg Gly Arg Asp Pro Glu Met
                        85                  90                  95

Gly Gly Lys Pro Gln Arg Arg Lys Asn Pro Gln Glu Gly Leu Tyr Asn
                        100                 105                 110

Glu Leu Gln Lys Asp Lys Met Ala Glu Ala Tyr Ser Glu Ile Gly Met
                        115                 120                 125

Lys Gly Glu Arg Arg Arg Gly Lys Gly His Asp Gly Leu Tyr Gln Gly
                        130                 135                 140

Leu Ser Thr Ala Thr Lys Asp Thr Tyr Asp Ala Leu His Met Gln Ala
        145                     150                 155                 160

Leu Pro Pro Arg

<210> SEQ ID NO 3
        <211> LENGTH: 23
        <212> TYPE: PRT
        <213> ORGANISM: Homo sapiens

<400> SEQUENCE: 3

Leu Gly Leu Leu Val Ala Gly Val Leu Val Leu Leu Val Ser Leu Gly
        1               5                   10                  15

Val Ala Ile His Leu Cys Cys
                        20

<210> SEQ ID NO 4
        <211> LENGTH: 26
        <212> TYPE: PRT
        <213> ORGANISM: Homo sapiens

<400> SEQUENCE: 4

Val Ala Ala Ile Leu Gly Leu Gly Leu Val Leu Gly Leu Leu Gly Pro
        1               5                   10                  15

Leu Ala Ile Leu Leu Ala Leu Tyr Leu Leu
                        20                  25

<210> SEQ ID NO 5
        <211> LENGTH: 25
        <212> TYPE: PRT
        <213> ORGANISM: Homo sapiens

<400> SEQUENCE: 5

Ala Leu Ile Val Leu Gly Gly Val Ala Gly Leu Leu Leu Phe Ile Gly
        1               5                   10                  15

Leu Gly Ile Phe Phe Cys Val Arg Cys
                        20                  25

<210> SEQ ID NO 6
        <211> LENGTH: 23
        <212> TYPE: PRT
        <213> ORGANISM: Homo sapiens
```

-continued

```
<400> SEQUENCE: 6

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 7
<211> LENGTH: 26
<212> TYPE: PRT
<213> ORGANISM: Homo sapiens

<400> SEQUENCE: 7

Trp Val Leu Val Val Gly Gly Val Leu Ala Cys Tyr Ser Leu Leu
1               5                   10                  15

Val Thr Val Ala Phe Ile Ile Phe Trp Val
            20                  25

<210> SEQ ID NO 8
<211> LENGTH: 24
<212> TYPE: PRT
<213> ORGANISM: Homo sapiens

<400> SEQUENCE: 8

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 9
<211> LENGTH: 24
<212> TYPE: PRT
<213> ORGANISM: Homo sapiens

<400> SEQUENCE: 9

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 10
<211> LENGTH: 250
<212> TYPE: PRT
<213> ORGANISM: Homo sapiens

<400> SEQUENCE: 10

Ser Lys Lys Asn Ser Leu Ala Leu Ser Leu Thr Ala Asp Gln Met Val
1               5                   10                  15

Ser Ala Leu Leu Asp Ala Glu Pro Pro Ile Leu Tyr Ser Glu Tyr Asp
            20                  25                  30

Pro Thr Arg Pro Phe Ser Glu Ala Ser Met Met Gly Leu Leu Thr Asn
        35                  40                  45

Leu Ala Asp Arg Glu Leu Val His Met Ile Asn Trp Ala Lys Arg Val
    50                  55                  60

Pro Gly Phe Val Asp Leu Thr Leu His Asp Gln Val His Leu Leu Glu
65                  70                  75                  80

Cys Ala Trp Leu Glu Ile Leu Met Ile Gly Leu Val Trp Arg Ser Met
                85                  90                  95

Glu His Pro Gly Lys Leu Leu Phe Ala Pro Asn Leu Leu Leu Asp Arg
            100                 105                 110
```

```
Asn Gln Gly Lys Cys Val Glu Gly Met Val Glu Ile Phe Asp Met Leu
            115                 120                 125

Leu Ala Thr Ser Ser Arg Phe Arg Met Met Asn Leu Gln Gly Glu Glu
130                 135                 140

Phe Val Cys Leu Lys Ser Ile Ile Leu Leu Asn Ser Gly Val Tyr Thr
145                 150                 155                 160

Phe Leu Ser Ser Thr Leu Lys Ser Leu Glu Glu Lys Asp His Ile His
                165                 170                 175

Arg Val Leu Asp Lys Ile Thr Asp Thr Leu Ile His Leu Met Ala Lys
            180                 185                 190

Ala Gly Leu Thr Leu Gln Gln Gln His Gln Arg Leu Ala Gln Leu Leu
        195                 200                 205

Leu Ile Leu Ser His Ile Arg His Met Ser Asn Lys Gly Met Glu His
    210                 215                 220

Leu Tyr Ser Met Lys Cys Lys Asn Val Val Pro Leu Tyr Asp Leu Leu
225                 230                 235                 240

Leu Glu Met Leu Asp Ala His Arg Leu His
                245                 250

<210> SEQ ID NO 11
<211> LENGTH: 248
<212> TYPE: PRT
<213> ORGANISM: Homo sapiens

<400> SEQUENCE: 11

Ala Leu Ser Leu Thr Ala Asp Gln Met Val Ser Ala Leu Leu Asp Ala
1               5                   10                  15

Glu Pro Pro Ile Leu Tyr Ser Glu Tyr Asp Pro Thr Arg Pro Phe Ser
            20                  25                  30

Glu Ala Ser Met Met Gly Leu Leu Thr Asn Leu Ala Asp Arg Glu Leu
        35                  40                  45

Val His Met Ile Asn Trp Ala Lys Arg Val Pro Gly Phe Val Asp Leu
    50                  55                  60

Thr Leu His Asp Gln Val His Leu Leu Glu Cys Ala Trp Leu Glu Ile
65                  70                  75                  80

Leu Met Ile Gly Leu Val Trp Arg Ser Met Glu His Pro Gly Lys Leu
                85                  90                  95

Leu Phe Ala Pro Asn Leu Leu Leu Asp Arg Asn Gln Gly Lys Cys Val
            100                 105                 110

Glu Gly Met Val Glu Ile Phe Asp Met Leu Leu Ala Thr Ser Ser Arg
        115                 120                 125

Phe Arg Met Met Asn Leu Gln Gly Glu Glu Phe Val Cys Leu Lys Ser
130                 135                 140

Ile Ile Leu Leu Asn Ser Gly Val Tyr Thr Phe Leu Ser Ser Thr Leu
145                 150                 155                 160

Lys Ser Leu Glu Glu Lys Asp His Ile His Arg Val Leu Asp Lys Ile
                165                 170                 175

Thr Asp Thr Leu Ile His Leu Met Ala Lys Ala Gly Leu Thr Leu Gln
            180                 185                 190

Gln Gln His Gln Arg Leu Ala Gln Leu Leu Leu Ile Leu Ser His Ile
        195                 200                 205

Arg His Met Ser Asn Lys Gly Met Glu His Leu Tyr Ser Met Lys Cys
    210                 215                 220

Lys Asn Val Val Pro Leu Tyr Asp Leu Leu Leu Glu Met Leu Asp Ala
225                 230                 235                 240
```

-continued

```
His Arg Leu His Ala Pro Thr Ser
            245

<210> SEQ ID NO 12
<211> LENGTH: 200
<212> TYPE: PRT
<213> ORGANISM: Homo sapiens

<400> SEQUENCE: 12

Ser Pro Gly Gln Asp Ile Gln Leu Ile Pro Pro Leu Ile Asn Leu Leu
1               5                   10                  15

Met Ser Ile Glu Pro Asp Val Ile Tyr Ala Gly His Asp Asn Thr Lys
            20                  25                  30

Pro Asp Thr Ser Ser Ser Leu Leu Thr Ser Leu Asn Gln Leu Gly Glu
        35                  40                  45

Arg Gln Leu Leu Ser Val Val Lys Trp Ser Lys Ser Leu Pro Gly Phe
    50                  55                  60

Arg Asn Leu His Ile Asp Asp Gln Ile Thr Leu Ile Gln Tyr Ser Trp
65                  70                  75                  80

Met Ser Leu Met Val Phe Gly Leu Gly Trp Arg Ser Tyr Lys His Val
                85                  90                  95

Ser Gly Gln Met Leu Tyr Phe Ala Pro Asp Leu Ile Leu Asn Glu Gln
            100                 105                 110

Arg Met Lys Glu Ser Ser Phe Tyr Ser Leu Cys Leu Thr Met Trp Gln
        115                 120                 125

Ile Pro Gln Glu Phe Val Lys Leu Gln Val Ser Gln Glu Glu Phe Leu
    130                 135                 140

Cys Met Lys Val Leu Leu Leu Leu Asn Thr Ile Pro Leu Glu Gly Leu
145                 150                 155                 160

Arg Ser Gln Thr Gln Phe Glu Glu Met Arg Ser Ser Tyr Ile Arg Glu
                165                 170                 175

Leu Ile Lys Ala Ile Gly Leu Arg Gln Lys Gly Val Val Ser Ser Ser
            180                 185                 190

Gln Arg Phe Tyr Gln Leu Thr Lys
        195                 200

<210> SEQ ID NO 13
<211> LENGTH: 261
<212> TYPE: PRT
<213> ORGANISM: Homo sapiens

<400> SEQUENCE: 13

Phe Thr Phe Ser Pro Gly Gln Asp Ile Gln Leu Ile Pro Pro Leu Ile
1               5                   10                  15

Asn Leu Leu Met Ser Ile Glu Pro Asp Val Ile Tyr Ala Gly His Asp
            20                  25                  30

Asn Thr Lys Pro Asp Thr Ser Ser Ser Leu Leu Thr Ser Leu Asn Gln
        35                  40                  45

Leu Gly Glu Arg Gln Leu Leu Ser Val Val Lys Trp Ser Lys Ser Leu
    50                  55                  60

Pro Gly Phe Arg Asn Leu His Ile Asp Asp Gln Ile Thr Leu Ile Gln
65                  70                  75                  80

Tyr Ser Trp Met Ser Leu Met Val Phe Gly Leu Gly Trp Arg Ser Tyr
                85                  90                  95

Lys His Val Ser Gly Gln Met Leu Tyr Phe Ala Pro Asp Leu Ile Leu
            100                 105                 110
```

```
Asn Glu Gln Arg Met Lys Glu Ser Ser Phe Tyr Ser Leu Cys Leu Thr
            115                 120                 125
Met Trp Gln Ile Pro Gln Glu Phe Val Lys Leu Gln Val Ser Gln Glu
130                 135                 140
Glu Phe Leu Cys Met Lys Val Leu Leu Leu Asn Thr Ile Pro Leu
145                 150                 155                 160
Glu Gly Leu Arg Ser Gln Thr Gln Phe Glu Glu Met Arg Ser Ser Tyr
            165                 170                 175
Ile Arg Glu Leu Ile Lys Ala Ile Gly Leu Arg Gln Lys Gly Val Val
            180                 185                 190
Ser Ser Ser Gln Arg Phe Tyr Gln Leu Thr Lys Leu Leu Asp Asn Leu
            195                 200                 205
His Asp Leu Val Lys Gln Leu His Leu Tyr Cys Leu Asn Thr Phe Ile
            210                 215                 220
Gln Ser Arg Ala Leu Ser Val Glu Phe Pro Glu Met Met Ser Glu Val
225                 230                 235                 240
Ile Ala Ala Gln Leu Pro Lys Ile Leu Ala Gly Met Val Lys Pro Leu
            245                 250                 255
Leu Phe His Lys Lys
            260

<210> SEQ ID NO 14
<211> LENGTH: 249
<212> TYPE: PRT
<213> ORGANISM: Homo sapiens

<400> SEQUENCE: 14

Pro Ile Phe Leu Asn Val Leu Glu Ala Ile Glu Pro Gly Val Val Cys
1               5                   10                  15
Ala Gly His Asp Asn Asn Gln Pro Asp Ser Phe Ala Ala Leu Leu Ser
            20                  25                  30
Ser Leu Asn Glu Leu Gly Glu Arg Gln Leu Val His Val Val Lys Trp
            35                  40                  45
Ala Lys Ala Leu Pro Gly Phe Arg Asn Leu His Val Asp Asp Gln Met
50                  55                  60
Ala Val Ile Gln Tyr Ser Trp Met Gly Leu Met Val Phe Ala Met Gly
65                  70                  75                  80
Trp Arg Ser Phe Thr Asn Val Asn Ser Arg Met Leu Tyr Phe Ala Pro
            85                  90                  95
Asp Leu Val Phe Asn Glu Tyr Arg Met His Lys Ser Arg Met Tyr Ser
            100                 105                 110
Gln Cys Val Arg Met Arg His Leu Ser Gln Glu Phe Gly Trp Leu Gln
            115                 120                 125
Ile Thr Pro Gln Glu Phe Leu Cys Met Lys Ala Leu Leu Leu Phe Ser
130                 135                 140
Ile Ile Pro Val Asp Gly Leu Lys Asn Gln Lys Phe Phe Asp Glu Leu
145                 150                 155                 160
Arg Met Asn Tyr Ile Lys Glu Leu Asp Arg Ile Ile Ala Cys Lys Arg
            165                 170                 175
Lys Asn Pro Thr Ser Cys Ser Arg Arg Phe Tyr Gln Leu Thr Lys Leu
            180                 185                 190
Leu Asp Ser Val Gln Pro Ile Ala Arg Glu Leu His Gln Phe Thr Phe
            195                 200                 205
Asp Leu Leu Ile Lys Ser His Met Val Ser Val Asp Phe Pro Glu Met
```

```
                210                 215                 220
Met Ala Glu Ile Ile Ser Val Gln Val Pro Lys Ile Leu Ser Gly Lys
225                 230                 235                 240

Val Lys Pro Ile Tyr Phe His Thr Gln
                245

<210> SEQ ID NO 15
<211> LENGTH: 283
<212> TYPE: PRT
<213> ORGANISM: Homo sapiens

<400> SEQUENCE: 15

Ser Leu Glu Glu Gly Glu Ala Ser Ser Thr Thr Ser Pro Thr Glu Glu
1               5                   10                  15

Thr Thr Gln Lys Leu Thr Val Ser His Ile Glu Gly Tyr Glu Cys Gln
                20                  25                  30

Pro Ile Phe Leu Asn Val Leu Glu Ala Ile Glu Pro Gly Val Val Cys
            35                  40                  45

Ala Gly His Asp Asn Asn Gln Pro Asp Ser Phe Ala Ala Leu Leu Ser
        50                  55                  60

Ser Leu Asn Glu Leu Gly Glu Arg Gln Leu Val His Val Val Lys Trp
65                  70                  75                  80

Ala Lys Ala Leu Pro Gly Phe Arg Asn Leu His Val Asp Asp Gln Met
                85                  90                  95

Ala Val Ile Gln Tyr Ser Trp Met Gly Leu Met Val Phe Ala Met Gly
            100                 105                 110

Trp Arg Ser Phe Thr Asn Val Asn Ser Arg Met Leu Tyr Phe Ala Pro
        115                 120                 125

Asp Leu Val Phe Asn Glu Tyr Arg Met His Lys Ser Arg Met Tyr Ser
130                 135                 140

Gln Cys Val Arg Met Arg His Leu Ser Gln Glu Phe Gly Trp Leu Gln
145                 150                 155                 160

Ile Thr Pro Gln Glu Phe Leu Cys Met Lys Ala Leu Leu Leu Phe Ser
                165                 170                 175

Ile Ile Pro Val Asp Gly Leu Lys Asn Gln Lys Phe Phe Asp Glu Leu
            180                 185                 190

Arg Met Asn Tyr Ile Lys Glu Leu Asp Arg Ile Ile Ala Cys Lys Arg
        195                 200                 205

Lys Asn Pro Thr Ser Cys Ser Arg Arg Phe Tyr Gln Leu Thr Lys Leu
    210                 215                 220

Leu Asp Ser Val Gln Pro Ile Ala Arg Glu Leu His Gln Phe Thr Phe
225                 230                 235                 240

Asp Leu Leu Ile Lys Ser His Met Val Ser Val Asp Phe Pro Glu Met
                245                 250                 255

Met Ala Glu Ile Ile Ser Val Gln Val Pro Lys Ile Leu Ser Gly Lys
            260                 265                 270

Val Lys Pro Ile Tyr Phe His Thr Gln Glu Gly
        275                 280

<210> SEQ ID NO 16
<211> LENGTH: 266
<212> TYPE: PRT
<213> ORGANISM: Homo sapiens

<400> SEQUENCE: 16

Glu Thr Thr Gln Lys Leu Thr Val Ser His Ile Glu Gly Tyr Glu Cys
```

-continued

```
1               5                   10                  15
Gln Pro Ile Phe Leu Asn Val Leu Glu Ala Ile Glu Pro Gly Val Val
            20                  25                  30

Cys Ala Gly His Asp Asn Asn Gln Pro Asp Ser Phe Ala Ala Leu Leu
            35                  40                  45

Ser Ser Leu Asn Glu Leu Gly Glu Arg Gln Leu Val His Val Val Lys
50                      55                  60

Trp Ala Lys Ala Leu Pro Gly Phe Arg Asn Leu His Val Asp Asp Gln
65                  70                  75                  80

Met Ala Val Ile Gln Tyr Ser Trp Met Gly Leu Met Val Phe Ala Met
                85                  90                  95

Gly Trp Arg Ser Phe Thr Asn Val Asn Ser Arg Met Leu Tyr Phe Ala
            100                 105                 110

Pro Asp Leu Val Phe Asn Glu Tyr Arg Met His Lys Ser Arg Met Tyr
            115                 120                 125

Ser Gln Cys Val Arg Met Arg His Leu Ser Gln Glu Phe Gly Trp Leu
130                     135                 140

Gln Ile Thr Pro Gln Glu Phe Leu Cys Met Lys Ala Leu Leu Leu Phe
145                 150                 155                 160

Ser Ile Ile Pro Val Asp Gly Leu Lys Asn Gln Lys Phe Phe Asp Glu
                165                 170                 175

Leu Arg Met Asn Tyr Ile Lys Glu Leu Asp Arg Ile Ile Ala Cys Lys
            180                 185                 190

Arg Lys Asn Pro Thr Ser Cys Ser Arg Arg Phe Tyr Gln Leu Thr Lys
            195                 200                 205

Leu Leu Asp Ser Val Gln Pro Ile Ala Arg Glu Leu His Gln Phe Thr
210                 215                 220

Phe Asp Leu Leu Ile Lys Ser His Met Val Ser Val Asp Phe Pro Glu
225                 230                 235                 240

Met Met Ala Glu Ile Ile Ser Val Gln Val Pro Lys Ile Leu Ser Gly
                245                 250                 255

Lys Val Lys Pro Ile Tyr Phe His Thr Gln
            260                 265
```

<210> SEQ ID NO 17
<211> LENGTH: 164
<212> TYPE: PRT
<213> ORGANISM: Homo sapiens

<400> SEQUENCE: 17

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110
```

```
Glu Leu Gln Lys Asp Lys Met Ala Glu Ala Tyr Ser Glu Ile Gly Met
            115                 120                 125

Lys Gly Glu Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 18
<211> LENGTH: 220
<212> TYPE: PRT
<213> ORGANISM: Homo sapiens

<400> SEQUENCE: 18

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
            210                 215                 220

<210> SEQ ID NO 19
<211> LENGTH: 255
<212> TYPE: PRT
<213> ORGANISM: Homo sapiens

<400> SEQUENCE: 19

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
```

-continued

```
                    50                  55                  60
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 20
<211> LENGTH: 10
<212> TYPE: PRT
<213> ORGANISM: Artificial Sequence
<220> FEATURE:
<223> OTHER INFORMATION: Linker sequence

<400> SEQUENCE: 20

```
Gly Ser Gly Ser Gly Ser Gly Ser Gly Ser
 1               5                   10
```

<210> SEQ ID NO 21
<211> LENGTH: 8
<212> TYPE: PRT
<213> ORGANISM: Artificial Sequence
<220> FEATURE:
<223> OTHER INFORMATION: Linker sequence

<400> SEQUENCE: 21

```
Gly Ser Gly Ser Gly Ser Gly Ser
 1               5
```

<210> SEQ ID NO 22
<211> LENGTH: 8
<212> TYPE: PRT
<213> ORGANISM: Artificial Sequence
<220> FEATURE:
<223> OTHER INFORMATION: Linker sequence

<400> SEQUENCE: 22

```
Arg Ser Gly Ser Gly Ser Gly Ser
 1               5
```

<210> SEQ ID NO 23

```
<211> LENGTH: 8
<212> TYPE: PRT
<213> ORGANISM: Artificial Sequence
<220> FEATURE:
<223> OTHER INFORMATION: Linker sequence

<400> SEQUENCE: 23

Gly Ser Gly Ser Gly Ser Gly Ser
1               5

<210> SEQ ID NO 24
<211> LENGTH: 30
<212> TYPE: DNA
<213> ORGANISM: Artificial Sequence
<220> FEATURE:
<223> OTHER INFORMATION: Linker sequence

<400> SEQUENCE: 24
ggatccggca gcggatctgg cagtggaagc                                      30

<210> SEQ ID NO 25
<211> LENGTH: 24
<212> TYPE: DNA
<213> ORGANISM: Artificial Sequence
<220> FEATURE:
<223> OTHER INFORMATION: Linker sequence

<400> SEQUENCE: 25
ggatctggct ctggaagcgg cagc                                            24

<210> SEQ ID NO 26
<211> LENGTH: 24
<212> TYPE: DNA
<213> ORGANISM: Artificial Sequence
<220> FEATURE:
<223> OTHER INFORMATION: Linker sequence

<400> SEQUENCE: 26
agatccggat ctggaagtgg ctcc                                            24

<210> SEQ ID NO 27
<211> LENGTH: 24
<212> TYPE: DNA
<213> ORGANISM: Artificial Sequence
<220> FEATURE:
<223> OTHER INFORMATION: Linker sequence

<400> SEQUENCE: 27
ggaagtggat ctgggagcgg ctct                                            24

<210> SEQ ID NO 28
<211> LENGTH: 297
<212> TYPE: PRT
<213> ORGANISM: Homo sapiens

<400> SEQUENCE: 28

Asp Arg Arg Gly Gly Arg Met Leu Lys His Lys Arg Gln Arg Asp Asp
1               5                   10                  15

Gly Glu Gly Arg Gly Glu Val Gly Ser Ala Gly Asp Met Arg Ala Ala
            20                  25                  30

Asn Leu Trp Pro Ser Pro Leu Met Ile Lys Arg Ser Lys Lys Asn Ser
        35                  40                  45

Leu Ala Leu Ser Leu Thr Ala Asp Gln Met Val Ser Ala Leu Leu Asp
    50                  55                  60
```

```
Ala Glu Pro Pro Ile Leu Tyr Ser Glu Tyr Asp Pro Thr Arg Pro Phe
 65                  70                  75                  80

Ser Glu Ala Ser Met Met Gly Leu Leu Thr Asn Leu Ala Asp Arg Glu
                 85                  90                  95

Leu Val His Met Ile Asn Trp Ala Lys Arg Val Pro Gly Phe Val Asp
            100                 105                 110

Leu Thr Leu His Asp Gln Val His Leu Leu Glu Cys Ala Trp Leu Glu
            115                 120                 125

Ile Leu Met Ile Gly Leu Val Trp Arg Ser Met Glu His Pro Gly Lys
            130                 135                 140

Leu Leu Phe Ala Pro Asn Leu Leu Leu Asp Arg Asn Gln Gly Lys Cys
145                 150                 155                 160

Val Glu Gly Met Val Glu Ile Phe Asp Met Leu Leu Ala Thr Ser Ser
                165                 170                 175

Arg Phe Arg Met Met Asn Leu Gln Gly Glu Glu Phe Val Cys Leu Lys
            180                 185                 190

Ser Ile Ile Leu Leu Asn Ser Gly Val Tyr Thr Phe Leu Ser Ser Thr
            195                 200                 205

Leu Lys Ser Leu Glu Glu Lys Asp His Ile His Arg Val Leu Asp Lys
            210                 215                 220

Ile Thr Asp Thr Leu Ile His Leu Met Ala Lys Ala Gly Leu Thr Leu
225                 230                 235                 240

Gln Gln Gln His Gln Arg Leu Ala Gln Leu Leu Leu Ile Leu Ser His
                245                 250                 255

Ile Arg His Met Ser Asn Lys Arg Met Glu His Leu Tyr Ser Met Lys
            260                 265                 270

Cys Lys Asn Val Val Pro Leu Phe Asp Leu Leu Leu Glu Met Leu Asp
            275                 280                 285

Ala His Arg Leu His Ala Pro Thr Ser
            290                 295

<210> SEQ ID NO 29
<211> LENGTH: 256
<212> TYPE: PRT
<213> ORGANISM: Homo sapiens

<400> SEQUENCE: 29

Gly Gln Asp Ile Gln Leu Ile Pro Pro Leu Ile Asn Leu Leu Met Ser
  1               5                  10                  15

Ile Glu Pro Asp Val Ile Tyr Ala Gly His Asp Asn Thr Lys Pro Asp
             20                  25                  30

Thr Ser Ser Ser Leu Leu Thr Ser Leu Asn Gln Leu Gly Glu Arg Gln
             35                  40                  45

Leu Leu Ser Val Val Lys Trp Ser Lys Ser Leu Pro Gly Phe Arg Asn
 50                  55                  60

Leu His Ile Asp Asp Gln Ile Thr Leu Ile Gln Tyr Ser Trp Met Ser
 65                  70                  75                  80

Leu Met Val Phe Gly Leu Gly Trp Arg Ser Tyr Lys His Val Ser Gly
                 85                  90                  95

Gln Met Leu Tyr Phe Ala Pro Asp Leu Ile Leu Asn Glu Gln Arg Met
            100                 105                 110

Lys Glu Ser Ser Phe Tyr Ser Leu Cys Leu Thr Met Trp Gln Ile Pro
            115                 120                 125

Gln Glu Phe Val Lys Leu Gln Val Ser Gln Glu Glu Phe Leu Cys Met
            130                 135                 140
```

```
Lys Val Leu Leu Leu Leu Asn Thr Ile Pro Leu Glu Gly Leu Arg Ser
145                 150                 155                 160

Gln Thr Gln Phe Glu Glu Met Arg Ser Ser Tyr Ile Arg Glu Leu Ile
            165                 170                 175

Lys Ala Ile Gly Leu Arg Gln Lys Gly Val Val Ser Ser Gln Arg
        180                 185                 190

Phe Tyr Gln Leu Thr Lys Leu Leu Asp Asn Leu His Asp Leu Val Lys
        195                 200                 205

Gln Leu His Leu Tyr Cys Leu Asn Thr Phe Ile Gln Ser Arg Ala Leu
    210                 215                 220

Ser Val Glu Phe Pro Glu Met Met Ser Glu Val Ile Ala Ala Gln Leu
225                 230                 235                 240

Pro Lys Ile Leu Ala Gly Met Val Lys Pro Leu Leu Phe His Lys Lys
                245                 250                 255

<210> SEQ ID NO 30
<211> LENGTH: 3183
<212> TYPE: DNA
<213> ORGANISM: Artificial Sequence
<220> FEATURE:
<223> OTHER INFORMATION: v.2 construct

<400> SEQUENCE: 30
atggctctgc ctgtgacagc tctgctgctg cctctggccc tgctgctgca tgccgctaga      60
cctgagcaga agctgatctc cgaagaggac ctggacatcc agatgaccca gaccaccagc     120
agcctgagcg ccagcctggg cgatagagtg accatcagct gcagagccag ccaggacatc     180
agcaagtacc tgaactggta tcagcagaaa cccgacggca ccgtgaagct gctgatctac     240
cacaccagca ctgcacag cggcgtgccc agcagatttt ctggcagcgg ctccggcacc     300
gactacagcc tgaccatctc caacctggaa caggaagata tcgctaccta cttctgtcag     360
caaggcaaca cccctgccta caccttcggc ggaggcacca agctggaaat cacaggcggc     420
ggaggatctg gcggaggcgg aagtggcgga ggggatctg aagtgaaact gcaggaaagc     480
ggccctggcc tggtggcccc atctcagtct ctgagcgtga cctgtaccgt gtccggcgtg     540
tccctgcctg actatggcgt gtcctggatc agacagcccc cagaaagggg cctggaatgg     600 ctggagtga tctggggcag cgagacaacc tactacaaca gcgccctgaa gtcccggctg     660
accatcatca aggacaactc caagagccag gtgttcctga gatgaacag cctgcagacc     720 gacgacaccg ccatctacta ctgcgccaag cactactact acggcggcag ctacgccatg     780
gactactggg gccagggcac aagcgtgacc gtgtctagca accacccc tgcccctaga     840 cctccaaccc cagcccctac aatcgccagc cagcctctgt ctctgaggcc cgaggcttgt     900
agaccagctg ctggcggagc cgtgcacacc agaggactgg atttcgcctg cgacatctac     960
atctgggccc ctctggccgg acatgtggc gtgctgctgc tgagcctcgt gatcaccctg    1020
tactgcggat ccaagcgggg cagaaagaaa ctgctgtaca tctttaagca gcccttcatg    1080
cggcccgtgc agaccacccca ggaagaggac ggctgctcct gcagattccc gaggaagaa    1140 gaaggcggct gcgagctggg cagcggatct ggcagtggaa gcgatagaag aggcggaga    1200 atgctgaaac acaagcggca gagggacgac ggggaaggca ggcgaagt gggatctgcc    1260 ggcgatatga gaccgccaa cctgtggcct agcccctga tgatcaagcg agcaagaag    1320 aactccctgg ccctgagcct gaccgccgac cagatggtgt ctgccctgct ggatgccgag    1380
ccccccatcc tgtacagcga gtacgacccc accagaccct tcagcgaggc cagcatgatg    1440
```

-continued

```
ggcctgctga ccaacctggc cgaccgggaa ctggtgcaca tgatcaactg ggccaagcgg    1500
gtgcccggct tcgtggatct gacactgcac gaccaggtgc acctgctgga atgcgcttgg    1560
ctggaaatcc tgatgatcgg cctcgtgtgg cggagcatgg aacaccctgg caagctgctg    1620
ttcgccccca acctgctgct ggaccggaac cagggcaaat gcgtggaagg catggtggaa    1680
atcttcgaca tgctgctggc cacctccagc cggttccgga tgatgaacct gcagggcgaa    1740
gagttcgtgt gtctgaagtc catcatcctg ctgaatagcg gcgtgtacac cttcctgagc    1800
agcaccctga aaagcctgga agaaaaggac cacatccacc gggtgctgga caagatcacc    1860 gacacccctga ttcacctgat ggccaaggcc ggactgaccc tgcagcagca gcatcagaga    1920
ctggctcagc tgctgctgat cctgtcccac atccggcaca tgagcaacaa gcggatggaa    1980
catctgtaca gcatgaagtg caagaacgtg gtgcctctgt tcgatctgct gctgaaaatg    2040
ctggacgccc acaggctgca cgccccaaca tccagatccg gatctggaag tggctccctg    2100
agagtgaagt ttagcagaag cgccgacgcc cctgcctatc agcagggaca gaaccagctg    2160
tataacgagc tgaacctggg caggcgggaa gagtacgacg tgctggataa gaggcggggc    2220
agggaccctg aaatgggcgg caaacccaga cggaagaacc cccaggaagg cctgtacaac    2280
gaactgcaga agacaagat ggccgaggcc tacagcgaga tcggaatgaa gggcgagcgg    2340
cggagaggca aggacatga tggcctgtac cagggcctgt ccaccgccac caaggacacc    2400
tatgacgccc tgcacatgca ggccctgcct ccaagaggaa gtggatctgg agcggctct    2460 atggtgtcta gggggaaga ggacaacatg gccatcatca agaattcat gcggttcaag    2520 gtgcacatgg aaggctccgt gaatggccac gaattcgaga tcgaggggga gggcgagggc    2580
agaccttatg agggaaccca gaccgccaag ctgaaagtga ccaagggcgg acccctgcct    2640
ttcgcctggg atatcctgtc tccccagttt atgtacggca gcaaggccta cgtgaagcac    2700
cccgccgaca tcccccgacta cctgaagctg agcttccctg agggcttcaa gtgggagaga    2760
gtgatgaatt tcgaggacgg cggagtcgtg acagtgaccc aggatagctc tctgcaggac    2820
ggcgagttca tctacaaagt gaagctgcgg ggcaccaact tccccagcga cggacccgtg    2880
atgcagaaaa agaccatggg ctgggaggcc agctccgaga gaatgtaccc agaggacggg    2940
gccctgaagg gggagatcaa gcagcggctg aaactgaagg atggcggcca ctacgacgca    3000
gaagtgaaaa ccacctacaa ggccaagaaa cctgtgcagc tgcctggcgc ctacaatgtg    3060
aacatcaagc tggacattac cagccacaac gaggactaca ccatcgtgga acagtacgag    3120 cggggccgagg gcaggcattc tacaggcgga atggatgaac tgtataagtg cgtgaccgac    3180
tag                                                                  3183
```

<210> SEQ ID NO 31
<211> LENGTH: 1060
<212> TYPE: PRT
<213> ORGANISM: Artificial Sequence
<220> FEATURE:
<223> OTHER INFORMATION: v.2 construct

<400> SEQUENCE: 31

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
        35                  40                  45
```

```
Arg Val Thr Ile Ser Cys Arg Ala Ser Gln Asp Ile Ser Lys Tyr Leu
     50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                 85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
        130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Gly Ser Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Gly Ser Gly Ser Gly Ser Gly Ser Asp Arg Arg Gly Gly Arg
385                 390                 395                 400

Met Leu Lys His Lys Arg Gln Arg Asp Asp Gly Glu Gly Arg Gly Glu
                405                 410                 415

Val Gly Ser Ala Gly Asp Met Arg Ala Ala Asn Leu Trp Pro Ser Pro
            420                 425                 430

Leu Met Ile Lys Arg Ser Lys Lys Asn Ser Leu Ala Leu Ser Leu Thr
        435                 440                 445

Ala Asp Gln Met Val Ser Ala Leu Leu Asp Ala Glu Pro Pro Ile Leu
    450                 455                 460
```

Tyr Ser Glu Tyr Asp Pro Thr Arg Pro Phe Ser Glu Ala Ser Met Met
465                 470                 475                 480

Gly Leu Leu Thr Asn Leu Ala Asp Arg Glu Leu Val His Met Ile Asn
            485                 490                 495

Trp Ala Lys Arg Val Pro Gly Phe Val Asp Leu Thr Leu His Asp Gln
        500                 505                 510

Val His Leu Leu Glu Cys Ala Trp Leu Glu Ile Leu Met Ile Gly Leu
    515                 520                 525

Val Trp Arg Ser Met Glu His Pro Gly Lys Leu Leu Phe Ala Pro Asn
530                 535                 540

Leu Leu Leu Asp Arg Asn Gln Gly Lys Cys Val Glu Gly Met Val Glu
545                 550                 555                 560

Ile Phe Asp Met Leu Leu Ala Thr Ser Ser Arg Phe Arg Met Met Asn
            565                 570                 575

Leu Gln Gly Glu Glu Phe Val Cys Leu Lys Ser Ile Ile Leu Leu Asn
        580                 585                 590

Ser Gly Val Tyr Thr Phe Leu Ser Ser Thr Leu Lys Ser Leu Glu Glu
    595                 600                 605

Lys Asp His Ile His Arg Val Leu Asp Lys Ile Thr Asp Thr Leu Ile
610                 615                 620

His Leu Met Ala Lys Ala Gly Leu Thr Leu Gln Gln Gln His Gln Arg
625                 630                 635                 640

Leu Ala Gln Leu Leu Leu Ile Leu Ser His Ile Arg His Met Ser Asn
            645                 650                 655

Lys Arg Met Glu His Leu Tyr Ser Met Lys Cys Lys Asn Val Val Pro
        660                 665                 670

Leu Phe Asp Leu Leu Leu Glu Met Leu Asp Ala His Arg Leu His Ala
    675                 680                 685

Pro Thr Ser Arg Ser Gly Ser Gly Ser Gly Ser Leu Arg Val Lys Phe
690                 695                 700

Ser Arg Ser Ala Asp Ala Pro Ala Tyr Gln Gln Gly Gln Asn Gln Leu
705                 710                 715                 720

Tyr Asn Glu Leu Asn Leu Gly Arg Arg Glu Glu Tyr Asp Val Leu Asp
            725                 730                 735

Lys Arg Arg Gly Arg Asp Pro Glu Met Gly Gly Lys Pro Arg Arg Lys
        740                 745                 750

Asn Pro Gln Glu Gly Leu Tyr Asn Glu Leu Gln Lys Asp Lys Met Ala
    755                 760                 765

Glu Ala Tyr Ser Glu Ile Gly Met Lys Gly Glu Arg Arg Arg Gly Lys
770                 775                 780

Gly His Asp Gly Leu Tyr Gln Gly Leu Ser Thr Ala Thr Lys Asp Thr
785                 790                 795                 800

Tyr Asp Ala Leu His Met Gln Ala Leu Pro Pro Arg Gly Ser Gly Ser
            805                 810                 815

Gly Ser Gly Ser Met Val Ser Lys Gly Glu Glu Asp Asn Met Ala Ile
        820                 825                 830

Ile Lys Glu Phe Met Arg Phe Lys Val His Met Glu Gly Ser Val Asn
    835                 840                 845

Gly His Glu Phe Glu Ile Glu Gly Glu Gly Glu Gly Arg Pro Tyr Glu
850                 855                 860

Gly Thr Gln Thr Ala Lys Leu Lys Val Thr Lys Gly Gly Pro Leu Pro
865                 870                 875                 880

Phe Ala Trp Asp Ile Leu Ser Pro Gln Phe Met Tyr Gly Ser Lys Ala

```
                  885                 890                 895
Tyr Val Lys His Pro Ala Asp Ile Pro Asp Tyr Leu Lys Leu Ser Phe
                900                 905                 910

Pro Glu Gly Phe Lys Trp Glu Arg Val Met Asn Phe Glu Asp Gly Gly
                915                 920                 925

Val Val Thr Val Thr Gln Asp Ser Ser Leu Gln Asp Gly Glu Phe Ile
            930                 935                 940

Tyr Lys Val Lys Leu Arg Gly Thr Asn Phe Pro Ser Asp Gly Pro Val
945                 950                 955                 960

Met Gln Lys Lys Thr Met Gly Trp Glu Ala Ser Ser Glu Arg Met Tyr
                    965                 970                 975

Pro Glu Asp Gly Ala Leu Lys Gly Glu Ile Lys Gln Arg Leu Lys Leu
                980                 985                 990

Lys Asp Gly Gly His Tyr Asp Ala  Glu Val Lys Thr Thr  Tyr Lys Ala
                995                 1000                1005

Lys Lys  Pro Val Gln Leu Pro  Gly Ala Tyr Asn Val  Asn Ile Lys
    1010                1015                1020

Leu Asp  Ile Thr Ser His Asn  Glu Asp Tyr Thr Ile  Val Glu Gln
    1025                1030                1035

Tyr Glu  Arg Ala Glu Gly Arg  His Ser Thr Gly Gly  Met Asp Glu
    1040                1045                1050

Leu Tyr  Lys Cys Val Thr Asp
    1055                1060
```

<210> SEQ ID NO 32
<211> LENGTH: 3183
<212> TYPE: DNA
<213> ORGANISM: Artificial Sequence
<220> FEATURE:
<223> OTHER INFORMATION: v.3 construct

<400> SEQUENCE: 32

| | | |
|---|---|---|
| atggctctgc ctgtgacagc tctgctgctg cctctggccc tgctgctgca tgccgctaga | 60 |
| cctgagcaga agctgatctc cgaagaggac ctggacatcc agatgaccca gaccaccagc | 120 |
| agcctgagcg ccagcctggg cgatagagtg accatcagct gcagagccag ccaggacatc | 180 |
| agcaagtacc tgaactggta tcagcagaaa cccgacggca ccgtgaagct gctgatctac | 240 |
| cacaccagca gactgcacag cggcgtgccc agcagatttt ctggcagcgg ctccggcacc | 300 |
| gactacagcc tgaccatctc caacctggaa caggaagata tcgctaccta cttctgtcag | 360 |
| caaggcaaca ccctgcccta caccttcggc ggaggcacca gctggaaat cacaggcggc | 420 |
| ggaggatctg gcggaggcgg aagtggcgga ggggatctg aagtgaaact gcaggaaagc | 480 |
| ggccctggcc tggtggcccc atctcagtct ctgagcgtga cctgtaccgt gtccggcgtg | 540 |
| tccctgcctg actatggcgt gtcctggatc agacagcccc cagaaagggg cctggaatgg | 600 |
| ctgggagtga tctggggcag cgagacaacc tactacaaca gcgccctgaa gtcccggctg | 660 |
| accatcatca aggacaactc caagagccag gtgttcctga gatgaacag cctgcagacc | 720 |
| gacgacaccg ccatctacta ctgcgccaag cactactact acggcggcag ctacgccatg | 780 |
| gactactggg gccagggcac aagcgtgacc gtgtctagca aaccaccccc tgcccctaga | 840 |
| cctccaaccc cagcccctac aatcgccagc cagcctctgt ctctgaggcc cgaggcttgt | 900 |
| agaccagctg ctggcggagc cgtgcacacc agaggactgg atttcgcctg cgacatctac | 960 |
| atctgggccc ctctggccgg cacatgtggc gtgctgctgc tgagcctcgt gatcaccctg | 1020 |

```
tactgcggat ccaagcgggg cagaaagaaa ctgctgtaca tctttaagca gcccttcatg    1080
cggcccgtgc agaccaccca ggaagaggac ggctgctcct gcagattccc cgaggaagaa    1140
gaaggcggct gcgagctgag atccggatct ggaagtggct ccctgagagt gaagtttagc    1200
agaagcgccg acgccctgc ctatcagcag ggacagaacc agctgtataa cgagctgaac    1260
ctgggcaggc gggaagagta cgacgtgctg ataagaggc ggggcaggga ccctgaaatg     1320
ggcggcaaac ccagacggaa gaaccccag gaaggcctgt acaacgaact gcagaaagac     1380
aagatggccg aggcctacag cgagatcgga atgaagggcg agcggcggag aggcaaggga    1440
catgatggcc tgtaccaggg cctgtccacc gccaccaagg acacctatga cgccctgcac    1500
atgcaggccc tgcctccaag aggcagcgga tctggcagtg aagcgatag aagaggcggc     1560 agaatgctga acacaagcg gcagagggac gacggggaag gcagaggcga agtgggatct    1620
gccggcgata tgagagccgc caacctgtgg cctagcccc tgatgatcaa gcggagcaag     1680
aagaactccc tggccctgag cctgaccgcc gaccagatgg tgtctgccct gctggatgcc    1740
gagcccccca tcctgtacag cgagtacgac cccaccagac ccttcagcga ggccagcatg    1800
atgggcctgc tgaccaacct ggccgaccgg gaactggtgc acatgatcaa ctgggccaag    1860
cgggtgcccg gcttcgtgga tctgacactg cacgaccagg tgcacctgct ggaatgcgct    1920
tggctggaaa tcctgatgat cggcctcgtg tggcggagca tggaacaccc tggcaagctg    1980
ctgttcgccc ccaacctgct gctggaccgg aaccagggca atgcgtgga aggcatggtg     2040 gaaatcttcg acatgctgct ggccacctcc agccggttcc ggatgatgaa cctgcagggc    2100
gaagagttcg tgtgtctgaa gtccatcatc ctgctgaata cggcgtgta caccttcctg     2160 agcagcaccc tgaaaagcct ggaagaaaag gaccacatcc accgggtgct ggacaagatc    2220
accgacaccc tgattcacct gatggccaag gccggactga ccctgcagca gcagcatcag    2280
agactggctc agctgctgct gatcctgtcc cacatccggc acatgagcaa caagcggatg    2340
gaacatctgt acagcatgaa gtgcaagaac gtggtgcctc tgttcgatct gctgctggaa    2400
atgctggacg cccacaggct gcacgcccca acatccggat ctggctctgg aagcggcagc    2460
atggtgtcta agggggaaga ggacaacatg gccatcatca agaattcat gcggttcaag    2520 gtgcacatgg aaggctccgt gaatggccac gaattcgaga tcgaggggga gggcgagggc    2580 agacctttatg agggaaccca gaccgccaag ctgaaagtga ccaagggcgg acccctgcct    2640
ttcgcctggg atatcctgtc tcccagtttt atgtacggca gcaaggccta cgtgaagcac    2700
cccgccgaca tccccgacta cctgaagctg agcttccctg agggcttcaa gtgggagaga    2760
gtgatgaatt tcgaggacgg cggagtcgtg acagtgaccc aggatagctc tctgcaggac    2820
ggcgagttca tctacaaagt gaagctgcgg ggcaccaact tccccagcga cggacccgtg    2880
atgcagaaaa agaccatggg ctgggaggcc agctccgaga aatgtaccc agaggacggg     2940 gccctgaagg gggagatcaa gcagcggctg aaactgaagg atggcggcca ctacgacgca    3000
gaagtgaaaa ccacctacaa ggccaagaaa cctgtgcagc tgcctggcgc ctacaatgtg    3060
aacatcaagc tggacattac cagccacaac gaggactaca ccatcgtgga acagtacgag    3120
cgggccgagg gcaggcattc tacaggcgga atggatgaac tgtataagtg cgtgaccgac    3180
tag                                                                 3183
```

<210> SEQ ID NO 33
<211> LENGTH: 1060
<212> TYPE: PRT
<213> ORGANISM: Artificial Sequence

```
<220> FEATURE:
<223> OTHER INFORMATION: v.3 construct

<400> SEQUENCE: 33

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Gly Ser Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Gly Gly Cys
370                 375                 380

Glu Leu Arg Ser Gly Ser Gly Ser Gly Ser Leu Arg Val Lys Phe Ser
385                 390                 395                 400
```

```
Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg Gly Ser Gly Ser Gly
            500                 505                 510

Ser Gly Ser Asp Arg Arg Gly Gly Arg Met Leu Lys His Lys Arg Gln
        515                 520                 525

Arg Asp Asp Gly Glu Gly Arg Gly Glu Val Gly Ser Ala Gly Asp Met
    530                 535                 540

Arg Ala Ala Asn Leu Trp Pro Ser Pro Leu Met Ile Lys Arg Ser Lys
545                 550                 555                 560

Lys Asn Ser Leu Ala Leu Ser Leu Thr Ala Asp Gln Met Val Ser Ala
                565                 570                 575

Leu Leu Asp Ala Glu Pro Pro Ile Leu Tyr Ser Glu Tyr Asp Pro Thr
            580                 585                 590

Arg Pro Phe Ser Glu Ala Ser Met Met Gly Leu Leu Thr Asn Leu Ala
        595                 600                 605

Asp Arg Glu Leu Val His Met Ile Asn Trp Ala Lys Arg Val Pro Gly
    610                 615                 620

Phe Val Asp Leu Thr Leu His Asp Gln Val His Leu Leu Glu Cys Ala
625                 630                 635                 640

Trp Leu Glu Ile Leu Met Ile Gly Leu Val Trp Arg Ser Met Glu His
                645                 650                 655

Pro Gly Lys Leu Leu Phe Ala Pro Asn Leu Leu Leu Asp Arg Asn Gln
            660                 665                 670

Gly Lys Cys Val Glu Gly Met Val Glu Ile Phe Asp Met Leu Leu Ala
        675                 680                 685

Thr Ser Ser Arg Phe Arg Met Met Asn Leu Gln Gly Glu Glu Phe Val
    690                 695                 700

Cys Leu Lys Ser Ile Ile Leu Leu Asn Ser Gly Val Tyr Thr Phe Leu
705                 710                 715                 720

Ser Ser Thr Leu Lys Ser Leu Glu Glu Lys Asp His Ile His Arg Val
                725                 730                 735

Leu Asp Lys Ile Thr Asp Thr Leu Ile His Leu Met Ala Lys Ala Gly
            740                 745                 750

Leu Thr Leu Gln Gln Gln His Gln Arg Leu Ala Gln Leu Leu Leu Ile
        755                 760                 765

Leu Ser His Ile Arg His Met Ser Asn Lys Arg Met Glu His Leu Tyr
    770                 775                 780

Ser Met Lys Cys Lys Asn Val Val Pro Leu Phe Asp Leu Leu Leu Glu
785                 790                 795                 800

Met Leu Asp Ala His Arg Leu His Ala Pro Thr Ser Gly Ser Gly Ser
                805                 810                 815
```

```
Gly Ser Gly Ser Met Val Ser Lys Gly Glu Asp Asn Met Ala Ile
            820                 825                 830

Ile Lys Glu Phe Met Arg Phe Lys Val His Met Glu Gly Ser Val Asn
    835                 840                 845

Gly His Glu Phe Glu Ile Glu Gly Glu Gly Glu Gly Arg Pro Tyr Glu
850                 855                 860

Gly Thr Gln Thr Ala Lys Leu Lys Val Thr Lys Gly Gly Pro Leu Pro
865                 870                 875                 880

Phe Ala Trp Asp Ile Leu Ser Pro Gln Phe Met Tyr Gly Ser Lys Ala
                885                 890                 895

Tyr Val Lys His Pro Ala Asp Ile Pro Asp Tyr Leu Lys Leu Ser Phe
            900                 905                 910

Pro Glu Gly Phe Lys Trp Glu Arg Val Met Asn Phe Glu Asp Gly Gly
            915                 920                 925

Val Val Thr Val Thr Gln Asp Ser Ser Leu Gln Asp Gly Glu Phe Ile
930                 935                 940

Tyr Lys Val Lys Leu Arg Gly Thr Asn Phe Pro Ser Asp Gly Pro Val
945                 950                 955                 960

Met Gln Lys Lys Thr Met Gly Trp Glu Ala Ser Ser Glu Arg Met Tyr
                965                 970                 975

Pro Glu Asp Gly Ala Leu Lys Gly Glu Ile Lys Gln Arg Leu Lys Leu
            980                 985                 990

Lys Asp Gly Gly His Tyr Asp Ala  Glu Val Lys Thr Thr  Tyr Lys Ala
            995                 1000                1005

Lys Lys  Pro Val Gln Leu Pro  Gly Ala Tyr Asn Val  Asn Ile Lys
    1010                1015                1020

Leu Asp  Ile Thr Ser His Asn  Glu Asp Tyr Thr Ile  Val Glu Gln
    1025                1030                1035

Tyr Glu  Arg Ala Glu Gly Arg  His Ser Thr Gly Gly  Met Asp Glu
    1040                1045                1050

Leu Tyr  Lys Cys Val Thr Asp
    1055                1060

<210> SEQ ID NO 34
<211> LENGTH: 3206
<212> TYPE: DNA
<213> ORGANISM: Artificial Sequence
<220> FEATURE:
<223> OTHER INFORMATION: v.4 construct

<400> SEQUENCE: 34
atggctctgc ctgtgacagc tctgctgctg cctctggccc tgctgctgca tgccgctaga      60
cctgagcaga agctgatctc cgaagaggac ctggacatcc agatgaccca gaccaccagc     120
agcctgagcg ccagcctggg cgatagagtg accatcagct gcagagccag ccaggacatc     180
agcaagtacc tgaactggta tcagcagaaa cccgacggca ccgtgaagct gctgatctac     240
cacaccagca gactgcacag cggcgtgccc agcagatttt ctggcagcgg ctccggcacc     300
gactacagcc tgaccatctc caacctggaa caggaagata tcgctaccta cttctgtcag     360
caaggcaaca ccctgcccta caccttcggc ggaggcacca agctggaaat cacaggcggc     420
ggaggatctg gcggaggcgg aagtggcgga gggggatctg aagtgaaact gcaggaaagc     480
ggccctggcc tggtggcccc atctcagtct ctgagcgtga cctgtaccgt gtccggcgtg     540
tccctgcctg actatggcgt gtcctggatc agacagcccc cagaaagggg cctggaatgg     600
ctgggagtga tctggggcag cgagacaacc tactacaaca gcgccctgaa gtcccggctg     660
```

-continued

```
accatcatca aggacaactc caagagccag gtgttcctga agatgaacag cctgcagacc      720
gacgacaccg ccatctacta ctgcgccaag cactactact acggcggcag ctacgccatg      780
gactactggg gccagggcac aagcgtgacc gtgtctagca caaccacccc tgcccctaga      840
cctccaaccc cagcccctac aatcgccagc cagcctctgt ctctgaggcc cgaggcttgt      900
agaccagctg ctggcggagc cgtgcacacc agaggactgg atttcgcctg cgacatctac      960
atctgggccc ctctggccgg cacatgtggc gtgctgctgc tgagcctcgt gatcaccctg     1020
tactgcggat ccggcagcgg atctggcagt ggaagcgata aagaggcgg cagaatgctg      1080 aaacacaagc ggcagaggga cgacggggaa ggcagaggcg aagtgggatc tgccggcgat     1140
atgagagccg ccaacctgtg gcctagcccc ctgatgatca gcggagcaa aagaactcc       1200 ctggccctga gcctgaccgc cgaccagatg gtgtctgccc tgctggatgc cgagcccccc     1260
atcctgtaca gcgagtacga ccccaccaga cccttcagcg aggccagcat gatgggcctg     1320
ctgaccaacc tggccgaccg ggaactggtg cacatgatca actgggccaa gcgggtgccc     1380
ggcttcgtgg atctgacact gcacgaccag gtgcacctgc tggaatgcgc ttggctggaa     1440
atcctgatga tcggcctcgt gtggcggagc atggaacacc ctggcaagct gctgttcgcc     1500
cccaacctgc tgctggaccg gaaccagggc aaatgcgtgg aaggcatggt ggaaatcttc     1560
gacatgctgc tggccacctc cagccggttc cggatgatga acctgcaggg cgaagagttc     1620
gtgtgtctga agtccatcat cctgctgaat agcggcgtgt acaccttcct gagcagcacc     1680
ctgaaaagcc tggaagaaaa ggaccacatc accgggtgc tggacaagat caccgacacc     1740
ctgattcacc tgatggccaa ggccggactg accctgcagc agcagcatca gagactggct     1800
cagctgctgc tgatcctgtc ccacatccgg cacatgagca caagcggat ggaacatctg      1860 tacagcatga agtgcaagaa cgtggtgcct ctgttcgatc tgctgctgga aatgctggac     1920
gcccacaggc tgcacgcccc aacatccgga tctggctctg aagcggcag caagcggggc     1980 agaaagaaac tgctgtacat ctttaagcag cccttcatgc ggcccgtgca gaccacccag     2040
gaagaggacg gctgctcctg cagattcccc gaggaagaag aaggcggctg cgagctgaga     2100
tccggatctg gaagtggctc cctgagagtg aagtttagca aagcgccga cgcccctgcc     2160 tatcagcagg gacagaacca gctgtataac gagctgaacc tgggcaggcg gaagagtac     2220 gacgtgctgg ataagaggcg gggcagggac cctgaaatgg gcggcaaacc cagacggaag     2280 aaccccagg aaggcctgta caacgaactg cagaaagaca agatggccga ggcctacagc     2340
gagatcggaa tgaagggcga gcggcggaga ggcaaggac atgatggcct gtaccagggc     2400
ctgtccaccg ccaccaagga cacctatgac gccctgcaca tgcaggccct gcctccaaga     2460
ggaagtggat ctgggagcgg ctctatggtg tctaaggggg aagaggacaa catggccatc     2520
atcaaagaat tcatgcggtt caaggtgcac atggaaggct ccgtgaatgg ccacgaattc     2580
gagatcgagg gggagggcga gggcagacct tatgagggaa cccagaccgc caagctgaaa     2640
gtgaccaagg gcggacccct gccttttcgc ctgggatatc tgtctccca gtttatgtac     2700 ggcagcaagg cctacgtgaa gcaccccgcc gacatcccg actacctgaa gctgagcttc     2760
cctgagggct tcaagtggga gagagtgatg aatttcgagg acggcggagt cgtgacagtg     2820
acccaggata gctctctgca ggacggcgag ttcatctaca aagtgaagct gcggggcacc     2880
aacttcccca gcgacggacc cgtgatgcag aaaaagacca tgggctggga ggccagctcc     2940
gagagaatgt acccagagga cggggccctg aaggggaga tcaagcagcg gctgaaactg     3000
```

-continued

```
aaggatggcg gccactacga cgcagaagtg aaaaccacct acaaggccaa gaaacctgtg    3060
cagctgcctg cgccctacaa tgtgaacatc aagctggaca ttaccagcca caacgaggac    3120
tacaccatcg tggaacagta cgagcgggcc gagggcaggc attctacagg cggaatggat    3180
gaactgtata agtgcgtgac cgacta                                         3206
```

```
<210> SEQ ID NO 35
<211> LENGTH: 1068
<212> TYPE: PRT
<213> ORGANISM: Artificial Sequence
<220> FEATURE:
<223> OTHER INFORMATION: v.4 construct

<400> SEQUENCE: 35
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Glu | Gln | Lys | Leu | Ile | Ser | Glu | Glu | Asp | Leu | Asp |
| | | | 20 | | | | | 25 | | | | | 30 | | |
| Ile | Gln | Met | Thr | Gln | Thr | Thr | Ser | Ser | Leu | Ser | Ala | Ser | Leu | Gly | Asp |
| | | | 35 | | | | | 40 | | | | | 45 | | |
| Arg | Val | Thr | Ile | Ser | Cys | Arg | Ala | Ser | Gln | Asp | Ile | Ser | Lys | Tyr | Leu |
| 50 | | | | | 55 | | | | | 60 | | | | | |
| Asn | Trp | Tyr | Gln | Gln | Lys | Pro | Asp | Gly | Thr | Val | Lys | Leu | Leu | Ile | Tyr |
| 65 | | | | | 70 | | | | | 75 | | | | | 80 |
| His | Thr | Ser | Arg | Leu | His | Ser | Gly | Val | Pro | Ser | Arg | Phe | Ser | Gly | Ser |
| | | | | 85 | | | | | 90 | | | | | 95 | |
| Gly | Ser | Gly | Thr | Asp | Tyr | Ser | Leu | Thr | Ile | Ser | Asn | Leu | Glu | Gln | Glu |
| | | | 100 | | | | | 105 | | | | | 110 | | |
| Asp | Ile | Ala | Thr | Tyr | Phe | Cys | Gln | Gln | Gly | Asn | Thr | Leu | Pro | Tyr | Thr |
| | | | 115 | | | | | 120 | | | | | 125 | | |
| Phe | Gly | Gly | Gly | Thr | Lys | Leu | Glu | Ile | Thr | Gly | Gly | Gly | Gly | Ser | Gly |
| | | 130 | | | | | 135 | | | | | 140 | | | |
| Gly | Gly | Gly | Ser | Gly | Gly | Gly | Gly | Ser | Glu | Val | Lys | Leu | Gln | Glu | Ser |
| 145 | | | | | 150 | | | | | 155 | | | | | 160 |
| Gly | Pro | Gly | Leu | Val | Ala | Pro | Ser | Gln | Ser | Leu | Ser | Val | Thr | Cys | Thr |
| | | | | 165 | | | | | 170 | | | | | 175 | |
| Val | Ser | Gly | Val | Ser | Leu | Pro | Asp | Tyr | Gly | Val | Ser | Trp | Ile | Arg | Gln |
| | | | 180 | | | | | 185 | | | | | 190 | | |
| Pro | Pro | Arg | Lys | Gly | Leu | Glu | Trp | Leu | Gly | Val | Ile | Trp | Gly | Ser | Glu |
| | | 195 | | | | | 200 | | | | | 205 | | | |
| Thr | Thr | Tyr | Tyr | Asn | Ser | Ala | Leu | Lys | Ser | Arg | Leu | Thr | Ile | Ile | Lys |
| 210 | | | | | 215 | | | | | 220 | | | | | |
| Asp | Asn | Ser | Lys | Ser | Gln | Val | Phe | Leu | Lys | Met | Asn | Ser | Leu | Gln | Thr |
| 225 | | | | | 230 | | | | | 235 | | | | | 240 |
| Asp | Asp | Thr | Ala | Ile | Tyr | Tyr | Cys | Ala | Lys | His | Tyr | Tyr | Tyr | Gly | Gly |
| | | | | 245 | | | | | 250 | | | | | 255 | |
| Ser | Tyr | Ala | Met | Asp | Tyr | Trp | Gly | Gln | Gly | Thr | Ser | Val | Thr | Val | Ser |
| | | | 260 | | | | | 265 | | | | | 270 | | |
| Ser | Thr | Thr | Thr | Pro | Ala | Pro | Arg | Pro | Pro | Thr | Pro | Ala | Pro | Thr | Ile |
| | | 275 | | | | | 280 | | | | | 285 | | | |
| Ala | Ser | Gln | Pro | Leu | Ser | Leu | Arg | Pro | Glu | Ala | Cys | Arg | Pro | Ala | Ala |
| | 290 | | | | | 295 | | | | | 300 | | | | |
| Gly | Gly | Ala | Val | His | Thr | Arg | Gly | Leu | Asp | Phe | Ala | Cys | Asp | Ile | Tyr |
| 305 | | | | | 310 | | | | | 315 | | | | | 320 |
| Ile | Trp | Ala | Pro | Leu | Ala | Gly | Thr | Cys | Gly | Val | Leu | Leu | Leu | Ser | Leu |

```
                325                 330                 335
Val Ile Thr Leu Tyr Cys Gly Ser Gly Ser Gly Ser Gly Ser
            340                 345                 350

Asp Arg Arg Gly Gly Arg Met Leu Lys His Lys Arg Gln Arg Asp Asp
            355                 360                 365

Gly Glu Gly Arg Gly Glu Val Gly Ser Ala Gly Asp Met Arg Ala Ala
            370                 375                 380

Asn Leu Trp Pro Ser Pro Leu Met Ile Lys Arg Ser Lys Lys Asn Ser
385                 390                 395                 400

Leu Ala Leu Ser Leu Thr Ala Asp Gln Met Val Ser Ala Leu Leu Asp
                405                 410                 415

Ala Glu Pro Pro Ile Leu Tyr Ser Glu Tyr Asp Pro Thr Arg Pro Phe
            420                 425                 430

Ser Glu Ala Ser Met Met Gly Leu Leu Thr Asn Leu Ala Asp Arg Glu
            435                 440                 445

Leu Val His Met Ile Asn Trp Ala Lys Arg Val Pro Gly Phe Val Asp
            450                 455                 460

Leu Thr Leu His Asp Gln Val His Leu Leu Glu Cys Ala Trp Leu Glu
465                 470                 475                 480

Ile Leu Met Ile Gly Leu Val Trp Arg Ser Met Glu His Pro Gly Lys
                485                 490                 495

Leu Leu Phe Ala Pro Asn Leu Leu Leu Asp Arg Asn Gln Gly Lys Cys
            500                 505                 510

Val Glu Gly Met Val Glu Ile Phe Asp Met Leu Leu Ala Thr Ser Ser
            515                 520                 525

Arg Phe Arg Met Met Asn Leu Gln Gly Glu Glu Phe Val Cys Leu Lys
            530                 535                 540

Ser Ile Ile Leu Leu Asn Ser Gly Val Tyr Thr Phe Leu Ser Ser Thr
545                 550                 555                 560

Leu Lys Ser Leu Glu Glu Lys Asp His Ile His Arg Val Leu Asp Lys
                565                 570                 575

Ile Thr Asp Thr Leu Ile His Leu Met Ala Lys Ala Gly Leu Thr Leu
            580                 585                 590

Gln Gln Gln His Gln Arg Leu Ala Gln Leu Leu Leu Ile Leu Ser His
            595                 600                 605

Ile Arg His Met Ser Asn Lys Arg Met Glu His Leu Tyr Ser Met Lys
            610                 615                 620

Cys Lys Asn Val Val Pro Leu Phe Asp Leu Leu Leu Glu Met Leu Asp
625                 630                 635                 640

Ala His Arg Leu His Ala Pro Thr Ser Gly Ser Gly Ser Gly Ser Gly
                645                 650                 655

Ser Lys Arg Gly Arg Lys Lys Leu Leu Tyr Ile Phe Lys Gln Pro Phe
            660                 665                 670

Met Arg Pro Val Gln Thr Thr Gln Glu Glu Asp Gly Cys Ser Cys Arg
            675                 680                 685

Phe Pro Glu Glu Glu Glu Gly Gly Cys Glu Leu Arg Ser Gly Ser Gly
            690                 695                 700

Ser Gly Ser Leu Arg Val Lys Phe Ser Arg Ser Ala Asp Ala Pro Ala
705                 710                 715                 720

Tyr Gln Gln Gly Gln Asn Gln Leu Tyr Asn Glu Leu Asn Leu Gly Arg
                725                 730                 735

Arg Glu Glu Tyr Asp Val Leu Asp Lys Arg Arg Gly Arg Asp Pro Glu
            740                 745                 750
```

Met Gly Gly Lys Pro Arg Arg Lys Asn Pro Gln Glu Gly Leu Tyr Asn
        755                 760                 765

Glu Leu Gln Lys Asp Lys Met Ala Glu Ala Tyr Ser Glu Ile Gly Met
        770                 775                 780

Lys Gly Glu Arg Arg Arg Gly Lys Gly His Asp Gly Leu Tyr Gln Gly
785                 790                 795                 800

Leu Ser Thr Ala Thr Lys Asp Thr Tyr Asp Ala Leu His Met Gln Ala
        805                 810                 815

Leu Pro Pro Arg Gly Ser Gly Ser Gly Ser Met Val Ser Lys
        820                 825                 830

Gly Glu Glu Asp Asn Met Ala Ile Ile Lys Glu Phe Met Arg Phe Lys
        835                 840                 845

Val His Met Glu Gly Ser Val Asn Gly His Glu Phe Glu Ile Glu Gly
        850                 855                 860

Glu Gly Glu Gly Arg Pro Tyr Glu Gly Thr Gln Thr Ala Lys Leu Lys
865                 870                 875                 880

Val Thr Lys Gly Gly Pro Leu Pro Phe Ala Trp Asp Ile Leu Ser Pro
                885                 890                 895

Gln Phe Met Tyr Gly Ser Lys Ala Tyr Val Lys His Pro Ala Asp Ile
        900                 905                 910

Pro Asp Tyr Leu Lys Leu Ser Phe Pro Glu Gly Phe Lys Trp Glu Arg
        915                 920                 925

Val Met Asn Phe Glu Asp Gly Gly Val Val Thr Val Thr Gln Asp Ser
        930                 935                 940

Ser Leu Gln Asp Gly Glu Phe Ile Tyr Lys Val Lys Leu Arg Gly Thr
945                 950                 955                 960

Asn Phe Pro Ser Asp Gly Pro Val Met Gln Lys Lys Thr Met Gly Trp
                965                 970                 975

Glu Ala Ser Ser Glu Arg Met Tyr Pro Glu Asp Gly Ala Leu Lys Gly
                980                 985                 990

Glu Ile Lys Gln Arg Leu Lys Leu Lys Asp Gly Gly His Tyr Asp Ala
        995                 1000                1005

Glu Val Lys Thr Thr Tyr Lys Ala Lys Lys Pro Val Gln Leu Pro
        1010                1015                1020

Gly Ala Tyr Asn Val Asn Ile Lys Leu Asp Ile Thr Ser His Asn
        1025                1030                1035

Glu Asp Tyr Thr Ile Val Glu Gln Tyr Glu Arg Ala Glu Gly Arg
        1040                1045                1050

His Ser Thr Gly Gly Met Asp Glu Leu Tyr Lys Cys Val Thr Asp
        1055                1060                1065

<210> SEQ ID NO 36
<211> LENGTH: 2694
<212> TYPE: DNA
<213> ORGANISM: Artificial Sequence
<220> FEATURE:
<223> OTHER INFORMATION: v.5 construct

<400> SEQUENCE: 36
atggctctgc ctgtgacagc tctgctgctg cctctggccc tgctgctgca tgccgctaga      60
cctgagcaga agctgatctc cgaagaggac ctggacatcc agatgaccca gaccaccagc     120
agcctgagcg ccagcctggg cgatagagtg accatcagct gcagagccag ccaggacatc    180
agcaagtacc tgaactggta tcagcagaaa cccgacggca ccgtgaagct gctgatctac     240

```
cacaccagca gactgcacag cggcgtgccc agcagatttt ctggcagcgg ctccggcacc    300
gactacagcc tgaccatctc caacctggaa caggaagata tcgctaccta cttctgtcag    360
caaggcaaca ccctgcccta ccttcggc ggaggcacca agctggaaat cacaggcggc      420
ggaggatctg gcggaggcgg aagtggcgga ggggatctg aagtgaaact gcaggaaagc     480
ggccctggcc tggtggcccc atctcagtct ctgagcgtga cctgtaccgt gtccggcgtg    540
tccctgcctg actatggcgt gtcctggatc agacagcccc ccagaaaggg cctgaatgg     600 ctgggagtga tctgggcag cgagacaacc tactacaaca gcgccctgaa gtcccggctg      660
accatcatca aggacaactc caagagccag gtgttcctga agatgaacag cctgcagacc    720
gacgacaccg ccatctacta ctgcgccaag cactactact acggcggcag ctacgccatg    780
gactactggg gccagggcac aagcgtgacc gtgtctagca caaccacccc tgccccctaga   840 cctccaaccc cagcccctac aatcgccagc cagcctctgt ctctgaggcc cgaggcttgt    900
agaccagctg ctggcggagc cgtgcacacc agaggactgg atttcgcctg cgacatctac    960
atctgggccc ctctggccgg cacatgtggc gtgctgctgc tgagcctcgt gatcaccctg   1020
tactgcggat ccggcagcgg atctggcagt ggaagcgata aagaggcgg cagaatgctg    1080 aaacacaagc ggcagaggga cgacggggaa ggcagaggcg aagtgggatc tgccggcgat   1140
atgagagccg ccaacctgtg gcctagcccc ctgatgatca gcggagcaa gaagaactcc    1200 ctggccctga gcctgaccgc cgaccagatg gtgtctgccc tgctggatgc cgagcccccc   1260
atcctgtaca gcgagtacga ccccaccaga cccttcagcg aggccagcat gatgggcctg   1320
ctgaccaacc tggccgaccg ggaactggtg cacatgatca actgggccaa gcgggtgccc   1380
ggcttcgtgg atctgacact gcacgaccag gtgcacctgc tggaatgcgc ttggctggaa   1440
atcctgatga tcggcctcgt gtggcggagc atggaacacc ctggcaagct gctgttcgcc   1500
cccaacctgc tgctggaccg gaaccagggc aaatgcgtgg aaggcatggt ggaaatcttc   1560
gacatgctgc tggccacctc cagccggttc cggatgatga acctgcaggg cgaagagttc   1620
gtgtgtctga agtccatcat cctgctgaat agcggcgtgt acacctcct gagcagcacc   1680 ctgaaaagcc tggaagaaaa ggaccacatc accgggtgc tggacaagat caccgacacc   1740
ctgattcacc tgatggccaa ggccggactg accctgcagc agcagcatca gagactggct   1800
cagctgctgc tgatcctgtc ccacatccgg cacatgagca caagcggat ggaacatctg    1860 tacagcatga agtgcaagaa cgtggtgcct ctgttcgatc tgctgctgga aatgctggac   1920
gcccacaggc tgcacgcccc aacatccgga tctggctctg gaagcggcag catggtgtct   1980 aaggggaag aggacaacat ggccatcatc aaagaattca tgcggttcaa ggtgcacatg    2040
gaaggctccg tgaatggcca cgaattcgag atcgaggggg agggcgaggg cagaccttat   2100
gagggaaccc agaccgccaa gctgaaagtg accaagggcg gacccctgcc tttcgcctgg   2160
gatatcctgt ctccccagtt tatgtacggc agcaaggcct acgtgaagca ccccgccgac   2220
atccccgact acctgaagct gagcttccct gagggcttca gtgggagag agtgatgaat   2280 ttcgaggacg gcggagtcgt gacagtgacc caggatagct ctctgcagga cggcgagttc   2340
atctacaaag tgaagctgcg gggcaccaac ttccccagcg acggaccgt gatgcagaaa   2400 aagaccatgg gctgggaggc cagctccgag agaatgtacc cagaggacgg ggccctgaag   2460
ggggagatca gcagcggct gaaactgaag gatggcggcc actacgacgc agaagtgaaa   2520
accacctaca aggccaagaa acctgtgcag ctgcctggcg cctacaatgt gaacatcaag   2580
ctggacatta ccagccacaa cgaggactac accatcgtgg aacagtacga gcgggccgag   2640
```
ggcaggcatt ctacaggcgg aatggatgaa ctgtataagt gcgtgaccga ctag    2694

<210> SEQ ID NO 37
<211> LENGTH: 897
<212> TYPE: PRT
<213> ORGANISM: Artificial Sequence
<220> FEATURE:
<223> OTHER INFORMATION: v.5 construct

<400> SEQUENCE: 37

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Gly Ser Gly Ser Gly Ser Gly Ser
            340                 345                 350

```
Asp Arg Arg Gly Gly Arg Met Leu Lys His Lys Arg Gln Arg Asp Asp
        355                 360                 365
Gly Glu Gly Arg Gly Glu Val Gly Ser Ala Gly Asp Met Arg Ala Ala
    370                 375                 380
Asn Leu Trp Pro Ser Pro Leu Met Ile Lys Arg Ser Lys Lys Asn Ser
385                 390                 395                 400
Leu Ala Leu Ser Leu Thr Ala Asp Gln Met Val Ser Ala Leu Leu Asp
                405                 410                 415
Ala Glu Pro Pro Ile Leu Tyr Ser Glu Tyr Asp Pro Thr Arg Pro Phe
            420                 425                 430
Ser Glu Ala Ser Met Met Gly Leu Leu Thr Asn Leu Ala Asp Arg Glu
        435                 440                 445
Leu Val His Met Ile Asn Trp Ala Lys Arg Val Pro Gly Phe Val Asp
    450                 455                 460
Leu Thr Leu His Asp Gln Val His Leu Leu Glu Cys Ala Trp Leu Glu
465                 470                 475                 480
Ile Leu Met Ile Gly Leu Val Trp Arg Ser Met Glu His Pro Gly Lys
                485                 490                 495
Leu Leu Phe Ala Pro Asn Leu Leu Asp Arg Asn Gln Gly Lys Cys
            500                 505                 510
Val Glu Gly Met Val Glu Ile Phe Asp Met Leu Leu Ala Thr Ser Ser
        515                 520                 525
Arg Phe Arg Met Met Asn Leu Gln Gly Glu Glu Phe Val Cys Leu Lys
    530                 535                 540
Ser Ile Ile Leu Leu Asn Ser Gly Val Tyr Thr Phe Leu Ser Ser Thr
545                 550                 555                 560
Leu Lys Ser Leu Glu Glu Lys Asp His Ile His Arg Val Leu Asp Lys
                565                 570                 575
Ile Thr Asp Thr Leu Ile His Leu Met Ala Lys Ala Gly Leu Thr Leu
            580                 585                 590
Gln Gln Gln His Gln Arg Leu Ala Gln Leu Leu Leu Ile Leu Ser His
        595                 600                 605
Ile Arg His Met Ser Asn Lys Arg Met Glu His Leu Tyr Ser Met Lys
    610                 615                 620
Cys Lys Asn Val Val Pro Leu Phe Asp Leu Leu Leu Glu Met Leu Asp
625                 630                 635                 640
Ala His Arg Leu His Ala Pro Thr Ser Gly Ser Gly Ser Gly Ser Gly
                645                 650                 655
Ser Met Val Ser Lys Gly Glu Glu Asp Asn Met Ala Ile Ile Lys Glu
            660                 665                 670
Phe Met Arg Phe Lys Val His Met Glu Gly Ser Val Asn Gly His Glu
        675                 680                 685
Phe Glu Ile Glu Gly Glu Gly Glu Gly Arg Pro Tyr Glu Gly Thr Gln
    690                 695                 700
Thr Ala Lys Leu Lys Val Thr Lys Gly Gly Pro Leu Pro Phe Ala Trp
705                 710                 715                 720
Asp Ile Leu Ser Pro Gln Phe Met Tyr Gly Ser Lys Ala Tyr Val Lys
                725                 730                 735
His Pro Ala Asp Ile Pro Asp Tyr Leu Lys Leu Ser Phe Pro Glu Gly
            740                 745                 750
Phe Lys Trp Glu Arg Val Met Asn Phe Glu Asp Gly Gly Val Val Thr
        755                 760                 765
Val Thr Gln Asp Ser Ser Leu Gln Asp Gly Glu Phe Ile Tyr Lys Val
```

```
                   770               775               780
Lys Leu Arg Gly Thr Asn Phe Pro Ser Asp Gly Pro Val Met Gln Lys
785               790               795               800

Lys Thr Met Gly Trp Glu Ala Ser Ser Glu Arg Met Tyr Pro Glu Asp
                805               810               815

Gly Ala Leu Lys Gly Glu Ile Lys Gln Arg Leu Lys Leu Lys Asp Gly
            820               825               830

Gly His Tyr Asp Ala Glu Val Lys Thr Thr Tyr Lys Ala Lys Lys Pro
        835               840               845

Val Gln Leu Pro Gly Ala Tyr Asn Val Asn Ile Lys Leu Asp Ile Thr
850               855               860

Ser His Asn Glu Asp Tyr Thr Ile Val Glu Gln Tyr Glu Arg Ala Glu
865               870               875               880

Gly Arg His Ser Thr Gly Gly Met Asp Glu Leu Tyr Lys Cys Val Thr
                885               890               895

Asp

<210> SEQ ID NO 38
<211> LENGTH: 2391
<212> TYPE: DNA
<213> ORGANISM: Artificial Sequence
<220> FEATURE:
<223> OTHER INFORMATION: ERa-LBD fusion protein with FLAG construct

<400> SEQUENCE: 38
atgatccacc tgggacacat cctgtttttg ctgctgctgc cagtggctgc cgccgattac      60
aaagacgacg atgataaaca gacaacacca ggcgagagat ctagcctgcc cgccttctac     120
cctggcacca gcggctcttg ttctggctgt ggcagcctgt ctctgcccat ctatatttgg     180
gcacccctgg ctggaacctg cggagtgctg ctgctgtctc tcgtgattac actgtattgc     240
aaaaggggcc ggaaaaagct gctgtatatt ttcaaacagc cttttatgag gcctgtgcag     300
acaacacagg aagaggacgg ctgtagctgt cggttccccg aagaggaaga gggggggctgc    360 gaactgggat caggcagtgg ctctggcagc gatagaagag cggcagaat gctgaaacac      420 aagcggcaga gggacgacgg ggaaggcaga ggcgaagtgg gatctgccgg cgatatgaga     480
gccgccaacc tgtggcctag ccccctgatg atcaagcgga gcaagaagaa ctccctggcc     540
ctgagcctga ccgccgacca gatggtgtct gccctgctgg atgccgagcc ccccatcctg     600
tacagcgagt acgaccccac cagaccttc agcgaggcca gcatgatggg cctgctgacc      660
aacctggccg accgggaact ggtgcacatg atcaactggg ccaagcgggt gcccggcttc     720
gtggatctga cactgcacga ccaggtgcac ctgctggaat cgcttggct ggaaatcctg      780 atgatcggcc tcgtgtggcg gagcatggaa caccctggca agctgctgtt cgcccccaac     840
ctgctgctgg accggaacca gggcaaatgc gtggaaggca tggtggaaat cttcgacatg     900
ctgctggcca cctccagccg gttccggatg atgaacctgc agggcgaaga gttcgtgtgt     960
ctgaagtcca tcatcctgct gaatagcggc gtgtacacct tcctgagcag caccctgaaa    1020
agcctggaag aaaaggacca catccaccgg gtgctggaca gatcaccga caccctgatt     1080 cacctgatgg ccaaggccgg actgaccctg cagcagcagc atcagagact ggctcagctg    1140
ctgctgatcc tgtcccacat ccggcacatg agcaacaagc ggatggaaca tctgtacagc    1200
atgaagtgca agaacgtggt gcctctgttc gatctgctgc tggaaatgct ggacgcccac    1260
aggctgcacg ccccaacatc cagatccgga tctggaagtg ctcccctgag agtgaagttt    1320
```

-continued

```
agcagaagcg ccgacgcccc tgcctatcag cagggacaga accagctgta taacgagctg    1380
aacctgggca ggcgggaaga gtacgacgtg ctggataaga ggcggggcag ggaccctgaa    1440
atgggcggca aacccagacg gaagaacccc caggaaggcc tgtacaacga actgcagaaa    1500
gacaagatgg ccgaggccta cagcgagatc ggaatgaagg cgagcggcg gagaggcaag    1560
ggacatgatg gcctgtacca gggcctgtcc accgccacca aggacaccta tgacgccctg    1620
cacatgcagg ccctgcctcc aagaggaagt ggatctggga gcggctctat ggtgtctaag    1680
ggggaagagg acaacatggc catcatcaaa gaattcatgc ggttcaaggt gcacatggaa    1740
ggctccgtga atggccacga attcgagatc gaggggagg gcgagggcag accttatgag    1800
ggaacccaga ccgccaagct gaaagtgacc aagggcggac ccctgccttt cgcctgggat    1860
atcctgtctc cccagtttat gtacggcagc aaggcctacg tgaagcaccc cgccgacatc    1920
cccgactacc tgaagctgag cttccctgag ggcttcaagt gggagagagt gatgaatttc    1980
gaggacggcg gagtcgtgac agtgacccag gatagctctc tgcaggacgg cgagttcatc    2040
tacaaagtga agctgcgggg caccaacttc cccagcgacg gacccgtgat gcagaaaaag    2100
accatgggct gggaggccag ctccgagaga atgtacccag aggacggggc cctgaagggg    2160
gagatcaagc agcggctgaa actgaaggat ggcggccact acgacgcaga agtgaaaacc    2220
acctacaagg ccaagaaacc tgtgcagctg cctggcgcct acaatgtgaa catcaagctg    2280
gacattacca gccacaacga ggactacacc atcgtggaac agtacgagcg ggccgagggc    2340
aggcattcta caggcggaat ggatgaactg tataagtgcg tgaccgacta g             2391
```

<210> SEQ ID NO 39
<211> LENGTH: 796
<212> TYPE: PRT
<213> ORGANISM: Artificial Sequence
<220> FEATURE:
<223> OTHER INFORMATION: ERa-LBD fusion protein with FLAG construct

<400> SEQUENCE: 39

```
Met Ile His Leu Gly His Ile Leu Phe Leu Leu Leu Leu Pro Val Ala
1               5                   10                  15

Ala Ala Asp Tyr Lys Asp Asp Asp Lys Gln Thr Thr Pro Gly Glu
            20                  25                  30

Arg Ser Ser Leu Pro Ala Phe Tyr Pro Gly Thr Ser Gly Ser Cys Ser
        35                  40                  45

Gly Cys Gly Ser Leu Ser Leu Pro Ile Tyr Ile Trp Ala Pro Leu Ala
    50                  55                  60

Gly Thr Cys Gly Val Leu Leu Ser Leu Val Ile Thr Leu Tyr Cys
65                  70                  75                  80

Lys Arg Gly Arg Lys Leu Leu Tyr Ile Phe Lys Gln Pro Phe Met
                85                  90                  95

Arg Pro Val Gln Thr Thr Gln Glu Glu Asp Gly Cys Ser Cys Arg Phe
            100                 105                 110

Pro Glu Glu Glu Glu Gly Gly Cys Glu Leu Gly Ser Gly Ser Gly Ser
        115                 120                 125

Gly Ser Asp Arg Arg Gly Gly Arg Met Leu Lys His Lys Arg Gln Arg
    130                 135                 140

Asp Asp Gly Glu Gly Arg Gly Glu Val Gly Ser Ala Gly Asp Met Arg
145                 150                 155                 160

Ala Ala Asn Leu Trp Pro Ser Pro Leu Met Ile Lys Arg Ser Lys Lys
                165                 170                 175
```

```
Asn Ser Leu Ala Leu Ser Leu Thr Ala Asp Gln Met Val Ser Ala Leu
                180                 185                 190

Leu Asp Ala Glu Pro Pro Ile Leu Tyr Ser Glu Tyr Asp Pro Thr Arg
            195                 200                 205

Pro Phe Ser Glu Ala Ser Met Met Gly Leu Leu Thr Asn Leu Ala Asp
    210                 215                 220

Arg Glu Leu Val His Met Ile Asn Trp Ala Lys Arg Val Pro Gly Phe
225                 230                 235                 240

Val Asp Leu Thr Leu His Asp Gln Val His Leu Leu Glu Cys Ala Trp
                245                 250                 255

Leu Glu Ile Leu Met Ile Gly Leu Val Trp Arg Ser Met Glu His Pro
                260                 265                 270

Gly Lys Leu Leu Phe Ala Pro Asn Leu Leu Leu Asp Arg Asn Gln Gly
            275                 280                 285

Lys Cys Val Glu Gly Met Val Glu Ile Phe Asp Met Leu Leu Ala Thr
    290                 295                 300

Ser Ser Arg Phe Arg Met Met Asn Leu Gln Gly Glu Glu Phe Val Cys
305                 310                 315                 320

Leu Lys Ser Ile Ile Leu Leu Asn Ser Gly Val Tyr Thr Phe Leu Ser
                325                 330                 335

Ser Thr Leu Lys Ser Leu Glu Glu Lys Asp His Ile His Arg Val Leu
                340                 345                 350

Asp Lys Ile Thr Asp Thr Leu Ile His Leu Met Ala Lys Ala Gly Leu
            355                 360                 365

Thr Leu Gln Gln Gln His Gln Arg Leu Ala Gln Leu Leu Leu Ile Leu
    370                 375                 380

Ser His Ile Arg His Met Ser Asn Lys Arg Met Glu His Leu Tyr Ser
385                 390                 395                 400

Met Lys Cys Lys Asn Val Val Pro Leu Phe Asp Leu Leu Leu Glu Met
                405                 410                 415

Leu Asp Ala His Arg Leu His Ala Pro Thr Ser Arg Ser Gly Ser Gly
                420                 425                 430

Ser Gly Ser Leu Arg Val Lys Phe Ser Arg Ser Ala Asp Ala Pro Ala
            435                 440                 445

Tyr Gln Gln Gly Gln Asn Gln Leu Tyr Asn Glu Leu Asn Leu Gly Arg
    450                 455                 460

Arg Glu Glu Tyr Asp Val Leu Asp Lys Arg Arg Gly Arg Asp Pro Glu
465                 470                 475                 480

Met Gly Gly Lys Pro Arg Arg Lys Asn Pro Gln Glu Gly Leu Tyr Asn
                485                 490                 495

Glu Leu Gln Lys Asp Lys Met Ala Glu Ala Tyr Ser Glu Ile Gly Met
                500                 505                 510

Lys Gly Glu Arg Arg Arg Gly Lys Gly His Asp Gly Leu Tyr Gln Gly
            515                 520                 525

Leu Ser Thr Ala Thr Lys Asp Thr Tyr Asp Ala Leu His Met Gln Ala
    530                 535                 540

Leu Pro Pro Arg Gly Ser Gly Ser Gly Ser Met Val Ser Lys
545                 550                 555                 560

Gly Glu Glu Asp Asn Met Ala Ile Ile Lys Glu Phe Met Arg Phe Lys
                565                 570                 575

Val His Met Glu Gly Ser Val Asn Gly His Glu Phe Glu Ile Glu Gly
                580                 585                 590

Glu Gly Glu Gly Arg Pro Tyr Glu Gly Thr Gln Thr Ala Lys Leu Lys
```

```
                595                 600                 605

Val Thr Lys Gly Gly Pro Leu Pro Phe Ala Trp Asp Ile Leu Ser Pro
        610                 615                 620

Gln Phe Met Tyr Gly Ser Lys Ala Tyr Val Lys His Pro Ala Asp Ile
625                 630                 635                 640

Pro Asp Tyr Leu Lys Leu Ser Phe Pro Glu Gly Phe Lys Trp Glu Arg
                645                 650                 655

Val Met Asn Phe Glu Asp Gly Gly Val Val Thr Val Thr Gln Asp Ser
            660                 665                 670

Ser Leu Gln Asp Gly Glu Phe Ile Tyr Lys Val Lys Leu Arg Gly Thr
        675                 680                 685

Asn Phe Pro Ser Asp Gly Pro Val Met Gln Lys Lys Thr Met Gly Trp
690                 695                 700

Glu Ala Ser Ser Glu Arg Met Tyr Pro Glu Asp Gly Ala Leu Lys Gly
705                 710                 715                 720

Glu Ile Lys Gln Arg Leu Lys Leu Lys Asp Gly Gly His Tyr Asp Ala
                725                 730                 735

Glu Val Lys Thr Thr Tyr Lys Ala Lys Lys Pro Val Gln Leu Pro Gly
            740                 745                 750

Ala Tyr Asn Val Asn Ile Lys Leu Asp Ile Thr Ser His Asn Glu Asp
        755                 760                 765

Tyr Thr Ile Val Glu Gln Tyr Glu Arg Ala Glu Gly Arg His Ser Thr
770                 775                 780

Gly Gly Met Asp Glu Leu Tyr Lys Cys Val Thr Asp
785                 790                 795

<210> SEQ ID NO 40
<211> LENGTH: 18
<212> TYPE: PRT
<213> ORGANISM: Homo sapiens

<400> SEQUENCE: 40

Met Ile His Leu Gly His Ile Leu Phe Leu Leu Leu Leu Pro Val Ala
1               5                   10                  15

Ala Ala

<210> SEQ ID NO 41
<211> LENGTH: 8
<212> TYPE: PRT
<213> ORGANISM: Artificial Sequence
<220> FEATURE:
<223> OTHER INFORMATION: FLAG tag

<400> SEQUENCE: 41

Asp Tyr Lys Asp Asp Asp Asp Lys
1               5

<210> SEQ ID NO 42
<211> LENGTH: 30
<212> TYPE: PRT
<213> ORGANISM: Homo sapiens

<400> SEQUENCE: 42

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro
            20                  25                  30
```

```
<210> SEQ ID NO 43
<211> LENGTH: 24
<212> TYPE: PRT
<213> ORGANISM: Homo sapiens

<400> SEQUENCE: 43

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 44
<211> LENGTH: 42
<212> TYPE: PRT
<213> ORGANISM: Homo sapiens

<400> SEQUENCE: 44

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 45
<211> LENGTH: 8
<212> TYPE: PRT
<213> ORGANISM: Artificial Sequence
<220> FEATURE:
<223> OTHER INFORMATION: Linker sequence

<400> SEQUENCE: 45

Gly Ser Gly Ser Gly Ser Gly Ser
1               5

<210> SEQ ID NO 46
<211> LENGTH: 297
<212> TYPE: PRT
<213> ORGANISM: Artificial Sequence
<220> FEATURE:
<223> OTHER INFORMATION: Modified ERa ligand binding domain

<400> SEQUENCE: 46

Asp Arg Arg Gly Gly Arg Met Leu Lys His Lys Arg Gln Arg Asp Asp
1               5                   10                  15

Gly Glu Gly Arg Gly Glu Val Gly Ser Ala Gly Asp Met Arg Ala Ala
                20                  25                  30

Asn Leu Trp Pro Ser Pro Leu Met Ile Lys Arg Ser Lys Lys Asn Ser
            35                  40                  45

Leu Ala Leu Ser Leu Thr Ala Asp Gln Met Val Ser Ala Leu Leu Asp
        50                  55                  60

Ala Glu Pro Pro Ile Leu Tyr Ser Glu Tyr Asp Pro Thr Arg Pro Phe
65                  70                  75                  80

Ser Glu Ala Ser Met Met Gly Leu Leu Thr Asn Leu Ala Asp Arg Glu
                85                  90                  95

Leu Val His Met Ile Asn Trp Ala Lys Arg Val Pro Gly Phe Val Asp
            100                 105                 110

Leu Thr Leu His Asp Gln Val His Leu Leu Glu Cys Ala Trp Leu Glu
        115                 120                 125

Ile Leu Met Ile Gly Leu Val Trp Arg Ser Met Glu His Pro Gly Lys
    130                 135                 140
```

```
Leu Leu Phe Ala Pro Asn Leu Leu Asp Arg Asn Gln Gly Lys Cys
145                 150                 155                 160

Val Glu Gly Met Val Glu Ile Phe Asp Met Leu Leu Ala Thr Ser Ser
                165                 170                 175

Arg Phe Arg Met Met Asn Leu Gln Gly Glu Glu Phe Val Cys Leu Lys
            180                 185                 190

Ser Ile Ile Leu Leu Asn Ser Gly Val Tyr Thr Phe Leu Ser Ser Thr
        195                 200                 205

Leu Lys Ser Leu Glu Glu Lys Asp His Ile His Arg Val Leu Asp Lys
    210                 215                 220

Ile Thr Asp Thr Leu Ile His Leu Met Ala Lys Ala Gly Leu Thr Leu
225                 230                 235                 240

Gln Gln Gln His Gln Arg Leu Ala Gln Leu Leu Leu Ile Leu Ser His
                245                 250                 255

Ile Arg His Met Ser Asn Lys Arg Met Glu His Leu Tyr Ser Met Lys
            260                 265                 270

Cys Lys Asn Val Val Pro Leu Phe Asp Leu Leu Leu Glu Met Leu Asp
        275                 280                 285

Ala His Arg Leu His Ala Pro Thr Ser
    290                 295

<210> SEQ ID NO 47
<211> LENGTH: 8
<212> TYPE: PRT
<213> ORGANISM: Artificial Sequence
<220> FEATURE:
<223> OTHER INFORMATION: Linker sequence

<400> SEQUENCE: 47

Arg Ser Gly Ser Gly Ser Gly Ser
1               5

<210> SEQ ID NO 48
<211> LENGTH: 113
<212> TYPE: PRT
<213> ORGANISM: Homo sapiens

<400> SEQUENCE: 48

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
                20                  25                  30

Tyr Asp Val Leu Asp Lys Arg Gly Arg Asp Pro Glu Met Gly Gly
            35                  40                  45

Lys Pro Arg Arg Lys Asn Pro Gln Glu Gly Leu Tyr Asn Glu Leu Gln
50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 49
<211> LENGTH: 8
<212> TYPE: PRT
```

<213> ORGANISM: Artificial Sequence
<220> FEATURE:
<223> OTHER INFORMATION: Linker sequence

<400> SEQUENCE: 49

Gly Ser Gly Ser Gly Ser Gly Ser
1               5

<210> SEQ ID NO 50
<211> LENGTH: 240
<212> TYPE: PRT
<213> ORGANISM: Artificial Sequence
<220> FEATURE:
<223> OTHER INFORMATION: mCherry

<400> SEQUENCE: 50

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Cys Val Thr Asp
225                 230                 235                 240

<210> SEQ ID NO 51
<211> LENGTH: 2265
<212> TYPE: DNA
<213> ORGANISM: Artificial Sequence
<220> FEATURE:
<223> OTHER INFORMATION: PR ligand-binding domain construct

<400> SEQUENCE: 51
atgatccacc tgggacacat cctgtttttg ctgctgctgc cagtggctgc cgccgattac      60
aaagacgacg atgataaaca gacaacacca ggcgagagat ctagcctgcc cgccttctac     120
cctggcacca gcggctcttg ttctggctgt ggcagcctgt ctctgcccat ctatatttgg     180

-continued

```
gcacccctgg ctggaacctg cggagtgctg ctgctgtctc tcgtgattac actgtattgc      240
aaaaggggcc ggaaaaagct gctgtatatt ttcaaacagc cttttatgag gcctgtgcag      300
acaacacagg aagaggacgg ctgtagctgt cggttccccg aagaggaaga gggggctgc       360 gaactgggat caggcagtgg ctctggcagc gggcaagaca ttcagctcat acctcctttg      420
ataaatttgc tgatgtctat agaaccagat gtcatatacg ctggtcacga caatacgaaa      480
ccggacacat cttcatcttt gcttacctct ctgaatcaac tgggtgaacg acagctcctg      540
agtgttgtta gtggtctaa aagcctcccg ggcttcagga atttgcacat agacgaccaa       600
atcacgctca tccaatattc ctggatgagt ctcatggtct ttggtctcgg ttggcgcagc      660
tataagcacg tctctggcca gatgttgtat ttcgcaccag acctgatcct gaacgaacag      720
aggatgaagg aatcaagctt ttactctctc tgcttgacta tgtggcaaat cccccaagaa      780
ttcgtgaaac ttcaagtttc ccaagaagaa ttcctctgca tgaaagtcct tcttttgctc      840
aacacgattc ccctggaagg cttgaggtct caaacgcaat tcgaggagat gcggagtagc      900
tatatacgcg aactcatcaa ggccatcggt ttgcggcaaa agggagtggt ctctagtagc      960
caacgatttt accagctgac taagctcctt gacaaccttc acgatctcgt caaacaactg     1020
cacctgtact gtcttaacac atttatacaa tcacgggcac tttctgtaga gttcccagag     1080
atgatgtctg aggtcatcgc agcccaactt ccgaaaattc ttgcaggaat ggtgaagcca     1140
cttctgttcc ataagaaaag atccggatct ggaagtggct ccctgagagt gaagtttagc     1200
agaagcgccg acgcccctgc ctatcagcag ggacagaacc agctgtataa cgagctgaac     1260
ctgggcaggc gggaagagta cgacgtgctg gataagaggc ggggcaggga ccctgaaatg     1320
ggcggcaaac ccagacggaa gaaccccag gaaggcctgt acaacgaact gcagaaagac      1380
aagatggccg aggcctacag cgagatcgga atgaagggcg agcggcggag aggcaaggga     1440
catgatggcc tgtaccaggg cctgtccacc gccaccaagg acacctatga cgccctgcac     1500
atgcaggccc tgcctccaag aggaagtgga tctgggagcg ctctatggt gtctaagggg      1560 gaagaggaca acatggccat catcaaagaa ttcatgcggt tcaaggtgca catggaaggc     1620
tccgtgaatg gccacgaatt cgagatcgag ggggagggcg agggcagacc ttatgaggga     1680
acccagaccg ccaagctgaa agtgaccaag gcggacccc tgccttttcgc ctgggatatc     1740 ctgtctcccc agtttatgta cggcagcaag gcctacgtga agcaccccgc cgacatcccc     1800
gactacctga gctgagcttc cctgagggc ttcaagtggg agagtgat gaatttcgag       1860 gacggcggag tcgtgacagt gacccaggat agctctctgc aggacggcga gttcatctac     1920
aaagtgaagc tgcggggcac caacttcccc agcgacggac ccgtgatgca gaaaaagacc     1980
atgggctggg aggccagctc cgagagaatg tacccagagg acggggccct gaaggggggag    2040 atcaagcagc ggctgaaact gaaggatggc ggccactacg acgcagaagt gaaaaccacc     2100
tacaaggcca gaaacctgt gcagctgcct ggcgcctaca tgtgaacat caagctggac      2160 attaccagcc acaacgagga ctacaccatc gtggaacagt acgagcgggc cgagggcagg     2220
cattctacag gcggaatgga tgaactgtat aagtgcgtga ccgac                    2265
```

<210> SEQ ID NO 52
<211> LENGTH: 755
<212> TYPE: PRT
<213> ORGANISM: Artificial Sequence
<220> FEATURE:
<223> OTHER INFORMATION: PR ligand-binding domain construct

```
<400> SEQUENCE: 52

Met Ile His Leu Gly His Ile Leu Phe Leu Leu Leu Pro Val Ala
1               5                   10                  15

Ala Ala Asp Tyr Lys Asp Asp Asp Lys Gln Thr Thr Pro Gly Glu
            20                  25                  30

Arg Ser Ser Leu Pro Ala Phe Tyr Pro Gly Thr Ser Gly Ser Cys Ser
        35                  40                  45

Gly Cys Gly Ser Leu Ser Leu Pro Ile Tyr Ile Trp Ala Pro Leu Ala
50                  55                      60

Gly Thr Cys Gly Val Leu Leu Ser Leu Val Ile Thr Leu Tyr Cys
65                  70                  75                  80

Lys Arg Gly Arg Lys Lys Leu Leu Tyr Ile Phe Lys Gln Pro Phe Met
                85                  90                  95

Arg Pro Val Gln Thr Thr Gln Glu Glu Asp Gly Cys Ser Cys Arg Phe
            100                 105                 110

Pro Glu Glu Glu Glu Gly Gly Cys Glu Leu Gly Ser Gly Ser Gly Ser
            115                 120                 125

Gly Ser Gly Gln Asp Ile Gln Leu Ile Pro Pro Leu Ile Asn Leu Leu
    130                 135                 140

Met Ser Ile Glu Pro Asp Val Ile Tyr Ala Gly His Asp Asn Thr Lys
145                 150                 155                 160

Pro Asp Thr Ser Ser Ser Leu Leu Thr Ser Leu Asn Gln Leu Gly Glu
                165                 170                 175

Arg Gln Leu Leu Ser Val Val Lys Trp Ser Lys Ser Leu Pro Gly Phe
            180                 185                 190

Arg Asn Leu His Ile Asp Asp Gln Ile Thr Leu Ile Gln Tyr Ser Trp
        195                 200                 205

Met Ser Leu Met Val Phe Gly Leu Gly Trp Arg Ser Tyr Lys His Val
210                 215                 220

Ser Gly Gln Met Leu Tyr Phe Ala Pro Asp Leu Ile Leu Asn Glu Gln
225                 230                 235                 240

Arg Met Lys Glu Ser Ser Phe Tyr Ser Leu Cys Leu Thr Met Trp Gln
            245                 250                 255

Ile Pro Gln Glu Phe Val Lys Leu Gln Val Ser Gln Glu Glu Phe Leu
            260                 265                 270

Cys Met Lys Val Leu Leu Leu Asn Thr Ile Pro Leu Glu Gly Leu
        275                 280                 285

Arg Ser Gln Thr Gln Phe Glu Glu Met Arg Ser Ser Tyr Ile Arg Glu
    290                 295                 300

Leu Ile Lys Ala Ile Gly Leu Arg Gln Lys Gly Val Val Ser Ser Ser
305                 310                 315                 320

Gln Arg Phe Tyr Gln Leu Thr Lys Leu Leu Asp Asn Leu His Asp Leu
            325                 330                 335

Val Lys Gln Leu His Leu Tyr Cys Leu Asn Thr Phe Ile Gln Ser Arg
        340                 345                 350

Ala Leu Ser Val Glu Phe Pro Glu Met Met Ser Glu Val Ile Ala Ala
            355                 360                 365

Gln Leu Pro Lys Ile Leu Ala Gly Met Val Lys Pro Leu Leu Phe His
    370                 375                 380

Lys Lys Arg Ser Gly Ser Gly Ser Leu Arg Val Lys Phe Ser
385                 390                 395                 400

Arg Ser Ala Asp Ala Pro Ala Tyr Gln Gln Gly Gln Asn Gln Leu Tyr
                405                 410                 415
```

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
            435                 440                 445

Pro Gln Glu Gly Leu Tyr Asn Glu Leu Gln Lys Asp Lys Met Ala Glu
            450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg Gly Ser Gly Ser Gly
            500                 505                 510

Ser Gly Ser Met Val Ser Lys Gly Glu Glu Asp Asn Met Ala Ile Ile
            515                 520                 525

Lys Glu Phe Met Arg Phe Lys Val His Met Glu Gly Ser Val Asn Gly
            530                 535                 540

His Glu Phe Glu Ile Glu Gly Glu Gly Glu Gly Arg Pro Tyr Glu Gly
545                 550                 555                 560

Thr Gln Thr Ala Lys Leu Lys Val Thr Lys Gly Gly Pro Leu Pro Phe
                565                 570                 575

Ala Trp Asp Ile Leu Ser Pro Gln Phe Met Tyr Gly Ser Lys Ala Tyr
            580                 585                 590

Val Lys His Pro Ala Asp Ile Pro Asp Tyr Leu Lys Leu Ser Phe Pro
            595                 600                 605

Glu Gly Phe Lys Trp Glu Arg Val Met Asn Phe Glu Asp Gly Gly Val
            610                 615                 620

Val Thr Val Thr Gln Asp Ser Ser Leu Gln Asp Gly Glu Phe Ile Tyr
625                 630                 635                 640

Lys Val Lys Leu Arg Gly Thr Asn Phe Pro Ser Asp Gly Pro Val Met
                645                 650                 655

Gln Lys Lys Thr Met Gly Trp Glu Ala Ser Ser Glu Arg Met Tyr Pro
            660                 665                 670

Glu Asp Gly Ala Leu Lys Gly Glu Ile Lys Gln Arg Leu Lys Leu Lys
            675                 680                 685

Asp Gly Gly His Tyr Asp Ala Glu Val Lys Thr Thr Tyr Lys Ala Lys
            690                 695                 700

Lys Pro Val Gln Leu Pro Gly Ala Tyr Asn Val Asn Ile Lys Leu Asp
705                 710                 715                 720

Ile Thr Ser His Asn Glu Asp Tyr Thr Ile Val Glu Gln Tyr Glu Arg
                725                 730                 735

Ala Glu Gly Arg His Ser Thr Gly Gly Met Asp Glu Leu Tyr Lys Cys
            740                 745                 750

Val Thr Asp
        755

<210> SEQ ID NO 53
<211> LENGTH: 18
<212> TYPE: PRT
<213> ORGANISM: Homo sapiens

<400> SEQUENCE: 53

Met Ile His Leu Gly His Ile Leu Phe Leu Leu Leu Leu Pro Val Ala
1               5                   10                  15

Ala Ala

```
<210> SEQ ID NO 54
<211> LENGTH: 8
<212> TYPE: PRT
<213> ORGANISM: Artificial Sequence
<220> FEATURE:
<223> OTHER INFORMATION: FLAG tag

<400> SEQUENCE: 54

Asp Tyr Lys Asp Asp Asp Asp Lys
1               5

<210> SEQ ID NO 55
<211> LENGTH: 30
<212> TYPE: PRT
<213> ORGANISM: Homo sapiens

<400> SEQUENCE: 55

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro
            20                  25                  30

<210> SEQ ID NO 56
<211> LENGTH: 24
<212> TYPE: PRT
<213> ORGANISM: Homo sapiens

<400> SEQUENCE: 56

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 57
<211> LENGTH: 42
<212> TYPE: PRT
<213> ORGANISM: Homo sapiens

<400> SEQUENCE: 57

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 58
<211> LENGTH: 8
<212> TYPE: PRT
<213> ORGANISM: Artificial Sequence
<220> FEATURE:
<223> OTHER INFORMATION: Linker sequence

<400> SEQUENCE: 58

Gly Ser Gly Ser Gly Ser Gly Ser
1               5

<210> SEQ ID NO 59
<211> LENGTH: 256
<212> TYPE: PRT
<213> ORGANISM: Homo sapiens

<400> SEQUENCE: 59
```

Gly Gln Asp Ile Gln Leu Ile Pro Pro Leu Ile Asn Leu Leu Met Ser
1               5                   10                  15

Ile Glu Pro Asp Val Ile Tyr Ala Gly His Asp Asn Thr Lys Pro Asp
            20                  25                  30

Thr Ser Ser Ser Leu Leu Thr Ser Leu Asn Gln Leu Gly Glu Arg Gln
        35                  40                  45

Leu Leu Ser Val Val Lys Trp Ser Lys Ser Leu Pro Gly Phe Arg Asn
50                  55                  60

Leu His Ile Asp Asp Gln Ile Thr Leu Ile Gln Tyr Ser Trp Met Ser
65                  70                  75                  80

Leu Met Val Phe Gly Leu Gly Trp Arg Ser Tyr Lys His Val Ser Gly
                85                  90                  95

Gln Met Leu Tyr Phe Ala Pro Asp Leu Ile Leu Asn Glu Gln Arg Met
            100                 105                 110

Lys Glu Ser Ser Phe Tyr Ser Leu Cys Leu Thr Met Trp Gln Ile Pro
            115                 120                 125

Gln Glu Phe Val Lys Leu Gln Val Ser Gln Glu Glu Phe Leu Cys Met
            130                 135                 140

Lys Val Leu Leu Leu Leu Asn Thr Ile Pro Leu Glu Gly Leu Arg Ser
145                 150                 155                 160

Gln Thr Gln Phe Glu Glu Met Arg Ser Ser Tyr Ile Arg Glu Leu Ile
                165                 170                 175

Lys Ala Ile Gly Leu Arg Gln Lys Gly Val Val Ser Ser Ser Gln Arg
            180                 185                 190

Phe Tyr Gln Leu Thr Lys Leu Leu Asp Asn Leu His Asp Leu Val Lys
            195                 200                 205

Gln Leu His Leu Tyr Cys Leu Asn Thr Phe Ile Gln Ser Arg Ala Leu
        210                 215                 220

Ser Val Glu Phe Pro Glu Met Met Ser Glu Val Ile Ala Ala Gln Leu
225                 230                 235                 240

Pro Lys Ile Leu Ala Gly Met Val Lys Pro Leu Leu Phe His Lys Lys
            245                 250                 255

<210> SEQ ID NO 60
<211> LENGTH: 8
<212> TYPE: PRT
<213> ORGANISM: Artificial Sequence
<220> FEATURE:
<223> OTHER INFORMATION: Linker sequence

<400> SEQUENCE: 60

Arg Ser Gly Ser Gly Ser Gly Ser
1               5

<210> SEQ ID NO 61
<211> LENGTH: 113
<212> TYPE: PRT
<213> ORGANISM: Homo sapiens

<400> SEQUENCE: 61

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
 50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
            100                 105                 110

Arg

<210> SEQ ID NO 62
<211> LENGTH: 8
<212> TYPE: PRT
<213> ORGANISM: Artificial Sequence
<220> FEATURE:
<223> OTHER INFORMATION: Linker sequence

<400> SEQUENCE: 62

Gly Ser Gly Ser Gly Ser Gly Ser
1               5

<210> SEQ ID NO 63
<211> LENGTH: 54
<212> TYPE: DNA
<213> ORGANISM: Artificial Sequence
<220> FEATURE:
<223> OTHER INFORMATION: Dap10 signal

<400> SEQUENCE: 63
atgatccacc tgggacacat cctgtttttg ctgctgctgc cagtggctgc cgcc            54

<210> SEQ ID NO 64
<211> LENGTH: 24
<212> TYPE: DNA
<213> ORGANISM: Artificial Sequence
<220> FEATURE:
<223> OTHER INFORMATION: FLAG tag

<400> SEQUENCE: 64
gattacaaag acgacgatga taaa                                            24

<210> SEQ ID NO 65
<211> LENGTH: 90
<212> TYPE: DNA
<213> ORGANISM: Artificial Sequence
<220> FEATURE:
<223> OTHER INFORMATION: Dap10 extracellular domain

<400> SEQUENCE: 65
cagacaacac caggcgagag atctagcctg cccgccttct accctggcac cagcggctct      60
tgttctggct gtggcagcct gtctctgccc                                      90

<210> SEQ ID NO 66
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 66
atctatattt gggcaccccT ggctggaacc tgcggagtgc tgctgctgtc tctcgtgatt      60
acactgtatt gc                                                         72

<210> SEQ ID NO 67
<211> LENGTH: 126
<212> TYPE: DNA
<213> ORGANISM: Artificial Sequence
<220> FEATURE:
<223> OTHER INFORMATION: 4-1BB costimulatory domain

<400> SEQUENCE: 67

```
aaaaggggcc ggaaaaagct gctgtatatt ttcaaacagc cttttatgag gcctgtgcag     60
acaacacagg aagaggacgg ctgtagctgt cggttccccg aagaggaaga gggggggctgc    120 gaactg                                                               126
```

<210> SEQ ID NO 68
<211> LENGTH: 24
<212> TYPE: DNA
<213> ORGANISM: Artificial Sequence
<220> FEATURE:
<223> OTHER INFORMATION: Linker sequence

<400> SEQUENCE: 68

```
ggatcaggca gtggctctgg cagc                                            24
```

<210> SEQ ID NO 69
<211> LENGTH: 768
<212> TYPE: DNA
<213> ORGANISM: Artificial Sequence
<220> FEATURE:
<223> OTHER INFORMATION: Progesterone receptor ligand binding domain

<400> SEQUENCE: 69

```
gggcaagaca ttcagctcat acctcctttg ataaatttgc tgatgtctat agaaccagat     60
gtcatatacg ctggtcacga caatacgaaa ccggacacat cttcatcttt gcttacctct    120
ctgaatcaac tgggtgaacg acagctcctg agtgttgtta gtggtctaa aagcctcccg    180 ggcttcagga atttgcacat agacgaccaa atcacgctca tccaatattc ctggatgagt    240
ctcatggtct ttggtctcgg ttggcgcagc tataagcacg tctctggcca gatgttgtat    300
ttcgcaccag acctgatcct gaacgaacag aggatgaagg aatcaagctt ttactctctc    360
tgcttgacta tgtggcaaat cccccaagaa ttcgtgaaac ttcaagtttc ccaagaagaa    420
ttcctctgca tgaaagtcct tcttttgctc aacacgattc ccctggaagg cttgaggtct    480
caaacgcaat cgaggagat gcggagtagc tatatacgcg aactcatcaa ggccatcggt    540
ttgcggcaaa agggagtggt ctctagtagc aacgattttt accagctgac taagctcctt    600
gacaaccttc acgatctcgt caaacaactg cacctgtact gtcttaacac atttatacaa    660
tcacgggcac tttctgtaga gttcccagag atgatgtctg aggtcatcgc agcccaactt    720
ccgaaaattc ttgcaggaat ggtgaagcca cttctgttcc ataagaaa              768
```

<210> SEQ ID NO 70
<211> LENGTH: 18
<212> TYPE: DNA
<213> ORGANISM: Artificial Sequence
<220> FEATURE:
<223> OTHER INFORMATION: Linker sequence

<400> SEQUENCE: 70

```
ggatctggaa gtggctcc                                                   18
```

<210> SEQ ID NO 71
<211> LENGTH: 339

<212> TYPE: DNA
<213> ORGANISM: Artificial Sequence
<220> FEATURE:
<223> OTHER INFORMATION: Sequence encoding CD3 zeta signaling domain

<400> SEQUENCE: 71

```
ctgagagtga agtttagcag aagcgccgac gcccctgcct atcagcaggg acagaaccag      60
ctgtataacg agctgaacct gggcaggcgg gaagagtacg acgtgctgga taagaggcgg     120
ggcagggacc ctgaaatggg cggcaaaccc agacggaaga accccaggga aggcctgtac     180
aacgaactgc agaaagacaa gatggccgag gcctacagcg agatcggaat gaagggcgag     240
cggcggagag gcaagggaca tgatggcctg taccagggcc tgtccaccgc caccaaggac     300
acctatgacg ccctgcacat gcaggccctg cctccaaga                            339
```

<210> SEQ ID NO 72
<211> LENGTH: 24
<212> TYPE: DNA
<213> ORGANISM: Artificial Sequence
<220> FEATURE:
<223> OTHER INFORMATION: Linker sequence

<400> SEQUENCE: 72

```
ggaagtggat ctgggagcgg ctct                                             24
```

<210> SEQ ID NO 73
<211> LENGTH: 720
<212> TYPE: DNA
<213> ORGANISM: Artificial Sequence
<220> FEATURE:
<223> OTHER INFORMATION: mCherry

<400> SEQUENCE: 73

```
atggtgtcta aggggaaga ggacaacatg gccatcatca agaattcat gcggttcaag        60
gtgcacatgg aaggctccgt gaatggccac gaattcgaga tcgaggggga gggcgagggc     120
agaccttatg agggaaccca gaccgccaag ctgaaagtga ccaagggcgg accctgcct     180
ttcgcctggg atatcctgtc tccccagttt atgtacggca gcaaggccta cgtgaagcac     240
cccgccgaca tccccgacta cctgaagctg agcttccctg agggcttcaa gtgggagaga     300
gtgatgaatt tcgaggacgg cggagtcgtg acagtgaccc aggatagctc tctgcaggac     360
ggcgagttca tctacaaagt gaagctgcgg ggcaccaact tccccagcga cggacccgtg     420
atgcagaaaa agaccatggg ctgggaggcc agctccgaga gaatgtaccc agaggacggg     480
gccctgaagg gggagatcaa gcagcggctg aaactgaagg atggcggcca ctacgacgca     540
gaagtgaaaa ccacctacaa ggccaagaaa cctgtgcagc tgcctggcgc ctacaatgtg     600
aacatcaagc tggacattac cagccacaac gaggactaca ccatcgtgga acagtacgag     660
cgggccgagg gcaggcattc tacaggcgga atggatgaac tgtataagtg cgtgaccgac     720
```

<210> SEQ ID NO 74
<211> LENGTH: 480
<212> TYPE: PRT
<213> ORGANISM: Homo sapiens

<400> SEQUENCE: 74

```
Met Glu Arg Asp Glu Pro Pro Ser Gly Gly Gly Gly Gly Gly
1               5                   10                  15

Ser Ala Gly Phe Leu Glu Pro Pro Ala Ala Leu Pro Pro Pro Arg
            20                  25                  30
```

```
Asn Gly Phe Cys Gln Asp Glu Leu Ala Glu Leu Asp Pro Gly Thr Ile
         35                  40                  45
Ser Val Ser Asp Asp Arg Ala Glu Gln Arg Thr Cys Leu Ile Cys Gly
 50                  55                  60
Asp Arg Ala Thr Gly Leu His Tyr Gly Ile Ile Ser Cys Glu Gly Cys
 65                  70                  75                  80
Lys Gly Phe Phe Lys Arg Ser Ile Cys Asn Lys Arg Val Tyr Arg Cys
                 85                  90                  95
Ser Arg Asp Lys Asn Cys Val Met Ser Arg Lys Gln Arg Asn Arg Cys
             100                 105                 110
Gln Tyr Cys Arg Leu Leu Lys Cys Leu Gln Met Gly Met Asn Arg Lys
         115                 120                 125
Ala Ile Arg Glu Asp Gly Met Pro Gly Gly Arg Asn Lys Ser Ile Gly
 130                 135                 140
Pro Val Gln Ile Ser Glu Glu Ile Glu Arg Ile Met Ser Gly Gln
 145                 150                 155                 160
Glu Phe Glu Glu Glu Ala Asn His Trp Ser Asn His Gly Asp Ser Asp
                 165                 170                 175
His Ser Ser Pro Gly Asn Arg Ala Ser Glu Ser Asn Gln Pro Ser Pro
             180                 185                 190
Gly Ser Thr Leu Ser Ser Arg Ser Val Glu Leu Asn Gly Phe Met
         195                 200                 205
Ala Phe Arg Glu Gln Tyr Met Gly Met Ser Val Pro Pro His Tyr Gln
 210                 215                 220
Tyr Ile Pro His Leu Phe Ser Tyr Ser Gly His Ser Pro Leu Leu Pro
 225                 230                 235                 240
Gln Gln Ala Arg Ser Leu Asp Pro Gln Ser Tyr Ser Leu Ile His Gln
             245                 250                 255
Leu Leu Ser Ala Glu Asp Leu Glu Pro Leu Gly Thr Pro Met Leu Ile
             260                 265                 270
Glu Asp Gly Tyr Ala Val Thr Gln Ala Glu Leu Phe Ala Leu Leu Cys
         275                 280                 285
Arg Leu Ala Asp Glu Leu Leu Phe Arg Gln Ile Ala Trp Ile Lys Lys
 290                 295                 300
Leu Pro Phe Phe Cys Glu Leu Ser Ile Lys Asp Tyr Thr Cys Leu Leu
 305                 310                 315                 320
Ser Ser Thr Trp Gln Glu Leu Ile Leu Leu Ser Ser Leu Thr Val Tyr
                 325                 330                 335
Ser Lys Gln Ile Phe Gly Glu Leu Ala Asp Val Thr Ala Lys Tyr Ser
             340                 345                 350
Pro Ser Asp Glu Glu Leu His Arg Phe Ser Asp Glu Gly Met Glu Val
         355                 360                 365
Ile Glu Arg Leu Ile Tyr Leu Tyr His Lys Phe His Gln Leu Lys Val
 370                 375                 380
Ser Asn Glu Glu Tyr Ala Cys Met Lys Ala Ile Asn Phe Leu Asn Gln
 385                 390                 395                 400
Asp Ile Arg Gly Leu Thr Ser Ala Ser Gln Leu Glu Gln Leu Asn Lys
                 405                 410                 415
Arg Tyr Trp Tyr Ile Cys Gln Asp Phe Thr Glu Tyr Lys Tyr Thr His
             420                 425                 430
Gln Pro Asn Arg Phe Pro Asp Leu Met Met Cys Leu Pro Glu Ile Arg
         435                 440                 445
Tyr Ile Ala Gly Lys Met Val Asn Val Pro Leu Glu Gln Leu Pro Leu
```

```
                    450                 455                 460
Leu Phe Lys Val Val Leu His Ser Cys Lys Thr Ser Val Gly Lys Glu
465                 470                 475                 480

<210> SEQ ID NO 75
<211> LENGTH: 505
<212> TYPE: PRT
<213> ORGANISM: Homo sapiens

<400> SEQUENCE: 75

Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
                20                  25                  30

Asp Thr Glu Met Pro Phe Trp Pro Thr Asn Phe Gly Ile Ser Ser Val
                35                  40                  45

Asp Leu Ser Val Met Glu Asp His Ser His Ser Phe Asp Ile Lys Pro
        50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
                100                 105                 110

Pro Pro Tyr Tyr Ser Glu Lys Thr Gln Leu Tyr Asn Lys Pro His Glu
            115                 120                 125

Glu Pro Ser Asn Ser Leu Met Ala Ile Glu Cys Arg Val Cys Gly Asp
            130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
            195                 200                 205

Arg Phe Gly Arg Met Pro Gln Ala Glu Lys Glu Lys Leu Leu Ala Glu
        210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
            290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350
```

```
Ile Ile Tyr Thr Met Leu Ala Ser Leu Met Asn Lys Asp Gly Val Leu
            355                 360                 365
Ile Ser Glu Gly Gln Gly Phe Met Thr Arg Glu Phe Leu Lys Ser Leu
370                 375                 380
Arg Lys Pro Phe Gly Asp Phe Met Glu Pro Lys Phe Glu Phe Ala Val
385                 390                 395                 400
Lys Phe Asn Ala Leu Glu Leu Asp Asp Ser Asp Leu Ala Ile Phe Ile
                405                 410                 415
Ala Val Ile Ile Leu Ser Gly Asp Arg Pro Gly Leu Leu Asn Val Lys
            420                 425                 430
Pro Ile Glu Asp Ile Gln Asp Asn Leu Leu Gln Ala Leu Glu Leu Gln
            435                 440                 445
Leu Lys Leu Asn His Pro Glu Ser Ser Gln Leu Phe Ala Lys Leu Leu
        450                 455                 460
Gln Lys Met Thr Asp Leu Arg Gln Ile Val Thr Glu His Val Gln Leu
465                 470                 475                 480
Leu Gln Val Ile Lys Lys Thr Glu Thr Asp Met Ser Leu His Pro Leu
                485                 490                 495
Leu Gln Glu Ile Tyr Lys Asp Leu Tyr
            500                 505

<210> SEQ ID NO 76
<211> LENGTH: 777
<212> TYPE: PRT
<213> ORGANISM: Homo sapiens

<400> SEQUENCE: 76

Met Asp Ser Lys Glu Ser Leu Thr Pro Gly Arg Glu Glu Asn Pro Ser
1               5                   10                  15
Ser Val Leu Ala Gln Glu Arg Gly Asp Val Met Asp Phe Tyr Lys Thr
            20                  25                  30
Leu Arg Gly Gly Ala Thr Val Lys Val Ser Ala Ser Ser Pro Ser Leu
        35                  40                  45
Ala Val Ala Ser Gln Ser Asp Ser Lys Gln Arg Arg Leu Leu Val Asp
    50                  55                  60
Phe Pro Lys Gly Ser Val Ser Asn Ala Gln Gln Pro Asp Leu Ser Lys
65                  70                  75                  80
Ala Val Ser Leu Ser Met Gly Leu Tyr Met Gly Glu Thr Glu Thr Lys
                85                  90                  95
Val Met Gly Asn Asp Leu Gly Phe Pro Gln Gln Gly Gln Ile Ser Leu
            100                 105                 110
Ser Ser Gly Glu Thr Asp Leu Lys Leu Leu Glu Glu Ser Ile Ala Asn
        115                 120                 125
Leu Asn Arg Ser Thr Ser Val Pro Glu Asn Pro Lys Ser Ser Ala Ser
    130                 135                 140
Thr Ala Val Ser Ala Ala Pro Thr Glu Lys Glu Phe Pro Lys Thr His
145                 150                 155                 160
Ser Asp Val Ser Ser Glu Gln Gln His Leu Lys Gly Gln Thr Gly Thr
                165                 170                 175
Asn Gly Gly Asn Val Lys Leu Tyr Thr Thr Asp Gln Ser Thr Phe Asp
            180                 185                 190
Ile Leu Gln Asp Leu Glu Phe Ser Ser Gly Ser Pro Gly Lys Glu Thr
        195                 200                 205
Asn Glu Ser Pro Trp Arg Ser Asp Leu Leu Ile Asp Glu Asn Cys Leu
    210                 215                 220
```

```
Leu Ser Pro Leu Ala Gly Glu Asp Ser Phe Leu Glu Gly Asn
225                 230                 235                 240

Ser Asn Glu Asp Cys Lys Pro Leu Ile Leu Pro Asp Thr Lys Pro Lys
            245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
            275                 280                 285

Pro Gly Val Ile Lys Gln Glu Lys Leu Gly Thr Val Tyr Cys Gln Ala
            290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
            325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Gly Pro
            405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
            435                 440                 445

Val Glu Gly Gln His Asn Tyr Leu Cys Ala Gly Arg Asn Asp Cys Ile
450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
            485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
            515                 520                 525

Thr Pro Thr Leu Val Ser Leu Leu Glu Val Ile Glu Pro Glu Val Leu
            530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
            565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
            595                 600                 605

Gly Trp Arg Ser Tyr Arg Gln Ser Ser Ala Asn Leu Leu Cys Phe Ala
            610                 615                 620

Pro Asp Leu Ile Ile Asn Glu Gln Arg Met Thr Leu Pro Cys Met Tyr
625                 630                 635                 640
```

Asp Gln Cys Lys His Met Leu Tyr Val Ser Ser Glu Leu His Arg Leu
                    645                 650                 655

Gln Val Ser Tyr Glu Glu Tyr Leu Cys Met Lys Thr Leu Leu Leu Leu
                660                 665                 670

Ser Ser Val Pro Lys Asp Gly Leu Lys Ser Gln Glu Leu Phe Asp Glu
                675                 680                 685

Ile Arg Met Thr Tyr Ile Lys Glu Leu Gly Lys Ala Ile Val Lys Arg
            690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
                740                 745                 750

Leu Ala Glu Ile Ile Thr Asn Gln Ile Pro Lys Tyr Ser Asn Gly Asn
                755                 760                 765

Ile Lys Lys Leu Leu Phe His Gln Lys
            770                 775

<210> SEQ ID NO 77
<211> LENGTH: 490
<212> TYPE: PRT
<213> ORGANISM: Homo sapiens

<400> SEQUENCE: 77

Met Glu Gln Lys Pro Ser Lys Val Glu Cys Gly Ser Asp Pro Glu Glu
1               5                   10                  15

Asn Ser Ala Arg Ser Pro Asp Gly Lys Arg Lys Arg Lys Asn Gly Gln
                20                  25                  30

Cys Ser Leu Lys Thr Ser Met Ser Gly Tyr Ile Pro Ser Tyr Leu Asp
            35                  40                  45

Lys Asp Glu Gln Cys Val Val Cys Gly Asp Lys Ala Thr Gly Tyr His
        50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95

Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
        115                 120                 125

Ser Lys Arg Val Ala Lys Arg Lys Leu Ile Glu Gln Asn Arg Glu Arg
    130                 135                 140

Arg Arg Lys Glu Glu Met Ile Arg Ser Leu Gln Gln Arg Pro Glu Pro
145                 150                 155                 160

Thr Pro Glu Glu Trp Asp Leu Ile His Ile Ala Thr Glu Ala His Arg
                165                 170                 175

Ser Thr Asn Ala Gln Gly Ser His Trp Lys Gln Arg Arg Lys Phe Leu
            180                 185                 190

Pro Asp Asp Ile Gly Gln Ser Pro Ile Val Ser Met Pro Asp Gly Asp
        195                 200                 205

Lys Val Asp Leu Glu Ala Phe Ser Glu Phe Thr Lys Ile Ile Thr Pro
    210                 215                 220

Ala Ile Thr Arg Val Val Asp Phe Ala Lys Lys Leu Pro Met Phe Ser
225                 230                 235                 240

```
Glu Leu Pro Cys Glu Asp Gln Ile Ile Leu Leu Lys Gly Cys Cys Met
                245                 250                 255

Glu Ile Met Ser Leu Arg Ala Ala Val Arg Tyr Asp Pro Glu Ser Asp
            260                 265                 270

Thr Leu Thr Leu Ser Gly Glu Met Ala Val Lys Arg Glu Gln Leu Lys
        275                 280                 285

Asn Gly Gly Leu Gly Val Val Ser Asp Ala Ile Phe Glu Leu Gly Lys
    290                 295                 300

Ser Leu Ser Ala Phe Asn Leu Asp Asp Thr Glu Val Ala Leu Leu Gln
305                 310                 315                 320

Ala Val Leu Leu Met Ser Thr Asp Arg Ser Gly Leu Leu Cys Val Asp
                325                 330                 335

Lys Ile Glu Lys Ser Gln Glu Ala Tyr Leu Leu Ala Phe Glu His Tyr
            340                 345                 350

Val Asn His Arg Lys His Asn Ile Pro His Phe Trp Pro Lys Leu Leu
        355                 360                 365

Met Lys Glu Arg Glu Val Gln Ser Ser Ile Leu Tyr Lys Gly Ala Ala
    370                 375                 380

Ala Glu Gly Arg Pro Gly Gly Ser Leu Gly Val His Pro Glu Gly Gln
385                 390                 395                 400

Gln Leu Leu Gly Met His Val Val Gln Gly Pro Gln Val Arg Gln Leu
                405                 410                 415

Glu Gln Gln Leu Gly Glu Ala Gly Ser Leu Gln Gly Pro Val Leu Gln
            420                 425                 430

His Gln Ser Pro Lys Ser Pro Gln Gln Arg Leu Leu Glu Leu Leu His
        435                 440                 445

Arg Ser Gly Ile Leu His Ala Arg Ala Val Cys Gly Glu Asp Asp Ser
    450                 455                 460

Ser Glu Ala Asp Ser Pro Ser Ser Ser Glu Glu Pro Glu Val Cys
465                 470                 475                 480

Glu Asp Leu Ala Gly Asn Ala Ala Ser Pro
                485                 490

<210> SEQ ID NO 78
<211> LENGTH: 924
<212> TYPE: PRT
<213> ORGANISM: Homo sapiens

<400> SEQUENCE: 78

Met Glu Thr Lys Gly Tyr His Ser Leu Pro Glu Gly Leu Asp Met Glu
1               5                   10                  15

Arg Arg Trp Gly Gln Val Ser Gln Ala Val Glu Arg Ser Ser Leu Gly
            20                  25                  30

Pro Thr Glu Arg Thr Asp Glu Asn Asn Tyr Met Glu Ile Val Asn Val
        35                  40                  45

Ser Cys Val Ser Gly Ala Ile Pro Asn Asn Ser Thr Gln Gly Ser Ser
    50                  55                  60

Lys Glu Lys Gln Glu Leu Leu Pro Cys Leu Gln Asp Asn Asn Arg
65                  70                  75                  80

Pro Gly Ile Leu Thr Ser Asp Ile Lys Thr Glu Leu Glu Ser Lys Glu
            85                  90                  95

Leu Ser Ala Thr Val Ala Glu Ser Met Gly Leu Tyr Met Asp Ser Val
            100                 105                 110

Arg Asp Ala Asp Tyr Ser Tyr Glu Gln Gln Asn Gln Gln Gly Ser Met
```

```
            115                 120                 125
Ser Pro Ala Lys Ile Tyr Gln Asn Val Glu Gln Leu Val Lys Phe Tyr
    130                 135                 140

Lys Gly Asn Gly His Arg Pro Ser Thr Leu Ser Cys Val Asn Thr Pro
145                 150                 155                 160

Leu Arg Ser Phe Met Ser Asp Ser Gly Ser Val Asn Gly Gly Val
                165                 170                 175

Met Arg Ala Ile Val Lys Ser Pro Ile Met Cys His Glu Lys Ser Pro
            180                 185                 190

Ser Val Cys Ser Pro Leu Asn Met Thr Ser Ser Val Cys Ser Pro Ala
        195                 200                 205

Gly Ile Asn Ser Val Ser Ser Thr Ala Ser Phe Gly Ser Phe Pro
    210                 215                 220

Val His Ser Pro Ile Thr Gln Gly Thr Pro Leu Thr Cys Ser Pro Asn
225                 230                 235                 240

Ala Glu Asn Arg Gly Ser Arg Ser His Ser Pro Ala His Ala Ser Asn
                245                 250                 255

Val Gly Ser Pro Leu Ser Ser Pro Leu Ser Ser Met Lys Ser Ser Ile
            260                 265                 270

Ser Ser Pro Pro Ser His Cys Ser Val Lys Ser Pro Val Ser Ser Pro
        275                 280                 285

Asn Asn Val Thr Leu Arg Ser Ser Val Ser Ser Pro Ala Asn Ile Asn
    290                 295                 300

Asn Ser Arg Cys Ser Val Ser Ser Pro Ser Asn Thr Asn Asn Arg Ser
305                 310                 315                 320

Thr Leu Ser Ser Pro Ala Ala Ser Thr Val Gly Ser Ile Cys Ser Pro
                325                 330                 335

Val Asn Asn Ala Phe Ser Tyr Thr Ala Ser Gly Thr Ser Ala Gly Ser
            340                 345                 350

Ser Thr Leu Arg Asp Val Val Pro Ser Pro Asp Thr Gln Glu Lys Gly
        355                 360                 365

Ala Gln Glu Val Pro Phe Pro Lys Thr Glu Glu Val Glu Ser Ala Ile
    370                 375                 380

Ser Asn Gly Val Thr Gly Gln Leu Asn Ile Val Gln Tyr Ile Lys Pro
385                 390                 395                 400

Glu Pro Asp Gly Ala Phe Ser Ser Cys Leu Gly Gly Asn Ser Lys
                405                 410                 415

Ile Asn Ser Asp Ser Ser Phe Ser Val Pro Ile Lys Gln Glu Ser Thr
            420                 425                 430

Lys His Ser Cys Ser Gly Thr Ser Phe Lys Gly Asn Pro Thr Val Asn
        435                 440                 445

Pro Phe Pro Phe Met Asp Gly Ser Tyr Phe Ser Phe Met Asp Asp Lys
    450                 455                 460

Asp Tyr Tyr Ser Leu Ser Gly Ile Leu Gly Pro Pro Val Pro Gly Phe
465                 470                 475                 480

Asp Gly Asn Cys Glu Gly Ser Gly Phe Pro Val Gly Ile Lys Gln Glu
                485                 490                 495

Pro Asp Asp Gly Ser Tyr Tyr Pro Glu Ala Ser Ile Pro Ser Ser Ala
            500                 505                 510

Ile Val Gly Val Asn Ser Gly Gly Gln Ser Phe His Tyr Arg Ile Gly
        515                 520                 525

Ala Gln Gly Thr Ile Ser Leu Ser Arg Ser Ala Arg Asp Gln Ser Phe
    530                 535                 540
```

```
Gln His Leu Ser Ser Phe Pro Pro Val Asn Thr Leu Val Glu Ser Trp
545                 550                 555                 560

Lys Ser His Gly Asp Leu Ser Ser Arg Arg Ser Asp Gly Tyr Pro Val
            565                 570                 575

Leu Glu Tyr Ile Pro Glu Asn Val Ser Ser Thr Leu Arg Ser Val
        580                 585                 590

Ser Thr Gly Ser Ser Arg Pro Ser Lys Ile Cys Leu Val Cys Gly Asp
        595                 600                 605

Glu Ala Ser Gly Cys His Tyr Gly Val Val Thr Cys Gly Ser Cys Lys
    610                 615                 620

Val Phe Phe Lys Arg Ala Val Glu Gly Gln His Asn Tyr Leu Cys Ala
625                 630                 635                 640

Gly Arg Asn Asp Cys Ile Ile Asp Lys Ile Arg Arg Lys Asn Cys Pro
                645                 650                 655

Ala Cys Arg Leu Gln Lys Cys Leu Gln Ala Gly Met Asn Leu Gly Ala
                660                 665                 670

Arg Lys Ser Lys Lys Leu Gly Lys Leu Lys Gly Ile His Glu Glu Gln
            675                 680                 685

Pro Gln Gln Gln Gln Pro Pro Pro Pro Pro Pro Pro Gln Ser Pro
    690                 695                 700

Glu Glu Gly Thr Thr Tyr Ile Ala Pro Ala Lys Glu Pro Ser Val Asn
705                 710                 715                 720

Thr Ala Leu Val Pro Gln Leu Ser Thr Ile Ser Arg Ala Leu Thr Pro
                725                 730                 735

Ser Pro Val Met Val Leu Glu Asn Ile Glu Pro Glu Ile Val Tyr Ala
                740                 745                 750

Gly Tyr Asp Ser Ser Lys Pro Asp Thr Ala Glu Asn Leu Leu Ser Thr
                755                 760                 765

Leu Asn Arg Leu Ala Gly Lys Gln Met Ile Gln Val Val Lys Trp Ala
770                 775                 780

Lys Val Leu Pro Gly Phe Lys Asn Leu Pro Leu Glu Asp Gln Ile Thr
785                 790                 795                 800

Leu Ile Gln Tyr Ser Trp Met Cys Leu Ser Ser Phe Ala Leu Ser Trp
                805                 810                 815

Arg Ser Tyr Lys His Thr Asn Ser Gln Phe Leu Tyr Phe Ala Pro Asp
                820                 825                 830

Leu Val Phe Asn Glu Glu Lys Met Lys Glu Leu Arg Lys Met Val Thr
                835                 840                 845

Lys Cys Pro Asn Asn Ser Gly Gln Ser Trp Gln Arg Phe Tyr Gln Leu
                850                 855                 860

Thr Lys Leu Leu Asp Ser Met His Asp Leu Val Ser Asp Leu Leu Glu
865                 870                 875                 880

Phe Cys Phe Tyr Thr Phe Arg Glu Ser His Ala Leu Lys Val Glu Phe
                885                 890                 895

Pro Ala Met Leu Val Glu Ile Ile Ser Asp Gln Leu Pro Lys Val Glu
                900                 905                 910

Ser Gly Asn Ala Lys Pro Leu Tyr Phe His Arg Lys
            915                 920

<210> SEQ ID NO 79
<211> LENGTH: 427
<212> TYPE: PRT
<213> ORGANISM: Homo sapiens
```

<400> SEQUENCE: 79

```
Met Glu Ala Met Ala Ala Ser Thr Ser Leu Pro Asp Pro Gly Asp Phe
 1               5                  10                  15

Asp Arg Asn Val Pro Arg Ile Cys Gly Val Cys Gly Asp Arg Ala Thr
                20                  25                  30

Gly Phe His Phe Asn Ala Met Thr Cys Glu Gly Cys Lys Gly Phe Phe
            35                  40                  45

Arg Arg Ser Met Lys Arg Lys Ala Leu Phe Thr Cys Pro Phe Asn Gly
        50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Glu Val Gln Arg Lys Arg Glu Met Ile Leu Lys Arg Lys Glu
                100                 105                 110

Glu Glu Ala Leu Lys Asp Ser Leu Arg Pro Lys Leu Ser Glu Glu Gln
            115                 120                 125

Gln Arg Ile Ile Ala Ile Leu Leu Asp Ala His His Lys Thr Tyr Asp
        130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Ser Ser Ser Cys Ser Asp His Cys Ile Thr
                180                 185                 190

Ser Ser Asp Met Met Asp Ser Ser Phe Ser Asn Leu Asp Leu Ser
            195                 200                 205

Glu Glu Asp Ser Asp Asp Pro Ser Val Thr Leu Glu Leu Ser Gln Leu
                210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
                260                 265                 270

Leu Arg Ser Asn Glu Ser Phe Thr Met Asp Asp Met Ser Trp Thr Cys
            275                 280                 285

Gly Asn Gln Asp Tyr Lys Tyr Arg Val Ser Asp Val Thr Lys Ala Gly
        290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
                340                 345                 350

Glu Ala Ile Gln Asp Arg Leu Ser Asn Thr Leu Gln Thr Tyr Ile Arg
            355                 360                 365

Cys Arg His Pro Pro Pro Gly Ser His Leu Leu Tyr Ala Lys Met Ile
        370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415
```

-continued

```
Leu Val Leu Glu Val Phe Gly Asn Glu Ile Ser
            420             425

<210> SEQ ID NO 80
<211> LENGTH: 468
<212> TYPE: PRT
<213> ORGANISM: Homo sapiens

<400> SEQUENCE: 80

Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
        35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
            260                 265                 270

Phe His Cys Cys Gln Cys Thr Ser Val Glu Thr Val Thr Glu Leu Thr
        275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
```

```
                355                 360                 365
Glu Leu Asp Asp Ser Asp Ile Ser Leu Phe Val Ala Ala Ile Ile Cys
    370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
            420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
    450                 455                 460

Arg Asp Met Tyr
465

<210> SEQ ID NO 81
<211> LENGTH: 441
<212> TYPE: PRT
<213> ORGANISM: Homo sapiens

<400> SEQUENCE: 81

Met Glu Gln Pro Gln Glu Glu Ala Pro Glu Val Arg Glu Glu Glu
1               5                   10                  15

Lys Glu Glu Val Ala Glu Ala Glu Gly Ala Pro Glu Leu Asn Gly Gly
                20                  25                  30

Pro Gln His Ala Leu Pro Ser Ser Ser Tyr Thr Asp Leu Ser Arg Ser
            35                  40                  45

Ser Ser Pro Pro Ser Leu Leu Asp Gln Leu Gln Met Gly Cys Asp Gly
        50                  55                  60

Ala Ser Cys Gly Ser Leu Asn Met Glu Cys Arg Val Cys Gly Asp Lys
65                  70                  75                  80

Ala Ser Gly Phe His Tyr Gly Val His Ala Cys Glu Gly Cys Lys Gly
                85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
        115                 120                 125

Arg Phe Gln Lys Cys Leu Ala Leu Gly Met Ser His Asn Ala Ile Arg
130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
                165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
        195                 200                 205

Ala Pro Phe Val Ile His Asp Ile Glu Thr Leu Trp Gln Ala Glu Lys
210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
                245                 250                 255
```

Val Arg Glu Leu Thr Glu Phe Ala Lys Ser Ile Pro Ser Phe Ser Ser
            260                 265                 270

Leu Phe Leu Asn Asp Gln Val Thr Leu Leu Lys Tyr Gly Val His Glu
        275                 280                 285

Ala Ile Phe Ala Met Leu Ala Ser Ile Val Asn Lys Asp Gly Leu Leu
    290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
                325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
        355                 360                 365

Arg Val Glu Ala Ile Gln Asp Thr Ile Leu Arg Ala Leu Glu Phe His
    370                 375                 380

Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
                405                 410                 415

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440

<210> SEQ ID NO 82
<211> LENGTH: 434
<212> TYPE: PRT
<213> ORGANISM: Homo sapiens

<400> SEQUENCE: 82

Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
            20                  25                  30

Glu Glu Val Gly Gly Pro Gln Ile Cys Arg Val Cys Gly Asp Lys Ala
        35                  40                  45

Thr Gly Tyr His Phe Asn Val Met Thr Cys Glu Gly Cys Lys Gly Phe
    50                  55                  60

Phe Arg Arg Ala Met Lys Arg Asn Ala Arg Leu Arg Cys Pro Phe Arg
65                  70                  75                  80

Lys Gly Ala Cys Glu Ile Thr Arg Lys Thr Arg Arg Gln Cys Gln Ala
                85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
        115                 120                 125

Lys Ser Glu Arg Thr Gly Thr Gln Pro Leu Gly Val Gln Gly Leu Thr
    130                 135                 140

Glu Glu Gln Arg Met Met Ile Arg Glu Leu Met Asp Ala Gln Met Lys
145                 150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
            195                 200                 205

Leu Lys Val Ser Leu Gln Leu Arg Gly Glu Asp Gly Ser Val Trp Asn
    210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
                260                 265                 270

Ile Ser Leu Leu Lys Gly Ala Ala Phe Glu Leu Cys Gln Leu Arg Phe
            275                 280                 285

Asn Thr Val Phe Asn Ala Glu Thr Gly Thr Trp Glu Cys Gly Arg Leu
            290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
                340                 345                 350

Arg Pro Gly Val Leu Gln His Arg Val Val Asp Gln Leu Gln Glu Gln
            355                 360                 365

Phe Ala Ile Thr Leu Lys Ser Tyr Ile Glu Cys Asn Arg Pro Gln Pro
    370                 375                 380

Ala His Arg Phe Leu Phe Leu Lys Ile Met Ala Met Leu Thr Glu Leu
385                 390                 395                 400

Arg Ser Ile Asn Ala Gln His Thr Gln Arg Leu Leu Arg Ile Gln Asp
                405                 410                 415

Ile His Pro Phe Ala Thr Pro Leu Met Gln Glu Leu Phe Gly Ile Thr
            420                 425                 430

Gly Ser

<210> SEQ ID NO 83
<211> LENGTH: 257
<212> TYPE: PRT
<213> ORGANISM: Homo sapiens

<400> SEQUENCE: 83

Gly Ser His Met Ser Gln Gly Ser Gly Glu Gly Glu Gly Val Gln Leu
1               5                   10                  15

Thr Ala Ala Gln Glu Leu Met Ile Gln Gln Leu Val Ala Ala Gln Leu
                20                  25                  30

Gln Cys Asn Lys Arg Ser Phe Ser Asp Gln Pro Lys Val Thr Pro Trp
            35                  40                  45

Pro Leu Gly Ala Asp Pro Gln Ser Arg Asp Ala Arg Gln Gln Arg Phe
    50                  55                  60

Ala His Phe Thr Glu Leu Ala Ile Ile Ser Val Gln Glu Ile Val Asp
65                  70                  75                  80

Phe Ala Lys Gln Val Pro Gly Phe Leu Gln Leu Gly Arg Glu Asp Gln
                85                  90                  95

Ile Ala Leu Leu Lys Ala Ser Thr Ile Glu Ile Met Leu Leu Glu Thr
            100                 105                 110

Ala Arg Arg Tyr Asn His Glu Thr Glu Cys Ile Thr Phe Leu Lys Asp
        115                 120                 125

```
Phe Thr Tyr Ser Lys Asp Asp Phe His Arg Ala Gly Leu Gln Val Glu
            130                 135                 140

Phe Ile Asn Pro Ile Phe Glu Phe Ser Arg Ala Met Arg Arg Leu Gly
145                 150                 155                 160

Leu Asp Asp Ala Glu Tyr Ala Leu Leu Ile Ala Ile Asn Ile Phe Ser
                165                 170                 175

Ala Asp Arg Pro Asn Val Gln Glu Pro Gly Arg Val Glu Ala Leu Gln
            180                 185                 190

Gln Pro Tyr Val Glu Ala Leu Leu Ser Tyr Thr Arg Ile Lys Arg Pro
        195                 200                 205

Gln Asp Gln Leu Arg Phe Pro Arg Met Leu Met Lys Leu Val Ser Leu
    210                 215                 220

Arg Thr Leu Ser Ser Val His Ser Glu Gln Val Phe Ala Leu Arg Leu
225                 230                 235                 240

Gln Asp Lys Lys Leu Pro Pro Leu Leu Ser Glu Ile Trp Asp Val His
                245                 250                 255

Glu

<210> SEQ ID NO 84
<211> LENGTH: 472
<212> TYPE: PRT
<213> ORGANISM: Homo sapiens

<400> SEQUENCE: 84

Met Gly Ser Lys Met Asn Leu Ile Glu His Ser His Leu Pro Thr Thr
1               5                   10                  15

Asp Glu Phe Ser Phe Ser Glu Asn Leu Phe Gly Val Leu Thr Glu Gln
                20                  25                  30

Val Ala Gly Pro Leu Gly Gln Asn Leu Glu Val Glu Pro Tyr Ser Gln
            35                  40                  45

Tyr Ser Asn Val Gln Phe Pro Gln Val Gln Pro Gln Ile Ser Ser Ser
        50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
        195                 200                 205

Arg Lys Asn Val Lys Gln His Ala Asp Gln Thr Val Asn Glu Asp Ser
    210                 215                 220

Glu Gly Arg Asp Leu Arg Gln Val Thr Ser Thr Thr Lys Ser Cys Arg
225                 230                 235                 240
```

-continued

```
Glu Lys Thr Glu Leu Thr Pro Asp Gln Gln Thr Leu His Phe Ile
                245                 250                 255

Met Asp Ser Tyr Asn Lys Gln Arg Met Pro Gln Glu Ile Thr Asn Lys
            260                 265                 270

Ile Leu Lys Glu Glu Phe Ser Ala Glu Glu Asn Phe Leu Ile Leu Thr
            275                 280                 285

Glu Met Ala Thr Asn His Val Gln Val Leu Val Glu Phe Thr Lys Lys
        290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
    370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
    450                 455                 460

Leu Cys Glu Ile Trp Asp Val Gln
465                 470

<210> SEQ ID NO 85
<211> LENGTH: 468
<212> TYPE: PRT
<213> ORGANISM: Homo sapiens

<400> SEQUENCE: 85

Met Met Tyr Phe Val Ile Ala Ala Met Lys Ala Gln Ile Glu Ile Ile
1               5                   10                  15

Pro Cys Lys Ile Cys Gly Asp Lys Ser Ser Gly Ile His Tyr Gly Val
            20                  25                  30

Ile Thr Cys Glu Gly Cys Lys Gly Phe Phe Arg Arg Ser Gln Gln Ser
        35                  40                  45

Asn Ala Thr Tyr Ser Cys Pro Arg Gln Lys Asn Cys Leu Ile Asp Arg
    50                  55                  60

Thr Ser Arg Asn Arg Cys Gln His Cys Arg Leu Gln Lys Cys Leu Ala
65                  70                  75                  80

Val Gly Met Ser Arg Asp Ala Val Lys Phe Gly Arg Met Ser Lys Lys
                85                  90                  95

Gln Arg Asp Ser Leu Tyr Ala Glu Val Gln Lys His Arg Met Gln Gln
            100                 105                 110

Gln Gln Arg Asp His Gln Gln Pro Gly Glu Ala Glu Pro Leu Thr
        115                 120                 125

Pro Thr Tyr Asn Ile Ser Ala Asn Gly Leu Thr Glu Leu His Asp Asp
```

```
                130               135               140
Leu Ser Asn Tyr Ile Asp Gly His Thr Pro Glu Gly Ser Lys Ala Asp
145                 150                 155                 160

Ser Ala Val Ser Ser Phe Tyr Leu Asp Ile Gln Pro Ser Pro Asp Gln
                165                 170                 175

Ser Gly Leu Asp Ile Asn Gly Ile Lys Pro Glu Pro Ile Cys Asp Tyr
            180                 185                 190

Thr Pro Ala Ser Gly Phe Phe Pro Tyr Cys Ser Phe Thr Asn Gly Glu
        195                 200                 205

Thr Ser Pro Thr Val Ser Met Ala Glu Leu Glu His Leu Ala Gln Asn
    210                 215                 220

Ile Ser Lys Ser His Leu Glu Thr Cys Gln Tyr Leu Arg Glu Glu Leu
225                 230                 235                 240

Gln Gln Ile Thr Trp Gln Thr Phe Leu Gln Glu Ile Glu Asn Tyr
                245                 250                 255

Gln Asn Lys Gln Arg Glu Val Met Trp Gln Leu Cys Ala Ile Lys Ile
                260                 265                 270

Thr Glu Ala Ile Gln Tyr Val Val Glu Phe Ala Lys Arg Ile Asp Gly
            275                 280                 285

Phe Met Glu Leu Cys Gln Asn Asp Gln Ile Val Leu Leu Lys Ala Gly
        290                 295                 300

Ser Leu Glu Val Val Phe Ile Arg Met Cys Arg Ala Phe Asp Ser Gln
305                 310                 315                 320

Asn Asn Thr Val Tyr Phe Asp Gly Lys Tyr Ala Ser Pro Asp Val Phe
                325                 330                 335

Lys Ser Leu Gly Cys Glu Asp Phe Ile Ser Phe Val Phe Glu Phe Gly
                340                 345                 350

Lys Ser Leu Cys Ser Met His Leu Thr Glu Asp Glu Ile Ala Leu Phe
            355                 360                 365

Ser Ala Phe Val Leu Met Ser Ala Asp Arg Ser Trp Leu Gln Glu Lys
        370                 375                 380

Val Lys Ile Glu Lys Leu Gln Gln Lys Ile Gln Leu Ala Leu Gln His
385                 390                 395                 400

Val Leu Gln Lys Asn His Arg Glu Asp Gly Ile Leu Thr Lys Leu Ile
                405                 410                 415

Cys Lys Val Ser Thr Leu Arg Ala Leu Cys Gly Arg His Thr Glu Lys
                420                 425                 430

Leu Met Ala Phe Lys Ala Ile Tyr Pro Asp Ile Val Arg Leu His Phe
            435                 440                 445

Pro Pro Leu Tyr Lys Glu Leu Phe Thr Ser Glu Phe Glu Pro Ala Met
        450                 455                 460

Gln Ile Asp Gly
465

<210> SEQ ID NO 86
<211> LENGTH: 518
<212> TYPE: PRT
<213> ORGANISM: Homo sapiens

<400> SEQUENCE: 86

Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
                20                  25                  30
```

```
Ile Cys Gly Asp Lys Ser Ser Gly Ile His Tyr Gly Val Ile Thr Cys
         35                  40                  45

Glu Gly Cys Lys Gly Phe Phe Arg Arg Ser Gln Arg Cys Asn Ala Ala
 50                  55                  60

Tyr Ser Cys Thr Arg Gln Gln Asn Cys Pro Ile Asp Arg Thr Ser Arg
 65                  70                  75                  80

Asn Arg Cys Gln His Cys Arg Leu Gln Lys Cys Leu Ala Leu Gly Met
             85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
            115                 120                 125

Gln Gln Glu Pro Val Val Lys Thr Pro Pro Ala Gly Ala Gln Gly Ala
        130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
            195                 200                 205

Gly Lys Ala Glu Gly Arg Glu Ser Phe Tyr Ser Thr Gly Ser Gln Leu
            210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
                260                 265                 270

Leu Val Gln Ser Val Cys Lys Ser Tyr Arg Glu Thr Cys Gln Leu Arg
            275                 280                 285

Leu Glu Asp Leu Leu Arg Gln Arg Ser Asn Ile Phe Ser Arg Glu Glu
            290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
            355                 360                 365

Tyr Asn Ala Asp Asn Arg Thr Val Phe Phe Glu Gly Lys Tyr Gly Gly
370                 375                 380

Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
                405                 410                 415

Ile Ala Leu Tyr Thr Ala Leu Val Leu Ile Asn Ala His Arg Pro Gly
            420                 425                 430

Leu Gln Glu Lys Arg Lys Val Glu Gln Leu Gln Tyr Asn Leu Glu Leu
            435                 440                 445

Ala Phe His His His Leu Cys Lys Thr His Arg Gln Ser Ile Leu Ala
```

```
                    450                 455                 460
Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
                500                 505                 510

Pro Val Gly Leu Ser Lys
            515

<210> SEQ ID NO 87
<211> LENGTH: 431
<212> TYPE: PRT
<213> ORGANISM: Homo sapiens

<400> SEQUENCE: 87

Met Leu Gly Gly Leu Ser Pro Pro Gly Ala Leu Thr Thr Leu Gln His
1               5                   10                  15

Gln Leu Pro Val Ser Gly Tyr Ser Thr Pro Ser Pro Ala Thr Ile Glu
                20                  25                  30

Thr Gln Ser Ser Ser Glu Glu Ile Val Pro Ser Pro Pro Ser Pro
            35                  40                  45

Pro Pro Leu Pro Arg Ile Tyr Lys Pro Cys Phe Val Cys Gln Asp Lys
50                  55                  60

Ser Ser Gly Tyr His Tyr Gly Val Ser Ala Cys Glu Gly Val Lys Gly
65                  70                  75                  80

Phe Phe Arg Arg Ser Ile Gln Lys Asn Met Val Tyr Thr Val His Arg
                85                  90                  95

Asp Lys Asn Cys Ile Ile Asn Lys Val Thr Arg Asn Arg Cys Gln Tyr
            100                 105                 110

Cys Arg Leu Gln Lys Cys Phe Glu Val Gly Met Ser Lys Glu Ser Val
        115                 120                 125

Arg Asn Asp Arg Asn Lys Lys Lys Glu Val Pro Lys Pro Glu Cys
130                 135                 140

Ser Glu Ser Tyr Thr Val Thr Pro Glu Val Gly Glu Leu Ile Glu Lys
145                 150                 155                 160

Val Arg Lys Ala His Gln Glu Thr Phe Pro Ala Leu Cys Gln Leu Gly
                165                 170                 175

Lys Tyr Thr Thr Asn Asn Ser Ser Glu Gln Arg Val Ser Leu Asp Ile
            180                 185                 190

Asp Leu Trp Asp Lys Phe Ser Glu Leu Ser Thr Lys Cys Ile Ile Lys
        195                 200                 205

Thr Val Glu Phe Ala Lys Gln Leu Pro Gly Phe Thr Thr Leu Thr Ile
    210                 215                 220

Ala Asp Gln Ile Thr Leu Leu Lys Ala Ala Cys Leu Asp Ile Leu Ile
225                 230                 235                 240

Leu Arg Ile Cys Thr Arg Tyr Thr Pro Glu Gln Asp Thr Met Thr Phe
                245                 250                 255

Ser Asp Gly Leu Thr Leu Asn Arg Thr Gln Met His Asn Ala Gly Phe
            260                 265                 270

Gly Pro Leu Thr Asp Leu Val Phe Ala Phe Ala Asn Gln Leu Leu Pro
        275                 280                 285

Leu Glu Met Asp Asp Ala Glu Thr Gly Leu Leu Ser Ala Ile Cys Leu
    290                 295                 300
```

Ile Cys Gly Asp Arg Gln Asp Leu Glu Gln Pro Asp Arg Val Asp Met
305                 310                 315                 320

Leu Gln Glu Pro Leu Leu Glu Ala Leu Lys Val Tyr Val Arg Lys Arg
            325                 330                 335

Arg Pro Ser Arg His Met Phe Pro Lys Met Leu Met Lys Ile Thr Asp
            340                 345                 350

Leu Arg Ser Ile Ser Ala Lys Gly Ala Glu Arg Val Ile Thr Leu Lys
            355                 360                 365

Met Glu Ile Pro Gly Ser Met Pro Pro Leu Ile Gln Glu Met Leu Glu
            370                 375                 380

Asn Ser Glu Gly Leu Asp Thr Leu Ser Gly Gln Pro Gly Gly Gly
385                 390                 395                 400

Arg Asp Gly Gly Gly Leu Ala Pro Pro Gly Ser Cys Ser Pro Ser
            405                 410                 415

Leu Ser Pro Ser Ser Asn Arg Ser Ser Pro Ala Thr His Ser Pro
            420                 425                 430

<210> SEQ ID NO 88
<211> LENGTH: 599
<212> TYPE: PRT
<213> ORGANISM: Mus musculus

<400> SEQUENCE: 88

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Ala Phe Ser Ala Asn
            85                  90                  95

Ser Leu Gly Ala Phe Pro Gln Leu Asn Ser Val Ser Pro Ser Pro Leu
            100                 105                 110

Met Leu Leu His Pro Pro Gln Leu Ser Pro Phe Leu His Pro His
            115                 120                 125

Gly Gln Gln Val Pro Tyr Tyr Leu Glu Asn Glu Pro Ser Ala Tyr Ala
130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Ser Asn Glu Lys Gly
            165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
            195                 200                 205

Cys Lys Ala Phe Phe Lys Arg Ser Ile Gln Gly His Asn Asp Tyr Met
210                 215                 220

Cys Pro Ala Thr Asn Gln Cys Thr Ile Asp Lys Asn Arg Arg Lys Ser
225                 230                 235                 240

Cys Gln Ala Cys Arg Leu Arg Lys Cys Tyr Glu Val Gly Met Met Lys
            245                 250                 255

-continued

```
Gly Gly Ile Arg Lys Asp Arg Arg Gly Gly Arg Met Leu Lys His Lys
            260                 265                 270

Arg Gln Arg Asp Asp Leu Glu Gly Arg Asn Glu Met Gly Ala Ser Gly
        275                 280                 285

Asp Met Arg Ala Ala Asn Leu Trp Pro Ser Pro Leu Val Ile Lys His
    290                 295                 300

Thr Lys Lys Asn Ser Pro Ala Leu Ser Leu Thr Ala Asp Gln Met Val
305                 310                 315                 320

Ser Ala Leu Leu Asp Ala Glu Pro Pro Met Ile Tyr Ser Glu Tyr Asp
                325                 330                 335

Pro Ser Arg Pro Phe Ser Glu Ala Ser Met Met Gly Leu Leu Thr Asn
            340                 345                 350

Leu Ala Asp Arg Glu Leu Val His Met Ile Asn Trp Ala Lys Arg Val
        355                 360                 365

Pro Gly Phe Gly Asp Leu Asn Leu His Asp Gln Val His Leu Leu Glu
    370                 375                 380

Cys Ala Trp Leu Glu Ile Leu Met Ile Gly Leu Val Trp Arg Ser Met
385                 390                 395                 400

Glu His Pro Gly Lys Leu Leu Phe Ala Pro Asn Leu Leu Leu Asp Arg
                405                 410                 415

Asn Gln Gly Lys Cys Val Glu Gly Met Val Glu Ile Phe Asp Met Leu
            420                 425                 430

Leu Ala Thr Ser Ser Arg Phe Arg Met Met Asn Leu Gln Gly Glu Glu
        435                 440                 445

Phe Val Cys Leu Lys Ser Ile Ile Leu Leu Asn Ser Gly Val Tyr Thr
    450                 455                 460

Phe Leu Ser Ser Thr Leu Lys Ser Leu Glu Glu Lys Asp His Ile His
465                 470                 475                 480

Arg Val Leu Asp Lys Ile Thr Asp Thr Leu Ile His Leu Met Ala Lys
                485                 490                 495

Ala Gly Leu Thr Leu Gln Gln Gln His Arg Arg Leu Ala Gln Leu Leu
            500                 505                 510

Leu Ile Leu Ser His Ile Arg His Met Ser Asn Lys Gly Met Glu His
        515                 520                 525

Leu Tyr Asn Met Lys Cys Lys Asn Val Val Pro Leu Tyr Asp Leu Leu
    530                 535                 540

Leu Glu Met Leu Asp Ala His Arg Leu His Ala Pro Ala Ser Arg Met
545                 550                 555                 560

Gly Val Pro Pro Glu Glu Pro Ser Gln Thr Gln Leu Ala Thr Thr Ser
                565                 570                 575

Ser Thr Ser Ala His Ser Leu Gln Thr Tyr Tyr Ile Pro Pro Glu Ala
            580                 585                 590

Glu Gly Phe Pro Asn Thr Ile
        595

<210> SEQ ID NO 89
<211> LENGTH: 600
<212> TYPE: PRT
<213> ORGANISM: Rattus rattus

<400> SEQUENCE: 89

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
```

-continued

```
               20                  25                  30
Met Pro Met Glu Arg Ala Leu Gly Glu Val Tyr Val Asp Asn Ser Lys
            35                  40                  45
Pro Ala Val Phe Asn Tyr Pro Glu Gly Ala Ala Tyr Glu Phe Asn Ala
            50                  55                  60
Ala Ala Ala Ala Ala Ala Gly Ala Ser Ala Pro Val Tyr Gly Gln
 65                  70                  75                  80
Ser Ser Ile Thr Tyr Gly Pro Gly Ser Glu Ala Ala Phe Gly Ala
                85                  90                  95
Asn Ser Leu Gly Ala Phe Pro Gln Leu Asn Ser Val Ser Pro Ser Pro
            100                 105                 110
Leu Met Leu Leu His Pro Pro His Val Ser Pro Phe Leu His Pro
            115                 120                 125
His Gly His Gln Val Pro Tyr Tyr Leu Glu Asn Glu Pro Ser Ala Tyr
            130                 135                 140
Ala Val Arg Asp Thr Gly Pro Pro Ala Phe Tyr Arg Ser Asn Ser Asp
145                 150                 155                 160
Asn Arg Arg Gln Asn Gly Arg Glu Arg Leu Ser Ser Ser Glu Lys
                165                 170                 175
Gly Asn Met Ile Met Glu Ser Ala Lys Glu Thr Arg Tyr Cys Ala Val
            180                 185                 190
Cys Asn Asp Tyr Ala Ser Gly Tyr His Tyr Gly Val Trp Ser Cys Glu
            195                 200                 205
Gly Cys Lys Ala Phe Phe Lys Arg Ser Ile Gln Gly His Asn Asp Tyr
            210                 215                 220
Met Cys Pro Ala Thr Asn Gln Cys Thr Ile Asp Lys Asn Arg Arg Lys
225                 230                 235                 240
Ser Cys Gln Ala Cys Arg Leu Arg Lys Cys Tyr Glu Val Gly Met Met
                245                 250                 255
Lys Gly Gly Ile Arg Lys Asp Arg Arg Gly Gly Arg Met Leu Lys His
            260                 265                 270
Lys Arg Gln Arg Asp Asp Leu Glu Gly Arg Asn Glu Met Gly Thr Ser
            275                 280                 285
Gly Asp Met Arg Ala Ala Asn Leu Trp Pro Ser Pro Leu Val Ile Lys
            290                 295                 300
His Thr Lys Lys Asn Ser Pro Ala Leu Ser Leu Thr Ala Asp Gln Met
305                 310                 315                 320
Val Ser Ala Leu Leu Asp Ala Glu Pro Pro Leu Ile Tyr Ser Glu Tyr
                325                 330                 335
Asp Pro Ser Arg Pro Phe Ser Glu Ala Ser Met Met Gly Leu Leu Thr
            340                 345                 350
Asn Leu Ala Asp Arg Glu Leu Val His Met Ile Asn Trp Ala Lys Arg
            355                 360                 365
Val Pro Gly Phe Gly Asp Leu Asn Leu His Asp Gln Val His Leu Leu
            370                 375                 380
Glu Cys Ala Trp Leu Glu Ile Leu Met Ile Gly Leu Val Trp Arg Ser
385                 390                 395                 400
Met Glu His Pro Gly Lys Leu Leu Phe Ala Pro Asn Leu Leu Leu Asp
                405                 410                 415
Arg Asn Gln Gly Lys Cys Val Glu Gly Met Val Glu Ile Phe Asp Met
            420                 425                 430
Leu Leu Ala Thr Ser Ser Arg Phe Arg Met Met Asn Leu Gln Gly Glu
            435                 440                 445
```

-continued

```
Glu Phe Val Cys Leu Lys Ser Ile Ile Leu Leu Asn Ser Gly Val Tyr
    450                 455                 460

Thr Phe Leu Ser Ser Thr Leu Lys Ser Leu Glu Glu Lys Asp His Ile
465                 470                 475                 480

His Arg Val Leu Asp Lys Ile Asn Asp Thr Leu Ile His Leu Met Ala
                485                 490                 495

Lys Ala Gly Leu Thr Leu Gln Gln Gln His Arg Arg Leu Ala Gln Leu
                500                 505                 510

Leu Leu Ile Leu Ser His Ile Arg His Met Ser Asn Lys Gly Met Glu
            515                 520                 525

His Leu Tyr Asn Met Lys Cys Lys Asn Val Val Pro Leu Tyr Asp Leu
    530                 535                 540

Leu Leu Glu Met Leu Asp Ala His Arg Leu His Ala Pro Ala Ser Arg
545                 550                 555                 560

Met Gly Val Pro Pro Glu Pro Ser Gln Ser Gln Leu Thr Thr Thr
                565                 570                 575

Ser Ser Thr Ser Ala His Ser Leu Gln Thr Tyr Tyr Ile Pro Pro Glu
                580                 585                 590

Ala Glu Gly Phe Pro Asn Thr Ile
                595                 600

<210> SEQ ID NO 90
<211> LENGTH: 595
<212> TYPE: PRT
<213> ORGANISM: Papio anubis

<400> SEQUENCE: 90

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Val Asp Ser Ser Lys
        35                  40                  45

Pro Ala Val Tyr Ser Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
```

```
              210                 215                 220
Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                    260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys His Ser Lys Lys Asn
290                 295                 300

Ser Pro Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Arg Arg Leu Ala Gln Leu Leu Leu Ile Leu Ser
                500                 505                 510

His Ile Arg His Met Ser Asn Lys Gly Met Glu His Leu Tyr Ser Met
                515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Pro Met
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Asp Ala Glu Gly Phe Pro
                580                 585                 590

Ala Thr Val
        595

<210> SEQ ID NO 91
<211> LENGTH: 866
<212> TYPE: PRT
<213> ORGANISM: Mus musculus
```

<400> SEQUENCE: 91

```
Met Thr Glu Leu Gln Ala Lys Asp Pro Gln Val Leu His Thr Ser Gly
1               5                   10                  15

Ala Ser Pro Ser Pro Pro His Ile Gly Ser Pro Leu Leu Ala Arg Leu
            20                  25                  30

Asp Ser Gly Pro Phe Gln Gly Ser Gln His Ser Asp Val Ser Ser Val
        35                  40                  45

Val Ser Pro Ile Pro Ile Ser Leu Asp Gly Leu Leu Phe Pro Arg Ser
    50                  55                  60

Cys Arg Gly Pro Glu Leu Pro Asp Gly Lys Thr Gly Asp Gln Gln Ser
65                  70                  75                  80

Leu Ser Asp Val Glu Gly Ala Phe Ser Gly Val Glu Ala Thr His Arg
                85                  90                  95

Glu Gly Gly Arg Asn Ser Arg Ala Pro Glu Lys Asp Ser Arg Leu Leu
            100                 105                 110

Asp Ser Val Leu Asp Ser Leu Leu Thr Pro Ser Gly Thr Glu Gln Ser
        115                 120                 125

His Ala Ser Pro Pro Ala Cys Glu Ala Ile Thr Ser Trp Cys Leu Phe
    130                 135                 140

Gly Pro Glu Leu Pro Glu Asp Pro Arg Ser Val Pro Ala Thr Lys Gly
145                 150                 155                 160

Leu Leu Ser Pro Leu Met Ser Arg Pro Glu Ile Lys Ala Gly Asp Ser
                165                 170                 175

Ser Gly Thr Gly Ala Gly Gln Lys Val Leu Pro Lys Gly Leu Ser Pro
            180                 185                 190

Pro Arg Gln Leu Leu Leu Pro Thr Ser Gly Ser Ala His Trp Pro Gly
        195                 200                 205

Ala Gly Val Lys Pro Ser Pro Gln Pro Ala Ala Gly Glu Val Glu Glu
    210                 215                 220

Asp Ser Gly Leu Glu Thr Glu Gly Ser Ala Ala Pro Leu Leu Lys Ser
225                 230                 235                 240

Lys Pro Arg Ala Leu Glu Gly Thr Gly Ser Gly Gly Val Ala Ala
                245                 250                 255

Asn Ala Ala Ser Ala Ala Pro Gly Gly Val Thr Leu Val Pro Lys Glu
            260                 265                 270

Asp Ser Arg Phe Ser Ala Pro Arg Val Ser Leu Glu Gln Asp Ser Pro
        275                 280                 285

Ile Ala Pro Gly Arg Ser Pro Leu Ala Thr Thr Val Val Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Gly Asp Ser Tyr Asp Gly Gly Ala Thr Ala Gln
                325                 330                 335

Gly Pro Phe Ala Pro Pro Arg Gly Ser Pro Ser Ala Pro Ser Pro Pro
            340                 345                 350

Val Pro Cys Gly Asp Phe Pro Asp Cys Thr Tyr Pro Leu Glu Gly Asp
        355                 360                 365

Pro Lys Glu Asp Val Phe Pro Leu Tyr Gly Asp Phe Gln Thr Pro Gly
    370                 375                 380

Leu Lys Ile Lys Glu Glu Glu Gly Ala Asp Ala Ala Val Arg Ser
385                 390                 395                 400

Pro Arg Pro Tyr Leu Ser Ala Gly Ala Ser Ser Ser Thr Phe Pro Asp
```

```
                    405                 410                 415
Phe Pro Leu Ala Pro Ala Pro Gln Arg Ala Pro Ser Ser Arg Pro Gly
            420                 425                 430

Glu Ala Ala Val Ala Gly Gly Pro Ser Ser Ala Val Ser Pro Ala
            435                 440                 445

Ser Ser Ser Gly Ser Ala Leu Glu Cys Ile Leu Tyr Lys Ala Glu Gly
            450                 455                 460

Ala Pro Pro Thr Gln Gly Ser Phe Ala Pro Leu Pro Cys Lys Pro Pro
465                 470                 475                 480

Ala Ala Gly Ser Cys Leu Leu Pro Arg Asp Ser Leu Pro Ala Ala Pro
            485                 490                 495

Ala Thr Ala Ala Ala Pro Ala Ile Tyr Gln Pro Leu Gly Leu Asn Gly
            500                 505                 510

Leu Pro Gln Leu Gly Tyr Gln Ala Ala Val Leu Lys Asp Ser Leu Pro
            515                 520                 525

Gln Val Tyr Pro Pro Tyr Leu Asn Tyr Leu Arg Pro Asp Ser Glu Ala
            530                 535                 540

Ser Gln Ser Pro Gln Tyr Gly Phe Asp Ser Leu Pro Gln Lys Ile Cys
545                 550                 555                 560

Leu Ile Cys Gly Asp Glu Ala Ser Gly Cys His Tyr Gly Val Leu Thr
                565                 570                 575

Cys Gly Ser Cys Lys Val Phe Phe Lys Arg Ala Met Glu Gly Gln His
                580                 585                 590

Asn Tyr Leu Cys Ala Gly Arg Asn Asp Cys Ile Val Asp Lys Ile Arg
                595                 600                 605

Arg Lys Asn Cys Pro Ala Cys Arg Leu Arg Lys Cys Cys Gln Ala Gly
            610                 615                 620

Met Val Leu Gly Gly Arg Lys Phe Lys Lys Phe Asn Lys Val Arg Val
625                 630                 635                 640

Met Arg Thr Leu Asp Gly Val Ala Leu Pro Gln Ser Val Gly Leu Pro
                645                 650                 655

Asn Glu Ser Gln Ala Leu Gly Gln Arg Ile Thr Phe Ser Pro Asn Gln
            660                 665                 670

Glu Ile Gln Leu Val Pro Pro Leu Ile Asn Leu Leu Met Ser Ile Glu
            675                 680                 685

Pro Asp Val Val Tyr Ala Gly His Asp Asn Thr Lys Pro Asp Thr Ser
            690                 695                 700

Ser Ser Leu Leu Thr Ser Leu Asn Gln Leu Gly Glu Arg Gln Leu Leu
705                 710                 715                 720

Arg Met Lys Glu Leu Ser Phe Tyr Ser Leu Cys Leu Thr Met Trp Gln
                725                 730                 735

Ile Pro Gln Glu Phe Val Lys Leu Gln Val Thr His Glu Glu Phe Leu
            740                 745                 750

Cys Met Lys Val Leu Leu Leu Asn Thr Ile Pro Leu Glu Gly Leu
            755                 760                 765

Arg Ser Gln Ser Gln Phe Glu Glu Met Arg Ser Ser Tyr Ile Arg Glu
770                 775                 780

Leu Ile Lys Ala Ile Gly Leu Arg Gln Lys Gly Val Val Pro Ser Ser
785                 790                 795                 800

Gln Arg Phe Tyr Gln Leu Thr Lys Leu Leu Asp Ser Leu His Asp Leu
                805                 810                 815

Val Lys Gln Leu His Leu Tyr Cys Leu Asn Thr Phe Ile Gln Ser Arg
                820                 825                 830
```

```
Thr Leu Ala Val Glu Phe Pro Glu Met Met Ser Glu Val Ile Ala Ala
        835                 840                 845

Gln Leu Pro Lys Ile Leu Ala Gly Met Val Lys Pro Leu Leu Phe His
    850                 855                 860

Lys Lys
865

<210> SEQ ID NO 92
<211> LENGTH: 923
<212> TYPE: PRT
<213> ORGANISM: Rattus rattus

<400> SEQUENCE: 92

Met Thr Glu Leu Gln Ala Lys Asp Pro Arg Thr Leu His Thr Ser Gly
1               5                   10                  15

Ala Ala Pro Ser Pro Thr His Val Gly Ser Pro Leu Leu Ala Arg Leu
            20                  25                  30

Asp Pro Asp Pro Phe Gln Gly Ser Gln His Ser Asp Ala Ser Ser Val
        35                  40                  45

Val Ser Pro Ile Pro Ile Ser Leu Asp Arg Leu Leu Phe Ser Arg Ser
    50                  55                  60

Cys Gln Ala Gln Glu Leu Pro Asp Glu Lys Thr Gln Asn Gln Gln Ser
65                  70                  75                  80

Leu Ser Asp Val Glu Gly Ala Phe Ser Gly Val Glu Ala Ser Arg Arg
                85                  90                  95

Arg Ser Arg Asn Pro Arg Ala Pro Glu Lys Asp Ser Arg Leu Leu Asp
            100                 105                 110

Ser Val Leu Asp Thr Leu Leu Ala Pro Ser Gly Pro Glu Gln Ser Gln
        115                 120                 125

Thr Ser Pro Pro Ala Cys Glu Ala Ile Thr Ser Trp Cys Leu Phe Gly
    130                 135                 140

Pro Glu Leu Pro Glu Asp Pro Arg Ser Val Pro Ala Thr Lys Gly Leu
145                 150                 155                 160

Leu Ser Pro Leu Met Ser Arg Pro Glu Ser Lys Ala Gly Asp Ser Ser
                165                 170                 175

Gly Thr Gly Ala Gly Gln Lys Val Leu Pro Lys Ala Val Ser Pro Pro
            180                 185                 190

Arg Gln Leu Leu Leu Pro Thr Ser Gly Ser Ala His Trp Pro Gly Ala
        195                 200                 205

Gly Val Lys Pro Ser Gln Pro Ala Thr Val Glu Val Glu Glu Asp
    210                 215                 220

Gly Gly Leu Glu Thr Glu Gly Ser Ala Gly Pro Leu Leu Lys Ser Lys
225                 230                 235                 240

Pro Arg Ala Leu Glu Gly Met Cys Ser Gly Gly Val Thr Ala Asn
                245                 250                 255

Ala Pro Gly Ala Ala Pro Gly Gly Val Thr Leu Val Pro Lys Glu Asp
            260                 265                 270

Ser Arg Phe Ser Ala Pro Arg Val Ser Leu Glu Gln Asp Ala Pro Val
        275                 280                 285

Ala Pro Gly Arg Ser Pro Leu Ala Thr Thr Val Val Asp Phe Ile His
    290                 295                 300

Val Pro Ile Leu Pro Leu Asn His Ala Leu Leu Ala Ala Arg Thr Arg
305                 310                 315                 320

Gln Leu Leu Glu Gly Asp Ser Tyr Asp Gly Gly Ala Ala Ala Gln Val
```

-continued

```
                325                 330                 335
Pro Phe Ala Pro Pro Arg Gly Ser Pro Ser Ala Pro Ser Pro Pro Val
            340                 345                 350
Pro Cys Gly Asp Phe Pro Asp Cys Thr Tyr Pro Pro Glu Gly Asp Pro
            355                 360                 365
Lys Glu Asp Gly Phe Pro Val Tyr Gly Glu Phe Gln Pro Pro Gly Leu
            370                 375                 380
Lys Ile Lys Glu Glu Glu Gly Thr Glu Ala Ala Ser Arg Ser Pro
385                 390                 395                 400
Arg Pro Tyr Leu Leu Ala Gly Ser Ala Thr Phe Pro Asp Phe
            405                 410                 415
Pro Leu Pro Pro Arg Pro Arg Ala Pro Pro Ser Arg Pro Gly Glu
            420                 425                 430
Ala Ala Val Ala Ala Pro Ser Ala Val Ser Pro Val Ser Ser Ser
            435                 440                 445
Gly Ser Ala Leu Glu Cys Ile Leu Tyr Lys Ala Glu Gly Ala Pro Pro
            450                 455                 460
Thr Gln Gly Ser Phe Ala Pro Leu Pro Cys Lys Pro Pro Ala Ala Ser
465                 470                 475                 480
Ser Cys Leu Leu Pro Arg Asp Ser Leu Pro Ala Ala Pro Thr Ser Ser
                    485                 490                 495
Ala Ala Pro Ala Ile Tyr Pro Pro Leu Gly Leu Asn Gly Leu Pro Gln
            500                 505                 510
Leu Gly Tyr Gln Ala Ala Val Leu Lys Asp Ser Leu Pro Gln Val Tyr
            515                 520                 525
Pro Pro Tyr Leu Asn Tyr Leu Arg Pro Asp Ser Glu Ala Ser Gln Ser
            530                 535                 540
Pro Gln Tyr Gly Phe Asp Ser Leu Pro Gln Lys Ile Cys Leu Ile Cys
545                 550                 555                 560
Gly Asp Glu Ala Ser Gly Cys His Tyr Gly Val Leu Thr Cys Gly Ser
                    565                 570                 575
Cys Lys Val Phe Phe Lys Arg Ala Met Glu Gly Gln His Asn Tyr Leu
            580                 585                 590
Cys Ala Gly Arg Asn Asp Cys Ile Val Asp Lys Ile Arg Arg Lys Asn
            595                 600                 605
Cys Pro Ala Cys Arg Leu Arg Lys Cys Cys Gln Ala Gly Met Val Leu
            610                 615                 620
Gly Gly Arg Lys Phe Lys Lys Phe Asn Lys Val Arg Val Met Arg Ala
625                 630                 635                 640
Leu Asp Gly Val Ala Leu Pro Gln Ser Val Ala Phe Pro Asn Glu Ser
                    645                 650                 655
Gln Thr Leu Gly Gln Arg Ile Thr Phe Ser Pro Asn Gln Glu Ile Gln
            660                 665                 670
Leu Val Pro Pro Leu Ile Asn Leu Leu Met Ser Ile Glu Pro Asp Val
            675                 680                 685
Val Tyr Ala Gly His Asp Asn Thr Lys Pro Asp Thr Ser Ser Ser Leu
            690                 695                 700
Leu Thr Ser Leu Asn Gln Leu Gly Glu Arg Gln Leu Leu Ser Val Val
705                 710                 715                 720
Lys Trp Ser Lys Ser Leu Pro Gly Phe Arg Asn Leu His Ile Asp Asp
                    725                 730                 735
Gln Ile Thr Leu Ile Gln Tyr Ser Trp Met Ser Leu Met Val Phe Gly
            740                 745                 750
```

```
Leu Gly Trp Arg Ser Tyr Lys His Val Ser Gly Gln Met Leu Tyr Phe
            755                 760                 765

Ala Pro Asp Leu Ile Leu Asn Glu Gln Arg Met Lys Glu Leu Ser Phe
770                 775                 780

Tyr Ser Leu Cys Leu Thr Met Trp Gln Ile Pro Gln Glu Phe Val Lys
785                 790                 795                 800

Leu Gln Val Thr His Glu Glu Phe Leu Cys Met Lys Val Leu Leu Leu
                805                 810                 815

Leu Asn Thr Ile Pro Leu Glu Gly Leu Arg Ser Gln Ser Gln Phe Glu
                820                 825                 830

Glu Met Arg Ser Ser Tyr Ile Arg Glu Leu Ile Lys Ala Ile Gly Leu
                835                 840                 845

Arg Gln Lys Gly Val Val Pro Ser Ser Gln Arg Phe Tyr Gln Leu Thr
850                 855                 860

Lys Leu Leu Asp Ser Leu His Asp Leu Val Lys Gln Leu His Leu Tyr
865                 870                 875                 880

Cys Leu Asn Thr Phe Ile Gln Ser Arg Ala Leu Ala Val Glu Phe Pro
                885                 890                 895

Glu Met Met Ser Glu Val Ile Ala Ala Gln Leu Pro Lys Ile Leu Ala
                900                 905                 910

Gly Met Val Lys Pro Leu Leu Phe His Lys Lys
            915                 920

<210> SEQ ID NO 93
<211> LENGTH: 933
<212> TYPE: PRT
<213> ORGANISM: Papio anubis

<400> SEQUENCE: 93

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
                20                  25                  30

Ala Gly Pro Phe Gln Gly Ser Gln Thr Ser Asp Thr Leu Pro Glu Val
            35                  40                  45

Ser Ala Ile Pro Ile Ser Leu Asp Gly Leu Leu Phe Pro Arg Pro Cys
    50                  55                  60

Gln Gly Gln Asp Pro Leu Asp Glu Lys Thr Gln Asp Gln Gln Ser Leu
65                  70                  75                  80

Ser Asp Val Glu Gly Ala Tyr Ser Arg Ala Glu Ala Thr Arg Gly Thr
                85                  90                  95

Gly Gly Ser Ser Ser Arg Pro Pro Glu Lys Asp Ser Gly Leu Leu His
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Gly Val
145                 150                 155                 160

Leu Ser Pro Leu Met Ser Arg Ser Gly Cys Lys Ala Gly Asp Ser Ser
                165                 170                 175

Gly Thr Ala Ala Ala His Lys Val Leu Pro Arg Gly Leu Ser Pro Ser
            180                 185                 190

Arg Gln Leu Leu Leu Pro Ala Ser Gly Ser Pro His Trp Ser Gly Ala
```

```
              195                 200                 205
Pro Val Lys Pro Ser Pro Gln Pro Ala Ala Val Glu Val Glu Glu Glu
210                 215                 220

Asp Gly Ser Glu Ser Glu Glu Ser Ala Gly Pro Leu Leu Lys Gly Lys
225                 230                 235                 240

Pro Arg Ala Leu Gly Ala Ala Ala Gly Gly Ala Ala Ala Val
                245                 250                 255

Pro Pro Gly Ala Ala Gly Gly Val Ala Leu Val Pro Lys Glu Asp
                260                 265                 270

Ser Arg Phe Ser Ala Pro Arg Val Ala Leu Val Glu Gln Asp Ala Pro
                275                 280                 285

Met Ala Pro Gly Arg Ser Pro Leu Ala Thr Thr Thr Met Asp Phe Thr
290                 295                 300

His Val Pro Ile Leu Pro Leu Ser His Ala Leu Leu Ala Ala Arg Thr
305                 310                 315                 320

Arg Gln Leu Leu Glu Glu Glu Ser Tyr Asp Gly Gly Ala Gly Ala Ala
                325                 330                 335

Ser Ala Phe Ala Pro Pro Arg Ser Ser Pro Ser Ala Ser Ser Thr Pro
                340                 345                 350

Val Ala Val Gly Asp Phe Pro Asp Cys Ala Tyr Pro Pro Asp Ala Asp
                355                 360                 365

Pro Lys Asp Asp Ala Tyr Pro Leu Tyr Gly Asp Phe Gln Pro Pro Ala
370                 375                 380

Leu Lys Ile Lys Glu Glu Glu Gly Ala Glu Val Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Leu Pro Pro Arg Ala Pro Pro Ser
                420                 425                 430

Arg Pro Gly Glu Ala Ala Val Thr Ala Ala Pro Ala Gly Ala Ser Val
                435                 440                 445

Ser Ser Ala Ser Ser Ser Gly Ser Thr Leu Glu Cys Ile Leu Tyr Lys
450                 455                 460

Ala Glu Gly Ala Pro Pro Gln Gln Gly Pro Phe Ala Pro Pro Pro Cys
465                 470                 475                 480

Lys Ala Pro Gly Ala Gly Gly Cys Leu Leu Pro Arg Asp Gly Leu Pro
                485                 490                 495

Ser Thr Ser Ala Ser Ala Ala Ala Gly Ala Ala Pro Ala Leu Tyr
                500                 505                 510

Pro Ala Leu Gly Leu Asn Gly Leu Pro Gln Leu Gly Tyr Gln Ala Ala
                515                 520                 525

Val Leu Lys Glu Gly Leu Gln Gln Val Tyr Pro Pro Tyr Leu Asn Tyr
                530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
                580                 585                 590

Arg Ala Met Glu Gly Gln His Asn Tyr Leu Cys Ala Gly Arg Asn Asp
                595                 600                 605

Cys Ile Val Asp Lys Ile Arg Arg Lys Asn Cys Pro Ala Cys Arg Leu
610                 615                 620
```

```
Arg Lys Cys Cys Gln Ala Gly Met Val Leu Gly Gly Arg Lys Phe Lys
625                 630                 635                 640

Lys Phe Asn Lys Val Arg Val Met Arg Ala Leu Asp Ala Val Ala Leu
            645                 650                 655

Pro Gln Pro Val Gly Ile Pro Asn Glu Ser Gln Ala Leu Ser Gln Arg
            660                 665                 670

Phe Thr Phe Pro Pro Gly Gln Asp Ile Gln Leu Ile Pro Pro Leu Ile
            675                 680                 685

Asn Leu Leu Val Ser Ile Glu Pro Asp Val Ile Tyr Ala Gly His Asp
            690                 695                 700

Asn Ser Lys Pro Asp Thr Ser Ser Leu Leu Thr Ser Leu Asn Gln
705                 710                 715                 720

Leu Gly Glu Arg Gln Leu Leu Ser Val Val Lys Trp Ser Lys Leu Leu
            725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
            755                 760                 765

Lys His Val Ser Gly Gln Met Leu Tyr Phe Ala Pro Asp Leu Ile Leu
770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
            805                 810                 815

Glu Phe Leu Cys Met Lys Val Leu Leu Leu Asn Thr Ile Pro Leu
            820                 825                 830

Glu Gly Leu Arg Ser Gln Thr Gln Phe Glu Glu Met Arg Ser Ser Tyr
            835                 840                 845

Ile Arg Glu Leu Ile Lys Ala Ile Gly Leu Arg Gln Lys Gly Val Val
850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
            885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
            915                 920                 925

Leu Phe His Lys Lys
        930

<210> SEQ ID NO 94
<211> LENGTH: 899
<212> TYPE: PRT
<213> ORGANISM: Mus musculus

<400> SEQUENCE: 94

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
            35                  40                  45

Pro Pro Gly Ala Cys Leu Gln Gln Arg Gln Glu Thr Ser Pro Arg Arg
```

-continued

```
            50                  55                  60
Arg Arg Arg Gln Gln His Thr Glu Asp Gly Ser Pro Gln Ala His Ile
 65                  70                  75                  80

Arg Gly Pro Thr Gly Tyr Leu Ala Leu Glu Glu Gln Gln Pro Ser
                 85                  90                  95

Gln Gln Gln Ala Ala Ser Glu Gly His Pro Glu Ser Ser Cys Leu Pro
                100                 105                 110

Glu Pro Gly Ala Ala Thr Ala Pro Gly Lys Gly Leu Pro Gln Gln Pro
                115                 120                 125

Pro Ala Pro Pro Asp Gln Asp Asp Ser Ala Ala Pro Ser Thr Leu Ser
                130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln His Gln Gln His Gln Gln Gln
                180                 185                 190

Gln Glu Val Ile Ser Glu Gly Ser Ser Ala Arg Ala Arg Glu Ala Thr
                195                 200                 205

Gly Ala Pro Ser Ser Ser Lys Asp Ser Tyr Leu Gly Gly Asn Ser Thr
210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
                260                 265                 270

Arg Pro Thr Pro Cys Ala Pro Leu Pro Glu Cys Lys Gly Leu Pro Leu
                275                 280                 285

Asp Glu Gly Pro Gly Lys Ser Thr Glu Glu Thr Ala Glu Tyr Ser Ser
                290                 295                 300

Phe Lys Gly Gly Tyr Ala Lys Gly Leu Glu Gly Glu Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Tyr
                340                 345                 350

Gln Asn Arg Asp Tyr Tyr Asn Phe Pro Leu Ala Leu Ser Gly Pro Pro
                355                 360                 365

His Pro Pro Pro Thr His Pro His Ala Arg Ile Lys Leu Glu Asn
                370                 375                 380

Pro Leu Asp Tyr Gly Ser Ala Trp Ala Ala Ala Ala Gln Cys Arg
385                 390                 395                 400

Tyr Gly Asp Leu Gly Ser Leu His Gly Gly Ser Val Ala Gly Pro Ser
                405                 410                 415

Thr Gly Ser Pro Pro Ala Thr Thr Ser Ser Ser Trp His Thr Leu Phe
                420                 425                 430

Thr Ala Glu Glu Gly Gln Leu Tyr Gly Pro Gly Gly Gly Gly Gly Ser
                435                 440                 445

Ser Ser Pro Ser Asp Ala Gly Pro Val Ala Pro Tyr Gly Tyr Thr Arg
                450                 455                 460

Pro Pro Gln Gly Leu Thr Ser Gln Glu Ser Asp Tyr Ser Ala Ser Glu
465                 470                 475                 480
```

```
Val Trp Tyr Pro Gly Gly Val Asn Arg Val Pro Tyr Pro Ser Pro
                485             490             495

Asn Cys Val Lys Ser Glu Met Gly Pro Trp Met Glu Asn Tyr Ser Gly
                500             505             510

Pro Tyr Gly Asp Met Arg Leu Asp Ser Thr Arg Asp His Val Leu Pro
                515             520             525

Ile Asp Tyr Tyr Phe Pro Pro Gln Lys Thr Cys Leu Ile Cys Gly Asp
530             535             540

Glu Ala Ser Gly Cys His Tyr Gly Ala Leu Thr Cys Gly Ser Cys Lys
545             550             555             560

Val Phe Phe Lys Arg Ala Ala Glu Gly Lys Gln Lys Tyr Leu Cys Ala
                565             570             575

Ser Arg Asn Asp Cys Thr Ile Asp Lys Phe Arg Arg Lys Asn Cys Pro
                580             585             590

Ser Cys Arg Leu Arg Lys Cys Tyr Glu Ala Gly Met Thr Leu Gly Ala
                595             600             605

Arg Lys Leu Lys Lys Leu Gly Asn Leu Lys Leu Gln Glu Glu Gly Glu
                610             615             620

Asn Ser Asn Ala Gly Ser Pro Thr Glu Asp Pro Ser Gln Lys Met Thr
625             630             635             640

Val Ser His Ile Glu Gly Tyr Glu Cys Gln Pro Ile Phe Leu Asn Val
                645             650             655

Leu Glu Ala Ile Glu Pro Gly Val Val Cys Ala Gly His Asp Asn Asn
                660             665             670

Gln Pro Asp Ser Phe Ala Ala Leu Leu Ser Ser Leu Asn Glu Leu Gly
                675             680             685

Glu Arg Gln Leu Val His Val Val Lys Trp Ala Lys Ala Leu Pro Gly
                690             695             700

Phe Arg Asn Leu His Val Asp Asp Gln Met Ala Val Ile Gln Tyr Ser
705             710             715             720

Trp Met Gly Leu Met Val Phe Ala Met Gly Trp Arg Ser Phe Thr Asn
                725             730             735

Val Asn Ser Arg Met Leu Tyr Phe Ala Pro Asp Leu Val Phe Asn Glu
                740             745             750

Tyr Arg Met His Lys Ser Arg Met Tyr Ser Gln Cys Val Arg Met Arg
                755             760             765

His Leu Ser Gln Glu Phe Gly Trp Leu Gln Ile Thr Pro Gln Glu Phe
                770             775             780

Leu Cys Met Lys Ala Leu Leu Leu Phe Ser Ile Ile Pro Val Asp Gly
785             790             795             800

Leu Lys Asn Gln Lys Phe Phe Asp Glu Leu Arg Met Asn Tyr Ile Lys
                805             810             815

Glu Leu Asp Arg Ile Ile Ala Cys Lys Arg Lys Asn Pro Thr Ser Cys
                820             825             830

Ser Arg Arg Phe Tyr Gln Leu Thr Lys Leu Leu Asp Ser Val Gln Pro
                835             840             845

Ile Ala Arg Glu Leu His Gln Phe Thr Phe Asp Leu Leu Ile Lys Ser
                850             855             860

His Met Val Ser Val Asp Phe Pro Glu Met Met Ala Glu Ile Ile Ser
865             870             875             880

Val Gln Val Pro Lys Ile Leu Ser Gly Lys Val Lys Pro Ile Tyr Phe
                885             890             895
```

His Thr Gln

<210> SEQ ID NO 95
<211> LENGTH: 902
<212> TYPE: PRT
<213> ORGANISM: Rattus rattus
<400> SEQUENCE: 95

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Ser Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Pro Glu Asp Gly Ser Pro Gln Ala His Ile
65                  70                  75                  80

Arg Gly Thr Thr Gly Tyr Leu Ala Leu Glu Glu Glu Gln Pro Ser
            85                  90                  95

Gln Gln Gln Ser Ala Ser Glu Gly His Pro Glu Ser Gly Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Ser Glu Ala Gly Thr Met Gln Leu Leu Gln Gln Gln
            165                 170                 175

Gln Gln Gln Gln Gln Gln Gln Gln Gln Gln Gln Gln Gln Gln Gln
            180                 185                 190

Gln Gln Gln Glu Val Ile Ser Glu Gly Ser Ser Ser Val Arg Ala Arg
        195                 200                 205

Glu Ala Thr Gly Ala Pro Ser Ser Ser Lys Asp Ser Tyr Leu Gly Gly
    210                 215                 220

Asn Ser Thr Ile Ser Asp Ser Ala Lys Glu Leu Cys Lys Ala Val Ser
225                 230                 235                 240

Val Ser Met Gly Leu Gly Val Glu Ala Leu Glu His Leu Ser Pro Gly
            245                 250                 255

Glu Gln Leu Arg Gly Asp Cys Met Tyr Ala Ser Leu Leu Gly Gly Pro
            260                 265                 270

Pro Ala Val Arg Pro Thr Pro Cys Ala Pro Leu Ala Glu Cys Lys Gly
        275                 280                 285

Leu Ser Leu Asp Glu Gly Pro Gly Lys Gly Thr Glu Glu Thr Ala Glu
    290                 295                 300

Tyr Ser Ser Phe Lys Gly Gly Tyr Ala Lys Gly Leu Glu Gly Glu Ser
305                 310                 315                 320

Leu Gly Cys Ser Gly Ser Ser Glu Ala Gly Ser Ser Gly Thr Leu Glu
            325                 330                 335

Ile Pro Ser Ser Leu Ser Leu Tyr Lys Ser Gly Ala Val Asp Glu Ala
            340                 345                 350

Ala Ala Tyr Gln Asn Arg Asp Tyr Tyr Asn Phe Pro Leu Ala Leu Ser
        355                 360                 365
```

```
Gly Pro Pro His Pro Pro Pro Thr His Pro His Ala Arg Ile Lys
    370             375             380

Leu Glu Asn Pro Ser Asp Tyr Gly Ser Ala Trp Ala Ala Ala Ala
385             390             395                 400

Gln Cys Arg Tyr Gly Asp Leu Ala Ser Leu His Gly Ser Val Ala
            405             410                 415

Gly Pro Ser Thr Gly Ser Pro Ala Thr Ala Ser Ser Ser Trp His
            420             425             430

Thr Leu Phe Thr Ala Glu Glu Gly Gln Leu Tyr Gly Pro Gly Gly
            435             440             445

Gly Gly Ser Ser Pro Ser Asp Ala Gly Pro Val Ala Pro Tyr Gly
    450             455             460

Tyr Thr Arg Pro Pro Gln Gly Leu Ala Ser Gln Glu Gly Asp Phe Ser
465             470             475                 480

Ala Ser Glu Val Trp Tyr Pro Gly Gly Val Val Asn Arg Val Pro Tyr
                485             490             495

Pro Ser Pro Ser Cys Val Lys Ser Glu Met Gly Pro Trp Met Glu Asn
            500             505             510

Tyr Ser Gly Pro Tyr Gly Asp Met Arg Leu Asp Ser Thr Arg Asp His
            515             520             525

Val Leu Pro Ile Asp Tyr Tyr Phe Pro Pro Gln Lys Thr Cys Leu Ile
    530             535             540

Cys Gly Asp Glu Ala Ser Gly Cys His Tyr Gly Ala Leu Thr Cys Gly
545             550             555                 560

Ser Cys Lys Val Phe Phe Lys Arg Ala Ala Glu Gly Lys Gln Lys Tyr
            565             570             575

Leu Cys Ala Ser Arg Asn Asp Cys Thr Ile Asp Lys Phe Arg Arg Lys
            580             585             590

Asn Cys Pro Ser Cys Arg Leu Arg Lys Cys Tyr Glu Ala Gly Met Thr
            595             600             605

Leu Gly Ala Arg Lys Leu Lys Lys Leu Gly Asn Leu Lys Leu Gln Glu
    610             615             620

Glu Gly Glu Asn Ser Ser Ala Gly Ser Pro Thr Glu Asp Pro Ser Gln
625             630             635             640

Lys Met Thr Val Ser His Ile Glu Gly Tyr Glu Cys Gln Pro Ile Phe
            645             650             655

Leu Asn Val Leu Glu Ala Ile Glu Pro Gly Val Val Cys Ala Gly His
            660             665             670

Asp Asn Asn Gln Pro Asp Ser Phe Ala Ala Leu Leu Ser Ser Leu Asn
            675             680             685

Glu Leu Gly Glu Arg Gln Leu Val His Val Val Lys Trp Ala Lys Ala
    690             695             700

Leu Pro Gly Phe Arg Asn Leu His Val Asp Asp Gln Met Ala Val Ile
705             710             715                 720

Gln Tyr Ser Trp Met Gly Leu Met Val Phe Ala Met Gly Trp Arg Ser
            725             730             735

Phe Thr Asn Val Asn Ser Arg Met Leu Tyr Phe Ala Pro Asp Leu Val
            740             745             750

Phe Asn Glu Tyr Arg Met His Lys Ser Arg Met Tyr Ser Gln Cys Val
            755             760             765

Arg Met Arg His Leu Ser Gln Glu Phe Gly Trp Leu Gln Ile Thr Pro
    770             775             780

Gln Glu Phe Leu Cys Met Lys Ala Leu Leu Leu Phe Ser Ile Ile Pro
```

```
785                 790                 795                 800
Val Asp Gly Leu Lys Asn Gln Lys Phe Phe Asp Glu Leu Arg Met Asn
                805                 810                 815

Tyr Ile Lys Glu Leu Asp Arg Ile Ile Ala Cys Lys Arg Lys Asn Pro
                820                 825                 830

Thr Ser Cys Ser Arg Arg Phe Tyr Gln Leu Thr Lys Leu Leu Asp Ser
                835                 840                 845

Val Gln Pro Ile Ala Arg Glu Leu His Gln Phe Thr Phe Asp Leu Leu
                850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Lys Pro
                885                 890                 895

Ile Tyr Phe His Thr Gln
                900

<210> SEQ ID NO 96
<211> LENGTH: 895
<212> TYPE: PRT
<213> ORGANISM: Papio hamadryas

<400> SEQUENCE: 96

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
                35                  40                  45

Pro Pro Gly Ala Ser Leu Gln Gln Gln Gln Gln Gln Gln Gln Gln Glu
                50                  55                  60

Thr Ser Pro Arg Gln Gln Gln Gln Gln Gly Glu Asp Gly Ser Pro
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
                100                 105                 110

Gly Cys Val Pro Glu Pro Gly Ala Ala Val Ala Ala Gly Lys Gly Leu
                115                 120                 125

Pro Gln Gln Leu Pro Ala Pro Pro Asp Glu Asp Asp Ser Ala Ala Pro
                130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
                180                 185                 190

Arg Ala Arg Glu Ala Ser Gly Ala Pro Thr Ser Ser Lys Asp Asn Tyr
                195                 200                 205

Leu Gly Gly Thr Ser Thr Ile Ser Asp Ser Ala Lys Glu Leu Cys Lys
                210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
                245                 250                 255
```

```
Gly Val Pro Pro Ala Val Arg Pro Thr Pro Cys Ala Pro Leu Ala Glu
            260                 265                 270

Cys Lys Gly Ser Leu Leu Asp Asp Ser Ala Gly Lys Ser Thr Glu Asp
            275                 280                 285

Thr Ala Glu Tyr Ser Pro Phe Lys Gly Tyr Thr Lys Gly Leu Glu
        290                 295                 300

Gly Glu Ser Leu Gly Cys Ser Gly Ser Ala Ala Gly Ser Ser Gly
305                     310                 315                 320

Thr Leu Glu Leu Pro Ser Thr Leu Ser Leu Tyr Lys Ser Gly Ala Leu
                325                 330                 335

Asp Glu Ala Ala Ala Tyr Gln Ser Arg Asp Tyr Tyr Asn Phe Pro Leu
            340                 345                 350

Ala Leu Ala Gly Pro Pro Pro Pro Pro Pro Pro His Pro His Ala
        355                 360                 365

Arg Ile Lys Leu Glu Asn Pro Leu Asp Tyr Gly Ser Ala Trp Ala Ala
            370                 375                 380

Ala Ala Ala Gln Cys Arg Tyr Gly Glu Leu Ala Ser Leu His Gly Ala
385                 390                 395                 400

Gly Ala Ala Gly Pro Gly Ser Gly Ser Pro Ser Ala Ala Ala Ser Ser
                405                 410                 415

Ser Trp His Thr Leu Phe Thr Ala Glu Glu Gly Gln Leu Tyr Gly Pro
            420                 425                 430

Cys Gly Gly Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
450                 455                 460

Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
            500                 505                 510

Met Arg Leu Glu Thr Ala Arg Asp His Val Leu Pro Ile Asp Tyr Tyr
            515                 520                 525

Phe Pro Pro Gln Lys Thr Cys Leu Ile Cys Gly Asp Glu Ala Ser Gly
            530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
            595                 600                 605

Lys Leu Gly Asn Leu Lys Leu Gln Glu Glu Gly Glu Ala Ser Ser Thr
610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
            660                 665                 670

Phe Ala Ala Leu Leu Ser Ser Leu Asn Glu Leu Gly Glu Arg Gln Leu
```

|  |  | 675 |  |  |  | 680 |  |  |  | 685 |  |
|---|---|---|---|---|---|---|---|---|---|---|---|
| Val | His | Val | Val | Lys | Trp | Ala | Lys | Ala | Leu | Pro | Gly | Phe | Arg | Asn | Leu |
|  |  | 690 |  |  |  | 695 |  |  |  | 700 |  |
| His | Val | Asp | Asp | Gln | Met | Ala | Val | Ile | Gln | Tyr | Ser | Trp | Met | Gly | Leu |
| 705 |  |  |  | 710 |  |  |  | 715 |  |  |  | 720 |
| Met | Val | Phe | Ala | Met | Gly | Trp | Arg | Ser | Phe | Thr | Asn | Val | Asn | Ser | Arg |
|  |  |  |  | 725 |  |  |  | 730 |  |  |  | 735 |
| Met | Leu | Tyr | Phe | Ala | Pro | Asp | Leu | Val | Phe | Asn | Glu | Tyr | Arg | Met | His |
|  |  |  | 740 |  |  |  | 745 |  |  |  | 750 |
| Lys | Ser | Arg | Met | Tyr | Ser | Gln | Cys | Val | Arg | Met | Arg | His | Leu | Ser | Gln |
|  |  | 755 |  |  |  | 760 |  |  |  | 765 |
| Glu | Phe | Gly | Trp | Leu | Gln | Ile | Thr | Pro | Gln | Glu | Phe | Leu | Cys | Met | Lys |
|  | 770 |  |  |  | 775 |  |  |  | 780 |
| Ala | Leu | Leu | Leu | Phe | Ser | Ile | Ile | Pro | Val | Asp | Gly | Leu | Lys | Asn | Gln |
| 785 |  |  |  | 790 |  |  |  | 795 |  |  |  | 800 |
| Lys | Phe | Phe | Asp | Glu | Leu | Arg | Met | Asn | Tyr | Ile | Lys | Glu | Leu | Asp | Arg |
|  |  |  |  | 805 |  |  |  | 810 |  |  |  | 815 |
| Ile | Ile | Ala | Cys | Lys | Arg | Lys | Asn | Pro | Thr | Ser | Cys | Ser | Arg | Arg | Phe |
|  |  |  | 820 |  |  |  | 825 |  |  |  | 830 |
| Tyr | Gln | Leu | Thr | Lys | Leu | Leu | Asp | Ser | Val | Gln | Pro | Ile | Ala | Arg | Glu |
|  |  | 835 |  |  |  | 840 |  |  |  | 845 |
| Leu | His | Gln | Phe | Thr | Phe | Asp | Leu | Leu | Ile | Lys | Ser | His | Met | Val | Ser |
|  | 850 |  |  |  | 855 |  |  |  | 860 |
| Val | Asp | Phe | Pro | Glu | Met | Met | Ala | Glu | Ile | Ile | Ser | Val | Gln | Val | Pro |
| 865 |  |  |  | 870 |  |  |  | 875 |  |  |  | 880 |
| Lys | Ile | Leu | Ser | Gly | Lys | Val | Lys | Pro | Ile | Tyr | Phe | His | Thr | Gln |
|  |  |  | 885 |  |  |  | 890 |  |  |  | 895 |

<210> SEQ ID NO 97
<211> LENGTH: 2397
<212> TYPE: DNA
<213> ORGANISM: Artificial Sequence
<220> FEATURE:
<223> OTHER INFORMATION: ECD v.1 CAR

<400> SEQUENCE: 97

| atgcttctcc | tggtgacaag | ccttctgctc | tgtgagttac | cacacccagc | attcctcctg | 60 |
| attcctgaac | agaagctgat | aagtgaggag | gacttggaca | tccagatgac | ccagaccacc | 120 |
| agcagcctga | gcgccagcct | gggcgataga | gtgaccatca | gctgcagagc | cagccaggac | 180 |
| atcagcaagt | acctgaactg | gtatcagcag | aaacccgacg | gcaccgtgaa | gctgctgatc | 240 |
| taccacacca | gcagactgca | cagcggcgtg | cccagcagat | ttctggcag | cggctccggc | 300 |
| accgactaca | gcctgaccat | ctccaacctg | gaacaggaag | atatcgctac | ctacttctgt | 360 |
| cagcaaggca | acaccctgcc | ctacaccttc | ggcggaggca | ccaagctgga | aatcacaggc | 420 |
| ggcgaggat | ctggcggagg | cggaagtggc | ggaggggat | ctgaagtgaa | actgcaggaa | 480 |
| agcggccctg | gcctggtggc | ccatctcag | tctctgagcg | tgacctgtac | cgtgtccggc | 540 |
| gtgtccctgc | ctgactatgg | cgtgtcctgg | atcagacagc | cccccagaaa | gggcctggaa | 600 |
| tggctgggag | tgatctgggg | cagcgagaca | acctactaca | acagcgccct | gaagtcccgg | 660 |
| ctgaccatca | tcaaggacaa | ctccaagagc | caggtgttcc | tgaagatgaa | cagcctgcag | 720 |
| accgacgaca | ccgccatcta | ctactgcgcc | aagcactact | actacggcgg | cagctacgcc | 780 |
| atggactact | ggggccaggg | cacaagcgtg | accgtgtcta | gcggatccga | tagaagaggc | 840 |

```
ggcagaatgc tgaaacacaa gcggcagagg gacgacgggg aaggcagagg cgaagtggga    900
tctgccggcg atatgagagc cgccaacctg tggcctagcc ccctgatgat caagcggagc    960
aagaagaact ccctggccct gagcctgacc gccgaccaga tggtgtctgc cctgctggat   1020
gccgagcccc ccatcctgta cagcgagtac gaccccacca gcccttcag cgaggccagc    1080
atgatgggcc tgctgaccaa cctggccgac cgggaactgg tgcacatgat caactgggcc   1140
aagcgggtgc ccggcttcgt ggatctgaca ctgcacgacc aggtgcacct gctggaatgc   1200
gcttggctgg aaatcctgat gatcggcctc gtgtggcgga gcatggaaca ccctggcaag   1260
ctgctgttcg cccccaacct gctgctggac cggaaccagg gcaaatgcgt ggaaggcatg   1320
gtggaaatct tcgacatgct gctggccacc tccagccggt tccggatgat gaacctgcag   1380
ggcgaagagt tcgtgtgtct gaagtccatc atcctgctga atagcggcgt gtacaccttc   1440
ctgagcagca ccctgaaaag cctggaagaa aaggaccaca tccaccgggt gctggacaag   1500
atcaccgaca ccctgattca cctgatggcc aaggccggac tgaccctgca gcagcagcat   1560
cagagactgg ctcagctgct gctgatcctg tcccacatcc ggcacatgag caacaagcgg   1620
atggaacatc tgtacagcat gaagtgcaag aacgtggtgc ctctgttcga tctgctgctg   1680
gaaatgctgg acgccacag gctgcacgcc caacatccg gatccaccac gacgccagcg    1740
ccgcgaccac caacaccggc gcccaccatc gcgtcgcagc ccctgtccct gcgcccagag   1800
gcgtgccggc cagcggcggg gggcgcagtg cacacgaggg ggctggactt cgcctgtgat   1860
atctacatct gggcgccctt ggccgggact tgtggggtcc ttctcctgtc actggttatc   1920
accctttact gcaaacgggg cagaaagaaa ctcctgtata tattcaaaca accatttatg   1980
agaccagtac aaactactca agaggaagat ggctgtagct gccgatttcc agaagaagaa   2040
gaaggaggat gtgaactgag agtgaagttc agcaggagcg cagacgcccc cgcgtaccag   2100
cagggccaga accagctcta taacgagctc aatctaggac gaagagagga gtacgatgtt   2160
ttggacaaga cgtggccg ggaccctgag atgggggaa agccgagaag gaagaaccct     2220
caggaaggcc tgtacaatga actgcagaaa gataagatgg cggaggccta cagtgagatt   2280
gggatgaaag gcgagcgccg gagggggcaag ggcacgatg gcctttacca gggtctcagt   2340
acagccacca aggacaccta cgacgccctt cacatgcagg ccctgccccc tcgctag     2397
```

<210> SEQ ID NO 98
<211> LENGTH: 798
<212> TYPE: PRT
<213> ORGANISM: Artificial Sequence
<220> FEATURE:
<223> OTHER INFORMATION: ECD v.1 CAR

<400> SEQUENCE: 98

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Asp Ile Gln Met Thr Gln Thr Thr Ser Ser Leu Ser Ala Ser Leu Gly
        35                  40                  45

Asp Arg Val Thr Ile Ser Cys Arg Ala Ser Gln Asp Ile Ser Lys Tyr
    50                  55                  60

Leu Asn Trp Tyr Gln Gln Lys Pro Asp Gly Thr Val Lys Leu Leu Ile
65                  70                  75                  80

Tyr His Thr Ser Arg Leu His Ser Gly Val Pro Ser Arg Phe Ser Gly
                85                  90                  95

```
Ser Gly Ser Gly Thr Asp Tyr Ser Leu Thr Ile Ser Asn Leu Glu Gln
            100                 105                 110

Glu Asp Ile Ala Thr Tyr Phe Cys Gln Gln Gly Asn Thr Leu Pro Tyr
            115                 120                 125

Thr Phe Gly Gly Gly Thr Lys Leu Glu Ile Thr Gly Gly Gly Gly Ser
        130                 135                 140

Gly Gly Gly Gly Ser Gly Gly Gly Ser Glu Val Lys Leu Gln Glu
145                 150                 155                 160

Ser Gly Pro Gly Leu Val Ala Pro Ser Gln Ser Leu Ser Val Thr Cys
                165                 170                 175

Thr Val Ser Gly Val Ser Leu Pro Asp Tyr Gly Val Ser Trp Ile Arg
            180                 185                 190

Gln Pro Pro Arg Lys Gly Leu Glu Trp Leu Gly Val Ile Trp Gly Ser
        195                 200                 205

Glu Thr Thr Tyr Tyr Asn Ser Ala Leu Lys Ser Arg Leu Thr Ile Ile
    210                 215                 220

Lys Asp Asn Ser Lys Ser Gln Val Phe Leu Lys Met Asn Ser Leu Gln
225                 230                 235                 240

Thr Asp Asp Thr Ala Ile Tyr Tyr Cys Ala Lys His Tyr Tyr Gly
                245                 250                 255

Gly Ser Tyr Ala Met Asp Tyr Trp Gly Gln Gly Thr Ser Val Thr Val
            260                 265                 270

Ser Ser Gly Ser Asp Arg Arg Gly Gly Arg Met Leu Lys His Lys Arg
            275                 280                 285

Gln Arg Asp Asp Gly Glu Gly Arg Gly Glu Val Gly Ser Ala Gly Asp
        290                 295                 300

Met Arg Ala Ala Asn Leu Trp Pro Ser Pro Leu Met Ile Lys Arg Ser
305                 310                 315                 320

Lys Lys Asn Ser Leu Ala Leu Ser Leu Thr Ala Asp Gln Met Val Ser
                325                 330                 335

Ala Leu Leu Asp Ala Glu Pro Pro Ile Leu Tyr Ser Glu Tyr Asp Pro
            340                 345                 350

Thr Arg Pro Phe Ser Glu Ala Ser Met Met Gly Leu Leu Thr Asn Leu
        355                 360                 365

Ala Asp Arg Glu Leu Val His Met Ile Asn Trp Ala Lys Arg Val Pro
    370                 375                 380

Gly Phe Val Asp Leu Thr Leu His Asp Gln Val His Leu Leu Glu Cys
385                 390                 395                 400

Ala Trp Leu Glu Ile Leu Met Ile Gly Leu Val Trp Arg Ser Met Glu
                405                 410                 415

His Pro Gly Lys Leu Leu Phe Ala Pro Asn Leu Leu Leu Asp Arg Asn
            420                 425                 430

Gln Gly Lys Cys Val Glu Gly Met Val Glu Ile Phe Asp Met Leu Leu
        435                 440                 445

Ala Thr Ser Ser Arg Phe Arg Met Met Asn Leu Gln Gly Glu Glu Phe
    450                 455                 460

Val Cys Leu Lys Ser Ile Ile Leu Leu Asn Ser Gly Val Tyr Thr Phe
465                 470                 475                 480

Leu Ser Ser Thr Leu Lys Ser Leu Glu Glu Lys Asp His Ile His Arg
                485                 490                 495

Val Leu Asp Lys Ile Thr Asp Thr Leu Ile His Leu Met Ala Lys Ala
            500                 505                 510
```

Gly Leu Thr Leu Gln Gln Gln His Gln Arg Leu Ala Gln Leu Leu Leu
            515                 520                 525

Ile Leu Ser His Ile Arg His Met Ser Asn Lys Arg Met Glu His Leu
            530                 535                 540

Tyr Ser Met Lys Cys Lys Asn Val Val Pro Leu Phe Asp Leu Leu Leu
545                 550                 555                 560

Glu Met Leu Asp Ala His Arg Leu His Ala Pro Thr Ser Gly Ser Thr
            565                 570                 575

Thr Thr Pro Ala Pro Arg Pro Pro Pro Ala Pro Thr Ile Ala Ser
            580                 585                 590

Gln Pro Leu Ser Leu Arg Pro Glu Ala Cys Arg Pro Ala Ala Gly Gly
            595                 600                 605

Ala Val His Thr Arg Gly Leu Asp Phe Ala Cys Asp Ile Tyr Ile Trp
            610                 615                 620

Ala Pro Leu Ala Gly Thr Cys Gly Val Leu Leu Leu Ser Leu Val Ile
625                 630                 635                 640

Thr Leu Tyr Cys Lys Arg Gly Arg Lys Lys Leu Leu Tyr Ile Phe Lys
            645                 650                 655

Gln Pro Phe Met Arg Pro Val Gln Thr Thr Gln Glu Glu Asp Gly Cys
            660                 665                 670

Ser Cys Arg Phe Pro Glu Glu Glu Gly Gly Cys Glu Leu Arg Val
            675                 680                 685

Lys Phe Ser Arg Ser Ala Asp Ala Pro Ala Tyr Gln Gln Gly Gln Asn
            690                 695                 700

Gln Leu Tyr Asn Glu Leu Asn Leu Gly Arg Arg Glu Glu Tyr Asp Val
705                 710                 715                 720

Leu Asp Lys Arg Arg Gly Arg Asp Pro Glu Met Gly Gly Lys Pro Arg
            725                 730                 735

Arg Lys Asn Pro Gln Glu Gly Leu Tyr Asn Glu Leu Gln Lys Asp Lys
            740                 745                 750

Met Ala Glu Ala Tyr Ser Glu Ile Gly Met Lys Gly Glu Arg Arg Arg
            755                 760                 765

Gly Lys Gly His Asp Gly Leu Tyr Gln Gly Leu Ser Thr Ala Thr Lys
            770                 775                 780

Asp Thr Tyr Asp Ala Leu His Met Gln Ala Leu Pro Pro Arg
785                 790                 795

<210> SEQ ID NO 99
<211> LENGTH: 66
<212> TYPE: DNA
<213> ORGANISM: Artificial Sequence
<220> FEATURE:
<223> OTHER INFORMATION: CSF2RA Signal Sequence

<400> SEQUENCE: 99
atgcttctcc tggtgacaag ccttctgctc tgtgagttac cacacccagc attcctcctg      60
attcct                                                                66

<210> SEQ ID NO 100
<211> LENGTH: 22
<212> TYPE: PRT
<213> ORGANISM: Artificial Sequence
<220> FEATURE:
<223> OTHER INFORMATION: CSF2RA Signal Sequence

<400> SEQUENCE: 100

Met Leu Leu Leu Val Thr Ser Leu Leu Leu Cys Glu Leu Pro His Pro

```
1               5                10               15
Ala Phe Leu Leu Ile Pro
            20
```

<210> SEQ ID NO 101
<211> LENGTH: 30
<212> TYPE: DNA
<213> ORGANISM: Artificial Sequence
<220> FEATURE:
<223> OTHER INFORMATION: cMyc tag

<400> SEQUENCE: 101

```
gaacagaagc tgataagtga ggaggacttg                                        30
```

<210> SEQ ID NO 102
<211> LENGTH: 10
<212> TYPE: PRT
<213> ORGANISM: Artificial Sequence
<220> FEATURE:
<223> OTHER INFORMATION: cMyc tag

<400> SEQUENCE: 102

```
Glu Gln Lys Leu Ile Ser Glu Glu Asp Leu
1               5                10
```

<210> SEQ ID NO 103
<211> LENGTH: 321
<212> TYPE: DNA
<213> ORGANISM: Artificial Sequence
<220> FEATURE:
<223> OTHER INFORMATION: FMC63 VL

<400> SEQUENCE: 103

```
gacatccaga tgacccagac caccagcagc ctgagcgcca gcctgggcga tagagtgacc        60
atcagctgca gagccagcca ggacatcagc aagtacctga actggtatca gcagaaaccc       120
gacggcaccg tgaagctgct gatctaccac accagcagac tgcacagcgg cgtgcccagc       180
agatttctct gcagcggctc cggcaccgac tacagcctga ccatctccaa cctggaacag       240
gaagatatcg ctacctactt ctgtcagcaa ggcaacaccc tgccctacac cttcggcgga       300
ggcaccaagc tggaaatcac a                                                 321
```

<210> SEQ ID NO 104
<211> LENGTH: 107
<212> TYPE: PRT
<213> ORGANISM: Artificial Sequence
<220> FEATURE:
<223> OTHER INFORMATION: FMC63 VL

<400> SEQUENCE: 104

```
Asp Ile Gln Met Thr Gln Thr Thr Ser Ser Leu Ser Ala Ser Leu Gly
1               5                10               15

Asp Arg Val Thr Ile Ser Cys Arg Ala Ser Gln Asp Ile Ser Lys Tyr
            20               25               30

Leu Asn Trp Tyr Gln Gln Lys Pro Asp Gly Thr Val Lys Leu Leu Ile
        35               40               45

Tyr His Thr Ser Arg Leu His Ser Gly Val Pro Ser Arg Phe Ser Gly
        50               55               60

Ser Gly Ser Gly Thr Asp Tyr Ser Leu Thr Ile Ser Asn Leu Glu Gln
65               70               75               80

Glu Asp Ile Ala Thr Tyr Phe Cys Gln Gln Gly Asn Thr Leu Pro Tyr
                85               90               95
```

```
Thr Phe Gly Gly Gly Thr Lys Leu Glu Ile Thr
            100                 105
```

<210> SEQ ID NO 105
<211> LENGTH: 44
<212> TYPE: DNA
<213> ORGANISM: Artificial Sequence
<220> FEATURE:
<223> OTHER INFORMATION: Linker sequence

<400> SEQUENCE: 105

```
ggcggcggag gatctggcgg aggcggaagt ggcggagggg gatc        44
```

<210> SEQ ID NO 106
<211> LENGTH: 15
<212> TYPE: PRT
<213> ORGANISM: Artificial Sequence
<220> FEATURE:
<223> OTHER INFORMATION: Linker sequence

<400> SEQUENCE: 106

```
Gly Gly Gly Gly Ser Gly Gly Gly Gly Ser Gly Gly Gly Gly Ser
1               5                   10                  15
```

<210> SEQ ID NO 107
<211> LENGTH: 360
<212> TYPE: DNA
<213> ORGANISM: Artificial Sequence
<220> FEATURE:
<223> OTHER INFORMATION: FMC63 VH

<400> SEQUENCE: 107

```
gaagtgaaac tgcaggaaag cggccctggc ctggtggccc catctcagtc tctgagcgtg        60
acctgtaccg tgtccggcgt gtccctgcct gactatggcg tgtcctggat cagacagccc       120
cccagaaagg gcctggaatg gctgggagtg atctggggca gcgagacaac ctactacaac       180
agcgccctga gtcccggct gaccatcatc aaggacaact ccaagagcca ggtgttcctg       240
aagatgaaca gcctgcagac cgacgacacc gccatctact actgcgccaa gcactactac       300
tacggcggca gctacgccat ggactactgg ggccagggca agcgtgac cgtgtctagc        360
```

<210> SEQ ID NO 108
<211> LENGTH: 120
<212> TYPE: PRT
<213> ORGANISM: Artificial Sequence
<220> FEATURE:
<223> OTHER INFORMATION: FMC63 VH

<400> SEQUENCE: 108

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95
```

```
Lys His Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 109
<211> LENGTH: 891
<212> TYPE: DNA
<213> ORGANISM: Artificial Sequence
<220> FEATURE:
<223> OTHER INFORMATION: Estrogen receptor alpha ligand binding domain

<400> SEQUENCE: 109

```
gatagaagag gcggcagaat gctgaaacac aagcggcaga gggacgacgg ggaaggcaga      60
ggcgaagtgg gatctgccgg cgatatgaga gccgccaacc tgtggcctag ccccctgatg     120
atcaagcgga gcaagaagaa ctccctggcc ctgagcctga ccgccgacca gatggtgtct     180
gccctgctgg atgccgagcc ccccatcctg tacagcgagt acgaccccac cagacccttc     240
agcgaggcca gcatgatggg cctgctgacc aacctggccg accgggaact ggtgcacatg     300
atcaactggg ccaagcgggt gcccggcttc gtggatctga cactgcacga ccaggtgcac     360
ctgctggaat gcgcttggct ggaaatcctg atgatcggcc tcgtgtggcg agcatggaa      420
caccctggca agctgctgtt cgcccccaac ctgctgctgg accggaacca gggcaaatgc     480
gtggaaggca tggtggaaat cttcgacatg ctgctggcca cctccagccg gttccggatg     540
atgaacctgc agggcgaaga gttcgtgtgt ctgaagtcca tcatcctgct gaatagcggc     600
gtgtacacct tcctgagcag caccctgaaa agcctggaag aaaaggacca catccaccgg     660
gtgctggaca agatcaccga caccctgatt cacctgatgg ccaaggccgg actgaccctg     720
cagcagcagc atcagagact ggctcagctg ctgctgatcc tgtcccacat ccggcacatg     780
agcaacaagc ggatggaaca tctgtacagc atgaagtgca agaacgtggt gcctctgttc     840
gatctgctgc tggaaatgct ggacgcccac aggctgcacg ccccaacatc c              891
```

<210> SEQ ID NO 110
<211> LENGTH: 297
<212> TYPE: PRT
<213> ORGANISM: Artificial Sequence
<220> FEATURE:
<223> OTHER INFORMATION: Estrogen receptor alpha ligand binding domain

<400> SEQUENCE: 110

```
Asp Arg Arg Gly Gly Arg Met Leu Lys His Lys Arg Gln Arg Asp Asp
1               5                   10                  15

Gly Glu Gly Arg Gly Glu Val Gly Ser Ala Gly Asp Met Arg Ala Ala
            20                  25                  30

Asn Leu Trp Pro Ser Pro Leu Met Ile Lys Arg Ser Lys Lys Asn Ser
        35                  40                  45

Leu Ala Leu Ser Leu Thr Ala Asp Gln Met Val Ser Ala Leu Leu Asp
    50                  55                  60

Ala Glu Pro Pro Ile Leu Tyr Ser Glu Tyr Asp Pro Thr Arg Pro Phe
65                  70                  75                  80

Ser Glu Ala Ser Met Met Gly Leu Leu Thr Asn Leu Ala Asp Arg Glu
                85                  90                  95

Leu Val His Met Ile Asn Trp Ala Lys Arg Val Pro Gly Phe Val Asp
            100                 105                 110

Leu Thr Leu His Asp Gln Val His Leu Leu Glu Cys Ala Trp Leu Glu
        115                 120                 125
```

```
Ile Leu Met Ile Gly Leu Val Trp Arg Ser Met Glu His Pro Gly Lys
    130                 135                 140

Leu Leu Phe Ala Pro Asn Leu Leu Asp Arg Asn Gln Gly Lys Cys
145                 150                 155                 160

Val Glu Gly Met Val Glu Ile Phe Asp Met Leu Leu Ala Thr Ser Ser
                    165                 170                 175

Arg Phe Arg Met Met Asn Leu Gln Gly Glu Glu Phe Val Cys Leu Lys
                180                 185                 190

Ser Ile Ile Leu Leu Asn Ser Gly Val Tyr Thr Phe Leu Ser Ser Thr
            195                 200                 205

Leu Lys Ser Leu Glu Glu Lys Asp His Ile His Arg Val Leu Asp Lys
    210                 215                 220

Ile Thr Asp Thr Leu Ile His Leu Met Ala Lys Ala Gly Leu Thr Leu
225                 230                 235                 240

Gln Gln Gln His Gln Arg Leu Ala Gln Leu Leu Ile Leu Ser His
                245                 250                 255

Ile Arg His Met Ser Asn Lys Arg Met Glu His Leu Tyr Ser Met Lys
                260                 265                 270

Cys Lys Asn Val Val Pro Leu Phe Asp Leu Leu Leu Glu Met Leu Asp
                275                 280                 285

Ala His Arg Leu His Ala Pro Thr Ser
    290                 295

<210> SEQ ID NO 111
<211> LENGTH: 207
<212> TYPE: DNA
<213> ORGANISM: Homo sapiens

<400> SEQUENCE: 111
accacgacgc cagcgccgcg accaccaaca ccggcgccca ccatcgcgtc gcagcccctg     60
tccctgcgcc cagaggcgtg ccggccagcg gcggggggcg cagtgcacac gaggggctg    120 gacttcgcct gtgatatcta catctgggcg cccttggccg ggacttgtgg ggtccttctc    180
ctgtcactgg ttatcaccct ttactgc                                       207

<210> SEQ ID NO 112
<211> LENGTH: 44
<212> TYPE: PRT
<213> ORGANISM: Homo sapiens

<400> SEQUENCE: 112

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys
            35                  40

<210> SEQ ID NO 113
<211> LENGTH: 75
<212> TYPE: DNA
<213> ORGANISM: Homo sapiens

<400> SEQUENCE: 113
gatatctaca tctgggcgcc cttggccggg acttgtgggg tccttctcct gtcactggtt    60
atcacccttt actgc                                                     75
```

<210> SEQ ID NO 114
<211> LENGTH: 25
<212> TYPE: PRT
<213> ORGANISM: Homo sapiens

<400> SEQUENCE: 114

Asp Ile Tyr Ile Trp Ala Pro Leu Ala Gly Thr Cys Gly Val Leu Leu
1               5                   10                  15

Leu Ser Leu Val Ile Thr Leu Tyr Cys
            20                  25

<210> SEQ ID NO 115
<211> LENGTH: 123
<212> TYPE: DNA
<213> ORGANISM: Homo sapiens

<400> SEQUENCE: 115
aaacggggca gaaagaaact cctgtatata ttcaaacaac catttatgag accagtacaa     60
actactcaag aggaagatgg ctgtagctgc cgatttccag aagaagaaga aggaggatgt    120
gaa                                                                  123

<210> SEQ ID NO 116
<211> LENGTH: 41
<212> TYPE: PRT
<213> ORGANISM: Homo sapiens

<400> SEQUENCE: 116

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
            35                  40

<210> SEQ ID NO 117
<211> LENGTH: 339
<212> TYPE: DNA
<213> ORGANISM: Homo sapiens

<400> SEQUENCE: 117
ctgagagtga agttcagcag gagcgcagac gcccccgcgt accagcaggg ccagaaccag     60
ctctataacg agctcaatct aggacgaaga gaggagtacg atgttttgga caagagacgt    120
ggccgggacc ctgagatggg gggaaagccg agaaggaaga accctcagga aggcctgtac    180
aatgaactgc agaaagataa gatggcggag gcctacagtg agattgggat gaaaggcgag    240
cgccggaggg gcaaggggca cgatggcctt taccagggtc tcagtacagc caccaaggac    300
acctacgacg cccttcacat gcaggccctg ccccctcgc                           339

<210> SEQ ID NO 118
<211> LENGTH: 113
<212> TYPE: PRT
<213> ORGANISM: Homo sapiens

<400> SEQUENCE: 118

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

```
Tyr Asp Val Leu Asp Lys Arg Arg Gly Arg Asp Pro Glu Met Gly Gly
                35                  40                  45

Lys Pro Arg Arg Lys Asn Pro Gln Glu Gly Leu Tyr Asn Glu Leu Gln
 50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
                100                 105                 110

Arg

<210> SEQ ID NO 119
<211> LENGTH: 595
<212> TYPE: PRT
<213> ORGANISM: Artificial Sequence
<220> FEATURE:
<223> OTHER INFORMATION: Estrogen receptor ligand binding domain

<400> SEQUENCE: 119

Met Thr Met Thr Leu His Thr Lys Ala Ser Gly Met Ala Leu Leu His
 1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
                35                  40                  45

Pro Ala Val Tyr Asn Tyr Pro Glu Gly Ala Ala Tyr Glu Phe Asn Ala
 50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
                130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
                195                 200                 205

Phe Lys Arg Ser Ile Gln Gly His Asn Asp Tyr Met Cys Pro Ala Thr
                210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
```

-continued

```
                 275                 280                 285
Ala Asn Leu Trp Pro Ser Pro Leu Met Ile Lys Arg Ser Lys Lys Asn
            290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
                355                 360                 365
Asp Leu Thr Leu His Asp Gln Val His Leu Leu Glu Cys Ala Trp Leu
        370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
            530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595
```

CHIMERIC POLYPEPTIDES AND METHODS OF ALTERING THE MEMBRANE LOCALIZATION OF THE SAME

CROSS-REFERENCE TO RELATED APPLICATIONS

This application is a divisional of U.S. patent application Ser. No. 15/938,600, filed Mar. 28, 2018, which claims priority to U.S. Provisional Patent Application No. 62/477,733, filed Mar. 28, 2017, and U.S. Provisional Patent Application No. 62/587,262, filed Nov. 16, 2017; the entire contents of each of which are herein incorporated by reference.

SEQUENCE LISTING

The instant application contains a Sequence Listing which has been submitted electronically in ASCII format and is hereby incorporated by reference in its entirety. The ASCII copy, created on Jul. 27, 2021, is named CDL-100P2CD_Sequence_listing_ST25.txt and is 267.1 KB in size.

TECHNICAL FIELD

The present disclosure relates to the field of biotechnology, and more specifically, to the regulation of the cellular localization of a chimeric polypeptide.

BACKGROUND

Chimeric antigen receptors (CARs) are a subclass of single-chain and multi-chain polypeptides. Chimeric antigen receptors typically include, e.g., an antigen-binding domain, a transmembrane domain, a co-stimulatory domain, and a CD3ζ or other signaling domain. CARs have been investigated for use in the clinical treatment of different cancers, e.g., hematological cancers, in mammals with considerable success. A limiting factor, however, has been uncontrollable toxicity associated with CAR anticancer activity.

Nuclear hormone receptors are class of polypeptides that include several domains, including a DNA-binding motif and a ligand-binding domain. In the absence of ligand, naturally-occurring nuclear hormone receptors associate with various chaperones and other interacting proteins which sequester the nuclear hormone receptor outside of the nucleus. Ligand binding induces changes in nuclear hormone receptor conformation and interaction partners and allows the nuclear translocation and transcriptional activation or repression of nuclear hormone target genes. While the classical view of steroid signaling holds that these hormones bind intracellular receptors that act as ligand-activated transcription factors, it has been reported that steroids may also act by a non-genomic mechanism at the cell surface.

SUMMARY

The present disclosure is based, at least in part, on the discovery that the reversible extracellular membrane localization of chimeric polypeptides that include a transmembrane domain can be utilized for medical applications where it is desired to have reversibly expressed on the extracellular membrane a protein or peptide of interest. An exemplary feature of the present disclosure is that the toxicity associated with CAR T cells can be regulated by reversibly expressing on their surface an antigen binding domain of a CAR.

The present disclosure is further based, at least in part, on the discovery that the plasma membrane localization or extracellular membrane localization of chimeric polypeptides that include a transmembrane domain and a hormone receptor ligand binding domain, where the transmembrane domain and the hormone receptor ligand binding domain directly abut each other or are separated by 1 to about 700 amino acids (e.g., 1 to about 500 amino acids), and the transmembrane domain and the hormone receptor ligand binding domain are not both present in the same endogenous single-chain polypeptide in a mammal (e.g., a single-chain chimeric antigen receptor), in a mammalian cell can be regulated by contacting the mammalian cell with a hormone or a hormone analogue. In view of this discovery, provided herein are: single-chain chimeric polypeptides, single-chain chimeric antigen receptors, and multi-chain chimeric antigen receptors; nucleic acids encoding the same; vectors including any of these nucleic acids; mammalian cells including any of these vectors; and methods of reversibly inducing the extracellular membrane localization and methods of altering the membrane localization of these single-chain chimeric polypeptides, single-chain chimeric antigen receptors, and multi-chain chimeric polypeptides.

In some embodiments, reversibly inducing the plasma membrane localization or extracellular membrane localization of polypeptides (e.g., single-chain chimeric polypeptides, single-chain chimeric antigen receptors, and/or multi-chain chimeric antigen receptors) using one or more of the compositions or methods disclosed herein is useful in the area of cell-based adoptive immunotherapy, in which immune cells isolated from a subject can be modified to express synthetic proteins that enable the cells to perform new therapeutic functions after they are subsequently transferred back into the subject. Non-limiting examples of such synthetic proteins are chimeric antigen receptors (CARs) and engineered T cell Receptors (TCRs).

In some embodiments, reversibly inducing the plasma membrane localization or extracellular membrane localization of polypeptides (e.g., single-chain chimeric polypeptides, single-chain chimeric antigen receptors, and/or multi-chain chimeric antigen receptors) using one or more of the compositions or methods disclosed herein is useful in controlling the toxic effects of chimeric antigen T cells (CAR-T cells) involved in eliminating cancer cells by regulating the presence or absence of an antigen binding moiety on the plasma membrane or extracellular membrane of the cell.

Provided herein are single-chain chimeric polypeptides that include: a transmembrane domain; and a hormone receptor ligand binding domain, where: the transmembrane domain and the hormone receptor ligand binding domain directly abut each other or are separated by 1 to 500 amino acids; and the transmembrane domain and the hormone receptor ligand binding domain are not both present in the same endogenous single-chain polypeptide in a mammal. In some embodiments of any of the single-chain chimeric polypeptides described herein, the transmembrane domain is a transmembrane domain from: α chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the single-chain chimeric polypeptides described herein, the hormone receptor ligand binding domain is a ligand binding domain from an estrogen receptor, a progesterone receptor, or an androgen receptor. In some embodiments of any of the single-chain chimeric polypeptides described herein, the hormone receptor ligand binding domain is a ligand binding domain from an estrogen receptor.

In some embodiments of any of the single-chain chimeric polypeptides described herein, the transmembrane domain and the hormone receptor ligand binding domain directly abut each other. In some embodiments of any of the single-chain chimeric polypeptides described herein, the transmembrane domain and the hormone receptor ligand binding domain are separated by 1 to 500 amino acids (e.g., 1 to 250 amino acids, or about 1 to 50 amino acids).

Also provided herein are nucleic acids that include a nucleotide sequence encoding any of the single-chain chimeric polypeptides described herein. Also provided herein are vectors that include any of the nucleic acids that include a nucleotide sequence encoding any of the single-chain chimeric polypeptides described herein. Also provided herein are mammalian cells that include any of the vectors described herein.

Also provided herein are methods of inducing the membrane localization of a single-chain chimeric polypeptide in a mammalian cell that include: contacting a mammalian cell expressing any of the single-chain chimeric polypeptides described herein with an amount of a hormone or a hormone analogue sufficient to induce localization of the single-chain chimeric polypeptide to the extracellular side of the plasma membrane of the cell.

Also provided are methods of reversibly altering the membrane localization of a single-chain chimeric polypeptide in a mammalian cell that include: (a) contacting a mammalian cell expressing any of the single-chain chimeric polypeptides described herein with an amount of a hormone or a hormone analogue sufficient to induce localization of the single-chain chimeric polypeptide to the extracellular side of the plasma membrane of the cell; and (b) contacting the mammalian cell with a reduced amount of the hormone or the hormone analogue that results in a decreased level of the single-chain chimeric polypeptide on the extracellular side of the plasma membrane of the mammalian cell. Some embodiments of any of the methods described herein further include: (c) contacting the mammalian cell with an increased amount of the hormone or the hormone analogue that results in an increased level of the single-chain chimeric polypeptide on the extracellular side of the plasma membrane of the cell as compared to the level of in step (b).

Some embodiments of any of the methods described herein further include: introducing a nucleic acid encoding the single-chain chimeric polypeptide into a mammalian cell to generate the mammalian cell expressing the single-chain chimeric polypeptide. In some embodiments of any of the methods described herein, the mammalian cell is a T cell (e.g., a T-cell selected from the group of a $CD8^+$ T cell, a $CD4^+$ T cell, a memory T cell, a Treg cell, and natural killer T cell).

In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include: obtaining the mammalian cell from the subject. In some embodiments of any of the methods described herein, the contacting step is performed in vitro. In some embodiments of any of the methods described herein, the contacting step is performed in a mammal.

Also provided herein are single-chain chimeric antigen receptors that include: an extracellular antigen-binding domain; a transmembrane domain; a hormone receptor ligand binding domain; a costimulatory domain; and a immunoreceptor tyrosine-based activation motif (ITAM); where: the transmembrane domain and the hormone receptor ligand binding domain directly abut each other or are separated by 1 to 500 amino acids; and the transmembrane domain and the hormone receptor ligand binding domain are not both present in the same endogenous single-chain polypeptide in a mammal. In some embodiments of any of the single-chain chimeric antigen receptors described herein, the extracellular antigen-binding domain is selected from the group of: a scFv, a (scFv)$_2$, a V$_H$H domain, and a V$_{NAR}$ domain. In some embodiments of any of the single-chain chimeric antigen receptors described herein, the extracellular antigen-binding domain is a scFv.

In some embodiments of any of the single-chain chimeric antigen receptors described herein, the extracellular antigen-binding domain binds specifically to a single antigen. In some embodiments of any of the single-chain chimeric antigen receptors described herein, the single antigen is a tumor antigen. In some embodiments of any of the single-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the single-chain chimeric antigen receptors described herein, the tumor antigen is CD19. In some embodiments of any of the single-chain chimeric antigen receptors described herein, the extracellular antigen-binding domain binds specifically to two different antigens.

In some embodiments of any of the single chain chimeric antigen receptors described herein, the transmembrane domain is a transmembrane domain from: a chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the single-chain chimeric antigen receptors described herein, the hormone receptor ligand binding domain is a ligand binding domain from an estrogen receptor, a progesterone receptor, or an androgen receptor. In some embodiments of any of the single-chain chimeric antigen receptors described herein, the hormone receptor ligand binding domain is a ligand binding domain from an estrogen receptor.

In some embodiments of any of the single-chain chimeric antigen receptors described herein, the costimulatory domain is a cytoplasmic costimulatory domain from CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, and B7-H3. In some embodiments of any of the single-chain chimeric antigen receptors described herein, the costimulatory domain is 4-1BB or CD28. In some embodiments of any of the single-chain chimeric antigen receptors described herein, the ITAM includes a cytoplasmic signaling sequence from CD3ζ.

In some embodiments of any of the single-chain chimeric antigen receptors described herein, the transmembrane domain and the hormone receptor ligand binding domain directly abut each other. In some embodiments of any of the single-chain chimeric antigen receptors described herein, the transmembrane domain and the hormone receptor ligand binding domain are separated by 1 to 500 amino acids (e.g., 1 to 250 amino acids, or 1 to 50 amino acids).

Also provided herein are nucleic acids that include a nucleotide sequence encoding any of the single-chain chimeric antigen receptors described herein. Also provided herein are vectors that include a nucleic acid that includes a nucleotide sequence encoding any of the single-chain chimeric antigen receptors described herein. Also provided are mammalian cells that include any of the vectors described herein.

Also provided are methods of inducing the membrane localization of a single-chain chimeric antigen receptor in a mammalian cell that include: contacting a mammalian cell expressing any of the single-chain chimeric antigen receptors described herein with an amount of a hormone or a hormone analogue sufficient to induce localization of the single-chain chimeric antigen-binding receptor to the extracellular side of the plasma membrane of the cell.

Also provided herein are methods of altering the membrane localization of a single-chain chimeric antigen receptor in a mammalian cell that include: (a) contacting a mammalian cell expressing any of the single-chain chimeric antigen receptors described herein with an amount of a hormone or a hormone analogue sufficient to induce localization of the single-chain chimeric antigen-binding receptor to the extracellular side of the plasma membrane of the cell; and (b) contacting the mammalian cell with an amount of the hormone or the hormone analogue that results in a reduced level of the single-chain chimeric antigen receptor on the extracellular side of the plasma membrane of the cell. Some embodiments of these methods further include: (c) contacting the mammalian cell with an amount of the hormone or the hormone analogue that results in an increased level of single-chain chimeric antigen receptor to the extracellular side of the plasma membrane of the cell as compared to the level in (b).

Some embodiments of any of the methods described herein further include: introducing a nucleic acid encoding the single-chain chimeric antigen receptor into a mammalian cell to generate the mammalian cell expressing the single-chain chimeric antigen receptor. In some embodiments of any of the methods described herein, the mammalian cell is a T cell. In some embodiments of any of the methods described herein, the T cell is selected from the group of: a CD8+ T cell, a CD4+ T cell, a memory T cell, a Treg cell, and a natural killer T cell.

In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include: obtaining the mammalian cell from the subject. In some embodiments of any of the methods described herein, the contacting step is performed in vitro. In some embodiments of any of the methods described herein, the contacting step is performed in a mammal. In some embodiments of any of the methods described herein, the mammal has a cancer. In some embodiments of any of the methods described herein, the contacting step results in the treatment of the cancer in the mammal.

Also provided herein are multi-chain chimeric antigen receptors that include at least one first polypeptide including: an extracellular antigen-binding domain; a transmembrane domain; and a hormone receptor ligand binding domain; where: the transmembrane domain and the hormone receptor ligand binding domain directly abut each other or are separated by 1 to 500 amino acids; and the transmembrane domain and the hormone receptor ligand binding domain are not both present in the same endogenous single-chain polypeptide in a mammal. In some embodiments of any of the multi-chain chimeric antigen receptors described herein, the extracellular antigen-binding domain is selected from the group consisting of: a scFv, a (scFv)$_2$, a V$_H$H domain, and a V$_{NAR}$ domain. In some embodiments of any of the multi-chain chimeric antigen receptors described herein, the extracellular antigen-binding domain is a scFv.

In some embodiments of any of the multi-chain chimeric antigen receptors described herein, the extracellular antigen-binding domain binds specifically to a single antigen. In some embodiments of any of the multi-chain chimeric antigen receptors described herein, the single antigen is a tumor antigen. In some embodiments of any of the multi-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the multi-chain chimeric antigen receptors described herein, the tumor antigen is CD19. In some embodiments of any of the multi-chain chimeric antigen receptors described herein, the extracellular antigen-binding domain binds specifically to two different antigens.

In some embodiments of any of the multi-chain chimeric antigen receptors described herein, the transmembrane domain is a transmembrane domain from: α chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the multi-chain chimeric antigen receptors described herein, the hormone receptor ligand binding domain is a ligand binding domain from an estrogen receptor, a progesterone receptor, or an androgen receptor. In some embodiments of any of the multi-chain chimeric antigen receptors described herein, the hormone receptor ligand binding domain is a ligand binding domain from an estrogen receptor.

In some embodiments of any of the multi-chain chimeric antigen receptors described herein, the transmembrane domain and the hormone receptor ligand binding domain directly abut each other. In some embodiments of any of the multi-chain chimeric antigen receptors described herein, the transmembrane domain and the hormone receptor ligand binding domain are separated by 1 to 500 amino acids (e.g., 1 to 250 amino acids, or 1 to 50 amino acids).

In some embodiments of any of the multi-chain chimeric antigen receptors described herein, the at least one polypeptide further includes a costimulatory domain. In some embodiments of any of the multi-chain chimeric antigen receptors described herein, the costimulatory domain is a cytoplasmic costimulatory domain from CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments of any of the multi-chain chimeric antigen receptors described herein, the costimulatory domain is 4-1BB or CD28.

Also provided herein are methods of inducing membrane localization of a multi-chain chimeric antigen receptor in a mammalian cell that include: contacting a mammalian cell expressing any of the multi-chain chimeric antigen receptors described herein with an amount of a hormone or a hormone analogue sufficient to induce localization of the multi-chain chimeric antigen-binding receptor to the extracellular side of the plasma membrane of the cell.

Also provided herein are methods of altering the membrane localization of a multi-chain chimeric antigen receptor in a mammalian cell that include: (a) contacting a mammalian cell expressing any of the multi-chain chimeric antigen receptors described herein with an amount of a hormone or a hormone analogue sufficient to induce localization of the multi-chain chimeric antigen-binding receptor to the extracellular side of the plasma membrane of the cell; and (b) contacting the mammalian cell with an amount of the hormone or the hormone analogue with an amount of the hormone or the hormone analogue that results in a decreased level of the multi-chain chimeric antigen-binding receptor on the extracellular side of the plasma membrane of the cell. Some embodiments of any of the methods described herein further include: (c) contacting the mammalian cell with an amount of the hormone or the hormone analogue that results in an increase in the level of the multi-chain chimeric antigen-binding receptor on the extracellular side of the plasma membrane of the cell. Some embodiments of any of the methods described herein further include: introducing a nucleic acid encoding the single-chain chimeric antigen receptor into a mammalian cell to generate the mammalian cell expressing the single-chain chimeric antigen receptor. In some embodiments of any of the methods described herein, the mammalian cell is a T cell. In some embodiments of any of the methods described herein, the T cell is selected from the group of: a CD8+ T cell, a CD4+ T cell, a memory T cell, a Treg cell, and a natural killer T cell.

In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include: obtaining the mammalian cell from the subject. In some embodiments of any of the methods described herein, the contacting step is performed in vitro. In some embodiments of any of the methods described herein, the contacting step is performed in a mammal. In some embodiments of any of the methods described herein, the mammal has a cancer. In some embodiments of any of the methods described herein, the contacting step results in the treatment of the cancer in the mammal.

Also provided herein are methods of treating a cancer in a subject (e.g., a human) that include: (a) administering to the subject a mammalian cell expressing any of the single chain chimeric antigen receptors described herein or any of the multi-chain chimeric antigen receptors described herein, where the antigen binding domain binds specifically to an antigen expressed by the cancer in the subject; (b) administering to the subject an amount of a hormone or hormone sufficient to induce localization of the single-chain or multi-chain chimeric antigen receptor to the extracellular side of the plasma membrane of the cell; (c) determining the presence or severity of one or more symptoms associated with toxicity, the level of one or more cytokines associated with a cytokine storm, or both, in the subject following (b); (d) comparing the determined presence or severity of one or more symptoms associated with toxicity, the determined level of one or more cytokines associated with the cytokine storm, or both, to a control(s); and (e) administering to the subject an amount of the hormone or hormone analogue sufficient to reduce the level of the single-chain or multi-chain chimeric antigen receptor on the extracellular side of the plasma membrane of the cell, such that the presence or severity of one or more symptoms associated with toxicity, the level of one or more cytokines associated with a cytokine storm, or both, is reduced in the subject after (e).

In some embodiments of any of the methods described herein, the amount of the hormone or hormone analogue administered to the subject in step (e) is reduced by at least 25% as compared to the amount of the hormone or hormone analogue administered to the subject in step (b). In some embodiments of any of the methods described herein, the amount of the hormone or hormone analogue administered to the subject in step (e) is reduced by at least 50% as compared to the amount of the hormone or hormone analogue administered to the subject in step (b). In some embodiments of any of the methods described herein, the amount of the hormone or hormone analogue administered to the subject in step (e) is reduced by at least 75% as compared to the level of the hormone or hormone analogue administered to the subject in step (b). In some embodiments of any of the methods described herein, the amount of the hormone or hormone analogue administered to the subject in step (e) is reduced by 100% as compared to the level of the hormone or hormone analogue administered to the subject in step (b).

In some embodiments of any of the methods described herein, the one or more symptoms associated with toxicity are selected from the group consisting of: high fever, swelling, chills, hypotension, tachycardia, asthenia, headache, rash, scratchy throat, dyspnea, redness, extreme fatigue, nausea, and cerebral edema. In some embodiments of these methods, the one or more cytokines associated with a cytokine storm are selected from the group consisting of: include tumor necrosis factor-alpha, IFNγ, IL-10, IL-1β, IL-2, IL-6, IL-8, and IL-10, granulocyte macrophage-colony-stimulating factor (GM-CSF), and IL-5.

Also provided herein are single-chain chimeric polypeptides that include: an extracellular hormone receptor ligand binding domain; and a transmembrane domain, where: the hormone receptor ligand binding domain and the extracellular transmembrane domain directly abut each other or are separated by 1 to 700 amino acids; and the transmembrane domain and the extracellular hormone receptor ligand binding domain are not both present in a single endogenous single-chain polypeptide in a mammal. In some embodiments of any of the single-chain chimeric polypeptides described herein, the transmembrane domain is a transmembrane domain from: a chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the single chain chimeric polypeptides described herein, the extracellular hormone receptor ligand binding domain is a ligand binding domain from an estrogen receptor, a progesterone receptor, or an androgen receptor. In some embodiments of any of the single-chain chimeric polypeptides described herein, the extracellular hormone receptor ligand binding domain is a ligand binding domain from an estrogen receptor. In some embodiments of any of the single-chain chimeric polypeptides described herein, the extracellular hormone receptor ligand binding domain is a ligand binding domain from a human estrogen receptor. In some embodiments of any of the single-chain chimeric polypeptides described herein, the ligand binding domain of the human estrogen receptor has a wildtype sequence, except that it comprises one or both of a substitution at amino acid position 521 and a substitution at amino acid position 537, each numbered relative to the full-length wildtype sequence of human hormone receptor.

In some embodiments of any of the single-chain chimeric polypeptide described herein, the extracellular hormone receptor ligand binding domain and the transmembrane domain directly abut each other. In some embodiments of any of the single-chain chimeric polypeptides described herein, the extracellular hormone receptor ligand binding domain and the transmembrane domain are separated by 1 to 700 amino acids (e.g., 1 to 500 amino acids, 1 to 250 amino acids, 1 to 100 amino acids, 1 to 50 amino acids, or 1 to 25 amino acids).

In some embodiments of any of the single-chain chimeric polypeptides described herein, when going in the N-terminal to C-terminal direction, the single-chain chimeric polypeptide includes the extracellular antigen-binding domain, the extracellular hormone receptor ligand binding domain, and the transmembrane domain. In some embodiments of any of the single-chain chimeric polypeptides described herein, when going in the C-terminal to the N-terminal direction, the single-chain chimeric polypeptide includes the extracellular antigen-binding domain, the extracellular hormone receptor ligand binding domain, and the transmembrane domain. In some embodiments of any of the single-chain chimeric polypeptides described herein, when going in the N-terminal to the C-terminal direction, the single-chain chimeric polypeptide includes the extracellular hormone receptor ligand binding domain, the extracellular antigen-binding domain, and the transmembrane domain. In some embodiments of any of the single-chain chimeric polypeptides described herein, when going in the C-terminal to the N-terminal direction, the single-chain chimeric polypeptide includes the extracellular hormone receptor ligand binding domain, the extracellular antigen-binding domain, and the transmembrane domain.

Also provided herein are nucleic acids that include a nucleotide sequence encoding any of the single-chain chimeric polypeptides described herein. Also provided herein are vectors that include a nucleic acid that includes a nucleotide sequence encoding any of the single-chain chimeric polypeptides described herein. Also provided herein are mammalian cells that include any of the vectors described herein. In some embodiments of any of the mammalian cells described herein, the mammalian cell is a T cell. In some embodiments of any of the mammalian cells described herein, the T cell is selected from the group of: a CD8$^+$ T cell, a CD4$^+$ T cell, a memory T cell, a Treg cell, and natural killer T cell.

Also provided herein are methods of inducing the plasma membrane localization of a single-chain chimeric polypeptide in a mammalian cell that include: (a) contacting a mammalian cell expressing any of the single-chain chimeric polypeptides described herein with an amount of a hormone or a hormone analogue sufficient to induce localization of the single-chain chimeric polypeptide to the extracellular side of the plasma membrane of the cell.

Also provided herein are methods of reversibly altering the plasma membrane localization of a single-chain chimeric polypeptide in a mammalian cell that include: (a) contacting a mammalian cell expressing any of the single-chain chimeric polypeptides described herein with an amount of a hormone or a hormone analogue sufficient to induce localization of the single-chain chimeric polypeptide to the extracellular side of the plasma membrane of the cell; and (b) contacting the mammalian cell with a reduced amount of the hormone or the hormone analogue that results in a decreased level of the single-chain chimeric polypeptide on the extracellular side of the plasma membrane of the mammalian cell. Some embodiments of any of the methods described herein further include: (c) contacting the mammalian cell with an increased amount of the hormone or the hormone analogue that results in an increased level of the single-chain chimeric polypeptide on the extracellular side of the plasma membrane of the cell as compared to the level of in step (b). Some embodiments of any of the methods described herein further include, before step (a), introducing a nucleic acid encoding the single-chain chimeric polypeptide into a mammalian cell to generate the mammalian cell expressing the single-chain chimeric polypeptide.

In some embodiments of any of the methods described herein, the mammalian cell is a T cell. In some embodiments of any of the methods described herein, the T cell is selected from the group of: a CD8$^+$ T cell, a CD4$^+$ T cell, a memory T cell, a Treg cell, and natural killer T cell. In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include: obtaining the mammalian cell from the subject.

In some embodiments of any of the methods described herein, the contacting step(s) is performed in vitro. In some embodiments of any of the methods described herein, the contacting step(s) is performed in a mammal.

Also provided herein are single-chain chimeric antigen receptors that include: an extracellular antigen-binding domain; an extracellular hormone receptor ligand binding domain; a transmembrane domain; an intracellular costimulatory domain; and an intracellular immunoreceptor tyrosine-based activation motif (ITAM); where: the transmembrane domain and the extracellular hormone receptor ligand binding domain directly abut each other or are separated by 1 to 700 amino acids; and the transmembrane domain and the extracellular hormone receptor ligand binding domain are not both present in a single endogenous single-chain polypeptide in a mammal. In some embodiments of any of the single-chain chimeric antigen receptors described herein, the extracellular antigen-binding domain is selected from the group consisting of: a scFv, a (scFv)$_2$, a V$_H$H domain, and a V$_{NAR}$ domain. In some embodiments of any of the single-chain chimeric antigen receptors described herein, the extracellular antigen-binding domain is a scFv.

In some embodiments of any of the single-chain chimeric antigen receptors described herein, the extracellular antigen-binding domain binds specifically to a single antigen. In some embodiments of any of the single-chain chimeric antigen receptors, the single antigen is a tumor antigen. In some embodiments of any of the single-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the single-chain chimeric antigen receptors described herein, the tumor antigen is CD19. In some embodiments of any of the single-chain chimeric antigen receptors described herein, the extracellular antigen-binding domain binds specifically to two different antigens. In some embodiments of any of the single-chain chimeric antigen receptors described herein, at least one of the two different antigens is a tumor antigen. In some embodiments of any of the single-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the single-chain chimeric antigen receptors described herein, the tumor antigen is CD19.

In some embodiments of any of the single-chain chimeric antigen receptors described herein, the transmembrane domain is a transmembrane domain from: a chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the single-chain chimeric antigen receptors described herein, the extracellular hormone receptor ligand binding domain is a ligand binding domain from an estrogen receptor, a progesterone receptor, or an androgen receptor. In some embodiments of any of the single-chain chimeric antigen receptors described herein, the extracellular hormone receptor ligand binding domain is a ligand binding domain from an estrogen receptor. In some embodiments of any of the single-chain chimeric antigen receptors described herein, the extracellular hormone receptor ligand binding domain is a ligand binding domain from a human estrogen receptor. In some embodiments of any of the single-chain chimeric antigen receptors described herein, the ligand binding domain of the human estrogen receptor has a wildtype sequence, except that it comprises one or both of a substitution at amino acid position 521 and a substitution at amino acid position 537, each numbered relative to the full-length wildtype sequence of human hormone receptor. In some embodiments of any of the single-chain chimeric antigen receptors described herein, the intracellular costimulatory domain is a cytoplasmic costimulatory domain from CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments of any of the single-chain chimeric antigen receptors described herein, the intracellular costimulatory domain is the cytoplasmic costimulatory domain from 4-1BB or CD28. In some embodiments of any of the single-chain chimeric antigen receptors described herein, the intracellular ITAM comprises a cytoplasmic signaling sequence from CD3ζ.

In some embodiments of any of the single-chain chimeric antigen receptors described herein, the extracellular hormone receptor ligand binding domain and the transmembrane domain directly abut each other. In some embodiments of any of the single-chain chimeric antigen receptors described herein, the extracellular hormone receptor ligand binding domain and the transmembrane domain are separated by 1 to 700 amino acids (e.g., 1 to 500 amino acids, 1 to 250 amino acids, 1 to 100 amino acids, 1 to 50 amino acids, or 1 to 25 amino acids).

In some embodiments of any of the single-chain chimeric antigen receptors described herein, when going in the N-terminal to C-terminal direction, the single-chain chimeric antigen receptor includes the extracellular antigen-binding domain, the extracellular hormone receptor ligand binding domain, the transmembrane domain, the intracellular costimulatory domain, and the ITAM. In some embodiments of any of the single-chain chimeric antigen receptors described herein, when going in the C-terminal to the N-terminal direction, the single-chain chimeric antigen receptor includes the extracellular antigen-binding domain, the extracellular hormone receptor ligand binding domain, the transmembrane domain, the intracellular costimulatory domain, and the ITAM. In some embodiments of any of the single-chain chimeric antigen receptors described herein, when going in the N-terminal to the C-terminal direction, the single-chain chimeric antigen receptor comprises the extracellular hormone receptor ligand binding domain, the extracellular antigen-binding domain, the transmembrane domain, the intracellular costimulatory domain, and the ITAM. In some embodiments of any of the single-chain chimeric antigen receptors described herein, when going in the C-terminal to the N-terminal direction, the single-chain chimeric polypeptide includes the extracellular hormone receptor ligand binding domain, the extracellular antigen-binding domain, the transmembrane domain, the intracellular costimulatory domain, and the ITAM.

Also provided herein are nucleic acids that include a nucleotide sequence encoding any of the single-chain chimeric antigen receptors described herein. Also provided herein are vectors that include a nucleic acid that includes a nucleotide sequence encoding any of the single-chain chimeric antigen receptors described herein. Also provided are mammalian cells that include any of the vectors described herein. In some embodiments of any of the mammalian cells described herein, the mammalian cell is a T cell. In some embodiments of any of the mammalian cells described herein, the T cell is selected from the group of: a CD8$^+$ T cell, a CD4$^+$ T cell, a memory T cell, a Treg cell, and natural killer T cell.

Also provided are methods of inducing the plasma membrane localization of a single-chain chimeric antigen receptor in a mammalian cell that include: (a) contacting a mammalian cell expressing any of the single-chain chimeric antigen receptors described herein with an amount of a hormone or a hormone analogue sufficient to induce localization of the single-chain chimeric antigen-binding receptor to the extracellular side of the plasma membrane of the cell.

Also provided herein are methods of altering the plasma membrane localization of a single-chain chimeric antigen receptor in a mammalian cell that include: (a) contacting a mammalian cell expressing any of the single-chain chimeric antigen receptors described herein with an amount of a hormone or a hormone analogue sufficient to induce localization of the single-chain chimeric antigen-binding receptor to the extracellular side of the plasma membrane of the cell; and (b) contacting the mammalian cell with an amount of the hormone or the hormone analogue that results in a reduced level of the single-chain chimeric antigen receptor on the extracellular side of the plasma membrane of the cell. Some embodiments of any of the methods described herein further include: (c) contacting the mammalian cell with an amount of the hormone or the hormone analogue that results in an increased level of single-chain chimeric antigen receptor to the extracellular side of the plasma membrane of the cell as compared to the level in (b). Some embodiments of any of the methods described herein further include before step (a): introducing a nucleic acid encoding the single-chain chimeric antigen receptor into a mammalian cell to generate the mammalian cell expressing the single-chain chimeric antigen receptor.

In some embodiments of any of the methods described herein, the mammalian cell is a T cell. In some embodiments of any of the methods described herein, the T cell is selected from the group of: a CD8$^+$ T cell, a CD4$^+$ T cell, a memory T cell, a Treg cell, and a natural killer T cell. In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include: obtaining the mammalian cell from the subject. In some embodiments of any of the methods described herein, the contacting step(s) is performed in vitro. In some embodiments of any of the methods described herein, the contacting step(s) is performed in a mammal. In some embodiments of any of the methods described herein, the mammal has a cancer. In some embodiments of any of the methods described herein, the contacting step results in the treatment of the cancer in the mammal.

Also provided herein are multi-chain chimeric antigen receptors that include at least one first polypeptide including: an extracellular antigen-binding domain; an extracellular hormone receptor ligand binding domain; and a transmembrane domain; where: the transmembrane domain and the extracellular hormone receptor ligand binding domain directly abut each other or are separated by 1 to 700 amino acids; and the transmembrane domain and the extracellular hormone receptor ligand binding domain are not both present in a single endogenous single-chain polypeptide in a mammal. In some embodiments of any of the multi-chain chimeric antigen receptors described herein, the extracellular antigen-binding domain is selected from the group consisting of: a scFv, a (scFv)$_2$, a V$_H$H domain, and a V$_{NAR}$ domain. In some embodiments of any of the multi-chain chimeric antigen receptors described herein, the extracellular antigen-binding domain is a scFv.

In some embodiments of any of the multi-chain chimeric antigen receptors described herein, the extracellular antigen-binding domain binds specifically to a single antigen. In some embodiments of any of the multi-chain chimeric antigen receptors described herein, the single antigen is a tumor antigen. In some embodiments of any of the multi-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the multi-chain chimeric antigen receptors described herein, the tumor antigen is CD19. In some embodiments of any of the multi-chain chimeric antigen receptors described herein, the extracellular antigen-binding domain binds specifically to two different antigens. In some embodiments of any of the multi-chain chimeric antigen receptors described herein at least one of the two different antigens is a tumor antigen. In some embodiments of any of the multi-chain chimeric antigen receptors described herein, the tumor antigen is selected from the group of: CD19, WT-1, CD22, L1-CAM, ROR-1, CD30, CD125, AFP, CEA, ETA, MAGE, and MUC16. In some embodiments of any of the multi-chain chimeric antigen receptors described herein, the tumor antigen is CD19.

In some embodiments of any of the multi-chain chimeric antigen receptors described herein, the transmembrane domain is a transmembrane domain from: α chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, or CD154. In some embodiments of any of the multi-chain chimeric antigen receptors described herein, the hormone receptor ligand binding domain is a ligand binding domain from an estrogen receptor, a progesterone receptor, or an androgen receptor. In some embodiments of any of the multi-chain chimeric antigen receptors described herein, the hormone receptor ligand binding domain is a ligand binding domain from an estrogen receptor. In some embodiments of any of the multi-chain chimeric antigen receptors described herein, the extracellular hormone receptor ligand binding domain is a ligand binding domain from a human estrogen receptor. In some embodiments of any of the multi-chain chimeric antigen receptors described herein, the ligand binding domain of the human estrogen receptor has a wildtype sequence, except that it includes one or both of a substitution at amino acid position 521 and a substitution at amino acid position 537, each numbered relative to the full-length wildtype sequence of human hormone receptor.

In some embodiments of any of the multi-chain chimeric antigen receptors described herein, the extracellular hormone receptor ligand binding domain and the transmembrane domain directly abut each other. In some embodiments of any of the multi-chain chimeric antigen receptors described herein, the extracellular hormone receptor ligand binding domain and the transmembrane domain are separated by 1 to 700 amino acids (e.g., 1 to 500 amino acids, 1 to 250 amino acids, 1 to 100 amino acids, 1 to 50 amino acids, or 1 to 25 amino acids).

In some embodiments of any of the multi-chain chimeric antigen receptors described herein, the at least one polypeptide further includes an intracellular costimulatory domain. In some embodiments of any of the multi-chain chimeric antigen receptors described herein, the intracellular costimulatory domain is a cytoplasmic costimulatory domain from CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments of any of the multi-chain chimeric antigen receptors described herein, the intracellular costimulatory domain is the cytoplasmic costimulatory domain from 4-1BB or CD28.

In some embodiments of any of the multi-chain chimeric antigen receptors described herein, when going in the N-terminal to C-terminal direction, the at least one first polypeptide includes the extracellular antigen-binding domain, the extracellular hormone receptor ligand binding domain, and the transmembrane domain. In some embodiments of any of the multi-chain chimeric antigen receptors described herein, when going in the C-terminal to N-terminal direction, the at least one first polypeptide includes the extracellular antigen-binding domain, the extracellular hormone receptor ligand binding domain, and the transmembrane domain. In some embodiments of any of the multi-chain chimeric antigen receptors described herein, when going in the N-terminal to C-terminal direction, the at least one first polypeptide includes the extracellular hormone receptor ligand binding domain, the extracellular antigen-binding domain, and the transmembrane domain. In some embodiments of any of the multi-chain chimeric antigen receptors described herein, when going in the C-terminal to N-terminal direction, the at least one first polypeptide includes the extracellular hormone receptor ligand binding domain, the extracellular antigen-binding domain, and the transmembrane domain.

Also provided herein are nucleic acids that encode any of the multi-chain chimeric antigen receptors described herein. Also provided herein are sets of nucleic acids that together encode any of the multi-chain chimeric antigen receptors described herein. Also provided herein are mammalian cells that include a nucleic acid that encodes any of the multi-chain chimeric antigen receptors described herein. Also provided herein are mammalian cells that include a set of nucleic acids that together encode any of the multi-chain chimeric antigen receptors described herein. In some embodiments of any of the mammalian cells described herein, the mammalian cell is a T cell. In some embodiments of any of the mammalian cells described herein, the T cell is selected from the group consisting of: a CD8$^+$ T cell, a CD4$^+$ T cell, a memory T cell, a Treg cell, and natural killer T cell.

Also provided herein are methods of inducing the plasma membrane localization of a multi-chain chimeric antigen receptor in a mammalian cell that include: (a) contacting a mammalian cell expressing any of the multi-chain chimeric antigen receptors described herein with an amount of a hormone or a hormone analogue sufficient to induce localization of the multi-chain chimeric antigen-binding receptor to the extracellular side of the plasma membrane of the cell.

Also provided herein are methods of altering the plasma membrane localization of a multi-chain chimeric antigen receptor in a mammalian cell that include: (a) contacting a mammalian cell expressing any of the multi-chain chimeric antigen receptors described herein with an amount of a hormone or a hormone analogue sufficient to induce localization of the multi-chain chimeric antigen-binding receptor to the extracellular side of the plasma membrane of the cell; and (b) contacting the mammalian cell with an amount of the hormone or the hormone analogue with an amount of the hormone or the hormone analogue that results in a decreased level of the multi-chain chimeric antigen-binding receptor on the extracellular side of the plasma membrane of the cell. Some embodiments of any of the methods described herein further include: (c) contacting the mammalian cell with an amount of the hormone or the hormone analogue that results in an increase in the level of the multi-chain chimeric antigen-binding receptor on the extracellular side of the plasma membrane of the cell. Some embodiments of any of the methods described herein further include before step (a): introducing a nucleic acid encoding the multi-chain chimeric antigen receptor or a set of nucleic acids that together encode the multi-chain chimeric receptor, into a mammalian cell to generate the mammalian cell expressing the multi-chain chimeric antigen receptor. In some embodiments of any of the methods described herein, the mammalian cell is a T cell. In some embodiments of any of the methods described herein, the T cell is selected from the group of: a CD8$^+$ T cell, a CD4$^+$ T cell, a memory T cell, a Treg cell, and a natural killer T cell. In some embodiments of any of the methods described herein, the mammalian cell is a mammalian cell previously obtained from a subject. In some embodiments of any of the methods described herein, the subject has been identified or diagnosed as having a cancer. Some embodiments of any of the methods described herein further include obtaining the mammalian cell from the subject. In some embodiments of any of the methods described herein, the contacting step is performed in vitro. In some embodiments of any of the methods described herein, the contacting step is performed in a mammal. In some embodiments of any of the methods described herein, the mammal has a cancer. In some embodiments of any of the methods described herein, the contacting step results in the treatment of the cancer in the mammal.

Also provided herein are methods of treating a cancer in a subject that include: (a) administering to the subject a mammalian cell expressing any of the single-chain chimeric antigen receptors described herein or any of the multi-chain chimeric antigen receptors described herein, where the antigen binding domain binds specifically to an antigen expressed by the cancer in the subject; (b) administering to the subject an amount of a hormone or hormone sufficient to induce localization of the single-chain or multi-chain chimeric antigen receptor to the extracellular side of the plasma membrane of the cell; (c) determining the presence or severity of one or more symptoms associated with toxicity or the level of one or more cytokines associated with a cytokine storm, or both, in the subject following (b); (d) comparing the determined presence or severity of one or more symptoms associated with toxicity or the determined level of one or more cytokines associated with the cytokine storm, or both, to a control(s); and (e) administering to the subject an amount of the hormone or hormone analogue sufficient to reduce the level of the single-chain or multi-chain chimeric antigen receptor on the extracellular side of the plasma membrane of the cell, such that the presence or severity of one or more symptoms associated with toxicity or the level of one or more cytokines associated with a cytokine storm, or both, is reduced in the subject after (e).

In some embodiments of any of the methods described herein, the amount of the hormone or hormone analogue administered to the subject in step (e) is reduced by at least 25% as compared to the amount of the hormone or hormone analogue administered to the subject in step (b). In some embodiments of any of the methods described herein, the amount of the hormone or hormone analogue administered to the subject in step (e) is reduced by at least 50% as compared to the amount of the hormone or hormone analogue administered to the subject in step (b). In some embodiments of any of the methods described herein, the amount of the hormone or hormone analogue administered to the subject in step (e) is reduced by at least 75% as compared to the level of the hormone or hormone analogue administered to the subject in step (b). In some embodiments of any of the methods described herein, the amount of the hormone or hormone analogue administered to the subject in step (e) is reduced by 100% as compared to the level of the hormone or hormone analogue administered to the subject in step (b).

In some embodiments of any of the methods described herein, the one or more symptoms associated with toxicity are selected from the group of: high fever, swelling, chills, hypotension, tachycardia, asthenia, headache, rash, scratchy throat, dyspnea, redness, extreme fatigue, nausea, and cerebral edema. In some embodiments of any of the methods described herein, the one or more cytokines associated with a cytokine storm are selected from the group of: include tumor necrosis factor-alpha, IFNγ, IL-10, IL-1β, IL-2, IL-6, IL-8, and IL-10, granulocyte macrophage-colony-stimulating factor (GM-CSF), and IL-5.

The use of the term "a" before a noun is meant "one or more" of the particular noun. For example, the phrase "a mammalian cell" means "one or more mammalian cell."

The term "single-chain chimeric polypeptide" means a single-chain polypeptide that includes a first contiguous amino acid sequence (e.g., a first domain) and a second contiguous amino acid sequence (e.g., a second domain), where the first contiguous amino acid sequence and the second contiguous amino acid sequence are not present in the same endogenous single-chain polypeptide in a mammal. In some examples, the first contiguous amino acid sequence and the second contiguous amino acid sequence directly abut each other in the single-chain chimeric polypeptide. In some examples, the first contiguous amino acid sequence and the second contiguous amino acid sequence are separated by one or more intervening amino acids (e.g., one or more domains). The term "single-chain chimeric polypeptide" is not meant to limit in any way the relative positioning of the first contiguous amino acid sequence and the second contiguous sequence in the single-chain polypeptide. Non-limiting examples of single-chain chimeric polypeptides (e.g., single-chain chimeric antigen receptors) are described herein. Additional examples of single-chain chimeric polypeptides (e.g., single-chain chimeric antigen receptors) are known in the art.

The terms "chimeric antigen receptor" and "CAR" are used interchangeably herein, and refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. CAR molecules and derivatives thereof (e.g., CAR variants) are described, e.g., in PCT Application No. US2014/016527; Fedorov et al. *Sci Transl Med* (2013); 5(215):215ra172; Glienke et al. Front Pharmacol (2015) 6:21; Kakarla & Gottschalk 52 *Cancer J* (2014) 20(2):151-5; Riddell et al. *Cancer J* (2014) 20(2): 141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety.

The term "multi-chain chimeric polypeptide" means a polypeptide including two or more single-chain polypeptides, where at least one of the two or more single-chain polypeptides is a single-chain chimeric polypeptide as defined and described herein. Non-limiting examples of multi-chain chimeric polypeptides (e.g., multi-chain chimeric antigen receptors) are described herein. Additional examples of multi-chain chimeric polypeptides (e.g., multi-chain chimeric antigen receptors) are known in the art.

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

The term "hormone receptor ligand binding domain" means a domain in a hormone receptor polypeptide that binds specifically to a hormone or a hormone analogue. Non-limiting examples of a hormone receptor ligand binding domains (LBD) are described herein. In some cases, a LBD of a nuclear hormone receptor is selected from an estrogen receptor, an ecdysone receptor, a PPARγ receptor, a glucocorticoid receptor, an androgen receptor, a thyroid hormone receptor, a mineralocorticoid receptor, a progesterone receptor, a vitamin D receptor, a PPAR receptorα, a PPARβ/δ receptor, a pregnane X receptor, a liver X receptor, a farnesoid X receptor, a retinoid X receptor, a RAR-related orphan receptor, and a retinoic acid receptor. In some cases, a polypeptide chain of a heterodimeric polypeptide of the present disclosure comprises a single LBD of a nuclear hormone receptor. In some cases, a polypeptide chain of a heterodimeric polypeptide of the present disclosure comprises multiple (e.g., two or more) LBDs of a nuclear hormone receptor. In some cases, a polypeptide chain of a heterodimeric polypeptide of the present disclosure comprises two LBDs of a nuclear hormone receptor. In some cases, a polypeptide chain of a heterodimeric polypeptide of the present disclosure comprises three LBDs of a nuclear hormone receptor. Where a polypeptide chain of a heterodimeric polypeptide of the present disclosure comprises multiple (e.g., two or more) LBDs of a nuclear hormone receptor, in some cases the multiple LBDs comprise identical amino acid sequences. In some cases, the two or more LBD are in tandem, either directly or separated by a linker (e.g., any of the linkers described herein).

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The term "costimulatory domain" means a signaling domain from an endogenous co-stimulatory transmembrane polypeptide expressed in a T lymphocyte that promotes the downstream T-cell receptor signaling and/or T cell activation. Non-limiting examples of costimulatory domains are described herein. Additional examples of costimulatory domains are known in the art. See, e.g., Chen et al., *Nature Reviews Immunol.* 13:227-242, 2013.

The term "immunoreceptor tyrosine-based activation motif" or "ITAM)" means an amino acid motif that includes a four amino-acid consensus sequence of a tyrosine separated from a leucine or an isoleucine by two other amino acids (YxxL/I). The tyrosine residue in the four-amino acid consensus sequence becomes phosphorylated following interaction of a signaling pathway kinase (e.g., a lymphocyte signaling pathway kinase). Non-limiting examples of ITAMs are described herein. Additional examples of ITAMs are known in the art.

The term "hormone" means a naturally-occurring molecule that specifically binds to a ligand binding domain of a hormone receptor and regulates the activity and/or location of the hormone receptor. Non-limiting examples of hormones are described herein. Additional examples of hormones are known in the art.

The term "hormone analogue" means a molecule that mimics the structure of a hormone and specifically binds to a ligand binding domain of a hormone receptor. Non-limiting examples of hormone analogues are described herein. Additional examples of hormone analogues are known in the art.

The phrase "treatment of cancer" means a reduction in the number, frequency, or severity of one or more (e.g., two, three, four, or five) symptoms of a cancer in a subject having a cancer. Non-limiting symptoms of cancer are described herein. Additional symptoms of cancer are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 2A is a set of flow cytometry dot plots of Jurkat T cells transduced with lentiviral vectors encoding the canonical CAR or with anti-CD19 (FMC63) ERa-LBD containing the v2, v3, and v4 CAR constructs. FIG. 2B is a set of flow cytometry dot plots of primary CD4 and CD8 human T cells were transduced with lentiviral vectors encoding the v4 CAR construct.

DETAILED DESCRIPTION

Figure 1:
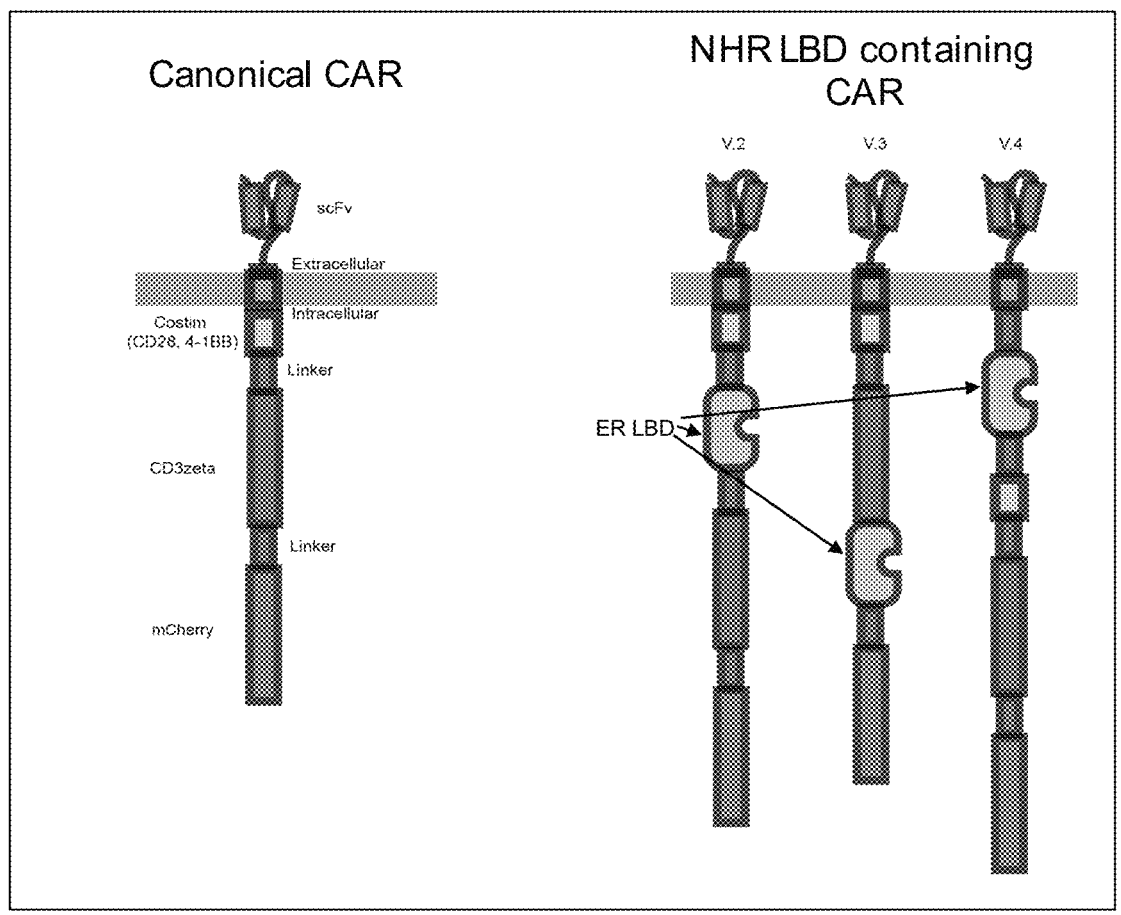
FIG. 1 is a diagram of different constructs tested. The labels extracellular and intracellular refer to the cell membrane, which is depicted as a gray box between these labels. The extracellular scFv domain, and intracellular costimulatory ("Costim"), CD3zeta, and mCherry domains are indicated.

Provided herein are single-chain chimeric polypeptides, single-chain chimeric antigen receptors (CARs), and multi-chain chimeric antigen receptors; nucleic acids encoding the same; vectors including any of these nucleic acids; mammalian cells including any of these vectors; and methods of reversibly inducing the extracellular membrane localization and methods of altering the membrane localization of these single-chain chimeric polypeptides, single-chain chimeric antigen receptors, and multi-chain chimeric polypeptides.

Also provided herein are genetically modified mammalian cells having a chimeric antigen receptor (CAR). In some cases, a genetically modified mammalian cell is derived from a stem cell, a progenitor cell, or a cell derived from a stem cell or a progenitor cell. In some cases, the mammalian cell is a T lymphocyte or an NK cell.

Non-limiting aspects of these single-chain chimeric polypeptides, single-chain chimeric antigen receptors, and multi-chain chimeric antigen receptors, nucleic acids, vectors, mammalian cells, and methods are described below, and can be used in any combination without limitation. Additional aspects of these single-chain chimeric polypeptides, single-chain chimeric antigen receptors, and multi-chain chimeric antigen receptors, nucleic acids, vectors, mammalian cells, and methods are known in the art.

In some embodiments, compositions and/or methods disclosed herein can be used to selectively kill cancer cells in a subject in the presence of a hormone or hormone analogue which binds to an LBD present in the polypeptide (e.g., a single-chain chimeric polypeptide, a single-chain chimeric antigen receptor, and/or a multi-chain chimeric antigen receptor). In some embodiments, in the presence of the hormone or hormone analogue, the polypeptide (e.g., the single-chain chimeric polypeptide, the single-chain chimeric antigen receptor, and/or the multi-chain chimeric antigen receptor) localizes to the extracellular surface, presenting an antigen binding domain (e.g., an scFv or other antigen-binding domain described herein or known in the art) on the exterior of the cell. The polypeptide (e.g., single-chain chimeric polypeptide, single-chain chimeric antigen receptor, or multi-chain chimeric antigen receptor) can recognize the antigen to which it binds, and thus can selectively kill a target cell expressing the antigen on its surface (e.g., a cancer cell).

In some embodiments, localization of the polypeptide (e.g., the single-chain chimeric polypeptide, the single-chain chimeric antigen receptor, or the multi-chain chimeric antigen receptor) to the extracellular surface can cause toxicity in the subject. In some embodiments, a subject experiencing toxicity to due hormone or hormone-analogue-induced localization of the polypeptide (e.g., the single-chain chimeric polypeptide, the single-chain chimeric antigen receptor, or the multi-chain chimeric antigen receptor) to the extracellular surface can be treated or ameliorated by reducing the dose of the hormone or hormone analogue, or eliminating hormone or hormone analogue treatment of the subject altogether. Such reduction in dose or elimination of hormone or hormone analogue treatment can cause the polypeptide (e.g., the single-chain chimeric polypeptide, the single-chain chimeric antigen receptor, or the multi-chain chimeric polypeptide) to be removed from the cell surface and reduce or eliminate presentation of the antigen binding domain on the cell surface, thus reducing or eliminating toxicity in the subject.

Single-Chain Chimeric Polypeptide
Single-Chain Chimeric Polypeptide-Intracellular Hormone Receptor LBD Provided herein are single-chain chimeric polypeptides that include a transmembrane domain (e.g., any of the transmembrane domains described herein or known in the art) and a hormone receptor ligand binding domain (e.g., any of the hormone receptor ligand binding domains described herein or known in the art), where the transmembrane domain and the hormone receptor ligand binding domain directly abut each other or are separated by 1 to about 800 amino acids (e.g., or any of the subranges of this range described herein), and the transmembrane domain and the hormone receptor ligand binding domain are not both present in the same (a single) endogenous single-chain polypeptide in a mammal (e.g., a human).

In some examples of the single-chain chimeric polypeptides, the transmembrane domain directly abuts the hormone receptor ligand binding domain (i.e., no intervening amino acids between the transmembrane domain and the hormone receptor ligand binding domain). In some examples of the single-chain chimeric polypeptides, the transmembrane domain and the hormone receptor ligand binding domain are separated by: 1 amino acid to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, about 5 amino acids, about 4 amino acids, or about 3 amino acids (inclusive); about 2 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, about 5 amino acids, or about 4 amino acids (inclusive); about 3 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, or about 5 amino acids (inclusive); about 4 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, or about 6 amino acids (inclusive); about 5 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, or about 8 amino acids (inclusive); about 6 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, or about 8 amino acids (inclusive); about 8 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, about 12 amino acids, or about 10 amino acids (inclusive); about 10 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, about 14 amino acids, or about 12 amino acids (inclusive); about 12 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, about 16 amino acids, or about 14 amino acids (inclusive); about 14 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 18 amino acids, or about 16 amino acids (inclusive); about 16 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, or about 18 amino acids (inclusive); about 18 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, or about 20 amino acids (inclusive); about 20 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, or about 40 amino acids (inclusive); about 40 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, about 75 amino acids, or about 70 amino acids (inclusive); about 70 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, about 80 amino acids, or about 75 amino acids (inclusive); about 75 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, about 85 amino acids, or about 80 amino acids (inclusive); about 80 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, about 90 amino acids, or about 85 amino acids (inclusive); about 85 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, about 95 amino acids, or about 90 amino acids (inclusive); about 90 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, about 100 amino acids, or about 95 amino acids (inclusive); about 95 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, about 105 amino acids, or about 100 amino acids (inclusive); about 100 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, about 110 amino acids, or about 105 amino acids (inclusive); about 105 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, about 115 amino acids, or about 110 amino acids (inclusive); about 110 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, about 125 amino acids, about 120 amino acids, or about 115 amino acids (inclusive); about 115 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, about 130 amino acids, or about 125 amino acids (inclusive); about 125 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, about 135 amino acids, or about 130 amino acids (inclusive); about 130 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, about 140 amino acids, or about 135 amino acids (inclusive); about 135 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, about 145 amino acids, or about 140 amino acids (inclusive); about 140 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, about 150 amino acids, or about 145 amino acids (inclusive); about 145 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, about 155 amino acids, or about 150 amino acids (inclusive); about 150 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, about 165 amino acids, about 160 amino acids, or about 155 amino acids (inclusive); about 155 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, about 170 amino acids, or about 165 amino acids (inclusive); about 165 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, about 175 amino acids, or about 170 amino acids (inclusive); about 170 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, about 180 amino acids, or about 175 amino acids (inclusive); about 175 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, about 185 amino acids, or about 180 amino acids (inclusive); about 180 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, about 190 amino acids, or about 185 amino acids (inclusive); about 185 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, about 195 amino acids, or about 190 amino acids (inclusive); about 190 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, about 200 amino acids, or about 195 amino acids (inclusive); about 195 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, about 210 amino acids, or about 200 amino acids (inclusive); about 200 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, about 220 amino acids, or about 210 amino acids (inclusive); about 210 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, about 230 amino acids, or about 220 amino acids (inclusive); about 220 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, about 240 amino acids, or about 230 amino acids (inclusive); about 230 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, about 250 amino acids, or about 240 amino acids (inclusive); about 240 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, about 260 amino acids, or about 250 amino acids (inclusive); about 250 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, about 270 amino acids, or about 260 amino acids (inclusive); about 260 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, about 280 amino acids, or about 270 amino acids (inclusive); about 270 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, about 290 amino acids, or about 280 amino acids (inclusive); about 280 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, or about 290 amino acids (inclusive); about 290 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, or about 300 amino acids (inclusive); about 300 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, about 300 amino acids, or about 290 amino acids (inclusive); about 290 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, about 310 amino acids, or about 300 amino acids (inclusive); about 300 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, about 320 amino acids, or about 310 amino acids (inclusive); about 310 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, about 330 amino acids, or about 320 amino acids (inclusive); about 320 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, about 340 amino acids, or about 330 amino acids (inclusive); about 330 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, about 350 amino acids, or about 340 amino acids (inclusive); about 340 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, about 360 amino acids, or about 350 amino acids (inclusive); about 350 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids, or about 360 amino acids (inclusive); about 360 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, about 380 amino acids, about 370 amino acids (inclusive); about 370 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, about 390 amino acids, or about 380 amino acids (inclusive); about 380 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, about 400 amino acids, or about 390 amino acids (inclusive); about 390 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, about 410 amino acids, or about 400 amino acids (inclusive); about 400 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, about 420 amino acids, or about 410 amino acids (inclusive); about 410 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, about 440 amino acids, about 430 amino acids, or about 420 amino acids (inclusive); about 420 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, or about 440 amino acids (inclusive); about 430 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, about 450 amino acids, or about 440 amino acids (inclusive); about 440 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, about 460 amino acids, or about 450 amino acids (inclusive); about 450 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids, or about 460 amino acids (inclusive); about 460 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, about 480 amino acids, about 470 amino acids (inclusive); about 470 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, about 490 amino acids, or about 480 amino acids (inclusive); about 480 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, about 500 amino acids, or about 490 amino acids (inclusive); about 490 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, about 520 amino acids, or about 500 amino acids (inclusive); about 500 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, about 540 amino acids, or about 520 amino acids (inclusive); about 520 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, about 560 amino acids, or about 540 amino acids (inclusive); about 540 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, about 580 amino acids, or about 560 amino acids (inclusive); about 560 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, about 600 amino acids, or about 580 amino acids (inclusive); about 580 amino acids to about 800 amino acids, about 780 amino acids, about 760 amino acids, about 740 amino acids, about 720 amino acids, about 700 amino acids, about 680 amino acids, about 660 amino acids, about 640 amino acids, about 620 amino acids, or about 600 amino acids (inclusive); about 600 amino acids to about 800 amino acids, about 780 amino acids, about 760 amino acids, about 740 amino acids, about 720 amino acids, about 700 amino acids, about 680 amino acids, about 660 amino acids, about 640 amino acids, or about 620 amino acids (inclusive); about 620 amino acids to about 800 amino acids, about 780 amino acids, about 760 amino acids, about 740 amino acids, about 720 amino acids, about 700 amino acids, about 680 amino acids, about 660 amino acids, or about 640 amino acids (inclusive); about 640 amino acids to about 800 amino acids, about 780 amino acids, about 760 amino acids, about 740 amino acids, about 720 amino acids, about 700 amino acids, about 680 amino acids, or about 660 amino acids (inclusive); about 660 amino acids to about 800 amino acids, about 780 amino acids, about 760 amino acids, about 740 amino acids, about 720 amino acids, about 700 amino acids, or about 680 amino acids (inclusive); about 680 amino acids to about 800 amino acids, about 780 amino acids, about 760 amino acids, about 740 amino acids, about 720 amino acids, or about 700 amino acids (inclusive); about 700 amino acids to about 800 amino acids, about 780 amino acids, about 760 amino acids, about 740 amino acids, or about 720 amino acids (inclusive); about 720 amino acids to about 800 amino acids, about 780 amino acids, about 760 amino acids, or about 740 amino acids (inclusive); about 740 amino acids to about 800 amino acids, about 780 amino acids, or about 760 amino acids (inclusive); about 760 amino acids to about 800 amino acids, or about 780 amino acids; (inclusive); or about 780 amino acids to about 800 amino acids (inclusive).

In some embodiments, one or more intervening amino acids between the transmembrane domain and the hormone receptor ligand binding domain can be or include a linker peptide. In some embodiments, a linker peptide can include one or more of the following amino acid sequences: GSGSGSGSGS (SEQ ID NO: 20), GSGSGSGS (SEQ ID NO: 21), RSGSGSGS (SEQ ID NO: 22), or GSGSGSGS (SEQ ID NO: 23). In some embodiments, linker peptide can be encoded by one or more of the following nucleic acid sequences: GGATCCGGCAGCGGATCTGGCAGTGGAAGC (SEQ ID NO: 24), GGATCTGGCTCTGGAAGCGGCAGC (SEQ ID NO: 25), AGATCCGGATCTGGAAGTGGCTCC (SEQ ID NO: 26), or GGAAGTGGATCTGGGAGCGGCTCT (SEQ ID NO: 27). In some embodiments, a linker peptide can include one or more (e.g., two, three, or four) copies of any one of SEQ ID NOs: 20-23, e.g., in tandem.

In some embodiments, one or more intervening amino acids between the transmembrane domain and the hormone receptor ligand binding domain can be or include an intracellular sequence that abuts the transmembrane domain in the endogenous polypeptide from which the transmembrane domain (e.g., any of the transmembrane domains described herein) is derived. In some embodiments, one or more intervening amino acids between the transmembrane domain and the hormone receptor ligand binding domain can be or include one or more additional domains (e.g., any of the exemplary additional domains described herein or known in the art). In some embodiments, a single-chain chimeric polypeptide can be a single-chain chimeric antigen receptor (e.g., any of the single-chain chimeric antigen receptors described herein). In some embodiments, the chimeric polypeptide can further include one or more additional domains. Non-limiting examples of additional domains that can be included in a single-chain chimeric polypeptide include one or more of: an extracellular ligand binding domain (e.g., an antigen-binding domain, e.g., any of the antigen-binding domains described herein), an ITIM (e.g., any of the ITIMs known in the art), an ITAM (e.g., any of ITAMs described herein or known in the art), a dimerization domain (e.g., capable of dimerizing with another dimerization domain present in another polypeptide (e.g., a recombinant polypeptide) expressed in a mammalian cell, e.g., any of the dimerization domains known in the art), and a peptide tag (e.g., a poly-His tag).

Single-Chain Chimeric Polypeptide-Extracellular Hormone Receptor LBD

Provided herein are single-chain chimeric polypeptides that include an extracellular hormone receptor ligand binding domain (e.g., any of the hormone receptor ligand binding domains described herein or known in the art) and a transmembrane domain (e.g., any of the transmembrane domains described herein or known in the art), where the transmembrane domain and the extracellular hormone receptor ligand binding domain directly abut each other or are separated by 1 to about 800 amino acids (e.g., or any of the subranges of this range described herein), and the transmembrane domain and the hormone receptor ligand binding domain are not both present in a single endogenous single-chain polypeptide in a mammal (e.g., a human).

In some examples of the single-chain chimeric polypeptides, the transmembrane domain directly abuts the hormone receptor ligand binding domain (i.e., no intervening amino acids between the transmembrane domain and the extracellular hormone receptor ligand binding domain). In some examples of the single-chain chimeric polypeptides, the transmembrane domain and the extracellular hormone receptor ligand binding domain are separated by: 1 amino acid to about 800 amino acids (e.g., any of the subranges of this range described herein).

In some embodiments, one or more intervening amino acids between the transmembrane domain and the extracellular hormone receptor ligand binding domain can be or include a linker peptide. In some embodiments, a linker peptide can include one or more of the following amino acid sequences: GSGSGSGSGS (SEQ ID NO: 20), GSGSGSGS (SEQ ID NO: 21), RSGSGSGS (SEQ ID NO: 22), or GSGSGSGS (SEQ ID NO: 23). In some embodiments, linker peptide can be encoded by one or more of the following nucleic acid sequences: GGATCCGGCAGCGGATCTGGCAGTGGAAGC (SEQ ID NO: 24), GGATCTGGCTCTGGAAGCGGCAGC (SEQ ID NO: 25), AGATCCGGATCTGGAAGTGGCTCC (SEQ ID NO: 26), or GGAAGTGGATCTGGGAGCGGCTCT (SEQ ID NO: 27). In some embodiments, a linker peptide can include one or more (e.g., two, three, or four) copies of any one of SEQ ID NOs: 20-23, e.g., in tandem. In some embodiments, a linker peptide can be or can include one or more of SEQ ID NO: 45, 47, 49, 58, 60, 62, and 106. In some embodiments, a linker peptide can be or include GS.

In some embodiments, one or more intervening amino acids between the transmembrane domain and the extracellular hormone receptor ligand binding domain can be or include a sequence that abuts the transmembrane domain in the endogenous polypeptide from which the transmembrane domain (e.g., any of the transmembrane domains described herein) is derived. In some embodiments, one or more intervening amino acids between the transmembrane domain and the extracellular hormone receptor ligand binding domain can be or include one or more additional domains (e.g., any of the exemplary additional domains described herein or known in the art). In some embodiments, a single-chain chimeric polypeptide can be a single-chain chimeric antigen receptor (e.g., any of the single-chain chimeric antigen receptors described herein). In some embodiments, the chimeric polypeptide can further include one or more (e.g., two, three, four, or five) additional domains. Non-limiting examples of additional domains that can be included in a single-chain chimeric polypeptide include one or more of: an extracellular ligand binding domain (e.g., an antigen-binding domain, e.g., any of the antigen-binding domains described herein), an ITIM (e.g., any of the ITIMs known in the art), an ITAM (e.g., any of ITAMs described herein or known in the art), a dimerization domain (e.g., capable of dimerizing with another dimerization domain present in another polypeptide (e.g., a recombinant polypeptide) expressed in a mammalian cell, e.g., any of the dimerization domains known in the art), and a peptide tag (e.g., a poly-His tag).

In some embodiments, when going in the N-terminal to C-terminal direction, the single-chain chimeric polypeptide includes the extracellular antigen-binding domain, the extracellular hormone receptor ligand binding domain, and the transmembrane domain. In some embodiments, when going in the C-terminal to the N-terminal direction, the single-chain chimeric polypeptide comprises the extracellular antigen-binding domain, the extracellular hormone receptor ligand binding domain, and the transmembrane domain. In some embodiments, when going in the N-terminal to the C-terminal direction, the single-chain chimeric polypeptide includes the extracellular hormone receptor ligand binding domain, the extracellular antigen-binding domain, and the transmembrane domain. In some embodiments, when going in the C-terminal to the N-terminal direction, the single-chain chimeric polypeptide includes the extracellular hormone receptor ligand binding domain, the extracellular antigen-binding domain, and the transmembrane domain.

Single-Chain Chimeric Antigen Receptor
Single-Chain Chimeric Antigen Receptor-Intracellular Hormone Receptor LBD Also provided herein are single-chain chimeric antigen receptors that include: an extracellular antigen-binding domain (e.g., any of the antigen-binding domains described herein or known in the art), a transmembrane domain (e.g., any of the transmembrane domains described herein or known in the art), a hormone receptor ligand binding domain (e.g., any of the hormone receptor ligand binding domain described herein or known in the art), a costimulatory domain (e.g., any of the costimulatory domains described herein or known in the art), and an immunoreceptor tyrosine-based activation motif (ITAM), where: the transmembrane domain and the hormone ligand binding domain directly abut each other or are separated by 1 to about 800 amino acids (e.g., any of the subranges of this range described herein), and the transmembrane domain and the hormone receptor ligand binding domain are not both present in the same (a single) endogenous single-chain polypeptide in a mammal. The single-chain chimeric antigen receptors described herein can bind to any of the exemplary antigens described herein or any other antigen known in the art. In some embodiments, the single-chain chimeric antigen receptor binds specifically to a single antigen (e.g., any of the exemplary antigens described herein). In some embodiments, the single-chain chimeric antigen receptor binds specifically to two different antigens (e.g., any combination of the exemplary antigens described herein).

In some embodiments of these single-chain chimeric antigen receptors, the transmembrane domain abuts the hormone receptor ligand binding domain. In some embodiments of these single-chain chimeric antigen receptors, the transmembrane domain and the hormone receptor ligand binding domain are separated by 1 to about 800 amino acids (e.g., or any of the subranges of this range described herein). In some embodiments, the amino acids between the transmembrane domain and the hormone receptor ligand binding domain do not comprise a domain. In other embodiments, the amino acids between the transmembrane domain and the hormone receptor ligand binding domain includes one or more intervening domain (e.g., one or more costimulatory domains and/or one or more ITAMs). In some embodiments, the amino acids between the transmembrane domain and the hormone receptor ligand binding domain includes a sequence from the same endogenous transmembrane protein from which the transmembrane domain is derived. In some embodiments, the amino acids between the transmembrane domain and the hormone receptor ligand binding domain include a linker sequence.

Some embodiments of these single-chain chimeric antigen receptors can include one or more (e.g., two, three, four, or five) costimulatory domain(s) (e.g., any combination of any of the exemplary costimulatory domains described herein or known in the art). Some embodiments of these single-chain chimeric antigen receptors include one or both of a 4-1BB costimulatory domain and a CD28 costimulatory domain.

Some embodiments of these single-chain chimeric antigen receptors can include one or more (e.g., two, three, four, or five) ITAMs (e.g., any of the ITAMs described herein or known in the art). In some embodiments of these single-chain chimeric antigen receptors, the ITAM includes a cytoplasmic signaling sequence from CD3ζ (e.g., human CD3ζ).

In some embodiments of any of these single-chain chimeric antigen receptors, any two neighboring domains can be separated by 1 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, about 4 amino acid, or about 3 amino acids (inclusive); about 2 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, or about 4 amino acid (inclusive); about 3 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, or about 5 amino acids (inclusive); about 4 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, or about 6 amino acids (inclusive); about 5 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, or about 7 amino acids (inclusive); about 6 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, or about 8 amino acids (inclusive); about 8 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, or about 10 amino acids (inclusive); about 10 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, or about 15 amino acids (inclusive); about 15 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, or about 20 amino acids (inclusive); about 20 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids (inclusive); about 40 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, or about 70 amino acids (inclusive); about 70 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, or about 75 amino acids (inclusive); about 75 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, or about 75 amino acids (inclusive); about 75 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, or about 80 amino acids (inclusive); about 80 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, or about 90 amino acids (inclusive); about 100 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, or about 110 amino acids (inclusive); about 110 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, or about 130 amino acids (inclusive); about 130 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, or about 140 amino acids (inclusive); about 140 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, or about 150 amino acids (inclusive); about 150 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, or about 160 amino acids (inclusive); about 160 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, or about 170 amino acids (inclusive); about 170 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, or about 180 amino acids (inclusive); about 180 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, or about 190 amino acids (inclusive); about 190 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, or about 200 amino acids (inclusive); about 200 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, or about 220 amino acids (inclusive); about 220 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, or about 240 amino acids (inclusive); about 240 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, or about 260 amino acids (inclusive); about 260 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, or about 280 amino acids (inclusive); about 280 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, or about 300 amino acids (inclusive); about 300 amino acids to about 500 amino acids, about 480 amino acids, about 460 amino acids, about 440 amino acids, about 420 amino acids, about 400 amino acids, about 380 amino acids, about 360 amino acids, about 340 amino acids, or about 320 amino acids (inclusive); about 320 amino acids to about 500 amino acids, about 480 amino acids, about 460 amino acids, about 440 amino acids, about 420 amino acids, about 400 amino acids, about 380 amino acids, about 360 amino acids, or about 340 amino acids (inclusive); about 340 amino acids to about 500 amino acids, about 480 amino acids, about 460 amino acids, about 440 amino acids, about 420 amino acids, about 400 amino acids, about 380 amino acids, or about 360 amino acids (inclusive); about 360 amino acids to about 500 amino acids, about 480 amino acids, about 460 amino acids, about 440 amino acids, about 420 amino acids, about 400 amino acids, or about 380 amino acids (inclusive); about 380 amino acids to about 500 amino acids, about 480 amino acids, about 460 amino acids, about 440 amino acids, about 420 amino acids, or about 400 amino acids (inclusive); about 400 amino acids to about 500 amino acids, about 480 amino acids, about 460 amino acids, about 440 amino acids, or about 420 amino acids (inclusive); about 420 amino acids to about 500 amino acids, about 480 amino acids, about 460 amino acids, or about 440 amino acids (inclusive); about 440 amino acids to about 500 amino acids, about 480 amino acids, or about 460 amino acids (inclusive); about 460 amino acids to about 500 amino acids or about 480 amino acids (inclusive); or about 480 amino acids to about 500 amino acids (inclusive).

In some embodiments, one or more amino acids between the extracellular antigen-binding domain and the transmembrane domain is a sequence from the same endogenous single-chain polypeptide from which the transmembrane domain is derived (e.g., a CD8α hinge region, e.g., SEQ ID NO: 112). In some embodiments, a sequence comprising SEQ ID NO: 42, 55, or 112 is positioned between the extracellular antigen-binding domain and the transmembrane domain. In some embodiments, one or more amino acids between the extracellular antigen-binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain and the transmembrane domain is or comprises a linker sequence (e.g., a non-naturally occurring linker sequence, e.g., GS or any of the other linker sequences described herein).

In some embodiments of the single-chain chimeric antigen receptors, after the hormone receptor ligand binding domain, the next domain is a costimulatory domain followed by an ITAM. In some of these embodiments, one or more amino acids between the hormone receptor ligand binding domain and the costimulatory domain is or includes a sequence from the same endogenous single-chain polypeptide from which the costimulatory domain is derived or the ITAM is derived. In some of these embodiments, one or more amino acids between the hormone receptor ligand binding domain and the costimulatory domain is or includes a linker sequence (e.g., a non-naturally occurring linker sequence). In some embodiments, one or more amino acids between the costimulatory domain and the ITAM is or includes a sequence from the same endogenous single-chain polypeptide from which the costimulatory domain is derived or the ITAM is derived.

In some embodiments of the single-chain chimeric antigen receptors, after the hormone receptor ligand binding domain, the next domain is a costimulatory domain followed by an ITAM. In some embodiments of the single-chain chimeric antigen receptors, after the ligand binding domain, the next domain is an ITAM, followed by the costimulatory domain. In some of these embodiments, one or more amino acids between the hormone receptor ligand binding domain and the ITAM is or includes a sequence from the same endogenous single-chain polypeptide from which the costimulatory domain is derived or the ITAM is derived. In some of these embodiments, one or more amino acids between the hormone receptor ligand binding domain and the ITAM is or includes a linker sequence (e.g., a non-naturally occurring linker sequence). In some embodiments, one or more amino acids between the ITAM and the costimulatory domain is or includes a sequence from the same endogenous single-chain polypeptide from which the ITAM is derived or the costimulatory domain is derived.

In some embodiments, where two or more costimulatory domains are included in the single-chain chimeric antigen receptor, the two or more costimulatory domains can be placed between the hormone receptor ligand binding domain and one or more ITAMs. In some embodiments of the single-chain chimeric antigen receptors described herein, the costimulatory domains and ITAMs can alternate in the primary amino acid sequence of the single-chain chimeric antigen receptor.

Some embodiments of any of the single-chain chimeric antigen receptors described herein can further include a dimerization domain and/or a peptide tag.

In some examples, a single-chain chimeric antigen receptor can comprise a sequence that is at least 80% (e.g., at least 82%, at least 84%, at least 86%, at least 88%, at least 90%, at least 92%, at least 94%, at least 96%, at least 98%, at least 99%, or 100%) identical to: SEQ ID NO: 31, 33, 35, 37, 39, or 52.

Single-Chain Chimeric Antigen Receptor-Extracellular Hormone Receptor LBD

Also provided herein are single-chain chimeric antigen receptors that include: an extracellular antigen-binding domain (e.g., any of the antigen-binding domains described herein or known in the art), an extracellular hormone receptor ligand binding domain (e.g., any of the hormone receptor ligand binding domain described herein or known in the art), a transmembrane domain (e.g., any of the transmembrane domains described herein or known in the art), a costimulatory domain (e.g., any of the costimulatory domains described herein or known in the art), and an immunoreceptor tyrosine-based activation motif (ITAM), where: the transmembrane domain and the extracellular hormone ligand binding domain directly abut each other or are separated by 1 to about 800 amino acids (e.g., any of the subranges of this range described herein), and the transmembrane domain and the extracellular hormone receptor ligand binding domain are not present in the same endogenous single-chain polypeptide in a mammal. The single-chain chimeric antigen receptors described herein can bind to any of the exemplary antigens described herein or any other antigen known in the art. In some embodiments, the single-chain chimeric antigen receptor binds specifically to a single antigen (e.g., any of the exemplary antigens described herein). In some embodiments, the single-chain chimeric antigen receptor binds specifically to two different antigens (e.g., any combination of the exemplary antigens described herein).

In some embodiments of these single-chain chimeric antigen receptors, the transmembrane domain abuts the extracellular hormone receptor ligand binding domain. In some embodiments of these single-chain chimeric antigen receptors, the transmembrane domain and the extracellular hormone receptor ligand binding domain are separated by 1 to about 800 amino acids (e.g., or any of the subranges of this range described herein). In some embodiments, the amino acids between the transmembrane domain and the extracellular hormone receptor ligand binding domain do not comprise a domain. In other embodiments, the amino acids between the transmembrane domain and the extracellular hormone receptor ligand binding domain includes one or more intervening domain (e.g., the antigen-binding domain or an additional antigen-binding domain). In some embodiments, the amino acids between the transmembrane domain and the extracellular hormone receptor ligand binding domain includes a sequence from the same endogenous transmembrane protein from which the transmembrane domain is derived. In some embodiments, the amino acids between the transmembrane domain and the extracellular hormone receptor ligand binding domain include a linker sequence.

Some embodiments of these single-chain chimeric antigen receptors can include one or more (e.g., two, three, four, or five) costimulatory domain(s) (e.g., any combination of any of the exemplary costimulatory domains described herein or known in the art). Some embodiments of these single-chain chimeric antigen receptors include one or both of a 4-1BB costimulatory domain and a CD28 costimulatory domain.

Some embodiments of these single-chain chimeric antigen receptors can include one or more (e.g., two, three, four, or five) ITAMs (e.g., any of the ITAMs described herein or known in the art). In some embodiments of these single-chain chimeric antigen receptors, the ITAM includes a cytoplasmic signaling sequence from CD3ζ (e.g., human CD3ζ).

In some embodiments of any of these single-chain chimeric antigen receptors, any two neighboring domains can be separated by 1 amino acids to about 500 amino acids (e.g., or any of the subranges of this range described herein).

In some embodiments, one or more amino acids between the extracellular hormone receptor ligand binding domain or the extracellular antigen-binding domain and the transmembrane domain is a sequence from the same endogenous single-chain polypeptide from which the transmembrane domain is derived (e.g., a hinge sequence from human CD8α, e.g., SEQ ID NO: 112). In some embodiments, a sequence comprising SEQ ID NO: 42, 55, or 112 is positioned between the extracellular hormone receptor ligand binding domain or the extracellular antigen-binding domain and the transmembrane domain. In some embodiments, one or more amino acids between the extracellular antigen-binding domain or the extracellular hormone receptor ligand binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain or the extracellular hormone receptor ligand binding domain (e.g., any of the hormone receptor ligand binding domain described herein or known in the art) and the transmembrane domain is or comprises a linker sequence (e.g., a non-naturally occurring linker sequence). In some embodiments, one or more amino acids between the extracellular antigen-binding domain and the extracellular hormone receptor ligand binding domain is or comprises a linker sequence (e.g., a non-naturally occurring linker sequence, e.g., GS or any of the other linker sequences described herein)).

In some embodiments of the single-chain chimeric antigen receptors, after the transmembrane domain, the next domain is a costimulatory domain followed by an ITAM. In some embodiments of the single-chain chimeric antigen receptors, after the transmembrane domain, the next domain is an ITAM, followed by the costimulatory domain. In some of these embodiments, one or more amino acids between the transmembrane domain and the costimulatory domain or the ITAM is or includes a sequence from the same endogenous single-chain polypeptide from which the costimulatory domain is derived or the ITAM is derived, respectively. In some of these embodiments, one or more amino acids between the transmembrane domain and the costimulatory domain or the ITAM is or includes a linker sequence (e.g., a non-naturally occurring linker sequence). In some of these embodiments, one or more amino acids between the the costimulatory domain and the ITAM is or includes a linker sequence (e.g., a non-naturally occurring linker sequence). In some embodiments, one or more amino acids between the costimulatory domain and the ITAM is or includes a sequence from the same endogenous single-chain polypeptide from which the costimulatory domain is derived or the ITAM is derived.

In some embodiments, where two or more costimulatory domains are included in the single-chain chimeric antigen receptor, the two or more costimulatory domains can be placed between the one or more ITAMs. In some embodiments, where two or more ITAMs are included in the single-chain chimeric antigen receptor, the two or more ITAMs can be placed between the one or more costimulatory molecules. In some embodiments of the single-chain chimeric antigen receptors described herein, the costimulatory domains and ITAMs can alternate in the primary amino acid sequence of the single-chain chimeric antigen receptor.

Some embodiments of any of the single-chain chimeric antigen receptors described herein can further include a dimerization domain and/or a peptide tag.

In some embodiments, when going in the N-terminal to C-terminal direction, the single-chain chimeric antigen receptor comprises the extracellular antigen-binding domain, the extracellular hormone receptor ligand binding domain, the transmembrane domain, the intracellular costimulatory domain, and the ITAM. In some embodiments, when going in the C-terminal to the N-terminal direction, the single-chain chimeric antigen receptor comprises the extracellular antigen-binding domain, the extracellular hormone receptor ligand binding domain, the transmembrane domain, the intracellular costimulatory domain, and the ITAM. In some embodiments, when going in the N-terminal to the C-terminal direction, the single-chain chimeric antigen receptor comprises the extracellular hormone receptor ligand binding domain, the extracellular antigen-binding domain, the transmembrane domain, the intracellular costimulatory domain, and the ITAM. In some embodiments, when going in the C-terminal to the N-terminal direction, the single-chain chimeric polypeptide comprises the extracellular hormone receptor ligand binding domain, the extracellular antigen-binding domain, the transmembrane domain, the intracellular costimulatory domain, and the ITAM.

In some examples, a single-chain chimeric antigen receptor can comprise a sequence that is at least 80% (e.g., at least 82%, at least 84%, at least 86%, at least 88%, at least 90%, at least 92%, at least 94%, at least 96%, at least 98%, at least 99%, or 100%) identical to SEQ ID NO: 98.

Multi-Chain Chimeric Antigen Receptor
Multi-Chain Chimeric Antigen Receptors-Intracellular Hormone Receptor LBD Also provided herein are multi-chain chimeric antigen receptors that include at least one first polypeptide including: an extracellular antigen-binding domain (e.g., any of the antigen-binding domains described herein or known in the art), a transmembrane domain (e.g., any of the transmembrane domains described herein or known in the art), and a hormone receptor ligand binding domain (e.g., any of the hormone receptor ligand binding domains described herein or known in the art), where the transmembrane domain and the hormone receptor ligand binding domain directly abut each other or are separated by 1 to about 800 amino acids (e.g., any of the subranges of this range described herein), and the transmembrane domain and the hormone receptor ligand binding domain are not both present in the same (a single) endogenous single-chain polypeptide. The antigen specifically bound by the antigen-binding domain in any of these multi-chain chimeric antigen receptors can be any of the antigens described herein or known in the art. In some embodiments, the multi-chain chimeric antigen receptor only binds specifically to a single antigen (e.g., any of the exemplary antigens described herein). In some embodiments, the multi-chain chimeric antigen receptor binds specifically to two different antigens (e.g., any combination of any of the exemplary antigens described herein).

In some embodiments of the multi-chain chimeric antigen receptors, the extracellular antigen-binding domain and the transmembrane domain in the at least one first polypeptide abut each other. In some embodiments of the multi-chain chimeric antigen receptors, 1 to about 500 amino acids (e.g., any of the subranges of this range described herein) are between the extracellular antigen-binding domain and the transmembrane domain in the at least one first polypeptide. In some embodiments, one or more amino acids between the extracellular antigen-binding domain and the transmembrane domain in the at least one first polypeptide is a sequence from the same endogenous single-chain polypeptide from which the transmembrane domain is derived. In some embodiments, one or more amino acids between the extracellular antigen-binding domain and the transmembrane domain of the at least one first polypeptide is or includes a hinge region sequence of human antibody (e.g., IgG1, IgG2, IgG3, or IgG4). In some embodiments, one or more amino acids between the extracellular antigen-binding domain and the transmembrane domain in the at least one first polypeptide is or includes a linker sequence (e.g., a non-naturally occurring linker sequence).

In some embodiments of these multi-chain chimeric antigen receptors, the transmembrane domain abuts the hormone receptor ligand binding domain in the at least one first polypeptide. In some embodiments of these multi-chain chimeric antigen receptors, the transmembrane domain and the hormone receptor ligand binding domain in the at least one first polypeptide are separated by 1 to about 800 amino acids (e.g., or any of the subranges of this range described herein). In some embodiments, the amino acids between the transmembrane domain and the hormone receptor ligand binding domain in the at least one first polypeptide do not comprise a domain. In other embodiments, the amino acids between the transmembrane domain and the hormone receptor ligand binding domain in the at least one first polypeptide includes one or more intervening domain (e.g., one or more costimulatory domains (e.g., any of the costimulatory domains described herein) and/or one or more ITAMs (e.g., any of the ITAMs described herein)). In some embodiments, the amino acids between the transmembrane domain and the hormone receptor ligand binding domain in the at least one first polypeptide includes a sequence from the same endogenous transmembrane protein from which the transmembrane domain is derived. In some embodiments, the amino acids between the transmembrane domain and the hormone receptor ligand binding domain in the at least one first polypeptide include a linker sequence (e.g., a non-naturally occurring linker sequence).

In some embodiments of these multi-chain chimeric antigen receptors, the at least one first polypeptide can further include one or more (e.g., two or three) of: a dimerizing domain (e.g., any dimerizing domain known in the art), a costimulatory domain (e.g., any of the costimulatory domains described herein), and/or a peptide tag (e.g., any peptide tag known in the art).

Some embodiments of these multi-chain chimeric antigen receptors further include a second polypeptide that can include one or more (e.g., two, three, or four) of: a transmembrane domain (e.g., any of the transmembrane domains described herein), a dimerizing domain (e.g., a dimerizing domain that can interact with a dimerizing domain in the at least one first polypeptide in a mammalian cell), one or more costimulatory domains (e.g., any of the costimulatory domains described herein), and one or more ITAM (e.g., any of the ITAMs described herein). As can be appreciated by those in the art, a pair or each pair of neighboring domains in the second polypeptide can abut each other or can be separated by 1 to about 800 amino acids (e.g., any of the subranges of this range described herein). The one or more amino acids between a pair of neighboring domains in the second polypeptide can be a sequence from an endogenous single-chain polypeptide from which a transmembrane, a costimulatory domain, or an ITAM present in the second polypeptide has been derived.

Multi-Chain Chimeric Antigen Receptors-Extracellular Hormone Receptor LBD

Also provided herein are multi-chain chimeric antigen receptors that include at least one first polypeptide including: an extracellular antigen-binding domain (e.g., any of the antigen-binding domains described herein or known in the art), an extracellular hormone receptor ligand binding domain (e.g., any of the hormone receptor ligand binding domains described herein or known in the art), and a transmembrane domain (e.g., any of the transmembrane domains described herein or known in the art), where the transmembrane domain and the extracellular hormone receptor ligand binding domain directly abut each other or are separated by 1 to about 800 amino acids (e.g., any of the subranges of this range described herein), and the transmembrane domain and the hormone receptor ligand binding domain are both not present in a single endogenous single-chain polypeptide. The antigen specifically bound by the antigen-binding domain in any of these multi-chain chimeric antigen receptors can be any of the antigens described herein or known in the art. In some embodiments, the multi-chain chimeric antigen receptor only binds specifically to a single antigen (e.g., any of the exemplary antigens described herein). In some embodiments, the multi-chain chimeric antigen receptor binds specifically to two different antigens (e.g., any combination of any of the exemplary antigens described herein).

In some embodiments of the multi-chain chimeric antigen receptors, the extracellular hormone receptor ligand binding domain and the transmembrane domain in the at least one first polypeptide abut each other. In some embodiments of the multi-chain chimeric antigen receptors, 1 to about 700 amino acids (e.g., any of the subranges of this range described herein) are between the extracellular hormone receptor ligand binding domain and the transmembrane domain in the at least one first polypeptide. In some embodiments, one or more amino acids between the extracellular hormone receptor ligand binding domain and the transmembrane domain in the at least one first polypeptide is a sequence from the same endogenous single-chain polypeptide from which the transmembrane domain is derived. In some embodiments, one or more amino acids between the extracellular hormone receptor ligand binding domain and the transmembrane domain of the at least one first polypeptide is or includes a hinge region sequence of human antibody (e.g., IgG1, IgG2, IgG3, or IgG4). In some embodiments, one or more amino acids between the extracellular hormone receptor ligand binding domain and the transmembrane domain in the at least one first polypeptide is or includes a linker sequence (e.g., a non-naturally occurring linker sequence). In some embodiments, one or more amino acids between the extracellular hormone receptor ligand binding domain and the antigen-binding domain is or includes a linker sequence (e.g., a non-naturally occurring linker sequence).

In some embodiments of these multi-chain chimeric antigen receptors, the transmembrane domain abuts the extracellular hormone receptor ligand binding domain in the at least one first polypeptide. In some embodiments of these multi-chain chimeric antigen receptors, the transmembrane domain and the extracellular hormone receptor ligand binding domain in the at least one first polypeptide are separated by 1 to about 800 amino acids (e.g., or any of the subranges of this range described herein). In some embodiments, the amino acids between the transmembrane domain and the extracellular hormone receptor ligand binding domain in the at least one first polypeptide do not comprise a domain.

In some embodiments, the amino acids between the transmembrane domain and the extracellular hormone receptor ligand binding domain in the at least one first polypeptide includes one or more intervening domain (e.g., the antigen-binding domain).

In some embodiments, the amino acids between the transmembrane domain and the antigen-binding domain in the at least one first polypeptide includes a sequence from the same endogenous transmembrane protein from which the transmembrane domain is derived. In some embodiments, the amino acids between the transmembrane domain and the antigen-binding domain in the at least one first polypeptide include a linker sequence (e.g., a non-naturally occurring linker sequence). In some embodiments, one or more amino acids between the antigen-binding domain and the transmembrane domain of the at least one first polypeptide is or includes a hinge region sequence of human antibody (e.g., IgG1, IgG2, IgG3, or IgG4). In some embodiments, one or more amino acids between the antigen-binding domain and the extracellular hormone receptor ligand binding domain in the at least one first polypeptide is or includes a linker sequence (e.g., a non-naturally occurring linker sequence).

In some embodiments, when going in the N-terminal to C-terminal direction, the at least one first polypeptide comprises the extracellular antigen-binding domain, the extracellular hormone receptor ligand binding domain, and the transmembrane domain. In some embodiments, when going in the C-terminal to N-terminal direction, the at least one first polypeptide comprises the extracellular antigen-binding domain, the extracellular hormone receptor ligand binding domain, and the transmembrane domain. In some embodiments, when going in the N-terminal to C-terminal direction, the at least one first polypeptide comprises the extracellular hormone receptor ligand binding domain, the extracellular antigen-binding domain, and the transmembrane domain. In some embodiments, when going in the C-terminal to N-terminal direction, the at least one first polypeptide comprises the extracellular hormone receptor ligand binding domain, the extracellular antigen-binding domain, and the transmembrane domain.

In some embodiments of these multi-chain chimeric antigen receptors, the at least one first polypeptide can further include one or more (e.g., two or three) of: a dimerizing domain (e.g., any dimerizing domain known in the art), a costimulatory domain (e.g., any of the costimulatory domains described herein), and/or a peptide tag (e.g., any peptide tag known in the art).

Some embodiments of these multi-chain chimeric antigen receptors further include a second polypeptide that can include one or more (e.g., two, three, or four, in any order or combination) of: a transmembrane domain (e.g., any of the transmembrane domains described herein), a dimerizing domain (e.g., a dimerizing domain that can interact with a dimerizing domain in the at least one first polypeptide in a mammalian cell), one or more costimulatory domains (e.g., any of the costimulatory domains described herein), and one or more ITAM (e.g., any of the ITAMs described herein). As can be appreciated by those in the art, a pair or each pair of neighboring domains in the second polypeptide can abut each other or can be separated by 1 to about 800 amino acids (e.g., any of the subranges of this range described herein). The one or more amino acids between a pair of neighboring domains in the second polypeptide can be a sequence from an endogenous single-chain polypeptide from which a transmembrane, a costimulatory domain, or an ITAM present in the second polypeptide has been derived. The one or more amino acids between a pair of neighboring domains in the second polypeptide can be or include a linker sequence (e.g., a non-naturally occurring linker sequence).

As can be appreciated in the art, the two or more polypeptides present in a multi-chain chimeric antigen receptor can associate via pair of domains that interact with each other (through dimerizing domains). In some embodiments, the interaction between dimerizing domains can be triggered by the addition of a small molecule. In some embodiments, the two or more polypeptides present in a multi-meric chimeric antigen receptor can associate through non-covalent interactions (e.g., between associations between dimerizing domains). In some embodiments, the two or more polypeptides present in a multi-meric chimeric antigen receptor can be through a covalent interaction (e.g., through a disulfide bond, through an ester bond, through an amide bond, through a thioester bond, or a combination thereof).

Transmembrane Domains

In some embodiments, a single-chain chimeric polypeptide, a single-chain chimeric antigen receptor, or a multi-chain chimeric antigen receptor includes a transmembrane domain, or portion thereof, from an endogenous polypeptide, where the endogenous polypeptide is selected from the group g of: an α chain of a T cell receptor, a β chain of a T cell receptor, a ζ chain of the T cell receptor, CD28 (also known as Tp44), CD3ε, CD3δ, CD3γ, CD33, CD37 (also known as GP52-40 or TSPAN26), CD64 (also known as FCGR1A), CD80 (also known as B7, B7-1, B7.1, BB1, CD28LG, CD28LG1, and LAB7), CD45 (also known as PTPRC, B220, CD45R, GP180, L-CA, LCA, LYS, T200, and protein tyrosine phosphatase, receptor type C), CD4, CD5 (also known as LEU1 and T1), CD8α(also known as Leu2, MAL, and p32), CD9 (also known as BTCC-1, DRAP-27, MIC3, MRP-1, TSPAN-29, and TSPAN29), CD16 (also known as FCGR3 and FCG3), CD22 (also known as SIGLEC-2 and SIGLEC2), CD86 (also known as B7-2, B7.2, B70, CD28LG2, and LAB72), CD134 (also known as TNFRSF4, ACT35, RP5-902P8.3, IMD16, OX40, TXGP1L, and tumor necrosis factor receptor superfamily member 4), CD137 (also known as TNFRSF9, 4-1BB, CDw137, ILA, and tumor necrosis factor receptor superfamily member 9), CD27 (also known as S152, S152.LPFS2, T14, TNFRSF7, and Tp55), CD152 (also known as CTLA4, ALPS5, CELIAC3, CTLA-4, GRD4, GSE, IDDM12, and cytotoxic T-lymphocyte associated protein 4), PD1 (also known as PDCD1, CD279, PD-1, SLEB2, hPD-1, hPD-1, hSLE1, and Programmed cell death 1), ICOS (also known as AILIM, CD278, and CVID1), CD272 (also known as BTLA and BTLA1), CD30 (also known as TNFRSF8, D1S166E, and Ki-1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), DAP10, and CD154 (also known as CD40LG, CD40L, HIGM1, IGM, IMD3, T-BAM, TNFSF5, TRAP, gp39, hCD40L, and CD40 ligand). The letters "CD" is the previous sentence stand for "Cluster of Differentiation." E.g., CD3 stands for "Cluster of Differentiation 3." In some embodiments, a single-chain chimeric polypeptide, a single-chain chimeric antigen receptor, or a multi-chain chimeric antigen receptor includes a transmembrane domain, or portion thereof, from an endogenous mammalian (e.g., human) polypeptide (e.g., a mammalian or human homolog of any of the polypeptides listed above).

Any transmembrane domain, or portion thereof, that serves to anchor an endogenous polypeptide in a lipid bilayer (e.g., plasma membrane) of a mammalian cell is suitable for use in accordance with compositions and methods disclosed herein. In some embodiments, a single-chain chimeric polypeptide, a single-chain chimeric antigen receptor, or a multi-chain chimeric antigen receptor includes a transmembrane domain, or portion thereof, from human CD28, e.g., Accession No. P01747, e.g., amino acids 153 to 179 of SEQ ID NO: 1. In some embodiments, a single-chain chimeric polypeptide, a single-chain chimeric antigen receptor, or a multi-chain chimeric antigen receptor includes a transmembrane domain that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 153 to 179 of SEQ ID NO: 1, or a portion thereof.

In some embodiments, transmembrane domain can comprise a sequence at least 80% (e.g., at least 82%, at least 84%, at least 86%, at least 88%, at least 90%, at least 92%, at least 94%, at least 96%, at least 98%, at least 99%, or 100% identical) to SEQ ID NO: 114 (or a portion thereof).

SEQ ID NO: 1
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS

In some embodiments, a single-chain chimeric polypeptide, a single-chain chimeric antigen receptor, or a multi-chain chimeric antigen receptor includes a transmembrane domain, or portion thereof, from human CD3, e.g., Accession No. P20963, e.g., amino acids 31 to 51 of SEQ ID NO: 2. In some embodiments, a single-chain chimeric polypeptide, a single-chain chimeric antigen receptor, or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 31 to 51 of SEQ ID NO: 2.

SEQ ID NO: 2
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR

In some embodiments, a single-chain chimeric polypeptide, a single-chain chimeric antigen receptor, or a multi-chain chimeric antigen receptor includes a transmembrane domain, or portion thereof, of any one of SEQ ID Nos. 3-9.

(SEQ ID NO: 3)
LGLLVAGVLVLLVSLGVAIHLCC;

(SEQ ID NO: 4)
VAAILGLGLVLGLLGPLAILLALYLL;

(SEQ ID NO: 5)
ALIVLGGVAGLLLFIGLGIFFCVRC;

(SEQ ID NO: 6)
LCYLLDGILFIYGVILTALFLRV;

(SEQ ID NO: 7)
WVLVVVGGVLACYSLLVTVAFIIFWV;

(SEQ ID NO: 8)
IYIWAPLAGTCGVLLLSLVITLYC;
and (SEQ ID NO: 9)
ALPAALAVISFLLGLGLGVACVLA.

In some embodiments, a single-chain chimeric polypeptide, a single-chain chimeric antigen receptor, or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to any one of SEQ ID Nos. 3-9.

In some embodiments, a single-chain chimeric polypeptide, a single-chain chimeric antigen receptor, or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to SEQ ID NO: 43, 56, or 114.

As will be appreciated by those of ordinary skill in the art, certain endogenous polypeptides have two or more isoforms that differ at least in their primary polypeptide sequence. A single-chain chimeric polypeptide, a single-chain chimeric antigen receptor, or a multi-chain chimeric antigen receptor disclosed herein can include a transmembrane domain that includes a sequence of amino acids from any isoform of an endogenous transmembrane protein (e.g., an endogenous mammalian, e.g., human, transmembrane protein) including, e.g., an isoform (e.g., a human isoform) of: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154.

In some embodiments, a transmembrane domain, or portion thereof, of a single-chain chimeric polypeptide, a single-chain chimeric antigen receptor, or a multi-chain chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to the transmembrane domains from one or more of the following endogenous mammalian (e.g., human) transmembrane proteins: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154. In some embodiments, a transmembrane domain, or portion thereof, of a single-chain chimeric polypeptide, a single-chain chimeric antigen receptor, or a multi-chain chimeric antigen receptor includes a sequence of amino acids having one or more amino acid substitutions, deletions, or additions as compared to the transmembrane domain of an endogenous mammalian (e.g., human) transmembrane protein: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, or CD154.

In some embodiments, a single-chain chimeric polypeptide, a single-chain chimeric antigen receptor, or a multi-chain chimeric antigen receptor includes a synthetic transmembrane domain. In some cases, a synthetic transmembrane domain can include predominantly hydrophobic residues such as, without limitation, leucine and valine. In some embodiments, a synthetic transmembrane domain includes a triplet of phenylalanine, tryptophan, and valine at each end of the domain.

In some embodiments, a single-chain chimeric polypeptide, a single-chain chimeric antigen receptor, or a multi-chain chimeric antigen receptor includes a transmembrane domain that is a chimeric transmembrane domain having portions of a transmembrane domain from two or more endogenous mammalian (e.g., human) transmembrane polypeptides such as, without limitation, an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD134, CD137, CD27, CD152, PD1, and CD154, such that the two or more portions of transmembrane domains together constitute a functional transmembrane domain. In some embodiments, such a portion of a chimeric transmembrane domain can include one or more amino acid substitutions, deletions, or additions as compared to a corresponding portion of a wild type transmembrane domain.

A transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Additional examples and features of transmembrane domains are known in the art.

Hormone Receptor Ligand Binding Domains

In some embodiments, the hormone receptor ligand binding domain is or comprises an estrogen receptor ligand binding domain, or a fragment thereof. Additional examples of hormone receptor ligand binding domains that can be used in any of the polypeptides described herein (e.g., single-chain chimeric polypeptide, single-chain chimeric antigen receptor, or multi-chain chimeric antigen receptor) include the ligand binding domains of, e.g., an estrogen receptor, an ecdysone receptor, a PPARγ receptor, a glucocorticoid receptor, an androgen receptor, a thyroid hormone receptor, a mineralocorticoid receptor, a progesterone receptor, a vitamin D receptor, a PPAR receptorα, a PPARβ/δ receptor, a pregnane X receptor, a liver X receptor, a farnesoid X receptor, a retinoid X receptor, a RAR-related orphan receptor, and a retinoic acid receptor.

A non-limiting example of a human estrogen receptor ligand binding domain is amino acids 10 of 247 of SEQ ID NO: 10. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 10 to 247 of SEQ ID NO: 10.

```
(Human)
                                                          SEQ ID NO: 10
  1 skknslalsl tadqmvsall daeppilyse ydptrpfsea smmglltnla drelvhminw 61 akrvpgfvdl tlhdqvhlle cawleilmig lvwrsmehpg kllfapnlll drnqgkcveg 121 mveifdmlla tssrfrmmnl qgeefvolks iillnsgvyt flsstlksle ekdhihrvld 181 kitdtlihlm akagltlqqq hqrlaqllli lshirhmsnk gmehlysmkc knvvplydll 241 lemldahrlh
```

Another non-limiting example of an estrogen receptor ligand binding domain is amino acids 4 to 241 of SEQ ID NO: 11. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 4 to 241 of SEQ ID NO: 11.

```
(Human)
                                                          SEQ ID NO: 11
  1 alsltadqmv salldaeppi lyseydptrp fseasmmgll tnladrelvh minwakrvpg 61 fvdltlhdqv hllecawlei lmiglvwrsm ehpgkllfap nllldrnqgk cvegmveifd 121 mllatssrfr mmnlqgeefv clksiillns gvytflsstl ksleekdhih rvldkitdtl 181 ihlmakaglt lqqqhqrlaq lllilshirh msnkgmehly smkcknvvpl ydlllemlda 241 hrlhapts
```

In some embodiments, the estrogen receptor ligand binding domain has a wildtype sequence, except that it comprises one or more (e.g., two, three, four, five, or six) amino acid substitutions. In some embodiments, the estrogen receptor ligand binding domain has a wildtype sequence, except that it comprises an amino acid substitution(s) at one or both of amino acid position 521 (e.g., a G521R substitution) and 537 (e.g., a G537F substitution) (each numbered relative to the full-length wildtype sequence of human estrogen receptor, e.g., SEQ ID NO: 119 below).

(Human)

SEQ ID NO: 119

```
  1 mtmtlhtkas gmallhqiqg neleplnrpq lkiplerplg evyldsskpa vynypegaay
 61 efnaaaaana qvygqtglpy gpgseaaafg snglggfppl nsvspsplml lhpppqlspf
121 lqphgqqvpy ylenepsgyt vreagppafy rpnsdnrrqg grerlastnd kgsmamesak
181 etrycavcnd yasgyhygvw scegckaffk rsiqghndym cpatnqctid knrrkscqac
241 rlrkcyevgm mkggirkdrr ggrmlkhkrq rddgegrgev gsagdmraan lwpsplmikr
301 skknslalsl tadqmvsall daeppilyse ydptrpfsea smmglltnla drelvhminw
361 akrvpgfvdl tlhdqvhlle cawleilmig lvwrsmehpg kllfapnlll drnqgkcveg
421 mveifdmlla tssrfrmmnl qgeefvclks iillnsgvyt flsstlksle ekdhihrvld
481 kitdtlihlm akagltlqqq hqrlaqllli lshirhmsnk gmehlysmkc knvvplydll
541 lemldahrlh aptsrggasv eetdqshlat agstsshslq kyyitgeaeg fpatv
```

Non-limiting examples of an estrogen receptor ligand binding domain can include a sequence at least 80% (e.g., at least 82%, at least 84%, at least 86%, at least 88%, at least 90%, at least 92%, at least 94%, at least 96%, at least 98%, at least 99% or 100%) identical to: SEQ ID NO: 110 (or a fragment thereof).

Additional non-limiting examples of a hormone receptor ligand binding domain is or includes a sequence at least 80% (e.g., at least 82%, at least 84%, at least 86%, at least 88%, at least 90%, at least 92%, at least 94%, at least 96%, at least 98%, at least 99% or 100%) identical to SEQ ID NO: 46, 59, or 110.

Another non-limiting example of an estrogen receptor ligand binding domain is amino acids 314 to 551 of SEQ ID NO: 88. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 314 to 551 of SEQ ID NO: 88.

(Mouse)

SEQ ID NO: 88

```
  1 mtmtlhtkas gmallhqiqg neleplnrpq lkmpmeralg evyvdnskpt vfnypegaay
 61 efnaaaaaaa aasapvygqs giaygpgsea aafsanslga fpqlnsvsps plmllhpppq
121 lspflhphgq qvpyylenep sayavrdtgp pafyrsnsdn rrqngrerls ssnekgnmim
181 esaketryca vcndyasgyh ygvwscegck affkrsiqgh ndymcpatnq ctidknrrks
241 cqacrlrkcy evgmmkggir kdrrggrmlk hkrqrddleg rnemgasgdm raanlwpspl
301 vikhtkknsp alsltadqmv salldaeppm iyseydpsrp fseasmmgll tnladrelvh
361 minwakrvpg fgdlnlhdqv hllecawlei lmiglvwrsm ehpgkllfap nllldrnqgk
421 cvegmveifd mllatssrfr mmnlqgeefv clksiillns gvytflsstl ksleekdhih
481 rvldkitdtl ihlmakaglt lqqqhrrlaq lllilshirh msnkgmehly nmkcknvvpl
541 ydlllemlda hrlhapasrm gvppeepsqt qlattsstsa hslqtyyipp eaegfpnti
```

Another non-limiting example of an estrogen receptor ligand binding domain is amino acids 315 to 552 of SEQ ID NO: 89. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 315 to 552 of SEQ ID NO: 89.

(Rat)

SEQ ID NO: 89

```
  1 mtmtlhtkas gmallhqiqg neleplnrpq lkmpmeralg evyvdnskpa vfnypegaay
 61 efnaaaaaaa agasapvygq ssitygpgse aaafganslg afpqlnsysp splmllhppp
121 hvspflhphg hqvpyylene psayavrdtg ppafyrsnsd nrrqngrerl ssssekgnmi
181 mesaketryc avcndyasgy hygvwscegc kaffkrsiqg hndymcpatn qctidknrrk
241 scqacrlrkc yevgmmkggi rkdrrggrml khkrqrddle grnemgtsgd mraanlwpsp
301 lvikhtkkns palsltadqm vsalldaepp liyseydpsr pfseasmmgl ltnladrelv
361 hminwakrvp gfgdlnlhdq vhllecawle ilmiglvwrs mehpgkllfa pnllldrnqg
421 kcvegmveif dmllatssrf rmmnlqgeef vclksiilln sgvytflsst lksleekdhi
481 hrvldkindt lihlmakagl tlqqqhrrla qlllilshir hmsnkgmehl ynmkcknvvp
541 lydlllemld ahrlhapasr mgvppeepsq sqltttssts ahslqtyyip peaegfpnti
```

Another non-limiting example of an estrogen receptor ligand binding domain is amino acids 310 to 547 of SEQ ID NO: 90. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 310 to 547 of SEQ ID NO: 90.

(Baboon)

SEQ ID NO: 90

```
  1 mtmtlhtkas gmallhqiqg neleplnrpq lkiplerplg evyvdsskpa vysypegaay
 61 efnaaaaana qvygqtglpy gpgseaaafg snglggfppl nsvspsplml lhpppqlspf
121 lqphgqqvpy ylenepsgyt vreagppafy rpnsdnrrqg grerlastnd kgsmamesak
181 etrycavcnd yasgyhygvw scegckaffk rsiqghndym cpatnqctid knrrkscqac
241 rlrkcyevgm mkggirkdrr ggrmlkhkrq rddgegrgev gsagdmraan lwpsplmikh
301 skknspalsl tadqmvsall daeppilyse ydptrpfsea smmglltnla drelvhminw
361 akrvpgfvdl tlhdqvhlle cawleilmig lvwrsmehpg kllfapnlll drnqgkcveg
421 mveifdmlla tssrfrmmnl qgeefvclks iillnsgvyt flsstlksle ekdhihrvld
481 kitdtlihlm akagltlqqq hrrlaqlllli lshirhmsnk gmehlysmkc knvvplydll
541 lemldahrlh aptsrggapm eetdqshlat agstsshslq kyyitgdaeg fpatv
```

In some embodiments, the hormone receptor ligand binding domain is or comprises a progesterone receptor ligand binding domain, or a fragment thereof. A non-limiting example of a human progesterone receptor ligand binding domain is amino acids 11 to 258 of SEQ ID NO: 12. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 11 to 258 of SEQ ID NO: 12.

(Human)

SEQ ID NO: 12

```
  1 spgqdiglip plinllmsie pdviyaghdn tkpdtsssll tslnqlgerq llsvvkwsks
 61 lpgfrnlhid dgitliqysw mslmvfglgw rsykhvsgqm lyfapdliln eqrmkessfy
121 slcltmwqip qefvklqvsq eeflcmkvll llntiplegl rsqtqfeemr ssyirelika
```

```
181 iglrqkgvvs ssqrfyqltk lldnlhdlvk qlhlyclntf iqsralsvef pemmseviaa 241 qlpkilagmv kpllfhkk
```

Another non-limiting example of a progesterone receptor ligand binding domain is amino acids 14 to 261 of SEQ ID NO: 13. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 14 to 261 of SEQ ID NO: 13.

```
(Human)
                                                    SEQ ID NO: 13
  1 ftfspgqdiq lipplinllm siepdviyag hdntkpdtss slltslnqlg erqllsvvkw 61 skslpgfrnl hiddqitliq yswmslmvfg lgwrsykhvs gqmlyfapdl ilneqrmkes 121 sfyslcltmw qipqefvklq vsgeeflcmk vllllntipl eglrsqtqfe emrssyirel 181 ikaiglrqkg vvsssqrfyq ltklldnlhd lvkqlhlycl ntfiqsrals vefpemmsev 241 iaaqlpkila gmvkpllfhk k
```

Another non-limiting example of a progesterone receptor ligand binding domain is amino acids 679 to 926 of SEQ ID NO: 91. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 679 to 926 of SEQ ID NO: 91.

```
(Mouse)
                                                    SEQ ID NO: 91
  1 mtelqakdpq vlhtsgasps pphigsplla rldsgpfqgs qhsdvssvvs pipisldgll 61 fprscrgpel pdgktgdqqs lsdvegafsg veathreggr nsrapekdsr lldsvldsll 121 tpsgteqsha sppaceaits wclfgpelpe dprsvpatkg llsplmsrpe ikagdssgtg 181 agqkvlpkgl spprqlllpt sgsahwpgag vkpspqpaag eveedsglet egsaapllks 241 kpralegtgs gggvaanaas aapggvtlvp kedsrfsapr vsleqdspia pgrsplattv 301 vdfihvpilp lnhallaart rqllegdsyd ggataqgpfa pprgspsaps ppvpcgdfpd 361 ctyplegdpk edvfplygdf qtpglkikee eegadaavrs prpylsagas sstfpdfpla 421 papqrapssr pgeaavaggp ssaavspass sgsalecily kaegapptqg sfaplpckpp 481 aagscllprd slpaapataa apaiyqplgl nglpqlgyqa avlkdslpqv yppylnylrp 541 dseasgspqy gfdslpqkic licgdeasgc hygvltcgsc kvffkrameg qhnylcagrn 601 dcivdkirrk ncpacrlrkc cqagmvlggr kfkkfnkvrv mrtldgvalp qsvglpnesq 661 algqritfsp nqeiqlvppl inllmsiepd vvyaghdntk pdtssllts lnqlgerqll 721 svvkwskslp gfrnlhiddq itliqyswms lmvfglgwrs ykhvsgqmly fapdlilneq 781 rmkelsfysl cltmwqipqe fvklqvthee flcmkvlllll ntipleglrs qsqfeemrss 841 yirelikaig lrqkgvvpss qrfyqltkll dslhdlvkql hlyclntfiq srtlavefpe 901 mmseviaaql pkilagmvkp llfhkk
```

Another non-limiting example of a progesterone receptor ligand binding domain is amino acids 676 to 923 of SEQ ID NO: 92. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 676 to 923 of SEQ ID NO: 92.

```
(Rat)
                                                          SEQ ID NO: 92
   1 mtelqakdpr tlhtsgaaps pthvgsplla rldpdpfqgs qhsdassvvs pipisldrll 61 fsrscqaqel pdektqnqqs lsdvegafsg veasrrrsrn prapekdsrl ldsvldtlla 121 psgpeqsqts ppaceaitsw clfgpelped prsvpatkgl lsplmsrpes kagdssgtga 181 gqkvlpkavs pprqlllpts gsahwpgagv kpsqqpatve veedgglete gsagpllksk 241 pralegmcsg ggvtanapga apggvtlvpk edsrfsaprv sleqdapvap grsplattvv 301 dfihvpilpl nhallaartr qllegdsydg gaaaqvpfap prgspsapsp pvpcgdfpdc 361 typpegdpke dgfpvygefq ppglkikeee egteaasrsp rpyllagasa atfpdfplpp 421 rpprappsrp geaavaapsa avspvsssgs alecilykae gapptqgsfa plpckppaas 481 scllprdslp aaptssaapa iypplglngl pqlgyqaavl kdslpqvypp ylnylrpdse 541 asqspqygfd slpqkiclic gdeasgchyg vltcgsckvf fkramegqhn ylcagrndci 601 vdkirrkncp acrlrkccqa gmvlggrkfk kfnkvrvmra ldgvalpqsv afpnesqtlg 661 qritfspnqe iqlvpplinl lmsiepdvvy aghdntkpdt ssslltslnq lgerqllsvv 721 kwskslpgfr nlhiddqitl iqyswmslmv fglgwrsykh vsgqmlyfap dlilneqrmk 781 elsfyslclt mwqipqefvk lqvtheeflc mkvllllnti pleglrsqsq feemrssyir 841 elikaiglrq kgvvpssqrf yqltklldsl hdlvkqlhly clntfiqsra lavefpemms 901 eviaaqlpki lagmvkpllf hkk
```

Another non-limiting example of a progesterone receptor ligand binding domain is amino acids 686 to 933 of SEQ ID NO: 93. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 686 to 933 of SEQ ID NO: 93.

```
(Baboon)
                                                          SEQ ID NO: 93
   1 mtelkakgpr aphvaggpps pevgspllcr paagpfqgsq tsdtlpevsa ipisldgllf 61 prpcqgqdpl dektqdqqsl sdvegaysra eatrgtggss srppekdsgl lhsvldtlla 121 psgpgqsqps ppacevtssw clfgpelped ppaapatqgv lsplmsrsgc kagdssgtaa 181 ahkvlprgls psrqlllpas gsphwsgapv kpspqpaave veeedgsese esagpllkgk 241 pralggaaag ggaaavppga aaggvalvpk edsrfsaprv alveqdapma pgrsplattt 301 mdfthvpilp lshallaart rqlleeesyd ggagaasafa pprsspsass tpvavgdfpd 361 cayppdadpk ddayplygdf qppalkikee eegaevsars prsylvagan paafpdfplg 421 ppplppprap psrpgeaavt aapagasvss asssgstlec ilykaegapp qqgpfapppc 481 kapgaggcll prdglpstsa saaaagaapa lypalglngl pqlgyqaavl keglqqvypp 541 ylnylrpdse asgspgysfe slpqkiclic gdeasgchyg vltcgsckvf fkramegqhn 601 ylcagrndci vdkirrkncp acrlrkccqa gmvlggrkfk kfnkvrvmra ldavalpqpv 661 gipnesqals qrftfppgqd iqlipplinl lvsiepdviy aghdnskpdt ssslltslnq
```

-continued

```
721 lgerqllsvv kwskllpgfr nlhiddqitl iqyswmslmv fglgwrsykh vsgqmlyfap 781 dlilneqrmk essfyslclt mwqipqefvk lqvsqeeflc mkvllllnti pleglrsqtq 841 feemrssyir elikaiglrq kgvvsssqrf yqltklldnl hdlvkqlhly clntfiqsra 901 lsvefpemms eviaaqlpki lagmvkpllf hkk
```

In some embodiments, the hormone receptor ligand binding domain is or comprises an androgen receptor ligand binding domain, or a fragment thereof. A non-limiting example of a human androgen receptor ligand binding domain is amino acids 2 of 247 of SEQ ID NO: 14. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 2 to 247 of SEQ ID NO: 14.

```
(Human)
                                                          SEQ ID NO: 14
  1 piflnvleai epgvvcaghd nnqpdsfaal lsslnelger qlvhvvkwak alpgfrnlhv 61 ddqmaviqys wmglmvfamg wrsftnvnsr mlyfapdlvf neyrmhksrm ysqcvrmrhl 121 sqefgwlqit pqeflcmkal llfsiipvdg lknqkffdel rmnyikeldr iiackrknpt 181 scsrrfyqlt klldsvqpia relhqftfdl likshmvsvd fpemmaeiis vqvpkilsgk 241 vkpiyfhtq
```

Another non-limiting example of an androgen receptor ligand binding domain is amino acids 34 to 279 of SEQ ID NO: 15. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 34 to 279 of SEQ ID NO: 15.

```
(Human)
                                                          SEQ ID NO: 15
  1 sleegeasst tspteettqk ltvshiegye cqpiflnvle aiepgvvcag hdnnqpdsfa 61 allsslnelg erqlvhvvkw akalpgfrnl hvddqmaviq yswmglmvfa mgwrsftnvn 121 srmlyfapdl vfneyrmhks rmysqcvrmr hlsqefgwlq itpqeflcmk alllfsiipv 181 dglknqkffd elrmnyikel driiackrkn ptscsrrfyq ltklldsvqp iarelhqftf 241 dllikshmvs vdfpemmaei isvqvpkils gkvkpiyfht qeg
```

Another non-limiting example of an androgen receptor ligand binding domain is amino acids 19 to 264 of SEQ ID NO: 16. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 19 to 264 of SEQ ID NO: 16.

```
(Human)
                                                          SEQ ID NO: 16
  1 ettqkltvsh iegyecqpif lnvleaiepg vvcaghdnnq pdsfaallss lnelgerqlv 61 hvvkwakalp gfrnlhvddq maviqyswmg lmvfamgwrs ftnvnsrmly fapdlvfney 121 rmhksrmysq cvrmrhlsqe fgwlqitpqe flcmkalllf siipvdglkn qkffdelrmn
```

```
181 yikeldriia ckrknptscs rrfyqltkll dsvqpiarel hqftfdllik shmvsvdfpe 241 mmaeiisvqv pkilsgkvkp iyfhtq
```

Another non-limiting example of an androgen receptor ligand binding domain is amino acids 652 to 897 of SEQ ID NO: 94. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 652 to 897 of SEQ ID NO: 94.

```
(Mouse)
                                                             SEQ ID NO: 94
  1 mevqlglgry yprppsktyr gafqnlfqsv reaiqnpgpr hpeaaniapp gaclqqrget 61 sprrrrrqqh tedgspqahi rgptgylale eeqqpsqqqa aseghpessc lpepgaatap 121 gkglpqqppa ppdqddsaap stlsllgptf pglsscsadi kdilneagtm qllqqqqqqq 181 qhqqqhqqhq qqqevisegs sarareatga pssskdsylg gnstisdsak elckaysysm 241 glgvealehl spgeqlrgdc myasllggpp avrptpcapl peckglplde gpgksteeta 301 eyssfkggya kglegeslgc sgsseagssg tleipsslsl yksgaldeaa ayqnrdyynf 361 plalsgpphp pppthphari klenpldygs awaaaaaqcr ygdlgslhgg svagpstgsp 421 pattssswht lftaeeggly gpgggggsss psdagpvapy gytrppqglt sqesdysase 481 vwypggvvnr vpypspncvk semgpwmeny sgpygdmrld strdhvlpid yyfppqktcl 541 icgdeasgch ygaltcgsck vffkraaegk qkylcasrnd ctidkfrrkn cpscrlrkcy 601 eagmtlgark lkklgnlklq eegensnags ptedpsqkmt vshiegyecq piflnvleai 661 epgvvcaghd nnqpdsfaal lsslnelger qlvhvvkwak alpgfrnlhv ddgmavigys 721 wmglmvfamg wrsftnvnsr mlyfapdlvf neyrmhksrm ysqcvrmrhl sgefgwlgit 781 pgeflcmkal llfsiipvdg lknqkffdel rmnyikeldr iiackrknpt scsrrfyqlt 841 klldsvqpia relhqftfdl likshmvsvd fpemmaeiis vqvpkilsgk vkpiyfhtq
```

Another non-limiting example of an androgen receptor ligand binding domain is amino acids 655 to 900 of SEQ ID NO: 95. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 655 to 900 of SEQ ID NO: 95.

```
(Rat)
                                                             SEQ ID NO: 95
  1 mevqlglgrv yprppsktyr gafqnlfqsv reaiqnpgpr hpeaasiapp gaclqqrqet 61 sprrrrrqqh pedgspqahi rgttgylale eeqqpsqqqs aseghpesgc lpepgaatap 121 gkglpqqppa ppdqddsaap stlsllgptf pglsscsadi kdilseagtm qllqqqqqqq 181 qqqqqqqqqq qqqqevise gsssvrarea tgapssskds ylggnstisd sakelckavs 241 vsmglgveal ehlspgeqlr gdcmyasllg gppavrptpc aplaeckgls ldegpgkgte 301 etaeyssfkg gyakgleges lgcsgsseag ssgtleipss lslyksgavd eaaayqnrdy 361 ynfplalsgp phppppthph ariklenpsd ygsawaaaaa qcrygdlasl hggsvagpst 421 gsppatasss whtlftaeeg qlygpgggggg ssspsdagpv apygytrppq glasqegdfs 481 asevwypggv vnrvpypsps cvksemgpwm enysgpygdm rldstrdhvl pidyyfppqk
```

-continued

```
541 tclicgdeas gchygaltcg sckvffkraa egkqkylcas rndctidkfr rkncpscrlr 601 kcyeagmtlg arklkklgnl klqeegenss agsptedpsq kmtvshiegy ecqpiflnvl 661 eaiepgvvca ghdnnqpdsf aallsslnel gerqlvhvvk wakalpgfrn lhvddqmavi 721 qyswmglmvf amgwrsftnv nsrmlyfapd lvfneyrmhk srmysqcvrm rhlsgefgwl 781 qitpqeflcm kalllfsiip vdglknqkff delrmnyike ldriiackrk nptscsrrfy 841 qltklldsvq piarelhqft fdllikshmv svdfpemmae iisvqvpkil sgkvkpiyfh 901 tq
```

Another non-limiting example of an androgen receptor ligand binding domain is amino acids 648 to 893 of SEQ ID NO: 96. In some embodiments, a hormone receptor ligand binding domain is or include a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 648 to 893 of SEQ ID NO: 96.

```
(Baboon)
                                                              SEQ ID NO: 96
  1 mevqlglgrv yprppsktyr gafqnlfqsv reviqnpgpr hpeaasaapp gaslqqqqqq 61 qqqetsprqq qqqgedgsp qahrrgptgy lvldeeqqps qpqsapechp ergcvpepga 121 avaagkglpq qlpappdedd saapstlsll gptfpglssc sadlkdilse astmqllqqq 181 qqeavsegss sgrareasga ptsskdnylg gtstisdsak elckavsvsm glgvealehl 241 spgeqlrgdc myapvlgvpp avrptpcapl aeckgslldd sagkstedta eyspfkggyt 301 kglegeslgc sgsaaagssg tlelpstlsl yksgaldeaa ayqsrdyynf plalagpppp 361 pppphphari klenpldygs awaaaaaqcr ygelaslhga gaagpgsgsp saaasssswht 421 lftaeegqly gpcgggggg gggggagea gavapygytr ppqglagqeg dftapdvwyp 481 ggmvsrvpyp sptcvksemg pwmdsysgpy gdmrletard hvlpidyyfp pqktclicgd 541 easgchygal tcgsckvffk raaegkqkyl casrndctid kfrrkncpsc rlrkcyeagm 601 tlgarklkkl gnlklqeege assttsptee taqkltvshi egyecqpifl nvleaiepgv 661 vcaghdnnqp dsfaallssl nelgerqlvh vvkwakalpg frnlhvddqm aviqyswmgl 721 mvfamgwrsf tnvnsrmlyf apdlvfneyr mhksrmysqc vrmrhlsqef gwlqitpqef 781 lcmkalllfs iipvdglknq kffdelrmny ikeldriiac krknptscsr rfyqltklld 841 svqpiarelh qftfdlliks hmvsvdfpem maeiisvqvp kilsgkvkpi yfhtq
```

Another non-limiting example of a ligand binding domain is SEQ ID NO: 28. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 28.

```
(Human)
                                                              SEQ ID NO: 28
  1 drrggrmlkh krqrddgegr gevgsagdmr aanlwpsplm ikrskknsla lsltadqmvs 61 alldaeppil yseydptrpf seasmmgllt nladrelvhm inwakrvpgf vdltlhdqvh 121 llecawleil miglvwrsme hpgkllfapn llldrnqgkc vegmveifdm llatssrfrm 181 mnlqgeefvc lksiillnsg vytflsstlk sleekdhihr vldkitdtli hlmakagltl 241 qqqhqrlaql llilshirhm snkrmehlys mkcknvvplf dlllemldah rlhapts
```

Another non-limiting example of a ligand binding domain is SEQ ID NO: 29. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 29.

(Human)
SEQ ID NO: 29

```
  1 gqdiqlippl inllmsiepd viyaghdntk pdtsssllts lnqlgerqll svvkwskslp
 61 gfrnlhiddq itliqyswms lmvfglgwrs ykhvsgqmly fapdlilneq rmkessfysl
121 cltmwqipqe fvklqvsqee flcmkvllll ntipleglrs qtqfeemrss yirelikaig
181 lrqkgvvsss qrfyqltkll dnlhdlvkql hlyclntfiq sralsvefpe mmseviaaql
241 pkilagmvkp llfhkk
```

Another non-limiting example of a ligand binding domain is a ligand binding domain of an ecdysone receptor. For example, a ligand binding domain of an ecdysone receptor can be amino acids 256 to 467 of SEQ ID NO: 74. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 256 to 467 of SEQ ID NO: 74.

(Human)
SEQ ID NO: 74

```
  1 merdepppsg gggggsagf leppaalppp prngfcqdel aeldpgtisv sddraeqrtc
 61 licgdratgl hygiiscegc kgffkrsicn krvyrcsrdk ncvmsrkqrn rcqycrllkc
121 lqmgmnrkai redgmpggrn ksigpvqise eeierimsgq efeeeanhws nhgdsdhssp
181 gnrasesnqp spgstlsssr svelngfmaf reqymgmsvp phyqyiphlf sysghspllp
241 qqarsldpqs yslihqllsa edleplgtpm liedgyavtq aelfallcrl adellfrqia
301 wikklpffce lsikdytcll sstwqelill ssltvyskqi fgeladvtak yspsdeelhr
361 fsdegmevie rliylyhkfh qlkvsneeya cmkainflnq dirgltsasq leqlnkrywy
421 icqdfteyky thqpnrfpdl mmclpeiryi agkmvnvple qlpllfkvvl hscktsvgke
```

Another non-limiting example of a ligand binding domain is a ligand binding domain of a PPARγ receptor. For example, a ligand binding domain of a PPARγ receptor can be amino acids 237 to 504 of SEQ ID NO: 75. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 237 to 504 of SEQ ID NO: 75.

(Human)
SEQ ID NO: 75

```
  1 mgetlgdspi dpesdsftdt lsanisqemt mvdtempfwp tnfgissvdl svmedhshsf
 61 dikpfttvdf ssistphyed ipftrtdpvv adykydlklq eyqsaikvep asppyysekt
121 qlynkpheep snslmaiecr vcgdkasgfh ygvhacegck gffrrtirlk liydrcdlnc
181 rihkksrnkc qycrfqkcla vgmshnairf grmpqaekek llaeissdid qlnpesadlr
241 alakhlydsy iksfpltkak arailtgktt dkspfviydm nslmmgedki kfkhitplqe
301 qskevairif qgcqfrsvea vqeiteyaks ipgfvnldln dqvtllkygv heiiytmlas
```

```
361 lmnkdgvlis egqgfmtref lkslrkpfgd fmepkfefav kfnalelddś dlaifiavii 421 lsgdrpglln vkpiediqdn llqalelqlk lnhpessqlf akllqkmtdl rqivtehvql 481 lqvikktetd mslhpllqei ykdly
```

Another non-limiting example of a ligand binding domain is a ligand binding domain of a glucocorticoid receptor. For example, a ligand binding domain of a glucocorticoid receptor can be amino acids 531 to 777 of SEQ ID NO: 76. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 531 to 777 of SEQ ID NO: 76.

```
(Human)
                                                            SEQ ID NO: 76
  1 mdskesltpg reenpssvla qergdvmdfy ktlrggatvk vsasspslav asqsdskqrr 61 llvdfpkgsv snaqqpdlsk avslsmglym getetkvmgn dlgfpqqgqi slssgetdlk 121 lleesianln rstsvpenpk ssastavsaa ptekefpkth sdvsseqqhl kgqtgtnggn 181 vklyttdqst fdilqdlefs sgspgketne spwrsdllid encllsplag eddsfllegn 241 snedckplil pdtkpkikdn gdlvlsspsn vtlpqvktek edfielctpg vikqeklgtv 301 ycqasfpgan iignkmsais vhgvstsggq myhydmntas lsqqqdqkpi fnvippipvg 361 senwnrcqgs gddnltslgt lnfpgrtvfs ngysspsmrp dvssppssss tattgpppkl 421 clvcsdeasg chygvltcgs ckvffkrave gqhnylcagr ndciidkirr kncpacryrk 481 clqagmnlea rktkkkikgi qqattgvsqe tsenpgnkti vpatlpqltp tlvsllevie 541 pevlyagyds svpdstwrim ttlnmlggrq viaavkwaka ipgfrnlhld dgmtllqysw 601 mflmafalgw rsyrqssanl lcfapdliin eqrmtlpcmy dqckhmlyvs selhrlqvsy 661 eeylcmktll llssvpkdgl ksqelfdeir mtyikelgka ivkregnssq nwqrfyqltk 721 lldsmhevve nllnycfqtf ldktmsiefp emlaeiitnq ipkysngnik kllfhqk
```

Another non-limiting example of a ligand binding domain is a ligand binding domain of a thyroid hormone receptor. For example, a ligand binding domain of a glucocorticoid receptor can be amino acids 162 to 370 of SEQ ID NO: 77. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 162 to 370 of SEQ ID NO: 77.

```
(Human)
                                                            SEQ ID NO: 77
  1 meqkpskvec gsdpeensar spdgkrkrkn gqcslktsms gyipsyldkd eqcvvcgdka 61 tgyhyrcitc egckgffrrt iqknlhptys ckydsccvid kitrnqcqlc rfkkciavgm 121 amdlvlddsk rvakrklieq nrerrrkeem irslqqrpep tpeewdlihi ateahrstna 181 qgshwkqrrk flpddigqsp ivsmpdgdkv dleafseftk iitpaitrvv dfakklpmfs 241 elpcedqiil lkgccmeims lraavrydpe sdtltlsgem avkreqlkng glgvvsdaif 301 elgkslsafn lddtevallq avllmstdrs gllcvdkiek sqeayllafe hyvnhrkhni
```

-continued

```
361 phfwpkllmk erevqssily kgaaaegrpg gslgvhpegq qllgmhvvqg pqvrqleqql 421 geagslqgpv lqhqspkspq qrllellhrs gilharavcg eddsseadsp ssseeepevc 481 edlagnaasp
```

Another non-limiting example of a ligand binding domain is a ligand binding domain of a mineralocorticoid receptor. For example, a ligand binding domain of a mineralocorticoid receptor can be amino acids 737 to 984 of SEQ ID NO: 78. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 737 to 984 of SEQ ID NO: 78.

```
(Human)
                                                              SEQ ID NO: 78
  1 metkgyhslp egldmerrwg qvsqaverss lgptertden nymeivnvsc vsgaipnnst 61 qgsskekqel lpclqqdnnr pgiltsdikt eleskelsat vaesmglymd svrdadysye 121 qqnqqgsmsp akiyqnveql vkfykgnghr pstlscvntp lrsfmsdsgs svnggvmrai 181 vkspimchek spsvcspinm tssvcspagi nsyssttasf gsfpvhspit qgtpltcspn 241 aenrgsrshs pahasnvgsp lssplssmks sissppshcs vkspvsspnn vtlrssvssp 301 aninnsrcsv sspsntnnrs tlsspaastv gsicspvnna fsytasgtsa gsstlrdvvp 361 spdtqekgaq evpfpkteev esaisngvtg qlnivqyikp epdgafsssc lggnskinsd 421 ssfsvpikqe stkhscsgts fkgnptvnpf pfmdgsyfsf mddkdyysls gilgppvpgf 481 dgncegsgfp vgikqepddg syypeasips saivgvnsgg qsfhyrigaq gtislsrsar 541 dqsfghlssf ppvntlvesw kshgdlssrr sdgypvleyi penvssstlr svstgssrps 601 kiclvcgdea sgchygvvtc gsckvffkra vegqhnylca grndciidki rrkncpacrl 661 qkclqagmnl garkskklgk lkgiheeqpq qqqpppppppp pqspeegtty iapakepsvn 721 talvpqlsti sraltpspvm vleniepeiv yagydsskpd taenllstln rlagkqmiqv 781 vkwakvlpgf knlpledgit liqyswmcls sfalswrsyk htnsqflyfa pdlvfneekm 841 hqsamyelcq gmhqislqfv rlqltfeeyt imkvllllst ipkdglksqa afeemrtnyi 901 kelrkmvtkc pnnsgqswqr fyqltkllds mhdlvsdlle fcfytfresh alkvefpaml 961 veiisdqlpk vesgnakply fhrk
```

Another non-limiting example of a ligand binding domain is a ligand binding domain of a vitamin D receptor. For example, a ligand binding domain of a vitamin D receptor can be amino acids 124 to 426 of SEQ ID NO: 79. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 124 to 426 of SEQ ID NO: 79.

```
(Human)
                                                              SEQ ID NO: 79
  1 meamaastsl pdpgdfdrnv pricgvcgdr atgfhfnamt cegckgffrr smkrkalftc 61 pfngdcritk dnrrhcqacr lkrcvdigmm kefiltdeev qrkremilkr keeealkdsl 121 rpklseeqqr iiailldahh ktydptysdf cqfrppvrvn dgggshpsrp nsrhtpsfsg 181 dssssscsdhc itssdmmdss sfsnldlsee dsddpsvtle lsqlsmlphl adlvsysiqk 241 vigfakmipg frdltsedqi vllkssaiev imlrsnesft mddmswtcgn qdykyrvsdv
```

-continued

```
301 tkaghsleli eplikfqvgl kklnlheeeh vllmaicivs pdrpgvqdaa lieaiqdrls 361 ntlqtyircr hpppgshlly akmiqkladl rslneehskq yrclsfqpec smkltplvle 421 vfgneis
```

Another non-limiting example of a ligand binding domain is a ligand binding domain of a PPARα receptor. For example, a ligand binding domain of a PPARα receptor can be amino acids 201 to 467 of SEQ ID NO: 80. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 201 to 467 of SEQ ID NO: 80.

```
(Human)
                                                        SEQ ID NO: 80
  1 mvdtesplcp lspleagdle splseeflqe mgniqeisqs igedssgsfg fteyqylgsc 61 pgsdgsvitd tlspasspss vtypvvpgsv despsgalni ecricgdkas gyhygvhace 121 gckgffrrti rlklvydkcd rsckiqkknr nkcqycrfhk clsvgmshna irfgrmprse 181 kaklkaeilt cehdiedset adlkslakri yeaylknfnm nkvkarvils gkasnnppfv 241 ihdmetlcma ektlvaklva ngiqnkeaev rifhccqcts vetvteltef akaipgfanl 301 dlndqvtllk ygvyeaifam lssvmnkdgm lvaygngfit reflkslrkp fcdimepkfd 361 famkfnalel ddsdislfva aiiccgdrpg llnvghiekm qegivhvlrl hlqsnhpddi 421 flfpkllqkm adlrqlvteh aqlvqiikkt esdaalhpll qeiyrdmy
```

Another non-limiting example of a ligand binding domain is a ligand binding domain of a PPARβ/δ receptor. For example, a ligand binding domain of a PPARβ/δ receptor can be amino acids 173 to 440 of SEQ ID NO: 81. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 173 to 440 of SEQ ID NO: 81.

```
(Human)
                                                        SEQ ID NO: 81
  1 meqpqeeape vreeeekeev aeaegapeln ggpqhalpss sytdlsrsss ppslldqlqm 61 gcdgascgsl nmecrvcgdk asgfhygvha cegckgffrr tirmkleyek cersckiqkk 121 nrnkcqycrf qkclalgmsh nairfgrmpe aekrklvagl tanegsqynp qvadlkafsk 181 hiynaylknf nmtkkkarsi ltgkashtap fvihdietlw qaekglvwkg lvnglppyke 241 isvhvfyrcq cttvetvrel tefaksipsf sslflndqvt llkygvheai famlasivnk 301 dgllvangsg fvtreflrsl rkpfsdiiep kfefavkfna lelddsdlal fiaaiilcgd 361 rpglmnvprv eaiqdtilra lefhlqanhp daqylfpkll qkmadlrqlv tehaqmmqri 421 kktetetslh pllqeiykdm y
```

Another non-limiting example of a ligand binding domain is a ligand binding domain of a pregnane X receptor. For example, a ligand binding domain of a pregnane X receptor can be amino acids 143 to 428 of SEQ ID NO: 82. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 143 to 428 of SEQ ID NO: 82.

(Human)

SEQ ID NO: 82

```
  1 mevrpkeswn hadfvhcedt esvpgkpsvn adeevggpqi crvcgdkatg yhfnvmtceg
 61 ckgffrramk rnarlrcpfr kgaceitrkt rrqcqacrlr kclesgmkke mimsdeavee
121 rralikrkks ertgtqplgv qglteeqrmm irelmdaqmk tfdttfshfk nfrlpgvlss
181 gcelpeslqa psreeaakws qvrkdlcslk vslqlrgedg svwnykppad sggkeifsll
241 phmadmstym fkgiisfakv isyfrdlpie dqisllkgaa felcqlrfnt vfnaetgtwe
301 cgrlsycled taggfqqlll epmlkfhyml kklqlheeey vlmgaislfs pdrpgvlqhr
361 vvdqlqeqfa itlksyiecn rpqpahrflf lkimamltel rsinaqhtqr llrigdihpf
421 atplmgelfg itgs
```

Another non-limiting example of a ligand binding domain is a ligand binding domain of a liver X receptor. For example, a ligand binding domain of a liver X receptor can be amino acids 20 to 255 of SEQ ID NO: 83. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 20 to 255 of SEQ ID NO: 83.

(Human)

SEQ ID NO: 83

```
  1 gshmsqgsge gegvqltaaq elmiqqlvaa qlqcnkrsfs dqpkvtpwpl gadpqsrdar
 61 qqrfahftel aiisvqeivd fakqvpgflq lgredqiall kastieimll etarrynhet
121 ecitflkdft yskddfhrag lqvefinpif efsramrrlg lddaeyalli ainifsadrp
181 nvqepgrvea lqqpyveall sytrikrpqd qlrfprmlmk lvslrtlssv hseqvfalrl
241 qdkklpplls eiwdvhe
```

Another non-limiting example of a ligand binding domain is a ligand binding domain of a farnesoid X receptor. For example, a ligand binding domain of a farnesoid X receptor can be amino acids 247 to 467 of SEQ ID NO: 84. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 247 to 467 of SEQ ID NO: 84.

(Human)

SEQ ID NO: 84

```
  1 mgskmnlieh shlpttdefs fsenlfgvlt eqvagplgqn levepysqys nvqfpqvqpq
 61 issssyysnl gfypqqpeew yspgiyelrr mpaetlyqge tevaempvtk kprmgasagr
121 ikgdelcvvc gdrasgyhyn altcegckgf frrsitknav ykcknggncv mdmymrrkcq
181 ecrlrkckem gmlaeclte iqckskrlrk nvkqhadqtv nedsegrdlr qvtsttkscr
241 ekteltpdgq tllhfimdsy nkqrmpqeit nkilkeefsa eenfliltem atnhvqvlve
301 ftkklpgfqt ldhedqiall kgsaveamfl rsaeifnkkl psghsdllee rirnsgisde
361 yitpmfsfyk sigelkmtqe eyalltaivi lspdrqyikd reaveklqep lldvlqklck
421 ihqpenpqhf acllgrltel rtfnhhhaem lmswrvndhk ftpllceiwd vq
```

Another non-limiting example of a ligand binding domain is a ligand binding domain of a RAR-related orphan receptor A. For example, a ligand binding domain of a RAR-related orphan receptor A can be amino acids 217 to 456 of SEQ ID NO: 85. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 217 to 456 of SEQ ID NO: 85.

```
(Human)
                                                         SEQ ID NO: 85
  1 mmyfviaamk aqieiipcki cgdkssgihy gvitcegckg ffrrsqqsna tyscprqknc 61 lidrtsrnrc qhcrlqkcla vgmsrdavkf grmskkqrds lyaevqkhrm qqqqrdhqqq 121 pgeaepltpt ynisanglte lhddlsnyid ghtpegskad sayssfyldi qspdqsgld 181 ingikpepic dytpasgffp ycsftngets ptvsmaeleh laqniskshl etcqylreel 241 qqitwqtflq eeienyqnkq revmwqlcai kiteaiqyvv efakridgfm elcqndqivl 301 lkagslevvf irmcrafdsq nntvyfdgky aspdvfkslg cedfisfvfe fgkslcsmhl 361 tedeialfsa fvlmsadrsw lqekvkiekl qqkiqlalqh vlqknhredg iltklickvs 421 tlralcgrht eklmafkaiy pdivrlhfpp lykelftsef epamqidg
```

Another non-limiting example of a ligand binding domain is a ligand binding domain of a RAR-related orphan receptor C. For example, a ligand binding domain of a RAR-related orphan receptor C can be amino acids 268 to 506 of SEQ ID NO: 86. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 268 to 506 of SEQ ID NO: 86.

```
(Human)
                                                         SEQ ID NO: 86
  1 mdrapqrqhr asrellaakk thtsqievip ckicgdkssg ihygvitceg ckgffrrsqr 61 cnaaysctrq qncpidrtsr nrcqhcrlqk clalgmsrda vkfgrmskkq rdslhaevqk 121 qlqqrqqqqq epvvktppag aqgadtltyt lglpdgqlpl gsspdlpeas acppgllkas 181 gsgpsysnnl akaglngasc hleyspergk aegresfyst gsqltpdrcg lrfeehrhpg 241 lgelgqgpds ygspsfrstp eapyasltei ehlvqsvcks yretcqlrle dllrqrsnif 301 sreevtgyqr ksmwemwerc ahhlteaiqy vvefakrlsg fmelcqndqi vllkagamev 361 vlvrmcrayn adnrtvffeg kyggmelfra lgcselissi fdfshslsal hfsedeialy 421 talvlinahr pglqekrkve qlgynlelaf hhhlckthrq silaklppkg klrslcsqhv 481 erlqifqhlh pivvqaafpp lykelfstet espvglsk
```

Another non-limiting example of a ligand binding domain is a ligand binding domain of a retinoic acid receptor. For example, a ligand binding domain of retinoic acid receptor can be amino acids 156 to 385 of SEQ ID NO: 87. In some embodiments, a hormone receptor ligand binding domain is or includes a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to amino acids 156 to 385 of SEQ ID NO: 87.

(Human)

SEQ ID NO: 87

```
  1 mlgglsppga lttlqhqlpv sgystpspat ietqssssee ivpsppsppp lpriykpcfv 61 cqdkssgyhy gvsacegvkg ffrrsiqknm vytvhrdknc iinkvtrnrc qycrlqkcfe 121 vgmskesvrn drnkkkkevp kpecsesytv tpevgeliek vrkahqetfp alcqlgkytt 181 nnsseqrvsl didlwdkfse lstkciiktv efakqlpgft tltiadqitl lkaacldili 241 lrictrytpe qdtmtfsdgl tlnrtqmhna gfgpltdlvf afanqllple mddaetglls 301 aiclicgdrq dleqpdrvdm lqepllealk vyvrkrrpsr hmfpkmlmki tdlrsisakg 361 aervitlkme ipgsmppliq emlensegld tlsgqpgggg rdggglappp gscspslsps 421 snrsspaths p
```

As can be appreciated in the art, amino acids that are not conserved between different mammalian homologues of hormone receptor ligand binding domains are more likely to not play an important role in the hormone or hormone analogue binding activity of the ligand binding domain, while those amino acids that are conserved between different mammalian homologues of hormone receptor ligand binding domains are more likely to play an important role in the hormone or hormone analogue binding activity of the ligand binding domain. Some ligand binding domains can include one or more (e.g., two, three, four, five, or six) amino acid substitutions of amino acids that are not conserved between different mammalian homologues of hormone receptor ligand binding domains.

Antigen-Binding Domains

In some embodiments of the single-chain chimeric antigen receptors or the multi-chain chimeric antigen receptors, the antigen-binding domain can be selected from a scFv, a scFv-Fc, a $V_H$H domain, a $V_{NAR}$ domain, a (scFv)$_2$, and a BiTE. Additional examples of antigen-binding domains that can be used in a single-chain chimeric antigen receptor or a multi-chain chimeric antigen receptor are known in the art.

A single-chain Fv or scFv fragment includes a $V_H$ domain and a $V_L$ domain in a single polypeptide chain. The $V_H$ and $V_L$ are generally linked by a peptide linker. In other examples, the linker can be a single amino acid. In some examples, the linker can be a chemical bond. See, e.g., Pluckthun, Antibodies from *E. coli*. In Rosenberg M. & Moore G P. (Eds.), The Pharmacology of Monoclonal Antibodies, Vol. 113, pp. 269-315, Spinger-Verlag, New York, 1994. An exemplary $V_L$ and $V_H$ sequences that can be used in a scFv are shown in SEQ ID NOs: 104 and 108 in the Examples. An exemplary linker that can be used between the $V_L$ and $V_H$ domains in an scFv can be any of the exemplary linkers described herein (e.g., a linker having the sequence of SEQ ID NO: 106)

Sc-Fv-Fc fragments include an scFv attached to an Fc domain. For example, an Fc domain can be attached, e.g., to the C-terminus of the scFv. The Fc domain can follow the $V_L$ or $V_H$, depending on the orientation of the variable domains in the scFv. The Fc domain can be any Fc domain known in the art. In some examples, the Fc domain is an IgG1, IgG2, IgG3, or IgG4 Fc domain (e.g., a human IgG1, IgG2, IgG3, or IgG4 Fc domain).

BiTEs are antigen-binding domains that include two $V_L$ and two $V_H$ in a single polypeptide that together form two scFvs, which can each bind to different epitopes on the same antigen or each bind to different antigens. See, e.g., Baeuerle et al., *Curr. Opin. Mol. Ther.* 11:22-30, 2009; Wolf et al., *Drug Discovery Today* 10:1237-1244, 2005; and Huehls et al., *Immunol. Cell Biol.* 93:290-296, 2015.

A $V_H$H domain is a single monomeric variable antibody domain found in camelids, and a $V_{NAR}$ domain is a single monomeric variable antibody domain found in cartilaginous fish. $V_H$H domains and $V_{NAR}$ domains are described in, e.g., Van Audenhove et al., *EBioMedicine* 8:40-48, 2016; Krah et al., *Immunopharmacol. Immunotoxicol.* 38:21-28, 2016; Cromie et al., *Curr. Top. Med. Chem.* 15:2543-2557, 2016; Kijanka et al., *Nanomedicine* 10:161-174, 2015; Kovaleva et al., *Expert. Opin. Biol. Ther.* 14:1527-1539, 2014; De Meyer et al., *Trends Biotechnol.* 32:263-270, 2014; Mujic-Delic et al., *Trends Pharmacol. Sci.* 35:247-255, 2014; Muyldermans, *Ann. Rev. Biochem.* 82:775-797, 2013; Vincke et al., *Methods Mol. Biol.* 911:15-26, 2012; Rahbarizadeh et al., *Immunol. Invest.* 40:299-338, 2011; Van Bockstaele et al., *Curr. Opin. Investig. Drugs* 10:1212-1224, 2009; Wesolowski et al., *Med. Microbiol. Immunol.* 198:157-174, 2009; De Genst et al., *Dev. Comp. Immunol.* 30:187-198, 2006; Muyldermans, *J. Biotechnol.* 74:277-302, 2001; and Muyldermans et al., *Trends Biochem. Sci.* 26:230-235, 2001.

In some embodiments of the multi-chain chimeric antigen receptors, at least two of the polypeptides that make up the multi-chain chimeric antigen receptor can interact together to form an antigen-binding domain. In such embodiments, the antigen-binding domain can be selected from the group of an antigen-binding antibody fragment, a dual-affinity re-targeting antibody (DART), Fab-scFv-Fc, a triomab, a crossmab, an ortho-Fab IgG, IgG-scFv, scFv2-Fc, a bi-nanobody, tanden antibody, a DART-Fe, a scFv-HAS-scFv, DNL-Fab3, DAF (two-in-one or four-in-one), DutaMab, DT-IgG knobs-in-holes common LC, knobs-in-holes assembly, Fab-arm exchange antibody, SEEDbody, Triomab, LUZ-Y, scDiabody-Fc, Fcab, kλ-body, orthogonal Fab, DVD-IgG, IgG(H)-scFv, scFv-(H)IgG IgG(L)-scFv, scFv-(L)-IgG IgG (L,H)-Fc, IgG(H)-V, V(H)—IgG IgG(L)-V, V(L)-IgG KIH IgG-scFab, 2scFv-IgG IgG-2scFv, scFv4-Ig, Zybody, nanobody, nanobody-HSA, a diabody, a TandAb, scDiabody, scDiabody-CH3, charge pair antibody, diabody-CH3, Cov-X-Bod, Triple Body, miniantibody, a DVD-Ig, minibody, a 2-in-1-IgG TriBi minibody, scFv-CH3 KIH, Fab-scFv, scFv-CH-CL-scFv, F(ab')2-scFV2, scFv-KIH, tetravalent HCAb, diabody-Fc, tandem scFv-Fc, intrabody, dock and lock bispecific antibody, ImmTAC, HSAbody, scDiabody-HAS, tandem scFv, IgG-IgG and scFv1-PEG-scFv2.

Non-limiting examples of an antigen-binding antibody fragments include an Fv fragment, a Fab fragment, a F(ab')2 fragment, and a Fab' fragment. Additional examples of an antigen-binding antibody fragment is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

Examples of DVD-Igs are described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645. Examples of DARTs are described in, e.g., Garber, *Nature Reviews Drug Discovery* 13:799-801, 2014. Examples of triomabs, kih IgG with a common LCs, crossmabs, ortho-Fab IgGs, 2-in-1-IgGs, IgG-ScFvs, scFv2-Fcs, bi-nanobodies, tanden antibodies, DART-Fcs, scFv-HAS-scFvs, and DNL-Fab3s are described in, e.g., Kontermann et al., *Drug Discovery Today* 20:838-847, 2015. Examples of DAFs (two-in-one or four-in-one), DutaMabs, DT-IgGs, knobs-in-holes common LCs, knobs-in-holes assemblies, charge pair antibodies, Fab-arm exchange antibodies, SEEDbodies, Triomabs, LUZ-Ys, Fcabs, kλ-bodies, orthogonal Fabs, DVD-IgGs, IgG(H)-scFvs, scFv-(H)IgGs, IgG(L)-scFvs, scFv-(L)-IgGs, IgG (L,H)-Fcs, IgG(H)-Vs, V(H)—IgGs, IgG(L)-Vs, V(L)-IgGs, KIH IgG-scFabs, 2scFv-IgGs, IgG-2scFvs, scFv4-Igs, Zybodies, DVI-IgGs, nanobodies, nanobody-HSAs, diabodies, TandAbs, scDiabodies, scDiabody-CH3s, Diabody-CH3s, Triple Bodies, miniantibodies, minibodies, TriBi minibodies, scFv-CH3 KIHs, Fab-scFvs, scFv-CH-CL-scFvs, F(ab')$_2$-scFV2s, scFv-KIHs, Fab-scFv-Fcs, tetravalent HCAbs, scDiabody-Fcs, diabody-Fcs, tandem scFv-Fcs, intrabodies, dock and lock bispecific antibodies, ImmTACs, HSAbodies, scDiabody-HASs, tandem scFvs, IgG-IgGs, Cov-X-Bodies, and scFv1-PEG-scFv2s are described in, e.g., Spiess et al., *Mol. Immunol.* 67:95-106, 2015.

Any of the antigen-binding domains described herein can bind to an antigen with a dissociation equilibrium constant ($K_D$) of less than $1\times10^{-7}$M, less than $1\times10^{-8}$M, less than $1\times10^{-9}$M, less than $1\times10^{-10}$ M, less than $1\times10^{-11}$M, less than $1\times10^{-12}$M, or less than $1\times10^{-13}$M. In some embodiments, the antigen-binding protein complexes provided herein can bind to a first and/or second antigen with a $K_D$ of about $1\times10^{-4}$M to about $1\times10^{-6}$M, about $1\times10^{-5}$M to about $1\times10^{-7}$M, about $1\times10^{-6}$M to about $1\times10^{-8}$M, about $1\times10^{-7}$M to about $1\times10^{-9}$M, about $1\times10^{-8}$M to about $1\times10^{-10}$ M, or about $1\times10^{-9}$M to about $1\times10^{-11}$M (inclusive). A variety of different methods known in the art can be used to determine the $K_D$ value of an antigen-binding domain (e.g., an electrophoretic mobility shift assay, a filter binding assay, surface plasmon resonance, and a biomolecular binding kinetics assay, etc.).

Antigens

In some embodiments, an antigen-binding domain described herein can bind to a single antigen (e.g., any of the exemplary antigens described herein or known in the art). In some embodiments, an antigen-binding domain described herein can bind to two or more different antigens (e.g., two or more of any of the exemplary antigens described herein or known in the art). Non-limiting examples of antigens include: HER2, A33 antigen, 9-0-acetyl-GD3, CA19-9 marker, BhCGm, CA-125 marker, carboanhydrase IX (MN/CA IX), calreticulin, CCR5, CCR8, CD2, CD3, CD8, CD16, CD19, CD20, CD22, CD24, CD25, CD27, CD28, CD30, CD33, CD38, CD40L, CD44, CD44V6, CD63, CD70, CD84, CD96, CD100, CC123, CD133, CD137, CD138, CD150, CD152 (CTLA-4), CD160, CRTAM, CS1 (CD319), DNAM-1 (CD226), CD229, CD244, CD272 (BTLA), CD274 (PDL-1, B7H1), CD279 (PD-1), CD319, CD352, CRTAM (CD355), CD358, DR3, GITR (TNFRSF 18), HVEM, ICOS, LIGHT, LTBR, OX40, activating forms of KIR, NKG2C, NKG2D, NKG2E, one or more natural cytotoxicity receptors, NTB-A, PEN-5, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), fucosyl GM1, GD2, GD3, GM2, ganglioside GM3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, MUC5AC, MUC5b, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-α precursor, 2B4 (CD244), β2-integrins, KIR, KIR2DL1, KIR2DL2, KIR2DL3, KIR3DL2, KIR-L, KLRGI, LAIR-1, NKG2A, NKR-P IA, Siglec-3, Siglec-7, Siglec-9, TCRa, TCRB, TCR5y, TIM1, LAG3, LAIR1, PD-1H, TIGIT, TIM2, and TIM3. Additional examples of antigens are known in the art.

Costimulatory Domains

In normal lymphocytes, T cell activation is mediated by two classes of intracellular signaling domains. Primary signaling is initiated via MHC-mediated antigen-dependent activation via the T cell receptor (e.g., a TCR/CD3 complex). A secondary or costimulatory signal is provided by a different receptor that includes a costimulatory signaling domain, which acts in an antigen-independent manner. Signals generated through the signaling domain of the TCR alone are insufficient for complete T cell activation; a co-stimulatory signal is also required.

In some embodiments, a single-chain chimeric polypeptide, a single-chain chimeric antigen receptor, or a multi-chain chimeric antigen receptor includes a costimulatory domain, or portion thereof, from an endogenous mammalian (e.g., human) transmembrane polypeptide selected from the group of: CD27 (also known as S152, S152.LPFS2, T14, TNFRSF7, and Tp55), CD28 (also known as Tp44), 4-1BB (also known as TNFRSF9, CD137, CDw137, ILA, and tumor necrosis factor receptor superfamily member 9), OX40 (also known as TNFRSF4, ACT35, RP5-902P8.3, IMD16, CD134, TXGP1L, and tumor necrosis factor receptor superfamily member 4), CD30 (also known as TNFRSF8, D1S166E, and Ki-1), CD40L (also known as CD40LG, CD154, HIGM1, IGM, IMD3, T-BAM, TNFSF5, TRAP, gp39, hCD40L, and CD40 ligand), CD40 (also known as Bp50, CDW40, TNFRSF5, p50, CD40 (protein), and CD40 molecule), PD-1 (also known as PDCD1, CD279, PD-1, SLEB2, hPD-1, hPD-1, hSLE1, and Programmed cell death 1), PD-L1 (also known as CD274, B7-H, B7H1, PD-L1, PDCD1L1, PDCD1LG1, PDL1, CD274 molecule, and Programmed cell death 1 ligand 1), ICOS (also known as AILIM, CD278, and CVID1), LFA-1 (also known as Lymphocyte function-associated antigen 1), CD2 (also known as LFA-2, SRBC, T11, and CD2 molecule), CD7 (also known as GP40, LEU-9, TP41, Tp40, and CD7 molecule), CD160 (also known as BY55, NK1, NK28, and CD160 molecule), LIGHT (also known as TNFSF14, CD258, HVEML, LIGHT, LTg, TR2, TNLG1D, and tumor necrosis factor superfamily member 14), BTLA (also known as CD272 and BTLA1), TIM3 (also known as HAVCR2, HAVcr-2, KIM-3, TIM3, TIMD-3, TIMD3, Tim-3, CD366, and hepatitis A virus cellular receptor 2), CD244 (also known as 2B4, NAIL, NKR2B4, Nmrk, SLAMF4, and CD244 molecule), CD80 (also known as B7, B7-1, B7.1, BB1, CD28LG, CD28LG1, LAB7, and CD80 molecule), LAG3 (also known as CD223 and lymphocyte activating 3), NKG2C (also known as CD314, D12S2489E, KLR, NKG2-D, NKG2D, and killer cell lectin like receptor K1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), TLR1, TLR2, TLR3, TLR4, TLR5, TLR6, TLR7, TLR8, TLR9, TLR10, CARD11, CD54 (ICAM), CD83, DAP10, LAT, SLP76, TRIM, ZAP70, and B7-H3 (also known as CD276, 41g-B7-H3, B7H3, B7RP-2, and CD276 molecule). The letters "CD" is the previous sentence stand for "Cluster of Differentiation." For example, CD3 stands for "Cluster of Differentiation 3." In some embodiments, a single-chain chimeric polypeptide, a single-chain chimeric antigen receptor, or a multi-chain chimeric antigen receptor includes a costimulatory domain, or portion thereof, from an endogenous mammalian (e.g., human) transmembrane polypeptide (e.g., a mammalian or human homolog of any of the polypeptides listed above).

Any costimulatory domain, or portion thereof, that serves to provide a costimulatory signal is suitable for use in accordance with compositions and methods disclosed herein. In some embodiments, a single-chain chimeric polypeptide, a single-chain chimeric antigen receptor, or a multi-chain chimeric antigen receptor includes a costimulatory domain, or portion thereof, from human CD28 (e.g. Accession No. P01747, e.g., from amino acids 180 to 220 of SEQ ID NO: 18). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 18, or a fragment thereof. In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% (or is identical) to SEQ ID NO: 116, or a fragment thereof.

SEQ ID NO: 18
MLRLLLALNLFPSIQVTGNKILVKQSPMLVAYDNAVNLSCKYSYNLFSREF

RASLHKGLDSAVEVCVVYGNYSQQLQVYSKTGFNCDGKLGNESVTFYLQNL

YVNQTDIYFCKIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRS

In some embodiments, a single-chain chimeric polypeptide, a single-chain chimeric antigen receptor, or a multi-chain chimeric antigen receptor includes a costimulatory domain, or portion thereof, from human 4-1BB (e.g. Accession No. Q07011, e.g., from amino acids 214 to 255 of SEQ ID NO: 19). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to amino acids 214 to 255 of SEQ ID NO: 19, or a portion thereof.

SEQ ID NO: 19
MGNSCYNIVATLLLVLNFERTRSLQDPCSNCPAGTFCDNNRNQICSPCPPN

SFSSAGGQRTCDICRQCKGVFRTRKECSSTSNAECDCTPGFHCLGAGCSMC

EQDCKQGQELTKKGCKDCCFGTFNDQKRGICRPWTNCSLDGKSVLVNGTKE

RDVVCGPSPADLSPGASSVTPPAPAREPGHSPQIISFFLALTSTALLFLLF

FLTLRFSVVKRGRKKLLYIFKQPFMRPVQTTQEEDGCSCRFPEEEEGGCEL

In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 44, 57, or 116, or a portion thereof.

A single-chain chimeric polypeptide, a single-chain chimeric antigen receptor, or a multi-chain chimeric antigen receptor disclosed herein can include a costimulatory domain that includes a sequence of amino acids from any isoform of an endogenous mammalian (e.g., human) transmembrane polypeptide having a costimulatory domain including, e.g., an isoform of: CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a costimulatory domain, or portion thereof, of a single-chain chimeric polypeptide, a single-chain chimeric antigen receptor, or a multi-chain chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to a costimulatory domain from one or more of a mammalian (e.g., human) CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments, a costimulatory domain, or portion thereof, of a single-chain chimeric polypeptide, a single-chain chimeric antigen receptor, or a multi-chain chimeric antigen receptor includes a sequence of amino acids having one or more amino acid substitutions, deletions, or additions as compared to a costimulatory domain of one or more of an endogenous mammalian (e.g., human) transmembrane polypeptide: an α chain of a T cell receptor, a β chain of the T cell receptor, a ζ chain of the T cell receptor, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a single-chain chimeric polypeptide, a single-chain chimeric antigen receptor, or a multi-chain chimeric antigen receptor includes a costimulatory domain that is a chimeric costimulatory domain having portions of a costimulatory domain from two or more endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides), such that the two or more portions of the transmembrane domains together constitute a functional costimulatory domain. In some embodiments, such a portion of a chimeric costimulatory domain can include one or more amino acid substitutions, deletions, or additions as compared to a corresponding portion of a wildtype costimulatory domain.

A costimulatory domain of a single-chain chimeric polypeptide, a single-chain chimeric antigen receptor, or a multi-chain chimeric antigen receptor disclosed herein can be of any suitable length. For example, a costimulatory domain can have a length of about 20 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, or about 40 amino acids (inclusive); about 40 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, or about 70 amino acids (inclusive); about 70 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, or about 80 amino acids (inclusive); about 80 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, or about 90 amino acids (inclusive); about 90 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, or about 100 amino acids (inclusive); about 100 amino acids to about 200 amino acids, about 190 amino acids, about 180 amino acids, about 170 amino acids, about 160 amino acids, about 150 amino acids, about 140 amino acids, about 130 amino acids, about 120 amino acids, or about 110 amino acids (inclusive); about 110 amino acids to about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 200 amino acids, about 190 amino acids, about 180 amino acids, about 170 amino acids, about 160 amino acids, about 150 amino acids, about 140 amino acids, or about 130 amino acids (inclusive); about 130 amino acids to about 200 amino acids, about 190 amino acids, about 180 amino acids, about 170 amino acids, about 160 amino acids, about 150 amino acids, or about 140 amino acids (inclusive); about 140 amino acids to about 200 amino acids, about 190 amino acids, about 180 amino acids, about 170 amino acids, about 160 amino acids, or about 150 amino acids (inclusive); about 150 amino acids to about 200 amino acids, about 190 amino acids, about 180 amino acids, about 170 amino acids, or about 160 amino acids (inclusive);

about 160 amino acids to about 200 amino acids, about 190 amino acids, about 180 amino acids, or about 170 amino acids (inclusive); about 170 amino acids to about 200 amino acids, about 190 amino acids, or about 180 amino acids (inclusive); about 180 amino acids to about 200 amino acids or about 190 amino acids (inclusive); or about 190 amino acids to about 200 amino acids (inclusive).

In some embodiments, a single-chain chimeric polypeptide, a single-chain chimeric antigen receptor, or a multi-chain chimeric antigen receptor includes two or more costimulatory domains, e.g., two, three, four, or five, or more costimulatory domains. In some embodiments, the two or more costimulatory domains are identical (e.g., they have the same amino acid sequence). In some embodiments, the costimulatory domains are not identical. For example, the costimulatory domains can be selected from different endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides). In some embodiments, the two or more costimulatory domains can differ from each other by one or more (e.g., two, three, four, or five) amino acid substitutions, deletions, or additions. In some embodiments, the two or more costimulatory domains exhibit at least 85%, 86%, 87%, 88%, 89%, 90%, 91%, 92%, 93%, 94%, 95%, 96%, 97%, 98%, 99% or more sequence identity to each other.

Immunoreceptor Tyrosine-Based Activation Motifs (ITAMs)

ITAMs include a tyrosine separated from a leucine or isoleucine by any two other amino acids, and can thus be represented as, e.g., Tyr-X-X-Leu/Ile. ITAMs are typically repeated (e.g., two or more times) in the cytoplasmic tails of certain cell surface proteins of the immune system, and are typically separated by between six and eight amino acids.

In some embodiments, a single-chain chimeric polypeptide, a single-chain chimeric antigen receptor, or a multi-chain chimeric antigen receptor includes an ITAM, or portion thereof, from an endogenous mammalian (e.g., human) polypeptide, wherein endogenous mammalian (e.g., human) polypeptide is selected from the group of: CD3ζ (also referred to as CD3 zeta), CD3-(CD3 delta), CD3ε(CD3 epsilon), CD3γ (CD3 gamma), DAP12, FCεR1γ (Fc epsilon receptor I gamma chain), FcRγ, FcRft, CD35, CD22, CD79A (antigen receptor complex-associated protein alpha chain), CD79B (antigen receptor complex-associated protein beta chain), and CD66d. The letters "CD" is the previous sentence stand for "Cluster of Differentiation." For example, CD3 stands for "Cluster of Differentiation 3."

Any ITAM, or portion thereof, that serves to mediate signaling in an endogenous mammalian (e.g., human) transmembrane protein suitable for use in accordance with compositions and methods disclosed herein. In some embodiments, a single-chain chimeric polypeptide, a single-chain chimeric antigen receptor, or a multi-chain chimeric antigen receptor includes an ITAM, or portion thereof, from human CD3 zeta (e.g. Accession No. P20963, e.g., an ITAM present in amino acids 52-164 of SEQ ID NO: 17, or a portion thereof; or SEQ ID NO: 118 or a portion thereof). In some embodiments, an ITAM comprises a sequence that is at least 80% (e.g., at least 82%, at least 84%, at least 86%, at least 88%, at least 90%, at least 92%, at least 94%, at least 96%, at least 98%, at least 99%, or 100% identical to: the sequence of amino acids 52-165 of SEQ ID NO: 17 (or a portion thereof), or the sequence of SEQ ID NO: 118 (or a portion thereof).

```
                                    SEQ ID NO: 17
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR
```

In some embodiments, an ITAM comprises a sequence that is or includes a sequence that is at least 80% (e.g., at least 82%, at least 84%, at least 86%, at least 88%, at least 90%, at least 92%, at least 94%, at least 96%, at least 98%, at least 99%, or 100%) identical to SEQ ID NO: 48, 61, or 118, or a portion thereof.

As will be appreciated by those of ordinary skill in the art, certain polypeptides have two or more isoforms that differ at least in their primary polypeptide sequence. For example, different isoforms can be generated as a result of alternative splicing. A single-chain chimeric polypeptide, a single-chain chimeric antigen receptor, or a multi-chain chimeric antigen receptor disclosed herein can include an ITAM that includes a sequence of amino acids from any isoform of an endogenous mammalian transmembrane polypeptide having an ITAM including, e.g., a mammalian (e.g., human) isoform of: CD3, CD3D, CD3E, CD3G, DAP12, FCER1G, FcRy, FcRft, CD35, CD22, CD79A, CD79B, or CD66d.

In some embodiments, an ITAM, or portion thereof, of a single-chain chimeric polypeptide, a single-chain chimeric antigen receptor, or a multi-chain chimeric antigen receptor includes a sequence of amino acids having one or more (e.g., two, three, four, or five) amino acid substitutions, deletions, or additions as compared to an ITAM of one or more of an ITAM in an endogenous mammalian (e.g., human) transmembrane protein, such as, CD3, CD3D, CD3E, CD3G, DAP12, FCER1G, FcRy, FcRft, CD35, CD22, CD79A, CD79B, or CD66d. For example, the tyrosine and leucine or isoleucine of an ITAM could be retained, while the two amino acids separating them could be replaced with different amino acids.

In some embodiments, a single-chain chimeric polypeptide, a single-chain chimeric antigen receptor, or a multi-chain chimeric antigen receptor includes an ITAM that is a chimeric ITAM having portions of an ITAM from two or more endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B, or CD66d (including, without limitation, a mammalian or human homolog of any of these polypeptides), such that the two or more ITAM portions together constitute a functional ITAM. In some embodiments, such a portion of a chimeric ITAM can include one or more amino acid substitutions, deletions, or additions as compared to a corresponding portion of a wild type ITAM.

In some embodiments, a single-chain chimeric polypeptide, a single-chain chimeric antigen receptor, or a multi-chain chimeric antigen receptor includes two or more ITAMs, e.g., two, three, four, or five, or more ITAMs. In some embodiments, the two or more ITAMs are identical (e.g., they have the same amino acid sequence). In some embodiments, the two or more ITAMs are not identical. For example, the ITAMs can be selected from different endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B (including, without limitation, a mammalian or human homolog of any of these polypeptides). In some embodiments, the two or more ITAMs can differ from each other by one or more amino acid substitutions, deletions, or additions.

Nucleic Acids

Also provided herein are nucleic acids that encode any of the single-chain chimeric polypeptides, single-chain chimeric antigen receptors, and multi-chain chimeric antigen receptors. Also provided herein are a set of nucleic acids that encode one or more single-chain polypeptides that make up a multi-chain chimeric polypeptide (e.g., where at least one single-chain polypeptide that makes up the multi-chain chimeric polypeptide is encoded by each nucleic acid in the set).

Vectors

Provided herein are vectors that include any of the nucleic acids provided herein. A "vector" according to the present disclosure is a polynucleotide capable of inducing the expression of a recombinant protein (e.g., a single-chain chimeric polypeptide, a single-chain chimeric antigen receptor, or a multi-chain chimeric antigen receptor) in a mammalian cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., Exp. Hematol. 28(10:1137-1146, 2000; Park et al., Trends Biotechnol. 29(11):550-557, 2011; and Alonso-Camino et al., Mol. Ther. Nucleic Acids 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., BioTechniques 7:980-990, 1989; Miller, Human Gene Therapy 1:5-14, 1990; Scarpa et al., Virology 180:849-852, 1991; Burns et al., Proc. Natl. Acad. Sci. U.S.A. 90:8033-8037, 1993; and Boris-Lawrie et al., Cur. Opin. Genet. Develop. 3:102-109, 1993. Exemplary lentiviral vectors are described in, e.g., Wang et al., J. Immunother. 35(9):689-701, 2003; Cooper et al., Blood 101:1637-1644, 2003; Verhoeyen et al., Methods Mol. Biol. 506:97-114, 2009; and Cavalieri et al., Blood 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter and/or enhancer operably linked to any of the nucleic acids described herein. Non-limiting examples of promoters include promoters from human cytomegalovirus (CMV), mouse phosphoglycerate kinase 1, polyoma adenovirus, thyroid stimulating hormone a, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQβ, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the single-chain chimeric polypeptide, the single-chain chimeric antigen receptor, or any of the polypeptides that make up the multi-chain chimeric antigen receptor. Non-limiting examples of a poly(A) sequence include those derived from bovine growth hormone (Woychik et al., Proc. Natl. Acad. Sci. U.S.A. 81(13): 3944-3948, 1984, and U.S. Pat. No. 5,122,458), mouse-β-globin, mouse-α-globin (Orkin et al., EMBO J. 4(2): 453-456, 1985), human collagen, polyoma virus (Batt et al., Mol. Cell Biol. 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., Mol. Therapy 15(7): 1340-1347, 2007), SV40 poly(A) site, e.g., SV40 late and early poly(A) site (Schek et al., Mol. Cell Biol. 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2).

A poly(A) sequence can, e.g., be a synthetic polyadenylation site. See, e.g., Levitt el al, Genes Dev. 3(7): 1019-1025, 1989). In some examples, a poly(A) sequence can be the polyadenylation signal of soluble neuropilin-1: AAATAAAATACGAAATG. Additional examples of poly (A) sequences are known in the art. Additional examples and aspects of vectors are also known in the art.

Methods of Introducing a Nucleic Acid or Vectors into a Mammalian Cell

A variety of different methods known in the art can be used to introduce any of the nucleic acids and vectors disclosed herein into a mammalian cell (e.g., any of the mammalian cells described herein, e.g., any of the T cells (e.g., human T cells) described herein). Non-limiting examples of methods that can be used to introduce a nucleic acid or vector into a mammalian cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. Additional methods of introducing a nucleic acid or vector into a mammalian cell are known in the art.

Mammalian Cells

Also provided herein are mammalian cells that include any of the nucleic acids or vectors described herein. In some embodiments, the mammalian cell is previously obtained from a subject (e.g., a human subject, e.g., a human subject identified or diagnosed as having a cancer).

Non-limiting examples of mammalian cells include a T cell (e.g., a human T cell). Non limiting examples of T cells (e.g., human T cells) include, e.g., an immature thymocyte, a peripheral blood lymphocyte, a naïve T cell, a pluripotent $T_H$ cell precursor, a lymphoid progenitor cell, a $T_{reg}$ cell, a memory T cell, a $T_H17$ cell, a $T_H22$ cell, a $T_H9$ cell, a $T_H2$ cell, a $T_H1$ cell, a $T_H3$ cell, γ6 T cell, an αβ T cell, a Treg cell, and a tumor-infiltrating T cell. Additional examples of a T cell (e.g., a human T cell) include a CD8+ T cell, a CD4+ T cell, and natural killer T cell. Additional examples of mammalian cells include a mast cell, a macrophage, a neutrophil, a dendritic cell, a basophil, an eosinophil, and a natural killer cell.

Hormones and Hormone Analogues

Non-limiting examples of hormones include estrogen (17β-estradiol), progesterone, testosterone, and dihydrotestosterone. Non-limiting examples of hormone analogues include estrogen hormone analogues, progesterone hormone analogues, and androgen hormone analogues.

Non-limiting examples of estrogen hormone analogues include: afimoxifene (also known as 4-hydroxytamoxifen, 4-OHT, 4-HT, and OHTAM); selective estrogen receptor modulators (SERMs), such as clomifene, ormeloxifene, raloxifene, tamoxifen, toremifene, lasofoxifene, and ospemifene; estradiol; estrone; raloxifene; estriol; genistein; phytoestrogens (e.g., isoflavones, such as genistein, daidzein, formononetin, and glycitein; coumestans, such as coumestrol and repensol andtrifoliol; and lignans, such as lariciresinol, matairesinol, pinoresinol, secoisolariciresinol, podophyllotoxin, and steganacin); and xenoestrogens (e.g., diethylstilbestrol, ethinyl estradiol, butylated hydroxyanisole, erythrosine, camphors (e.g., 4-methylbenzylidene camphor), parabens (e.g., methylparaben, ethylparaben and propylparaben), atrazine, dichlorodiphenyldichloroethylene, dichlorodiphenyltrichloroethane, methoxychlor, dieldrin, endosulfan, heptachlor, lindane, phenols (e.g., bisphenol A and nonylphenol), biphenyls (e.g., monochlorobiphenyl and dichlorobiphenyl), phthalates (e.g., di-2-ethylhexyl phthalate, diisodecyl phthalate and diisononyl phthalate), and metalloestrogens). In some embodiments, an estrogen hormone analogue can be, e.g., mifepristone (also known as RU-486). In some embodiments, an estrogen hormone analogue can be a selective progesterone receptor modulator (SPRM), such as onapristone (ZK98299), lonaprisan (ZK230211, BAY86-5044), APR19, EC304, WAY-255348, ORG31710, asoprisnil (J867), telapristone (Proellex, CDB-4124), and CDB-2914 (ulipristal acetates).

Non-limiting examples of progesterone hormone analogues include selective progesterone receptor modulators (SPRMs), such as onapristone (ZK98299), lonaprisan (ZK230211, BAY86-5044), APR19, EC304, WAY-255348, ORG31710, asoprisnil (J867), telapristone (Proellex, CDB-4124), and CDB-2914 (ulipristal acetates).

Non-limiting examples of androgen hormone analogues include enobosarm (also known as ostarine, MK-2866, GTx-024, and S-22), BMS-564,929, LGD-4033 (ligandrol), AC-262,356, JNJ-28330835, LGD-2226, LGD-3303, S-40503, S-23, RAD140, acetothiolutamide, Andarine, LG-121071, TFM-4AS-1, and YK-11.

As can be appreciated in the art, estrogen or an estrogen hormone analogue can be used in together with a single-chain chimeric polypeptide, a single-chain chimeric antigen receptor, or a multi-chain chimeric antigen receptor that includes an estrogen receptor ligand binding domain.

Compositions and Kits

Also provided herein are compositions (e.g., pharmaceutical compositions) that include any of the nucleic acids, vectors, sets of nucleic acids, sets of vectors, or mammalian cells described herein. For example, provided herein is a composition that includes any of the nucleic acids or sets of nucleic acids described herein, or any of the vectors or sets of vectors provided herein and a pharmaceutically acceptable solvent or carrier.

In some embodiments, a composition can be any of the mammalian cells described herein (e.g., any of the mammalian cells described herein previously obtained from a subject, e.g., a subject identified or diagnosed as having a cancer) comprising a nucleic acid encoding any of the single-chain chimeric polypeptides, single-chain chimeric antigen receptors, or multi-chain chimeric antigen receptors described herein. In a composition including any of the mammalian cells described herein, the composition can further include a cell culture medium or a pharmaceutically acceptable buffer (e.g., phosphate-buffered saline). A composition that includes any of the mammalian cells described herein can be formulated for intravenous or intraarterial administration.

Also provided are kits that include one or more of any of the compositions described herein. For example, a kit can include any of the compositions described herein and one or more doses of a hormone or hormone analogue formulated for administration to a subject (e.g., formulated for oral, intravenous, intramuscular, or subcutaneous administration). In some embodiments, a kit can further include instructions for performing any of the methods described herein.

Methods of Inducing the Membrane Localization of a Single-Chain Chimeric Polypeptide, a Single-Chain Chimeric Antigen Receptor, or a Multi-Chain Chimeric Polypeptide in a Mammalian Cell Also provided herein are methods of inducing the membrane localization of a single-chain chimeric polypeptide (e.g., any of the single-chain chimeric polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) in a mammalian cell (e.g., any of the mammalian cells described herein) that include: contacting a mammalian cell expressing a single-chain chimeric polypeptide (e.g., any of the single-chain chimeric polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) with an amount of a hormone or a hormone analogue sufficient to induce localization of the single-chain chimeric polypeptide, the single-chain chimeric antigen-binding receptor, or the multi-chain chimeric antigen receptor to the extracellular side of the plasma membrane of the cell, respectively.

Some embodiments of these methods further include introducing a nucleic acid encoding the single-chain chimeric polypeptide, the single-chain chimeric antigen receptor, or the multi-chain chimeric antigen receptor into a mammalian cell (e.g., any of the mammalian cells described herein or known in the art) to generate the mammalian cell expressing the single-chain chimeric polypeptide, the single-chain chimeric antigen receptor, or the multi-chain chimeric antigen receptor, respectively. In some examples of these methods, the mammalian cell is a T cell (e.g., a CD8+ T cell, a CD4+ T cell, a memory T cell, a Treg cell, and a natural killer T cell). In some examples, the mammalian cell (e.g., any of the mammalian cells described herein) is a mammalian cell previously obtained from a subject (e.g., a subject that has been identified or diagnosed as having a cancer, e.g., any of the cancers described herein). Some embodiments of these methods further include obtaining the mammalian cell from the subject.

In some embodiments of any of these methods, the contacting step is performed in vitro. In some embodiments of any of these methods, the contacting step is performed in a mammal (e.g., a mammal, e.g., a human, having a cancer, e.g., any of the cancers described herein). In some embodiments, the contacting step results in the treatment of the cancer in a mammal (e.g., a human).

Non-limiting examples of cancer that can be treated using any of the methods provided herein include: acute lymphoblastic leukemia, acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastric cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, gastric cancer, testicular cancer, throat cancer, thyroid cancer, urethral cancer, uterine cancer, vaginal cancer, and vulvar cancer.

In some embodiments of any of these methods, the methods result in a decrease in the tumor burden (e.g., tumor mass and/or volume) in a subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the tumor burden in a subject (e.g., as compared to the tumor burden in the subject prior to treatment).

In some embodiments, the methods result in a decrease in the rate of progression of a cancer in the subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the rate of progression of a cancer in a subject (e.g., as compared to the rate of progression of a cancer in the subject prior to treatment or in a control subject or a control population of subjects having the same cancer and administered no treatment or a different treatment).

In some embodiments of any of these methods, the methods result in an increase in the time of survival of a cancer in a subject. For example, any of the methods described herein can result in an about 1% to about 800% (e.g., about 1% to about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, about 10%, or about 5% (inclusive); about 5% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, or about 10% (inclusive); about 10% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, or about 20% (inclusive); about 20% to about 800%, about 750%, about 700%, about 650%, about 600%, about 550%, about 500%, about 450%, about 400%, about 350%, about 300%, about 250%, about 200%, about 150%, about 100%, about 80%, about 60%, or about 40% (inclusive); about 40% to about 800%, about 750%, about 700%, about 650%, about 600%, about 550%, about 500%, about 450%, about 400%, about 350%, about 300%, about 250%, about 200%, about 150%, about 100%, about 80%, or about 60% (inclusive); about 60% to about 800%, about 750%, about 700%, about 650%, about 600%, about 550%, about 500%, about 450%, about 400%, about 350%, about 300%, about 250%, about 200%, about 150%, about 100%, about 80% (inclusive); about 80% to about 800%, about 750%, about 700%, about 650%, about 600%, about 550%, about 500%, about 450%, about 400%, about 350%, about 300%, about 250%, about 200%, about 150%, or about 100% (inclusive); about 100% to about 800%, about 750%, about 700%, about 650%, about 600%, about 550%, about 500%, about 450%, about 400%, about 350%, about 300%, about 250%, about 200%, or about 150% (inclusive); about 150% to about 800%, about 750%, about 700%, about 650%, about 600%, about 550%, about 500%, about 450%, about 400%, about 350%, about 300%, about 250%, or about 200% (inclusive); about 200% to about 800%, about 750%, about 700%, about 650%, about 600%, about 550%, about 500%, about 450%, about 400%, about 350%, about 300%, or about 250% (inclusive); about 250% to about 800%, about 750%, about 700%, about 650%, about 600%, about 550%, about 500%, about 450%, about 400%, about 350%, or about 300% (inclusive); about 300% to about 800%, about 750%, about 700%, about 650%, about 600%, about 550%, about 500%, about 450%, about 400%, or about 350% (inclusive); about 350% to about 800%, about 750%, about 700%, about 650%, about 600%, about 550%, about 500%, about 450%, or about 400% (inclusive); about 400% to about 800%, about 750%, about 700%, about 650%, about 600%, about 550%, about 500%, or about 450% (inclusive); about 450% to about 800%, about 750%, about 700%, about 650%, about 600%, about 550%, or about 500% (inclusive); about 500% to about 800%, about 750%, about 700%, about 650%, about 600%, or about 550% (inclusive); about 550% to about 800%, about 750%, about 700%, about 650%, or about 600% (inclusive); about 600% to about 800%, about 750%, about 700%, or about 650% (inclusive); about 650% to about 800%, about 750%, or about 700% (inclusive); about 700% to about 800% or about 750% (inclusive); or about 750% to about 800% (inclusive)) increase in the time of survival of a cancer in a subject (e.g., as compared to the time of survival for a control subject or a population of control subjects having the same cancer and receiving no treatment or a different treatment).

Methods of Reversibly Altering the Membrane Localization of a Single-Chain Chimeric Polypeptide, a Single-Chain Chimeric Antigen Receptor, or a Multi-Chain Chimeric Polypeptide in a Mammalian Cell Also provided herein are methods of reversibly altering the membrane localization of a single-chain chimeric polypeptide (e.g., any of the single-chain polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) in a mammalian cell that include: (a) contacting a mammalian cell (e.g., any of the mammalian cells described herein) expressing a single-chain chimeric polypeptide (e.g., any of the single-chain polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) with an amount of a hormone or a hormone analogue sufficient to induce localization of the single-chain chimeric polypeptide, the single-chain chimeric antigen receptor, or the multi-chain chimeric antigen receptor to the extracellular side of the plasma membrane of the cell, respectively; and (b) contacting the mammalian cell with a reduced amount of the hormone or the hormone analogue that results in a decreased level of the single-chain chimeric polypeptide, the single-chain chimeric antigen receptor, or the multi-chain chimeric antigen receptor on the extracellular side of the plasma membrane of the mammalian cell (e.g., as compared to the level on the extracellular side of the plasma membrane in step (a)). In some embodiments, the decreased level in step (b) is at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease in the level of the single-chain chimeric polypeptide, the single-chain chimeric antigen receptor, or the multi-chain chimeric antigen receptor on the extracellular side of the plasma membrane in step (a). In some embodiments, the decreased level in step (b) is a 100% decrease in the level of the single-chain chimeric polypeptide, the single-chain chimeric antigen receptor, or the multi-chain chimeric antigen receptor on the extracellular side of the plasma membrane in step (a). In some embodiments, the mammalian cell is not contacted with any hormone or hormone analogue hormone in step (b). Some embodiments of these methods further include: (c) contacting the mammalian cell (e.g., any of the mammalian cells described herein) with an increased amount of the hormone or the hormone analogue that results in an increased level of the single-chain chimeric polypeptide, the single-chain chimeric antigen receptor, or the multi-chain chimeric antigen receptor on the extracellular side of the plasma membrane of the cell as compared to the level of in step (b).

Some embodiments of any of these methods further include introducing a nucleic acid encoding the single-chain chimeric polypeptide into a mammalian cell (e.g., any of the mammalian cells described herein) to generate the mammalian cell expressing the single-chain chimeric polypeptide, the single-chain chimeric antigen receptor, or the multi-chain chimeric antigen receptor. In some embodiments of any of the methods described herein, the mammalian cell is a T cell (e.g., a human T cell). In some embodiments, the T cell (e.g., human T cell) is selected from the group of a $CD8^+$ T cell, a $CD4^+$ T cell, a memory T cell, a Treg cell, and natural killer T cell. In some embodiments, the mammalian cell is a mammalian cell previously obtained from a subject (e.g., a human). In some examples, the subject (e.g., human) has been identified or diagnosed as having a cancer (e.g., any of the types of cancer described herein). Some embodiments further include obtaining the mammalian cell from the subject.

In some embodiments of any of the methods described herein, the contacting step is performed in vitro. In some embodiments, the contacting step is performed in a mammal (e.g., in a subject). In some embodiments, the contacting step results in the treatment of the cancer in a mammal (e.g., a human).

Non-limiting examples of cancer that can be treated using any of the methods provided herein include: acute lymphoblastic leukemia, acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastric cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, gastric cancer, testicular cancer, throat cancer, thyroid cancer, urethral cancer, uterine cancer, vaginal cancer, and vulvar cancer.

Methods of Controlling the Toxicity of a Single-Chain Chimeric Polypeptide, a Single-Chain Chimeric Antigen Receptor, or a Multi-Chain Chimeric Polypeptide in a Mammalian Cell by Reversibly Altering Membrane Localization of the Same In some embodiments, compositions and/or methods disclosed herein can be used to selectively kill cancer cells in a subject (e.g., a human) in the presence of a hormone or a hormone analogue which binds to an LBD present in the polypeptide (e.g., a single-chain chimeric polypeptide, a single-chain chimeric antigen receptor, or a multi-chain chimeric antigen receptor). In some embodiments, in the presence of the hormone or hormone analogue, the polypeptide (e.g., the single-chain chimeric polypeptide, the single-chain chimeric antigen receptor, or the multi-chain chimeric antigen receptor) localizes to the extracellular surface of a mammalian cell, presenting its antigen binding domain (e.g., an scFv or any other antigen binding domain described herein or known in the art) on the exterior of the cell. The polypeptide can then recognize the antigen to which it binds, and thus can selectively kill a target cell expressing the antigen on its surface.

In some embodiments, localization of the polypeptide (e.g., the single-chain chimeric polypeptide, the single-chain chimeric antigen receptor, or the multi-chain chimeric antigen receptor) on the extracellular surface can cause toxicity in the subject. Such toxicity can be caused by, for example, a cytokine storm (also referred to as hypercytokinemia or cytokine release syndrome). In some embodiments, a subject experiencing toxicity due hormone- or hormone analogue-induced localization of the polypeptide to the extracellular surface can be treated by reducing the dose of the hormone or hormone analogue administered to the subject, or eliminating hormone or hormone analogue treatment altogether. Such reduction in dose or elimination of the hormone or hormone analgue treatment can cause the polypeptide to be removed from the cell surface and reduce or eliminate presentation of the antigen binding domain on the cell surface, thus reducing or eliminating toxicity in the subject.

Exemplary symptoms of toxicity include, without limitation, high fever, swelling, chills, hypotension, tachycardia, asthenia, headache, rash, scratchy throat, dyspnea, redness, extreme fatigue, nausea, and cerebral edema (swelling in the brain). In some embodiments, toxicity in a subject can be determined by assessing the presence or severity of one or more of these symptoms in a subject following administration of one or more doses of the hormone or hormone analogue to the subject. In some embodiments, one or more of these or other symptoms associated with toxicity can be determined after introducing into a subject a mammalian cell (e.g., a T cell) that includes a single-chain chimeric polypeptide (e.g., any of the single-chain polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) having a LBD, and a hormone or hormone analogue that binds the LBD. In some embodiments, the determined level of one or more of these or other symptoms associated with toxicity can be compared to a baseline level that is associated with lack of a toxicity or a reduced level of toxicity. Such a baseline level can be, for example, the level of one or more of these or other symptoms in the subject prior to administration of the mammalian cell, the hormone or hormone analogue, or both. Additionally or alternatively, such a baseline level can be the level of one or more of these or other symptoms in a different subject that has not been administered the mammalian cell, the hormone or hormone analogue, or both. Those of ordinary skill in the art will be aware of suitable clinical and laboratory methods to determine the level of one or more symptoms associated with toxicity.

In some embodiments, toxicity can be the result of a cytokine storm. Both pro-inflammatory cytokines and anti-inflammatory cytokines are elevated in the serum of subjects experiencing a cytokine storm. Non-limiting examples of cytokines that are elevated in the serum of subjects experiencing a cytokine storm include tumor necrosis factor-alpha, IFNγ, IL-10, IL-1β, IL-2, IL-6, IL-8, and IL-10, granulocyte macrophage-colony-stimulating factor (GM-CSF), and IL-5. In some embodiments, one or more of these or other cytokines associated with a cytokine storm are determined after introducing into a subject a mammalian cell (e.g., a T cell) that includes a single-chain chimeric polypeptide (e.g., any of the single-chain polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) having a LBD, and a hormone or hormone analogue that binds the LBD. In some embodiments, the determined level of one or more of these or other cytokines associated with a cytokine storm can be compared to a baseline level that is associated with lack of a cytokine storm or a reduced level of a cytokine storm. Such a baseline level can be, for example, the level of one or more of these or other cytokines in the subject prior to administration of the mammalian cell, the hormone or hormone analogue, or both. Additionally or alternatively, such a baseline level can be the level of one or more of these or other cytokines in a different subject that has not been administered the mammalian cell, the hormone or hormone analogue, or both. The level of a cytokine (e.g., the level of cytokine after administering to a subject the mammalian cell and the hormone or hormone analogue and/or the baseline level of a cytokine), can be determined by any of a variety of methods and techniques, including, without limitation, ELISAs, Western blots, antibody array panels, multiplex arrays, Elispot assays, immunohistochemistry, or any of the variety of commercial assays available to determine cytokine levels.

In some embodiments, methods of treating cancer (e.g., any of the variety of cancers described herein) in a subject (e.g., a mammal, e.g., a human) are provided. In some embodiments, methods of treating cancer include: (a) administering to a subject a mammalian cell (e.g., a T cell) that includes a nucleic acid encoding a single-chain chimeric polypeptide (e.g., any of the single-chain polypeptides described herein), a single-chain chimeric antigen receptor (e.g., any of the single-chain chimeric antigen receptors described herein), or a multi-chain chimeric antigen receptor (e.g., any of the multi-chain chimeric antigen receptors described herein) having a hormone receptor LBD, (b) administering to the subject a hormone or hormone analogue that binds the LBD, (c) determining the level of one or more symptoms associated with toxicity and/or the level of one or more cytokines associated with a cytokine storm, (d) comparing the determined level of one or more symptoms associated with toxicity and/or the level of one or more cytokines associated with a cytokine storm to a baseline level of the symptom or cytokine, and (e) reducing the amount of the hormone or hormone analogue administered to the subject, such that the determined level of one or more symptoms associated with toxicity and/or the level of one or more cytokines associated with a cytokine storm is reduced. In some embodiments the level of the hormone or hormone analogue administered to the subject is reduced in step (e) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the level of the hormone or hormone analogue administered to the subject is reduced in step (e) by 100% (e.g., no mammalian cell is administered to the subject in step (e)). In some embodiments, after administering the hormone or hormone analogue in step (b), the single-chain chimeric polypeptide, the single-chain chimeric antigen receptor, and/or the multi-chain chimeric antigen receptor localizes the extracellular surface of the mammalian cell in a reversible manner. In some embodiments, after reducing the amount of the hormone or hormone analogue administered to the subject in step (e), the single-chain chimeric polypeptide, the single-chain chimeric antigen receptor, and/or the multi-chain chimeric antigen receptor is removed from the extracellular surface, thus reducing the toxicity (e.g., one or more symptoms associated with toxicity and/or one or more cytokines associated with a cytokine storm). In some embodiments, after reducing the amount of the hormone or hormone analogue administered to the subject in step (e), the toxicity (e.g., one or more symptoms associated with toxicity and/or one or more cytokines associated with a cytokine storm) is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, after reducing the amount of the hormone or hormone analogue administered to the subject in step (e), the toxicity (e.g., one or more symptoms associated with toxicity and/or one or more cytokines associated with a cytokine storm) is reduced by 100% (e.g., the subject experiences no toxicity, or only a baseline level of toxicity). In some embodiments, after reducing the amount of the hormone or hormone analogue administered to the subject in step (e), the toxicity (e.g., one or more symptoms associated with toxicity and/or one or more cytokines associated with a cytokine storm) normalizes towards a baseline level of toxicity (e.g., a level that is associated with lack of a cytokine storm or a reduced level of a cytokine storm). For example, after reducing the amount of the hormone or hormone analogue administered to the subject in step (e), the toxicity can normalize to a level that is less than 10-fold higher, 9-fold higher, 8-fold higher, 7-fold higher, 6-fold higher, 5-fold higher, 4-fold higher, 3-fold higher, 2-fold higher, or less than the baseline level of toxicity.

In some embodiments, a subject can be treated by administering to the subject a mammalian cell (e.g., a T cell) that includes a single-chain chimeric polypeptide (e.g., any of the single-chain polypeptides described herein), a single-chain chimeric antigen receptor (e.g., any of the single-chain chimeric antigen receptors described herein), and/or a multi-chain chimeric antigen receptor (e.g., any of the multi-chain chimeric antigen receptors described herein) having a LBD and a hormone or hormone analogue that binds the LBD. The level of toxicity in the subject can be monitored, and toxicity can be reduced by any of the methods described herein, e.g., by reducing the level of the hormone or hormone analogue. After toxicity has been reduced (e.g., to a baseline level, or a level above the baseline level that is sufficiently low), the level of the hormone or hormone analogue can be subsequently increased to increase the efficacy of treatment. In some embodiments, the level of the hormone or hormone analogue is decreased and subsequently increased multiple times to control toxicity while still providing an effective course of treatment. In some embodiments, the level of the hormone is subsequently increased to 100% of the level at which the hormone or hormone analogue was originally administered. In some embodiments, the level of the hormone or hormone analogue is subsequently increased to a level that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the level at which the hormone or hormone analogue was originally administered. In some embodiments, the level of the hormone or hormone analogue is subsequently increased to a level that is higher than the level at which the hormone or hormone analogue was originally administered. For example, the subsequently administered hormone or hormone analogue can be administered at a level that is at least 100%, at least 110%, at least 120%, at least 130%, at least 140%, at least 150%, at least 160%, at least 170%, at least 180%, at least 190%, at least 200%, at least 300%, at least 400%, or at least 500% of the level at which the hormone or hormone analogue was originally administered.

In some embodiments, toxicity arising after administering a first hormone or hormone analogue to a subject can be reduced by administering a second hormone or hormone analogue to the subject. For example, the second hormone or hormone analogue can have a reduced affinity for the LBD present in the single-chain chimeric polypeptide, the single-chain chimeric antigen receptor, and/or the multi-chain chimeric antigen receptor, such that plasma membrane localization of the single-chain chimeric polypeptide, the single-chain chimeric antigen receptor, and/or the multi-chain chimeric antigen receptor is reduced as compared to the plasma membrane localization facilitated by the first hormone or hormone analogue. In some embodiments, the second hormone or hormone analogue can be less effective than the first hormone or hormone analogue at facilitating plasma membrane localization of the single-chain chimeric polypeptide, the single-chain chimeric antigen receptor, and/ or the multi-chain chimeric antigen receptor. In some embodiments, the second hormone or hormone analogue competes with the first hormone or hormone analogue for binding to the LBD.

In some embodiments, in addition to or as an alternative to reducing the level of hormone or hormone analogue to reduce toxicity, toxicity can be further reduced by administering a composition that inactivates or sequesters the hormone or hormone analogue. For example, exogenous LBD can be administered to the subject (e.g., as a pharmaceutically acceptable formulation) to sequester the hormone or hormone analogue that was previously administered to the subject. As another example, a composition that inactivates, degrades, or otherwise sequesters the administered hormone or hormone analogue can be administered to the subject. A non-limiting example of such a composition is an antibody or antibody fragment that binds the administered hormone or hormone analogue and renders it unable to penetrate a cell membrane, renders it unable to bind the LBD, or facilitates its degradation.

EXAMPLES

The invention is further described in the following examples, which do not limit the scope of the invention described in the claims.

Example 1—Generation of Constructs

A canonical chimeric antigen receptor ("Canonical CAR", FIG. 1, left) was modified to include the estrogen receptor alpha ("ERa") ligand binding domain ("ERa-LBD," in green and indicated by arrows) at various locations within the protein. The ERa-LBD was introduced at different positions in the CAR (FIG. 1, right) to create different versions of the ERa-LBD, denoted as: "v.2" (also denoted as "v2" or "V2"), "v.3" (also denoted as "v3" or "V3"), and "v.4" (also denoted as "v4" or "V4"). An mCherry fusion was also included to allow tracking of cells containing the engineered protein. The nucleic acid and polypeptide sequences of v.2 (SEQ ID NOs: 30 and 31, respectively), v.3 (SEQ ID NOs: 32 and 33, respectively), and v.4 (SEQ ID NOs: 34 and 35, respectively) are provided below.

SEQ ID NO: 30
ATGGCTCTGCCTGTGACAGCTCTGCTGCTGCCTCTGGCCCTGCTGCTGCA
TGCCGCTAGACCTGAGCAGAAGCTGATCTCCGAAGAGGACCTGGACATCC
AGATGACCCAGACCACCAGCAGCCTGAGCGCCAGCCTGGGCGATAGAGTG
ACCATCAGCTGCAGAGCCAGCCAGGACATCAGCAAGTACCTGAACTGGTA
TCAGCAGAAACCCGACGGCACCGTGAAGCTGCTGATCTACCACACCAGCA
GACTGCACAGCGGCGTGCCCAGCAGATTTTCTGGCAGCGGCTCCGGCACC
GACTACAGCCTGACCATCTCCAACCTGGAACAGGAAGATATCGCTACCTA
CTTCTGTCAGCAAGGCAACACCCTGCCCTACACCTTCGGCGGAGGCACCA
AGCTGGAAATCACAGGCGGCGGAGGATCTGGCGGAGGCGGAAGTGGCGGA
GGGGGATCTGAAGTGAAACTGCAGGAAAGCGGCCCTGGCCTGGTGGCCCC
ATCTCAGTCTCTGAGCGTGACCTGTACCGTGTCCGGCGTGTCCCTGCCTG
ACTATGGCGTGTCCTGGATCAGACAGCCCCCAGAAAGGGCCTGGAATGG
CTGGGAGTGATCTGGGGCAGCGAGACAACCTACTACAACAGCGCCCTGAA
GTCCCGGCTGACCATCATCAAGGACAACTCCAAGAGCCAGGTGTTCCTGA
AGATGAACAGCCTGCAGACCGACGACACCGCCATCTACTACTGCGCCAAG
CACTACTACTACGGCGGCAGCTACGCCATGGACTACTGGGGCCAGGGCAC
AAGCGTGACCGTGTCTAGCACAACCACCCCTGCCCCTAGACCTCCAACCC
CAGCCCCTACAATCGCCAGCCAGCCTCTGTCTCTGAGGCCCGAGGCTTGT
AGACCAGCTGCTGGCGGAGCCGTGCACACCAGAGGACTGGATTTCGCCTG
CGACATCTACATCTGGGCCCCTCTGGCCGGCACATGTGGCGTGCTGCTGC
TGAGCCTCGTGATCACCCTGTACTGCGGATCCAAGCGGGGCAGAAAGAAA
CTGCTGTACATCTTTAAGCAGCCCTTCATGCGGCCCGTGCAGACCACCCA
GGAAGAGGACGGCTGCTCCTGCAGATTCCCCGAGGAAGAAGAAGGCGGCT
GCGAGCTGGGCAGCGGATCTGGCAGTGGAAGCGATAGAAGAGGCGGCAGA
ATGCTGAAACACAAGCGGCAGAGGGACGACGGGGAAGGCAGAGGCGAAGT
GGGATCTGCCGGCGATATGAGAGCCGCCAACCTGTGGCCTAGCCCCCTGA
TGATCAAGCGGAGCAAGAAGAACTCCCTGGCCCTGAGCCTGACCGCCGAC
CAGATGGTGTCTGCCCTGCTGGATGCCGAGCCCCCCATCCTGTACAGCGA
GTACGACCCCACCAGACCCTTCAGCGAGGCCAGCATGATGGGCCTGCTGA
CCAACCTGGCCGACCGGGAACTGGTGCACATGATCAACTGGGCCAAGCGG
GTGCCCGGCTTCGTGGATCTGACACTGCACGACCAGGTGCACCTGCTGGA
ATGCGCTTGGCTGGAAATCCTGATGATCGGCCTCGTGTGGCGGAGCATGG
AACACCCTGGCAAGCTGCTGTTCGCCCCCAACCTGCTGCTGGACCGGAAC

-continued

CAGGGCAAATGCGTGGAAGGCATGGTGGAAATCTTCGACATGCTGCTGGC

CACCTCCAGCCGGTTCCGGATGATGAACCTGCAGGGCGAAGAGTTCGTGT

GTCTGAAGTCCATCATCCTGCTGAATAGCGGCGTGTACACCTTCCTGAGC

AGCACCCTGAAAAGCCTGGAAGAAAAGGACCACATCCACCGGGTGCTGGA

CAAGATCACCGACACCCTGATTCACCTGATGGCCAAGGCCGGACTGACCC

TGCAGCAGCAGCATCAGAGACTGGCTCAGCTGCTGCTGATCCTGTCCCAC

ATCCGGCACATGAGCAACAAGCGGATGGAACATCTGTACAGCATGAAGTG

CAAGAACGTGGTGCCTCTGTTCGATCTGCTGCTGGAAATGCTGGACGCCC

ACAGGCTGCACGCCCCAACATCCAGATCCGGATCTGGAAGTGGCTCCCTG

AGAGTGAAGTTTAGCAGAAGCGCCGACGCCCCTGCCTATCAGCAGGGACA

GAACCAGCTGTATAACGAGCTGAACCTGGGCAGGCGGGAAGAGTACGACG

TGCTGGATAAGAGGCGGGGCAGGGACCCTGAAATGGGCGGCAAACCCAGA

CGGAAGAACCCCCAGGAAGGCCTGTACAACGAACTGCAGAAAGACAAGAT

GGCCGAGGCCTACAGCGAGATCGGAATGAAGGGCGAGCGGCGGAGAGGCA

AGGGACATGATGGCCTGTACCAGGGCCTGTCCACCGCCACCAAGGACACC

TATGACGCCCTGCACATGCAGGCCCTGCCTCCAAGAGGAAGTGGATCTGG

GAGCGGCTCTATGGTGTCTAAGGGGGAAGAGGACAACATGGCCATCATCA

AAGAATTCATGCGGTTCAAGGTGCACATGGAAGGCTCCGTGAATGGCCAC

GAATTCGAGATCGAGGGGGAGGGCGAGGGCAGACCTTATGAGGGAACCCA

GACCGCCAAGCTGAAAGTGACCAAGGGCGACCCCTGCCTTTCGCCTGGG

ATATCCTGTCTCCCCAGTTTATGTACGGCAGCAAGGCCTACGTGAAGCAC

CCCGCCGACATCCCCGACTACCTGAAGCTGAGCTTCCCTGAGGGCTTCAA

GTGGGAGAGAGTGATGAATTTCGAGGACGGCGAGTCGTGACAGTGACCC

AGGATAGCTCTCTGCAGGACGGCGAGTTCATCTACAAAGTGAAGCTGCGG

GGCACCAACTTCCCCAGCGACGGACCCGTGATGCAGAAAAAGACCATGGG

CTGGGAAGGCCAGCTCCGAGAGAATGTACCCAGAGGACGGGGCCCTGAAGG

GGGAGATCAAGCAGCGGCTGAAACTGAAGGATGGCGGCCACTACGACGCA

GAAGTGAAAACCACCTACAAGGCCAAGAAACCTGTGCAGCTGCCTGGCGC

CTACAATGTGAACATCAAGCTGGACATTACCAGCCACAACGAGGACTACA

CCATCGTGGAACAGTACGAGCGGGCCGAGGGCAGGCATTCTACAGGCGGA

ATGGATGAACTGTATAAGTGCGTGACCGACTAG

SEQ ID NO: 31
MALPVTALLLPLALLLHAARPEQKLISEEDLDIQMTQTTSSLSASLGDRV
TISCRASQDISKYLNWYQQKPDGTVKLLIYHTSRLHSGVPSRFSGSGSGT
DYSLTISNLEQEDIATYFCQQGNTLPYTFGGGTKLEITGGGSGGGGSGG
GGSEVKLQESGPGLVAPSQSLSVTCTVSGVSLPDYGVSWIRQPPRKGLEW
LGVIWGSETTYYNSALKSRLTIIKDNSKSQVFLKMNSLQTDDTAIYYCAK
HYYYGGSYAMDYWGQGTSVTVSSTTTPAPRPPTPAPTIASQPLSLRPEAC
RPAAGGAVHTRGLDFACDIYIWAPLAGTCGVLLLSLVITLYCGSKRGRKK
LLYIFKQPFMRPVQTTQEEDGCSCRFPEEEEGGCELGSGSGSGSDRRGGR
MLKHKRQRDDGEGRGEVGSAGDMRAANLWPSPLMIKRSKKNSLALSLTAD
QMVSALLDAEPPILYSEYDPTRPFSEASMMGLLTNLADRELVHMINWAKR
VPGFVDLTLHDQVULLECAWLEILMIGLVWRSMEHPGKLLFAPNLLLDRN
QGKCVEGMVEIFDMLLATSSRFRMMNLQGEEFVCLKSIILLNSGVYTFLS
STLKSLEEKDHIHRVLDKITDTLIHLMAKAGLTLQQQHQRLAQLLLILSH
IRHMSNKRMEHLYSMKCKNVVPLFDLLLEMLDAHRLHAPTSRSGSGSGSL
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPRGSGSGSGSMVSKGEEDNMAIIKEFMRFKVHMEGSVNGH
EFEIEGEGEGRPYEGTQTAKLKVTKGGPLPFAWDILSPQFMYGSKAYVKH
PADIPDYLKLSFPEGFKWERVMNFEDGGVVTVTQDSSLQDGEFIYKVKLR
GTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGG
MDELYKCVTD

SEQ ID NO: 32
ATGGCTCTGCCTGTGACAGCTCTGCTGCTGCCTCTGGCCCTGCTGCTGCA

TGCCGCTAGACCTGAGCAGAAGCTGATCTCCGAAGAGGACCTGGACATCC

AGATGACCCAGACCACCAGCAGCCTGAGCGCCAGCCTGGGCGATAGAGTG

ACCATCAGCTGCAGAGCCAGCCAGGACATCAGCAAGTACCTGAACTGGTA

TCAGCAGAAACCCGACGGCACCGTGAAGCTGCTGATCTACCACACCAGCA

GACTGCACAGCGGCGTGCCCAGCAGATTTTCTGGCAGCGGCTCCGGCACC

GACTACAGCCTGACCATCTCCAACCTGGAACAGGAAGATATCGCTACCTA

CTTCTGTCAGCAAGGCAACACCCTGCCCTACACCTTCGGCGGAGGCACCA

AGCTGGAAATCACAGGCGGCGGAGGATCTGGCGGAGGCGGAAGTGGCGGA

GGGGGATCTGAAGTGAAACTGCAGGAAAGCGGCCCTGGCCTGGTGGCCCC

ATCTCAGTCTCTGAGCGTGACCTGTACCGTGTCCGGCGTGTCCCTGCCTG

ACTATGGCGTGTCCTGGATCAGACAGCCCCCCAGAAAGGGCCTGGAATGG

CTGGGAGTGATCTGGGCAGCGAGACAACCTACTACAACAGCGCCCTGAA

GTCCCGGCTGACCATCATCAAGGACAACTCCAAGAGCCAGGTGTTCCTGA

AGATGAACAGCCTGCAGACCGACGACACCGCCATCTACTACTGCGCCAAG

CACTACTACTACGGCGGCAGCTACGCCATGGACTACTGGGGCCAGGGCAC

AAGCGTGACCGTGTCTAGCACAACCACCCCTGCCCCTAGACCTCCAACCC

CAGCCCCTACAATCGCCAGCCAGCCTCTGTCTCTGAGGCCCGAGGCTTGT

AGACCAGCTGCTGGCGGAGCCGTGCACACCAGAGGACTGGATTTCGCCTG

CGACATCTACATCTGGGCCCCTCTGGCCGGCACATGTGGCGTGCTGCTGC

TGAGCCTCGTGATCACCCTGTACTGCGGATCCAAGCGGGGCAGAAAGAAA

CTGCTGTACATCTTTAAGCAGCCCTTCATGCGGCCCGTGCAGACCACCCA

GGAAGAGGACGGCTGCTCCTGCAGATTCCCCGAGGAAGAAGAAGGCGGCT

GCGAGCTGGGATCCGGATCTGGAAGTGGCTCCCTGAGAGTGAAGTTTAGC

AGAAGCGCCGACGCCCCTGCCTATCAGCAGGGACAGAACCAGCTGTATAA

CGAGCTGAACCTGGGCAGGCGGGAAGAGTACGACGTGCTGGATAAGAGGC

GGGGCAGGGACCCTGAAATGGGCGGCAAACCCAGACGGAAGAACCCCCAG

```
GAAGGCCTGTACAACGAACTGCAGAAAGACAAGATGGCCGAGGCCTACAG
CGAGATCGGAATGAAGGGCGAGCGGCGGAGAGGCAAGGGACATGATGGCC
TGTACCAGGGCCTGTCCACCGCCACCAAGGACACCTATGACGCCCTGCAC
ATGCAGGCCCTGCCTCCAAGAGGCAGCGGATCTGGCAGTGGAAGCGATAG
AAGAGGCGGCAGAATGCTGAAACACAAGCGGCAGAGGGACGACGGGAAG
GCAGAGGCGAAGTGGGATCTGCCGGCGATATGAGAGCCGCCAACCTGTGG
CCTAGCCCCCTGATGATCAAGCGGAGCAAGAAGAACTCCCTGGCCCTGAG
CCTGACCGCCGACCAGATGGTGTCTGCCCTGCTGGATGCCGAGCCCCCA
TCCTGTACAGCGAGTACGACCCCACCAGACCCTTCAGCGAGGCCAGCATG
ATGGGCCTGCTGACCAACCTGGCCGACCGGGAACTGGTGCACATGATCAA
CTGGGCCAAGCGGGTGCCCGGCTTCGTGGATCTGACACTGCACGACCAGG
TGCACCTGCTGGAATGCGCTTGGCTGGAAATCCTGATGATCGGCCTCGTG
TGGCGGAGCATGGAACACCCTGGCAAGCTGCTGTTCGCCCCCAACCTGCT
GCTGGACCGGAACCAGGGCAAATGCGTGGAAGGCATGGTGGAAATCTTCG
ACATGCTGCTGGCCACCTCCAGCCGGTTCCGGATGATGAACCTGCAGGGC
GAAGAGTTCGTGTGTCTGAAGTCCATCATCCTGCTGAATAGCGGCGTGTA
CACCTTCCTGAGCAGCACCCTGAAAAGCCTGGAAGAAAAGGACCACATCC
ACCGGGTGCTGGACAAGATCACCGACACCCTGATTCACCTGATGGCCAAG
GCCGGACTGACCCTGCAGCAGCAGCATCAGAGACTGGCTCAGCTGCTGCT
GATCCTGTCCCACATCCGGCACATGAGCAACAAGCGGATGGAACATCTGT
ACAGCATGAAGTGCAAGAACGTGGTGCCTCTGTTCGATCTGCTGCTGGAA
ATGCTGGACGCCCACAGGCTGCACGCCCCAACATCCGGATCTGGCTCTGG
AAGCGGCAGCATGGTGTCTAAGGGGGAAGAGGACAACATGGCCATCATCA
AAGAATTCATGCGGTTCAAGGTGCACATGGAAGGCTCCGTGAATGGCCAC
GAATTCGAGATCGAGGGGGAGGGCGAGGGCAGACCTTATGAGGGAACCCA
GACCGCCAAGCTGAAAGTGACCAAGGGCGGACCCCTGCCTTTCGCCTGGG
ATATCCTGTCTCCCCAGTTTATGTACGGCAGCAAGGCCTACGTGAAGCAC
CCCGCCGACATCCCCGACTACCTGAAGCTGAGCTTCCCTGAGGGCTTCAA
GTGGGAGAGAGTGATGAATTTCGAGGACGGCGGAGTCGTGACAGTGACCC
AGGATAGCTCTCTGCAGGACGGCGAGTTCATCTACAAAGTGAAGCTGCGG
GGCACCAACTTCCCCAGCGACGGACCCGTGATGCAGAAAAAGACCATGGG
CTGGGAGGCCAGCTCCGAGAGAATGTACCCAGAGGACGGGGCCCTGAAGG
GGGAGATCAAGCAGCGGCTGAAACTGAAGGATGGCGGCCACTACGACGCA
GAAGTGAAAACCACCTACAAGGCCAAGAAACCTGTGCAGCTGCCTGGCGC
CTACAATGTGAACATCAAGCTGGACATTACCAGCCACAACGAGGACTACA
CCATCGTGGAACAGTACGAGCGGGCCGAGGGCAGGCATTCTACAGGCGGA
ATGGATGAACTGTATAAGTGCGTGACCGACTAG
                                            SEQ ID NO: 33
MALPVTALLLPLALLLHAARPEQKLISEEDLDIQMTQTTSSLSASLGDRV
TISCRASQDISKYLNWYQQKPDGTVKLLIYHTSRLHSGVPSRFSGSGSGT
DYSLTISNLEQEDIATYFCQQGNTLPYTFGGGTKLEITGGGSGGGGSGG
GGSEVKLQESGPGLVAPSQSLSVTCTVSGVSLPDYGVSWIRQPPRKGLEW
LGVIWGSETTYYNSALKSRLTIIKDNSKSQVFLKMNSLQTDDTAIYYCAK
HYYYGGSYAMDYWGQGTSVTVSSTTTPAPRPPTPAPTIASQPLSLRPEAC
RPAAGGAVHTRGLDFACDIYIWAPLAGTCGVLLLSLVITLYCGSKRGRKK
LLYIFKQPFMRPVQTTQEEDGCSCRFPEEEEGGCELRSGSGSGSLRVKFS
RSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALH
MQALPPRGSGSGSGSDRRGGRMLKHKQRDDGEGRGEVGSAGDMRAANLW
PSPLMIKRSKKNSLALSLTADQMVSALLDAEPPILYSEYDPTRPFSEASM
MGLLTNLADRELVHMINWAKRVPGFVDLTLHDQVHLLECAWLEILMIGLV
WRSMEHPGKLLFAPNLLLDRNQGKCVEGMVEIFDMLLATSSRFRMMNLQG
EEFVCLKSIILLNSGVYTFLSSTLKSLEEKDHIHRVLDKITDTLIHLMAK
AGLTLQQQHQRLAQLLLILSHIRHMSNKRMEHLYSMKCKNVVPLFDLLLE
MLDAHRLHAPTSGSGSGSGSMVSKGEEDNMAIIKEFMRFKVHMEGSVNGH
EFEIEGEGEGRPYEGTQTAKLKVTKGGPLPFAWDILSPQFMYGSKAYVKH
PADIPDYLKLSFPEGFKWERVMNFEDGGVVTVTQDSSLQDGEFIYKVKLR
GTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGG
MDELYKCVTD
                                            SEQ ID NO: 34
ATGGCTCTGCCTGTGACAGCTCTGCTGCTGCCTCTGGCCCTGCTGCTGCA
TGCCGCTAGACCTGAGCAGAAGCTGATCTCCGAAGAGGACCTGGACATCC
AGATGACCCAGACCACCAGCAGCCTGAGCGCCAGCCTGGGCGATAGAGTG
ACCATCAGCTGCAGAGCCAGCCAGGACATCAGCAAGTACCTGAACTGGTA
TCAGCAGAAACCCGACGGCACCGTGAAGCTGCTGATCTACCACACCAGCA
GACTGCACAGCGGCGTGCCCAGCAGATTTTCTGGCAGCGGCTCCGGCACC
GACTACAGCCTGACCATCTCCAACCTGGAACAGGAAGATATCGCTACCTA
CTTCTGTCAGCAAGGCAACACCCTGCCCTACACCTTCGGCGGAGGCACCA
AGCTGGAAATCACAGGCGGCGGAGGATCTGGCGGAGGCGGAAGTGGCGGA
GGGGGATCTGAAGTGAAACTGCAGGAAAGCGGCCCTGGCCTGGTGGCCCC
ATCTCAGTCTCTGAGCGTGACCTGTACCGTGTCCGGCGTGTCCCTGCCTG
ACTATGGCGTGTCCTGGATCAGACAGCCCCCAGAAAGGGCCTGGAATGG
CTGGGAGTGATCTGGGGCAGCGAGACAACCTACTACAACAGCGCCCTGAA
GTCCCGGCTGACCATCATCAAGGACAACTCCAAGAGCCAGGTGTTCCTGA
AGATGAACAGCCTGCAGACCGACGACACCGCCATCTACTACTGCGCCAAG
CACTACTACTACGGCGGCAGCTACGCCATGGACTACTGGGGCCAGGGCAC
AAGCGTGACCGTGTCTAGCACAACCACCCCTGCCCCTAGACCTCCAACCC
CAGCCCCTACAATCGCCAGCCAGCCTCTGTCTCTGAGGCCCGAGGCTTGT
AGACCAGCTGCTGGCGGAGCCGTGCACACCAGAGGACTGGATTTCGCCTG
CGACATCTACATCTGGGCCCCTCTGGCCGGCACATGGGCGTGCTGCTGC
TGAGCCTCGTGATCACCCTGTACTGCGGATCCGGCAGCGGATCTGGCAGT
```

```
GGAAGCGATAGAAGAGGCGGCAGAATGCTGAAACACAAGCGGCAGAGGGA

CGACGGGGAAGGCAGAGGCGAAGTGGGATCTGCCGGCGATATGAGAGCCG

CCAACCTGTGGCCTAGCCCCCTGATGATCAAGCGGAGCAAGAAGAACTCC

CTGGCCCTGAGCCTGACCGCCGACCAGATGGTGTCTGCCCTGCTGGATGC

CGAGCCCCCATCCTGTACAGCGAGTACGACCCCACCAGACCCTTCAGCG

AGGCCAGCATGATGGGCCTGCTGACCAACCTGGCCGACCGGGAACTGGTG

CACATGATCAACTGGGCCAAGCGGGTGCCCGGCTTCGTGGATCTGACACT

GCACGACCAGGTGCACCTGCTGGAATGCGCTTGGCTGGAAATCCTGATGA

TCGGCCTCGTGTGGCGGAGCATGGAACACCCTGGCAAGCTGCTGTTCGCC

CCCAACCTGCTGCTGGACCGGAACCAGGGCAAATGCGTGGAAGGCATGGT

GGAAATCTTCGACATGCTGCTGGCCACCTCCAGCCGGTTCCGGATGATGA

ACCTGCAGGGCGAAGAGTTCGTGTGTCTGAAGTCCATCATCCTGCTGAAT

AGCGGCGTGTACACCTTCCTGAGCAGCACCCTGAAAAGCCTGGAAGAAAA

GGACCACATCCACCGGGTGCTGGACAAGATCACCGACACCCTGATTCACC

TGATGGCCAAGGCCGGACTGACCCTGCAGCAGCAGCATCAGAGACTGGCT

CAGCTGCTGCTGATCCTGTCCCACATCCGGCACATGAGCAACAAGCGGAT

GGAACATCTGTACAGCATGAAGTGCAAGAACGTGGTGCCTCTGTTCGATC

TGCTGCTGGAAATGCTGGACGCCCACAGGCTGCACGCCCCAACATCCGGA

TCTGGCTCTGGAAGCGGCAGCAAGCGGGGCAGAAAGAAACTGCTGTACAT

CTTTAAGCAGCCCTTCATGCGGCCCGTGCAGACCACCCAGGAAGAGGACG

GCTGCTCCTGCAGATTCCCCGAGGAAGAAGAAGGCGGCTGCGAGCTGAGA

TCCGGATCTGGAAGTGGCTCCCTGAGAGTGAAGTTTAGCAGAAGCGCCGA

CGCCCCTGCCTATCAGCAGGGACAGAACCAGCTGTATAACGAGCTGAACC

TGGGCAGGCGGGAAGAGTACGACGTGCTGGATAAGAGGCGGGGCAGGGAC

CCTGAAATGGGCGGCAAACCCAGACGGAAGAACCCCCAGGAAGGCCTGTA

CAACGAACTGCAGAAAGACAAGATGGCCGAGGCCTACAGCGAGATCGGAA

TGAAGGGCGAGCGGCGGAGAGGCAAGGGACATGATGGCCTGTACCAGGGC

CTGTCCACCGCCACCAAGGACACCTATGACGCCCTGCACATGCAGGCCCT

GCCTCCAAGAGGAAGTGGATCTGGGAGCGGCTCTATGGTGTCTAAGGGGG

AAGAGGACAACATGGCCATCATCAAAGAATTCATGCGGTTCAAGGTGCAC

ATGGAAGGCTCCGTGAATGGCCACGAATTCGAGATCGAGGGGGAGGGCGA

GGGCAGACCTTATGAGGGAACCCAGACCGCCAAGCTGAAAGTGACCAAGG

GCGGACCCCTGCCTTTCGCCTGGGATATCCTGTCTCCCCAGTTTATGTAC

GGCAGCAAGGCCTACGTGAAGCACCCCGCCGACATCCCCGACTACCTGAA

GCTGAGCTTCCCTGAGGGCTTCAAGTGGGAGAGAGTGATGAATTTCGAGG

ACGGCGGAGTCGTGACAGTGACCCAGGATAGCTCTCTGCAGGACGGCGAG

TTCATCTACAAAGTGAAGCTGCGGGGCACCAACTTCCCCAGCGACGGACC

CGTGATGCAGAAAAAGACCATGGGCTGGGAGGCCAGCTCCGAGAGAATGT

ACCCAGAGGACGGGGCCCTGAAGGGGGAGATCAAGCAGCGGCTGAAACTG

AAGGATGGCGGCCACTACGACGCAGAAGTGAAAACCACCTACAAGGCCAA
```

```
GAAACCTGTGCAGCTGCCTGGCGCCTACAATGTGAACATCAAGCTGGACA

TTACCAGCCACAACGAGGACTACACCATCGTGGAACAGTACGAGCGGGCC

GAGGGCAGGCATTCTACAGGCGGAATGGATGAACTGTATAAGTGCGTGAC

CGACTA
```

SEQ ID NO: 35

```
MALPVTALLLPLALLLHAARPEQKLISEEDLDIQMTQTTSSLSASLGDRV

TISCRASQDISKYLNWYQQKPDGTVKLLIYHTSRLHSGVPSRFSGSGSGT

DYSLTISNLEQEDIATYFCQQGNTLPYTFGGGTKLEITGGGGSGGGGSGG

GGSEVKLQESGPGLVAPSQSLSVTCTVSGVSLPDYGVSWIRQPPRKGLEW

LGVIWGSETTYYNSALKSRLTIIKDNSKSQVFLKMNSLQTDDTAIYYCAK

HYYYGGSYAMDYWGQGTSVTVSSTTTPAPRPPTPAPTIASQPLSLRPEAC

RPAAGGAVHTRGLDFACDIYIWAPLAGTCGVLLLSLVITLYCGSGSGSGS

GSDRRGGRMLKHKRQRDDGEGRGEVGSAGDMRAANLWPSPLMIKRSKKNS

LALSLTADQMVSALLDAEPPILYSEYDPTRPFSEASMMGLLTNLADRELV

HMINWAKRVPGFVDLTLHDQVHLLECAWLEILMIGLVWRSMEHPGKLLFA

PNLLLDRNQGKCVEGMVEIFDMLLATSSRFRMMNLQGEEFVCLKSIILLN

SGVYTFLSSTLKSLEEKDHIHRVLDKITDTLIHLMAKAGLTLQQQHQRLA

QLLLILSHIRHMSNKRMEHLYSMKCKNVVPLFDLLLEMLDAHRLHAPTSG

SGSGSGSKRGRKKLLYIFKQPFMRPVQTTQEEDGCSCRFPEEEEGGCELR

SGSGSGSLRVKFSRSADAPAYQQGQNQLYNELNLGRREEYDVLDKRRGRD

PEMGGKPRRKNPQEGLYNELQKDKMAEAYSEIGMKGERRRGKGHDGLYQG

LSTATKDTYDALHMQALPPRGSGSGSGSMVSKGEEDNMAIIKEFMRFKVH

MEGSVNGHEFEIEGEGEGRPYEGTQTAKLKVTKGGPLPFAWDILSPQFMY

GSKAYVKHPADIPDYLKLSFPEGFKWERVMNFEDGGVVTVTQDSSLQDGE

FIYKVKLRGTNFPSDGPVMQKKTMGWEASSERMYPEDGALKGEIKQRLKL

KDGGHYDAEVKTTYKAKKPVQLPGAYNVNIKLDITSHNEDYTIVEQYERA

EGRHSTGGMDELYKCVTD
```

Figure 2A:
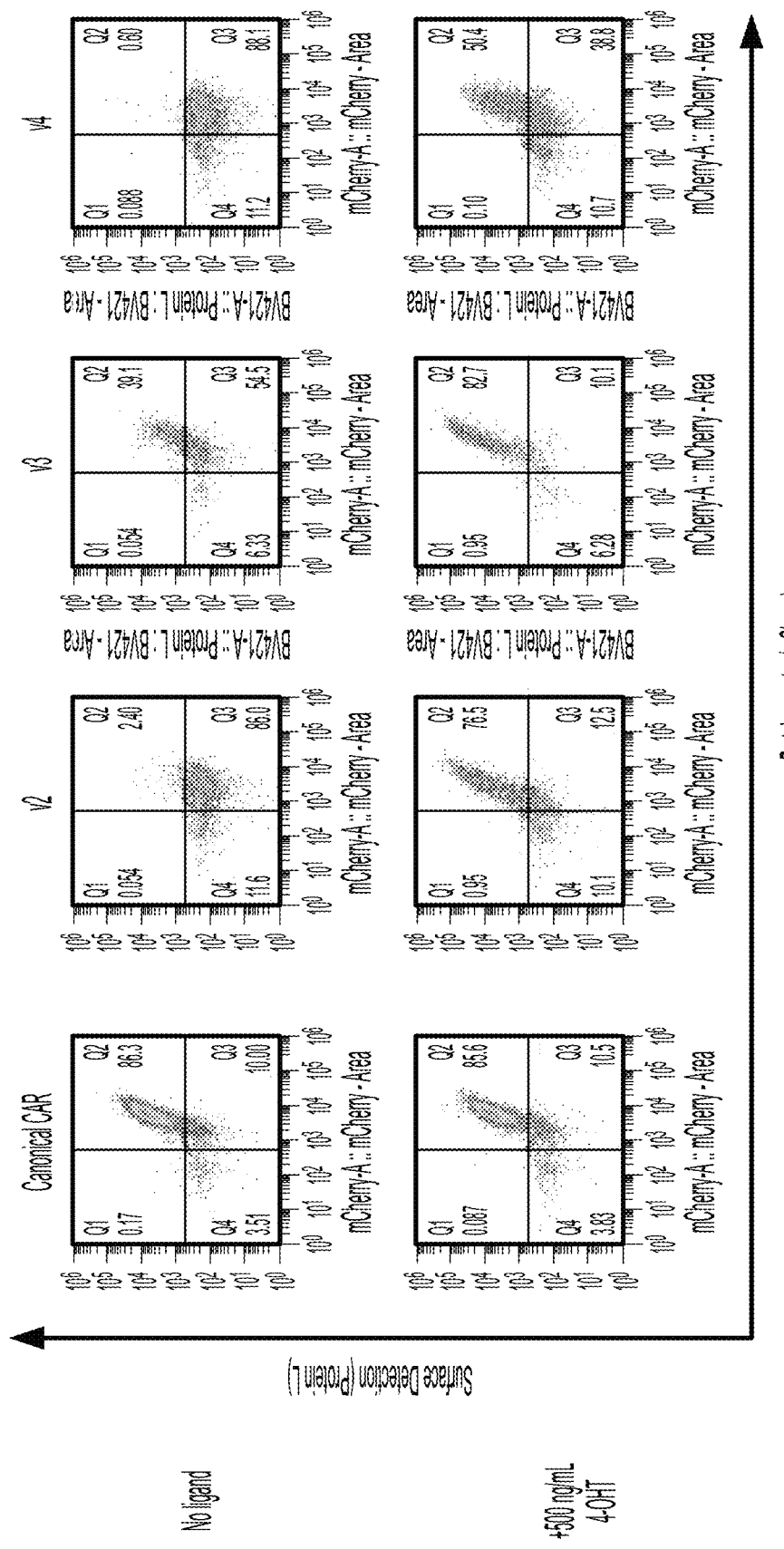
FIG. 2A and FIG. 2B are a set of flow cytometry dot plots for cells expressing one of the different constructs. The cells were either left untreated or were treated with 500 ng/mL 4-hydroxytamoxifen ("4-OHT").

Example 2—NHR-LBD Containing Anti-CD19 Chimeric Antigen Receptors Exhibit Ligand-Induced Surface Expression of the CAR Jurkat T cells were transduced with lentiviral vectors encoding the canonical CAR or with anti-CD19 (FMC63) ERa-LBD containing the v2, v3, and v4 CAR constructs described in Example 1. The cells were then either left untreated, or were treated with, a ligand for the ERa-LBD. After one hour of drug treatment, the cells were stained with Protein L-biotin (Protein L binds to the extracellular scFv), and then with streptavidin-BV421 to detect surface expression of the CAR. The cells were subsequently analyzed by flow cytometry for mCherry expression and for the presence of CAR on the cell surface (FIG. 2A). Canonical CAR was expressed on the surface at identical levels regardless of the presence or absence of the drug (FIG. 2A, dot plots under the heading "Canonical CAR"). In contrast, ERa-LBD-containing v2 and v4 CARs (exemplary single-chain chimeric antigen receptors described herein) are expressed in the presence of the ligand (as assayed by mCherry-positive expression), but in the absence of the ligand, no CAR is detected on the cell surface (FIG. 2A, top row, Protein L staining, dot plots under the headings "v2" and "v4"). After treatment with 500 ng/mL 4-OHT, CAR is detected on cell surface (FIG. 2A, bottom row, Protein L staining) at levels comparable to control CAR. Notably, not all designs behave identically: v3 has some basal surface expression of CAR in the absence of ligand (FIG. 2A, top dot plot under the heading "v3"), and expression is further increased upon ligand addition (FIG. 2A, bottom dot plot under the heading "v3").

Figure 2B:
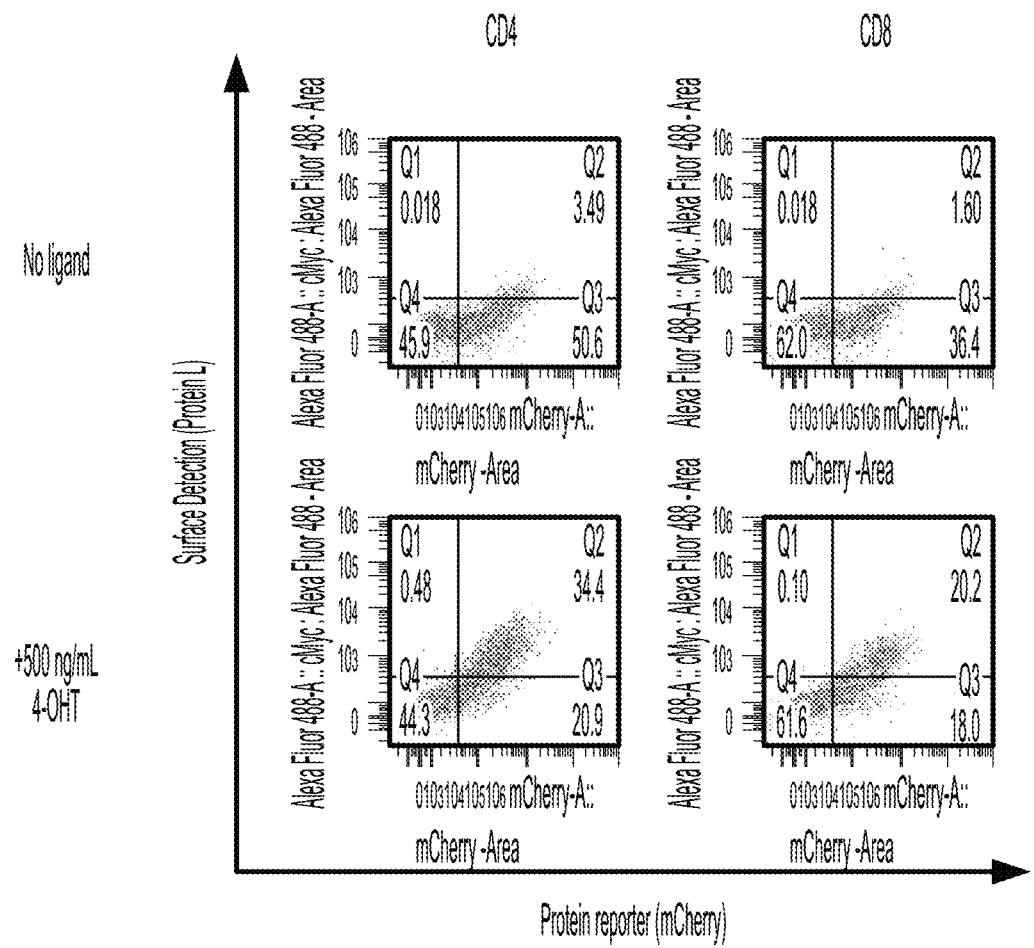

Primary CD4 and CD8 human T cells were transduced with lentiviral vectors encoding the v4 CAR constructs. Cells were treated as described in this Example, and were stained using an anti-cMyc antibody to detect the cMyc-tagged scFv on the cell surface. Surface induction was observed in both CD4 and CD8 T cells after co-culture of the T cells with 500 ng/mL 4-OHT ligand (FIG. 2B), demonstrating that the surface induction phenotype extends from Jurkat to primary human T cells.

Figure 3:
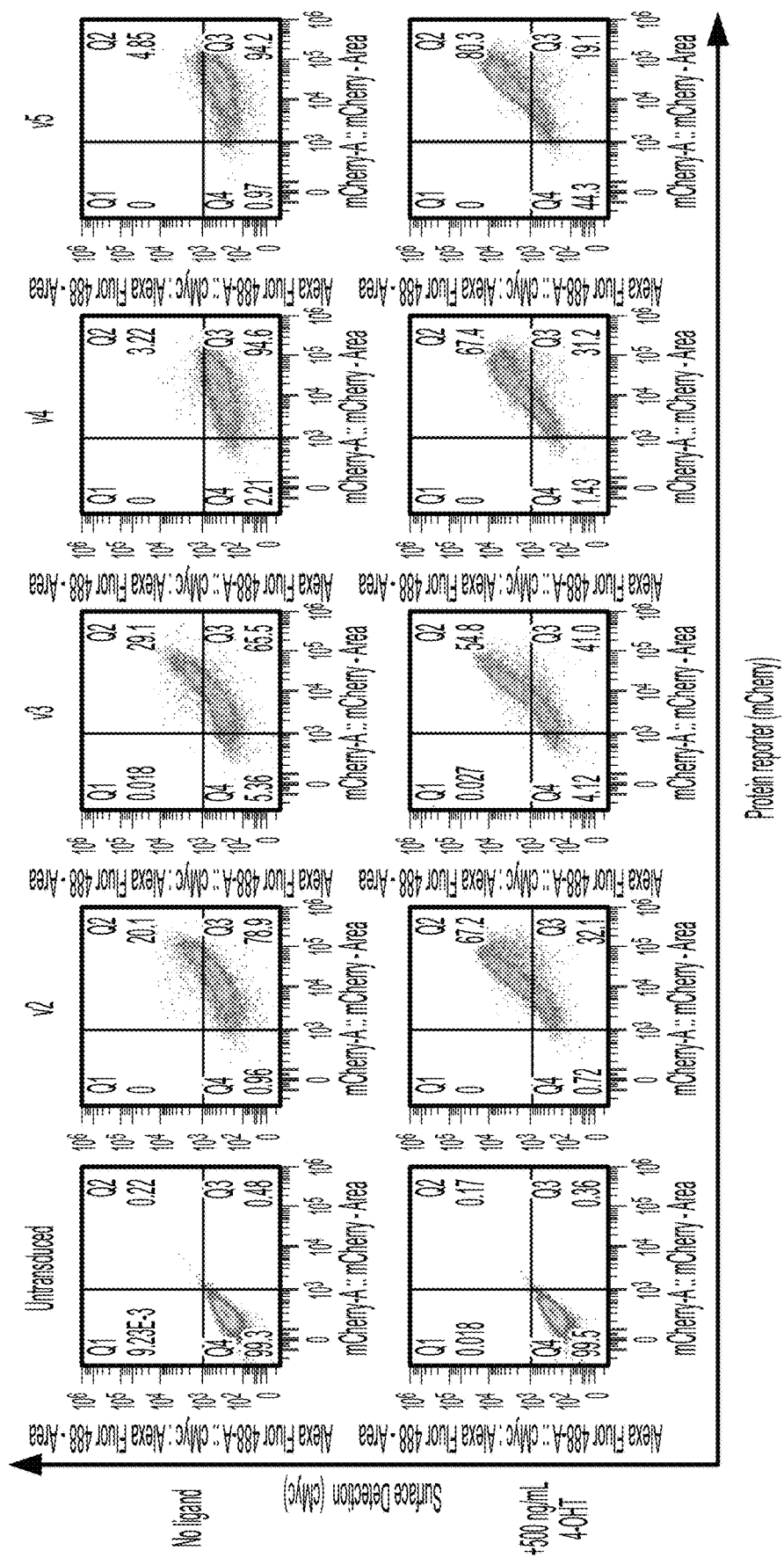
FIG. 3 is a set of flow cytometry dot plots for HEK-293T cells transduced with lentiviral vectors encoding ERa-LBD-containing FMC63 CAR fusions. The cells were either left untreated or were treated with 500 ng/mL 4-OHT.

Example 3—NHR-LBD Fusion Proteins Exhibit Ligand-Induced Surface Expression in Diverse Cell Types HEK-293T cells were transduced with lentiviral vectors encoding ERa-LBD-containing FMC63 CAR fusions described in Example 1. The cells were either left untreated, or were incubated with 500 ng/mL 4-OHT for two hours, and then stained for surface CAR expression. Consistent with ERa LBD results in Jurkat cells and primary T cells demonstrated in Example 2, several ERa-LBD CAR fusions exhibited minimal surface expression of CAR in the absence of ligand, and strongly up-regulated surface CAR upon ligand treatment (FIG. 3). These data indicate that ligand-induced surface expression of NHR-LBD CAR fusions operates in diverse cell types including immortalized (Jurkat and HEK-293T) and primary cells (Human CD4 and CD8 T cells), as well as lymphoid (Jurkat and human T) and non-lymphoid (HEK-293T) cell types.

Figure 4:
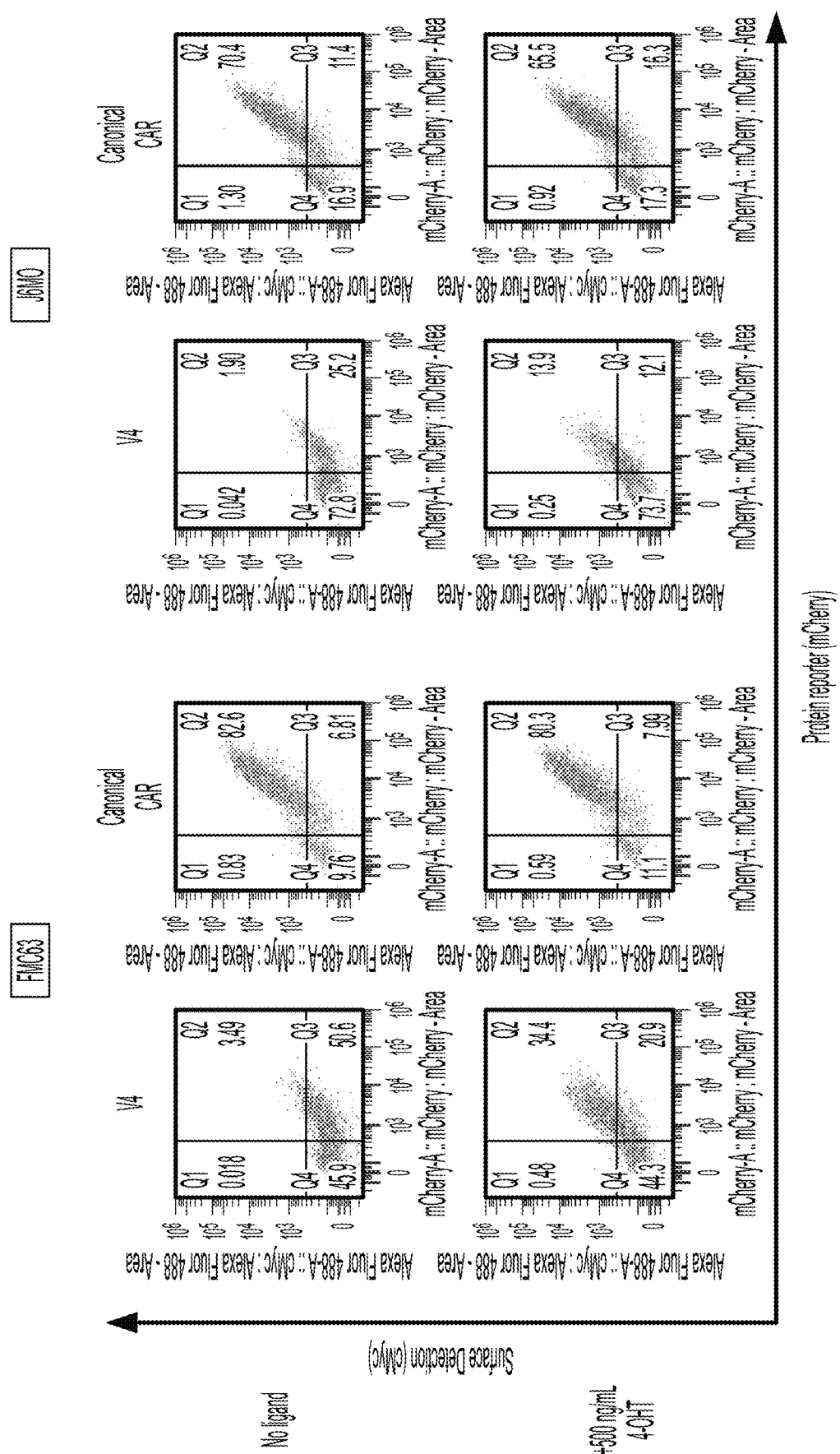
FIG. 4 is a set of flow cytometry dot plots for primary human CD4 T cells transduced with lentiviral vectors encoding a FMC63 NHR LBD-CAR fusions and a NHR LBD-CAR having the J6M0 scFv. The cells were either left untreated or were treated with 500 ng/mL 4-OHT.

Example 4—Ligand-Induced Surface Expression of NHR LBD-CAR Fusions is Conserved Between Different scFvs To demonstrate the conserved function and modularity of NHR LBD-CAR fusion proteins, the FMC63 scFv in V4 was replaced with a different scFv (J6M0) that recognizes B-cell maturation antigen ("BCMA"). Primary human CD4 T cells were transduced with lentiviral vectors encoding the NHR-LBD CAR fusions, and were either left untreated, or were treated with 500 ng/mL of the ERa ligand 4-OHT. Similar to the FMC63 NHR LBD-CAR fusions, the NHR LBD-CAR having the J6M0 scFv displayed ligand-induced surface expression (FIG. 4).

Figure 5A:
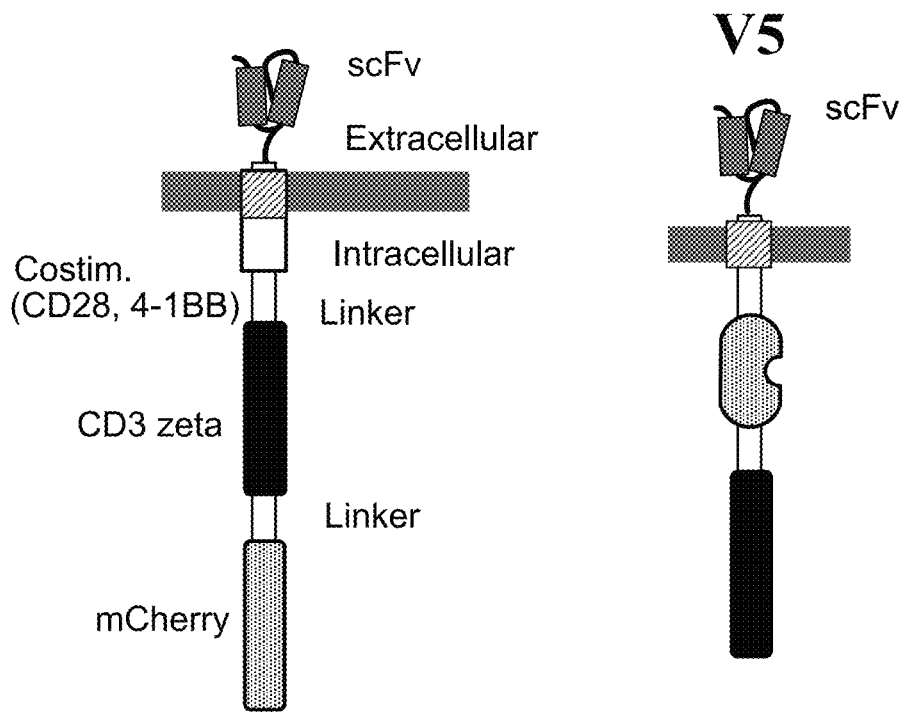
FIG. 5A is a diagram of the V5 nuclear hormone receptor ligand binding domain NHR-LBD CAR construct lacking the costimulatory and CD3zeta domains, and a set of flow cytometry dot plots for cells transduced with a lentiviral vector encoding the V5 construct. The cells were either left untreated or were treated with 500 ng/mL 4-OHT.
Figure 5A:
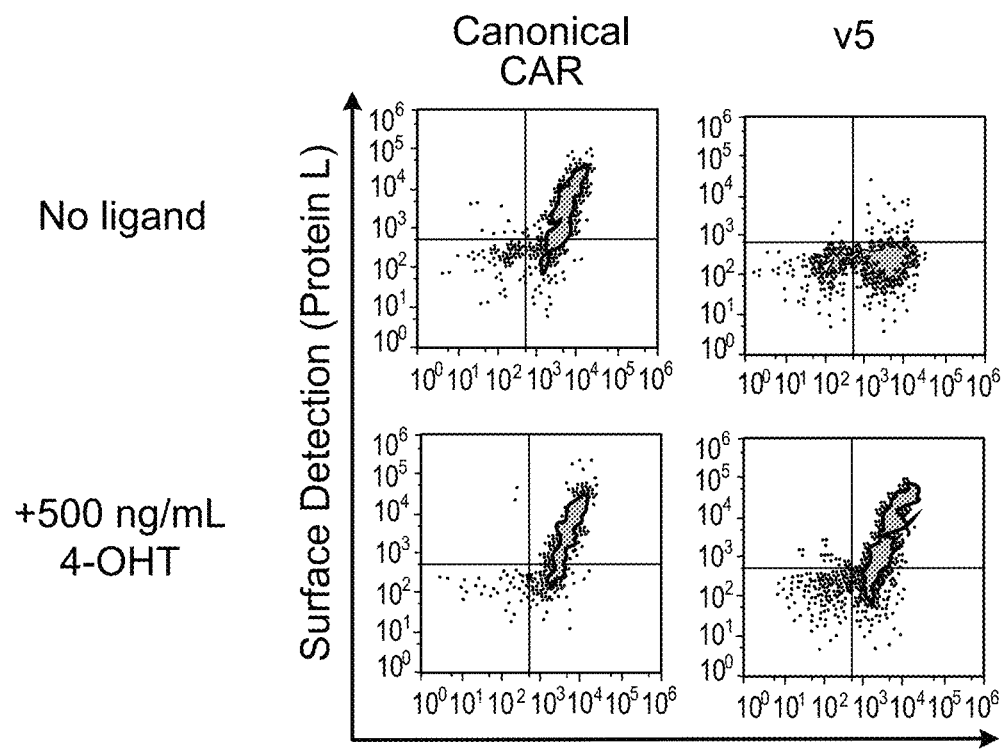

Example 5—Ligand-Induced Surface Trafficking of NHR LBD Fusion Proteins does not Require scFv or Intracellular Domains from the Canonical CAR The LBD-CAR fusions tested in Example 2 contain a number of protein motifs in addition to the NHR LBD domain, including a CD137 intracellular domain, a CD3z intracellular signaling domain, and an scFv domain. To determine if the intracellular portions of the CAR constructs (the CD137 intracellular domain and CD3z intracellular domain) were involved in ligand-induced surface trafficking, a construct lacking these regions ("v5", FIG. 5A, left) was generated and tested in primary human T cells. Construct v5 includes the scFv domain and the mCherry domain. Construct v5 exhibited ligand-induced trafficking comparable to that of constructs v2 and v4 in Example 2, indicating the CAR intracellular motifs were not responsible for the ligand-induced trafficking (FIG. 5A, right). The nucleotide (SEQ ID NO: 36) and amino acid (SEQ ID NO: 37) sequence of v5 are shown below.

SEQ ID NO: 36
ATGGCTCTGCCTGTGACAGCTCTGCTGCTGCCTCTGGCCCTGCTGCTGCA
TGCCGCTAGACCTGAGCAGAAGCTGATCTCCGAAGAGGACCTGGACATCC
AGATGACCCAGACCACCAGCAGCCTGAGCGCCAGCCTGGGCGATAGAGTG
ACCATCAGCTGCAGAGCCAGCCAGGACATCAGCAAGTACCTGAACTGGTA
TCAGCAGAAACCCGACGGCACCGTGAAGCTGCTGATCTACCACACCAGCA
GACTGCACAGCGGCGTGCCCAGCAGATTTTCTGGCAGCGGCTCCGGCACC
GACTACAGCCTGACCATCTCCAACCTGGAACAGGAAGATATCGCTACCTA
CTTCTGTCAGCAAGGCAACACCCTGCCCTACACCTTCGGCGGAGGCACCA
AGCTGGAAATCACAGGCGGCGGAGGATCTGGCGGAGGCGGAAGTGGCGGA
GGGGGATCTGAAGTGAAACTGCAGGAAAGCGGCCCTGGCCTGGTGGCCCC
ATCTCAGTCTCTGAGCGTGACCTGTACCGTGTCCGGCGTGTCCCTGCCTG
ACTATGGCGTGTCCTGGATCAGACAGCCCCCAGAAAGGGCCTGGAATGG
CTGGGAGTGATCTGGGGCAGCGAGACAACCTACTACAACAGCGCCCTGAA
GTCCCGGCTGACCATCATCAAGGACAACTCCAAGAGCCAGGTGTTCCTGA
AGATGAACAGCCTGCAGACCGACGACACCGCCATCTACTACTGCGCCAAG
CACTACTACTACGGCGGCAGCTACGCCATGGACTACTGGGGCCAGGGCAC
AAGCGTGACCGTGTCTAGCACAACCACCCCTGCCCCTAGACCTCCAACCC
CAGCCCCTACAATCGCCAGCCAGCCTCTGTCTCTGAGGCCCGAGGCTTGT
AGACCAGCTGCTGGCGGAGCCGTGCACACCAGAGGACTGGATTTCGCCTG
CGACATCTACATCTGGGCCCCTCTGGCCGGCACATGTGGCGTGCTGCTGC
TGAGCCTCGTGATCACCCTGTACTGCGGATCCGGCAGCGGATCTGGCAGT
GGAAGCGATAGAAGAGGCGGCAGAATGCTGAAACACAAGCGGCAGAGGGA
CGACGGGGAAGGCAGAGGCGAAGTGGGATCTGCCGGCGATATGAGAGCCG
CCAACCTGTGGCCTAGCCCCCTGATGATCAAGCGGAGCAAGAAGAACTCC
CTGGCCCTGAGCCTGACCGCCGACCAGATGGTGTCTGCCCTGCTGGATGC
CGAGCCCCCCATCCTGTACAGCGAGTACGACCCCACCAGACCCTTCAGCG
AGGCCAGCATGATGGGCCTGCTGACCAACCTGGCCGACCGGGAACTGGTG
CACATGATCAACTGGGCCAAGCGGGTGCCCGGCTTCGTGGATCTGACACT
GCACGACCAGGTGCACCTGCTGGAATGCGCTTGGCTGGAAATCCTGATGA
TCGGCCTCGTGTGGCGGAGCATGGAACACCCTGGCAAGCTGCTGTTCGCC
CCCAACCTGCTGCTGGACCGGAACCAGGGCAAATGCGTGGAAGGCATGGT
GGAAATCTTCGACATGCTGCTGGCCACCTCCAGCCGGTTCCGGATGATGA
ACCTGCAGGGCGAAGAGTTCGTGTGTCTGAAGTCCATCATCCTGCTGAAT
AGCGGCGTGTACACCTTCCTGAGCAGCACCCTGAAAAGCCTGGAAGAAAA
GGACCACATCCACCGGGTGCTGGACAAGATCACCGACACCCTGATTCACC

```
TGATGGCCAAGGCCGGACTGACCCTGCAGCAGCAGCATCAGAGACTGGCT

CAGCTGCTGCTGATCCTGTCCCACATCCGGCACATGAGCAACAAGCGGAT

GGAACATCTGTACAGCATGAAGTGCAAGAACGTGGTGCCTCTGTTCGATC

TGCTGCTGGAAATGCTGGACGCCCACAGGCTGCACGCCCCAACATCCGGA

TCTGGCTCTGGAAGCGGCAGCATGGTGTCTAAGGGGGAAGAGGACAACAT

GGCCATCATCAAAGAATTCATGCGGTTCAAGGTGCACATGGAAGGCTCCG

TGAATGGCCACGAATTCGAGATCGAGGGGGAGGGCGAGGGCAGACCTTAT

GAGGGAACCCAGACCGCCAAGCTGAAAGTGACCAAGGGCGGACCCCTGCC

TTTCGCCTGGGATATCCTGTCTCCCCAGTTTATGTACGGCAGCAAGGCCT

ACGTGAAGCACCCCGCCGACATCCCCGACTACCTGAAGCTGAGCTTCCCT

GAGGGCTTCAAGTGGGAGAGAGTGATGAATTTCGAGGACGGCGGAGTCGT

GACAGTGACCCAGGATAGCTCTCTGCAGGACGGCGAGTTCATCTACAAAG

TGAAGCTGCGGGGCACCAACTTCCCCAGCGACGGACCCGTGATGCAGAAA

AAGACCATGGGCTGGGAGGCCAGCTCCGAGAGAATGTACCCAGAGGACGG

GGCCCTGAAGGGGGAGATCAAGCAGCGGCTGAAACTGAAGGATGGCGGCC

ACTACGACGCAGAAGTGAAAACCACCTACAAGGCCAAGAAACCTGTGCAG

CTGCCTGGCGCCTACAATGTGAACATCAAGCTGGACATTACCAGCCACAA

CGAGGACTACACCATCGTGGAACAGTACGAGCGGGCCGAGGGCAGGCATT

CTACAGGCGGAATGGATGAACTGTATAAGTGCGTGACCGACTAG

SEQ ID NO: 37
MALPVTALLLPLALLLHAARPEQKLISEEDLDIQMTQTTSSLSASLGDRV

TISCRASQDISKYLNWYQQKPDGTVKLLIYHTSRLHSGVPSRFSGSGSGT

DYSLTISNLEQEDIATYFCQQGNTLPYTFGGGTKLEITGGGSGGGGSGG

GGSEVKLQESGPGLVAPSQSLSVTCTVSGVSLPDYGVSWIRQPPRKGLEW

LGVIWGSETTYYNSALKSRLTIIKDNSKSQVFLKMNSLQTDDTAIYYCAK

HYYYGGSYAMDYWGQGTSVTVSSTTTPAPRPPTPAPTIASQPLSLRPEAC

RPAAGGAVHTRGLDFACDIYIWAPLAGTCGVLLLSLVITLYCGSGSGSGS

GSDRRGGRMLKHKRQRDDGEGRGEVGSAGDMRAANLWPSPLMIKRSKKNS

LALSLTADQMVSALLDAEPPILYSEYDPTRPFSEASMMGLLTNLADRELV

HMINWAKRVPGFVDLTLHDQVHLLECAWLEILMIGLVWRSMEHPGKLLFA

PNLLLDRNQGKCVEGMVEIFDMLLATSSRFRMMNLQGEEFVCLKSIILLN

SGVYTFLSSTLKSLEEKDHIHRVLDKITDTLIHLMAKAGLTLQQQHQRLA

QLLLILSHIRHMSNKRMEHLYSMKCKNVVPLFDLLLEMLDAHRLHAPTSG

SGSGSGSMVSKGEEDNMAIIKEFMRFKVHMEGSVNGHEFEIEGEGEGRPY

EGTQTAKLKVTKGGPLPFAWDILSPQFMYGSKAYVKHPADIPDYLKLSFP

EGFKWERVMNFEDGGVVTVTQDSSLQDGEFIYKVKLRGTNFPSDGPVMQK

KTMGWEASSERMYPEDGALKGEIKQRLKLKDGGHYDAEVKTTYKAKKPVQ

LPGAYNVNIKLDITSHNEDYTIVEQYERAEGRHSTGGMDELYKCVTD
```

Figure 5B:
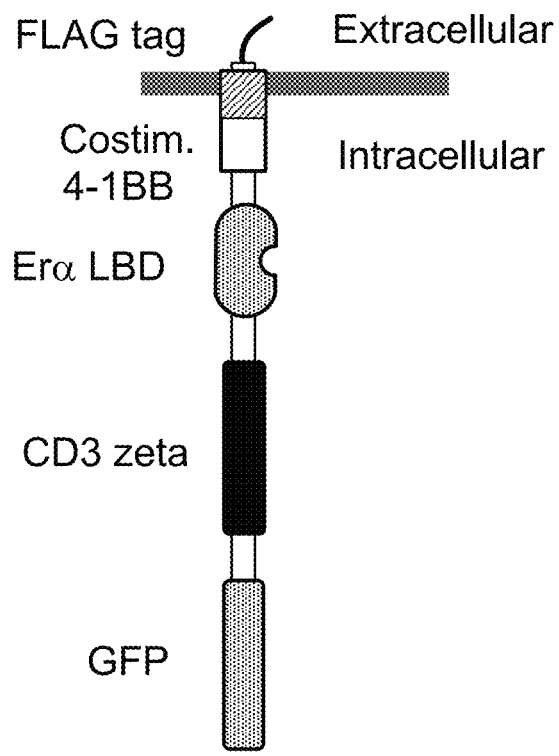
FIG. 5B is a set of flow cytometry diagrams of untransduced Jurkat T cells or Jurkat T cells transduced with a lentiviral vector encoding a CAR in which the scFv domain was replaced with a FLAG tag. The transduced cells were either left untreated or were treated with 500 ng/mL 4-OHT.
Figure 5B:
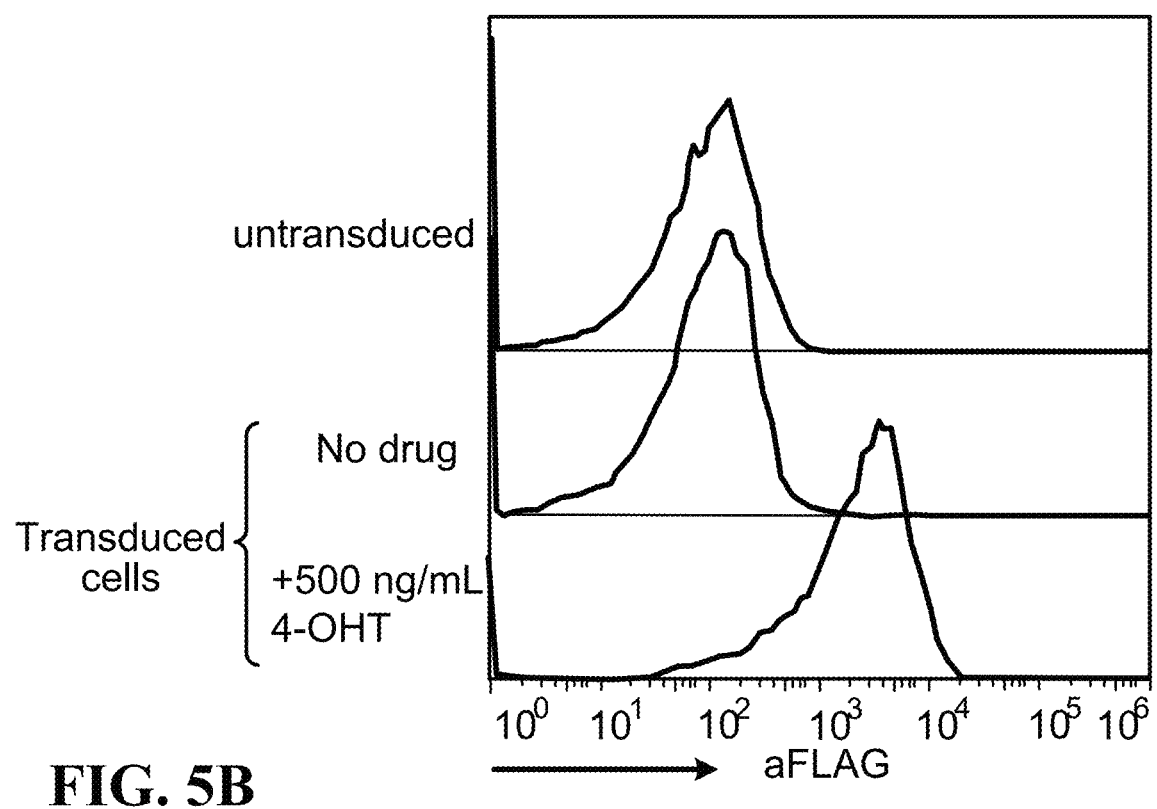

To test whether the extracellular scFv was involved in the ligand-induced surface expression, constructs lacking the scFv were generated; in its place a FLAG tag was inserted to allow surface detection of the protein (nucleic acid and polypeptide sequences for this construct are shown below as SEQ ID NOs: 38 and 39, respectively). Jurkat T cells were transduced with a lentiviral vector encoding the ERa-LBD fusion protein, and were stained for surface expression of the polypeptide in the presence and absence of the ERa ligand 4-OHT. Ligand treatment induced robust surface detection of the polypeptide (FIG. 5B), indicating that NHR-LBD-mediated surface expression does not require an scFv, and that the technology is broadly generalizable to diverse polypeptides.

```
                                            SEQ ID NO: 38
ATGATCCACCTGGGACACATCCTGTTTTTGCTGCTGCTGCCAGTGGCTGCC

GCCgattacaaagacgacgatgataaaCAGACAACACCAGGCGAGAGATCT

AGCCTGCCCGCCTTCTACCCTGGCACCAGCGGCTCTTGTTCTGGCTGTGGC

AGCCTGTCTCTGCCCatctatatttgggcacccctggctggaacctgcgga gtgctgctgctgtctctcgtgattacactgtattgcAAAAGGGGCCGGAAA

AAGCTGCTGTATATTTTCAAACAGCCTTTTATGAGGCCTGTGCAGACAACA

CAGGAAGAGGACGGCTGTAGCTGTCGGTTCCCCGAAGAGGAAGAGGGGGGC

TGCGAACTGggatcaggcagtggctctggcagcGATAGAAGAGGCGGCAGA

ATGCTGAAACACAAGCGGCAGAGGGACGACGGGGAAGGCAGAGGCGAAGTG

GGATCTGCCGGCGATATGAGAGCCGCCAACCTGTGGCCTAGCCCCCTGATG

ATCAAGCGGAGCAAGAAGAACTCCCTGGCCCTGAGCCTGACCGCCGACCAG

ATGGTGTCTGCCCTGCTGGATGCCGAGCCCCCATCCTGTACAGCGAGTAC

GACCCCACCAGACCCTTCAGCGAGGCCAGCATGATGGGCCTGCTGACCAAC

CTGGCCGACCGGGAACTGGTGCACATGATCAACTGGGCCAAGCGGGTGCCC

GGCTTCGTGGATCTGACACTGCACGACCAGGTGCACCTGCTGGAATGCGCT

TGGCTGGAAATCCTGATGATCGGCCTCGTGTGGCGGAGCATGGAACACCCT

GGCAAGCTGCTGTTCGCCCCCAACCTGCTGCTGGACCGGAACCAGGGCAAA

TGCGTGGAAGGCATGGTGGAAATCTTCGACATGCTGCTGGCCACCTCCAGC

CGGTTCCGGATGATGAACCTGCAGGGCGAAGAGTTCGTGTGTCTGAAGTCC

ATCATCCTGCTGAATAGCGGCGTGTACACCTTCCTGAGCAGCACCCTGAAA

AGCCTGGAAGAAAAGGACCACATCCACCGGGTGCTGGACAAGATCACCGAC

ACCCTGATTCACCTGATGGCCAAGGCCGGACTGACCCTGCAGCAGCAGCAT

CAGAGACTGGCTCAGCTGCTGCTGATCCTGTCCCACATCCGGCACATGAGC

AACAAGCGGATGGAACATCTGTACAGCATGAAGTGCAAGAACGTGGTGCCT

CTGTTCGATCTGCTGCTGGAAATGCTGGACGCCCACAGGCTGCACGCCCCA

ACATCCaGATCCggatctggaagtggctccCTGAGAGTGAAGTTTAGCAGA

AGCGCCGACGCCCCTGCCTATCAGCAGGGACAGAACCAGCTGTATAACGAG

CTGAACCTGGGCAGGCGGGAAGAGTACGACGTGCTGGATAAGAGGCGGGGC

AGGGACCCTGAAATGGGCGGCAAACCCAGACGGAAGAACCCCCAGGAAGGC

CTGTACAACGAACTGCAGAAAGACAAGATGGCCGAGGCCTACAGCGAGATC

GGAATGAAGGGCGAGCGGCGGAGAGGCAAGGGACATGATGGCCTGTACCAG

GGCCTGTCCACCGCCACCAAGGACACCTATGACGCCCTGCACATGCAGGCC

CTGCCTCCAAGGgaagtggatctgggagcggctctatggtgtctaagggg gaagaggacaacatggccatcatcaaagaattcatgcggttcaaggtgcac
```

-continued
```
atggaaggctccgtgaatggccacgaattcgagatcgaggggagggcgag ggcagaccttatgagggaacccagaccgccaagctgaaagtgaccaagggc ggacccctgcctttcgcctgggatatcctgtctcccagtttatgtacggc agcaaggcctacgtgaagcaccccgccgacatccccgactacctgaagctg agcttccctgagggcttcaagtgggagagagtgatgaatttcgaggacggc ggagtcgtgacagtgacccaggatagctactgcaggacggcgagttcatct acaaagtgaagctgcggggcaccaacttccccagcgacggacccgtgatgc agaaaaagaccatgggctgggaggccagctccgagagaatgtacccagagg acggggcctgaaggggagatcaagcagcggctgaaactgaaggatggcg gccactacgacgcagaagtgaaaaccacctacaaggccaagaaacctgtgc agagcctggcgcctacaatgtgaacatcaagaggacattaccagccacaac gaggactacaccatcgtggaacagtacgagcgggccgagggcaggcattct acaggcggaatggatgaactgtataagtgcgtgaccgacTAG
```

SEQ ID NO: 39
MIHLGHILFLLLLPVAAADYKDDDDKQTTPGERSSLPAFYPGTSGSCSGCG
SLSLPIYIWAPLAGTCGVLLLSLVITLYCKRGRKKLLYIFKQPFMRPVQTT
QEEDGCSCRFPEEEEGGCELGSGSGSGSDRRGGRMLKHKRQRDDGEGRGEV
GSAGDMRAANLWPSPLMIKRSKKNSLALSLTADQMVSALLDAEPPILYSEY
DPTRPFSEASMMGLLTNLADRELVHMINWAKRVPGFVDLTLHDQVHLLECA
WLEILMIGLVWRSMEHPGKLLFAPNLLLDRNQGKCVEGMVEIFDMLLATSS
RFRMMNLQGEEFVCLKSIILLNSGVYTFLSSTLKSLEEKDHIHRVLDKITD
TLIHLMAKAGLTLQQQHQRLAQLLLILSHIRHMSNKRMEHLYSMKCKNVVP
LFDLLLEMLDAHRLHAPTSRSGSGSGSLRVKFSRSADAPAYQQGQNQLYNE
LNLGRREEYDVLDKRRGRDPEMGGKPRRKNPQEGLYNELQKDKMAEAYSEI
GMKGERRRGKGHDGLYQGLSTATKDTYDALHMQALPPRGSGSGSGSMVSKG
EEDNMAIIKEFMRFKVHMEGSVNGHEFEIEGEGEGRPYEGTQTAKLKVTKG
GPLPFAWDILSPQFMYGSKAYVKHPADIPDYLKLSFPEGFKWERVMNFEDG
GVVTVTQDSSLQDGEFIYKVKLRGTNFPSDGPVMQKKTMGWEASSERMYPE
DGALKGEIKQRLKLKDGGHYDAEVKTTYKAKKPVQLPGAYNVNIKLDITSH
NEDYTIVEQYERAEGRHSTGGMDELYKCVTD

The polypeptide of SEQ ID NO: 39 includes the following domains: Dap10 signal peptide (MIHLGHIL-FLLLLPVAAA, SEQ ID NO: 40), flag tag (DYKDDDDK, SEQ ID NO: 41), Dap10 extracellular domain (QTTP GERSSLPAFYPGTSGSCSGCGSLSLP, SEQ ID NO: 42), CD8 transmembrane domain (IYIWAPLAGTCGV LLLSLVITLYC, SEQ ID NO: 43), 4-1BB costimulatory domain (KRGRKKLLYIFKQPFMRPVQTTQ EEDGCSC RFPEEEEGGCEL, SEQ ID NO: 44), first linker (GS GSGSGS, SEQ ID NO: 45), modified ERa domain (DRRG-GRMLKHKRQRDDGEGRGEVGSAGDMRAANL WPSP LMIKRSKKNSLALSLTADQMVSALLDAEPPILYSEY-DPTRPFSEASMMGLLT NLADRELVHMINWAKRVP GFVDLTLHDQVSALLECAWLEILMIGLVWRSMEHPG KLLFAPNLLLDRNQGKCVEGMVEIFDMLLATSSR-FRMMNLQGEEFVCLKSIILLN SGVYTFLSSTLKSLE EKD HIHRVLDKITDTLIHLMAKAGLTLQQQHQR-LAQLLLIL SHIRHMSNKRMEHLYSMKCKNVVPLFD LLLEMLDAHRLHAPTS, SEQ ID NO: 46), second linker (RSGSGSGS, SEQ ID NO: 47), CD3 zeta signaling domain (LRVKFSRSADAPAYQQGQNQLYNELNLGRREEY-DVLDKRRGRDPEMGGKPRRK NPQEGLYNELQKDK-MAEAYSEIGMKGERRRGKGHDGLYQGLSTATKDTY-DALH MQALPPR, SEQ ID NO: 48), third linker (GSGSGSGS, SEQ ID NO: 49), mCherry (MVSKGEEDN-MAIIKEFMRFKVHMEGSVNGHEFEIEGEGEGRPYE GTQTAKLKV TKGGPLPFAWDILSPQFMYGSKAYVK HPADIPDYLKLSFPEGFKWERVMNFEDG GVVTVT QDS SLQDGEFIYKVKLRGTNFPSDGPVMQKKTM GWEASSERMYPEDG ALKGEIKQRLKLKDGGHY-DAEVKTTYKAKKPVQLPGAYNVNIKLDITSHNEDYT IVEQYERAEGRHSTGGMDELYKCVTD, SEQ ID NO: 50).

Example 6—Ligand-Induced Surface Expression of NHR-LBD Fusion Constructs Extends to Different NHRs Including Progesterone Receptor (PR)

Figure 6:
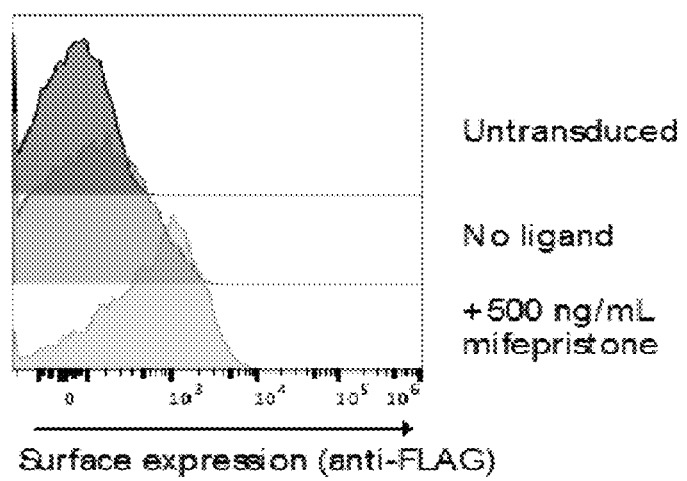
FIG. 6 is a set of flow cytometry diagrams of Jurkat T cells transduced with CAR constructs having progesterone receptor LBDs. The cells were either left untreated or were treated with 500 ng/mL mifepristone.

To test whether progesterone receptor ("PR") LBD fusions exhibited ligand-induced surface expression, a construct (v33) was generated (nucleic acid and polypeptide sequences for this construct are shown below as SEQ ID NOs: 51 and 52, respectively). The tested construct contained an N-terminal FLAG tag for surface detection. Jurkat T cells were transduced with lentiviral vectors encoding the construct, and were either left untreated, or were treated with 500 ng/mL mifepristone, a PR ligand. The cells were stained for surface protein expression after two hours of drug treatment. The construct exhibited ligand-induced surface expression of the polypeptide as detected by flow cytometry (FIG. 6), indicating that other NHR-LBDs (aside from ERa) could be used to generate constructs with ligand-inducible surface expression, and that ligand-induced surface expression of NHR-LBD fusions proteins is a generizable phenomenon.

SEQ ID NO: 51
```
ATGATCCACCTGGGACACATCCTGTTTTTGCTGCTGCTGCCAGTGGCTGC

CGCCgattacaaagacgacgatgataaaCAGACAACACCAGGCGAGAGAT

CTAGCCTGCCCGCCTTCTACCCTGGCACCAGCGGCTCTTGTTCTGGCTGT

GGCAGCCTGTCTCTGCCCatctatatttgggcacccctggctgaacctg cggagtgctgctgctgtctctcgtgattacactgtattgcAAAAGGGGCC

GGAAAAAGCTGCTGTATATTTTCAAACAGCCTTTTATGAGGCCTGTGCAG

ACAACACAGGAAGAGGACGGCTGTAGCTGTCGGTTCCCCGAAGAGGAAGA

GGGGGGCTGCGAACTGggatcaggcagtggctctggcagcGGGCAAGACA

TTCAGCTCATACCTCCTTTGATAAATTTGCTGATGTCTATAGAACCAGAT

GTCATATACGCTGGTCACGACAATACGAAACCGGACACATCTTCATCTTT

GCTTACCTCTCTGAATCAACTGGGTGAACGACAGCTCCTGAGTGTTGTTA

AGTGGTCTAAAAGCCTCCCGGGCTTCAGGAATTTGCACATAGACGACCAA

ATCACGCTCATCCAATATTCCTGGATGAGTCTCATGGTCTTTGGTCTCGG

TTGGCGCAGCTATAAGCACGTCTCTGGCCAGATGTTGTATTTCGCACCAG

ACCTGATCCTGAACGAACAGAGGATGAAGGAATCAAGCTTTTACTCTCTC
```

-continued
```
TGCTTGACTATGTGGCAAATCCCCCAAGAATTCGTGAAACTTCAAGTTTC

CCAAGAAGAATTCCTCTGCATGAAAGTCCTTCTTTTGCTCAACACGATTC

CCCTGGAAGGCTTGAGGTCTCAAACGCAATTCGAGGAGATGCGGAGTAGC

TATATACGCGAACTCATCAAGGCCATCGGTTTGCGGCAAAAGGGAGTGGT

CTCTAGTAGCCAACGATTTTACCAGCTGACTAAGCTCCTTGACAACCTTC

ACGATCTCGTCAAACAACTGCACCTGTACTGTCTTAACACATTTATACAA

TCACGGGCACTTTCTGTAGAGTTCCCAGAGATGATGTCTGAGGTCATCGC

AGCCCAACTTCCGAAAATTCTTGCAGGAATGGTGAAGCCACTTCTGTTCC

ATAAGAAAaGATCCggatctggaagtggctccCTGAGAGTGAAGTTTAGC

AGAAGCGCCGACGCCCCTGCCTATCAGCAGGGACAGAACCAGCTGTATAA

CGAGCTGAACCTGGGCAGGCGGGAAGAGTACGACGTGCTGGATAAGAGGC

GGGGCAGGGACCCTGAAATGGGCGGCAAACCCAGACGGAAGAACCCCCAG

GAAGGCCTGTACAACGAACTGCAGAAAGACAAGATGGCCGAGGCCTACAG

CGAGATCGGAATGAAGGGCGAGCGGCGGAGAGGCAAGGGACATGATGGCC

TGTACCAGGGCCTGTCCACCGCCACCAAGGACACCTATGACGCCCTGCAC

ATGCAGGCCCTGCCTCCAAGAggaagtggatctgggagcggctctatggt gtctaaggggggaagaggacaacatggccatcatcaaagaattcatgcggt tcaaggtgcacatggaaggctccgtgaatggccacgaattcgagatcgag ggggagggcgagggcagaccttatgagggaacccagaccgccaagagaaa gtgaccaagggcggacccctgcctttcgcctgggatatcctgtacccag tttatgtacggcagcaaggcctacgtgaagcaccccgccgacatccccga ctacctgaagctgagcttccctgagggcttcaagtgggagagagtgatga atttcgaggacggcggagtcgtgacagtgacccaggatagctactgcagg acggcgagttcatctacaaagtgaagagcggggcaccaacttccccagcg acggacccgtgatgcagaaaaagaccatgggctgggaggccagctccgag agaatgtacccagaggacggggccctgaaggggggagatcaagcagcggct gaaactgaaggatggcggccactacgacgcagaagtgaaaaccacctaca aggccaagaaacctgtgcagctgcctggcgcctacaatgtgaacatcaag aggacattaccagccacaacgaggactacaccatcgtggaacagtacgag cgggccgagggcaggcattctacaggcggaatggatgaactgtataagtg cgtgaccgac
```
SEQ ID NO: 52
```
MIHLGHILFLLLLPVAAADYKDDDDKQTTPGERSSLPAFYPGTSGSCSGC

GSLSLPIYIWAPLAGTCGVLLLSLVITLYCKRGRKKLLYIFKQPFMRPVQ

TTQEEDGCSCRFPEEEEGGCELGSGSGSGSGQDIQLIPPLINLLMSIEPD

VIYAGHDNTKPDTSSSLLTSLNQLGERQLLSVVKWSKSLPGFRNLHIDDQ

ITLIQYSWMSLMVFGLGWRSYKHVSGQMLYFAPDLILNEQRMKESSFYSL

CLTMWQIPQEFVKLQVSQEEFLCMKVLLLLNTIPLEGLRSQTQFEEMRSS

YIRELIKAIGLRQKGVVSSSQRFYQLTKLLDNLHDLVKQLHLYCLNTFIQ

SRALSVEFPEMMSEVIAAQLPKILAGMVKPLLFHKKRSGSGSGSLRVKFS

RSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALH

MQALPPRGSGSGSGSMVSKGEEDNMAIIKEFMRFKVHMEGSVNGHEFEIE

GEGEGRPYEGTQTAKLKVTKGGPLPFAWDILSPQFMYGSKAYVKHPADIP

DYLKLSFPEGFKWERVMNFEDGGVVTVTQDSSLQDGEFIYKVKLRGTNFP

SDGPVMQKKTMGWEASSERMYPEDGALKGEIKQRLKLKDGGHYDAEVKTT

YKAKKPVQLPGAYNVNIKLDITSHNEDYTIVEQYERAEGRHSTGGMDELY

KCVTD
```

The polypeptide of SEQ ID NO: 52 includes the following domains: Dap10 signal peptide (MIHLGHIL-FLLLLPVAAA, SEQ ID NO: 53), flag tag (DYKDDDDK, SEQ ID NO: 54), Dap10 extracellular domain (QTTP GERSSLPAFYPGTSGSCSGCGSLSLP, SEQ ID NO: 55), CD8 transmembrane domain (IYIWAPLAGTCGV LLLSLVITLYC, SEQ ID NO: 56), 4-1BB costimulatory domain (KRGRKKLLYIFKQPFMRPVQTTQ EEDGCSCR F PEEEEGGCEL, SEQ ID NO: 57), first linker (GSG SGSGS, SEQ ID NO: 58), Progesterone receptor LBD (GQDIQLIPPLINLLMSIEPDVIYAGHDNTKP DTSS SLLTSLNQLGERQLLSVVKWSKSLPGFRNLHIDDQIT LIQYSWMSLMVFGL GWRSYKHVSGQMLYFAPDLIL-NEQRMKESSFYSLCLTMWQIPQEFVKLQVSQEE FLCMKVLLLLNTIPLEGLRSQTQFEEMRSSYIRE-LIKAIGLRQKGVVSSSQRFYQLT KLLDNLHDLVK QLHLYCLNTFIQSRALSVEFPEMMSEVIAAQLP-KILAGMVKPLL FHKK, SEQ ID NO: 59), second linker (RSGSGSGS, SEQ ID NO: 60), CD3zeta signaling domain (LRVKFSRSADAPAYQQGQNQLYNELNLGRREEY-DVLDKRR GRDPEMGGKPRRKNPQEGLYNELQKDK-MAEAYSEIGMKGERRRGKGHDGLYQ GLSTATKDTY-DALHMQALPPR, SEQ ID NO: 61), third linker (GSGSG SGS, SEQ ID NO: 62), and mCherry (MVSKGEEDN-MAIIKEFMRFKVHMEGSVNGHEFEIEGEGE GRPYE GT QTAKLKVTKGGPLPFAWDILSPQFMYGSKAYVK H PADIPDYLKLSFPE GFKWERVMNFEDGGVV TVT QDSSLQDGEFIYKVKLRGTNFPSDGPVMQKKTMG WEASSERMYPEDGALKGEIKQRLKLKDGGHYDAE VKTTYKAKKPVQLPGAYN VNIKLDITSHNEDY-TIVEQYERAEGRHSTGGMDELYKCVTD, SEQ ID NO: 63).

The nucleotide sequence of SEQ ID NO: 51 includes the following sequences encoding the indicated domains: Dap10 signal peptide (ATGATCCACCTGGGACACAT CCTGTTTTTGCTGCTGCTGCCAGTGGCTGCCGCC, SEQ ID NO: 63), flag tag (gattacaaagacgacgatgataaa, SEQ ID NO: 64), Dap10 extracellular domain (CAGACAAC ACCAGGCGAGAGATCTAGCCTGCCCGCCTTCTACC CTGGCACCAGCGGCTCTT GTTCTGGCTGTGGC AGCCTGTCTCTGCCC, SEQ ID NO: 65), CD8 transmembrane domain (atctatatttgggcacccctggctggaacctgcggagtgctg ctgctgtctctcgtgattacactgtattgc, SEQ ID NO: 66), 4-1BB costimulatory domain (AAAAGGGGCCGGAAAAA GCTGCT GTATATTTTCAAACAGCCTTTTATGAGG CCTGTGCAGACAACACAGGAAGAGG ACGGCTGTA GCTGTCGGTTCCCCGAAGAGGAAGAGGGGGGC TGCGAACTGc SEQ ID NO: 67), first linker (ggatcaggcagtggctctggcagc, SEQ ID NO: 68), Progesterone receptor LBD (GGGCAAGACATTCAGCTCATACCTC CTTTGATAAATTTGCTG ATGTCTATAGAACCAGAT GTCATATACGCTGGTCACGACAATACGAAACCG GAC ACATCTTCATCTTTGCTTACCTCTCTGAAT- CAACTGGGTGAACGACAGCTCCTG AGTGTTGTTAA GTGGTCTAAAAGCCTCCCGGGCTTCAGGAAT-TTGCACATAGA CGACCAAATCACGCTCATCCAAT-ATTCCTGGATGAGTCTCATGGTCTTTGGTCT CGGT TGGCGCAGCTATAAGCACGTCTCTGGCCAGATG TTG TATTTCGCACCAG ACCTGATCCTGAACGA ACAGAGGATGAAGGAATCAAGCTTTTACTCTC TCTGC TTGACTATGTGGCAAATCCCCCAAGAAT-TCGTGAAACTTCAAGTTTCCCAAGA AGAATTCCT CT GCATGAAAGTCCTTCTTTTGCTCAACACGAT-TCCCCTGGAAG GCTTGAGGTCTCAAACGCAAT-TCGAGGAGATGCGGAGTAGCTATATACGCGAA CTCATCAAGGCCATCGGTTTGCGGCAAAAGG-GAGTGGTCTCTAGTAGCCAACG ATTTTACCAGCT GACTAAGCTCCTTGACAACCTTCACGATCTCGT-CAAACAAC TGCACCTGTACTGTCTTAACACATT-TATACAATCACGGGCACTTTCTGTAGAGT TCCCA GAGATGATGTCTGAGGTCATCGCAGCCCAAC TTC CGAAAATTCTTGCA GGAATGGTGAAGCCACTTC TGTTCCATAAGAAA, SEQ ID NO: 69), second linker (ggatctggaagtggctcc, SEQ ID NO: 70), CD3zeta signaling domain (CTGAGAGTGAA GTTTAGCAGAAGCG CCGACGCCCCTGCCTATCAGCAGGGACAGAACCAG CTG TATAACGAGCTGAACCTGGGCAGGCGGGAA GAGTACGACGTGCTGGATAAGA GGCGGGGCAGGG AC CCTGAAATGGGCGGCAAACCCAGACGGAAGA ACCCCC AGGAAGGCCTGTACAACGAACTGCAG AAA GACAAGATGGCCGAGGCCTACA GCGAGATCG GAATGAAGGGCGAGCGGCGGAGAGGCAAGGGA-CATGATGGCC TGTACCAGGGCCTGTCCACCGC-CACCAAGGACACCTATGACGCCCTGCACATG CAGGCCCTGCCTCCAAGA, SEQ ID NO: 71), third linker (ggaagtggatctgggagcggctct, SEQ ID NO: 72), and mCherry (atggtgtctaaggggggaagaggacaacatggccatcatcaaa gaattcatg cggttcaaggtgcacatggaaggctccgtgaatggccacgaat-tcgagatcgaggggggagggcgagggcagaccttatgag ggaacccagaccgc c aagctgaaagtgaccaagggcggaccccctgcctttcgcctgggatatcctgtctc cccagtttatgtac ggcagcaaggcctacgtgaagcacccccgccgacatcccc gactacctgaagctgagatccctgagggatcaagtgggaga gagtgatgaat-ttcgaggacggcggagtcgtgacagtgacccaggatagctctctgcagg acggcgagttcatctacaaagtg aagctgcggggcaccaacttccccagcgac ggacccgtgatgcagaaaaagaccatgggctggaggccagctccgagag aatgtacccagaggacggggccctgaaggggggagatcaagcagcggct-gaaactgaaggatggcggccactacgacgcag aagtgaaaaccacctacaa ggccaagaaacctgtgcagctgcctggcgcctacaatgtgaacatcaagctgga-cattaccagc cacaacgaggactacaccatcgtggaacagtacgagcgggcc gagggcaggcattctacaggcggaatggatgaactgtata agtgcgtgaccgac, SEQ ID NO: 73).

Figure 7A:
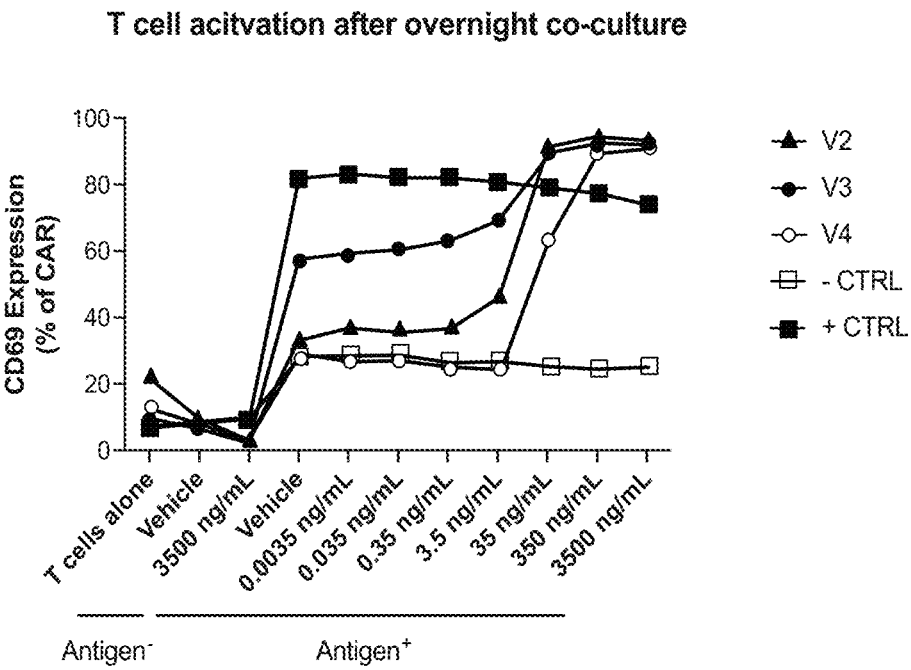
FIG. 7A is a graph showing T cell activation of primary human T cells transduced with lentiviral vectors encoding J6M0-ERa-LBD CAR construct after overnight co-culture with antigen-negative (K562 cell line) and antigen-positive (MM1S cell line) targets.

Example 7—Ligand-Induced NHR-LBD CAR T Cell Activation is Antigen- and Drug-Dependent Primary human T cells were transduced with lentiviral vectors encoding J6M0-ERa-LBD CAR construct. T cell activation was assessed by surface staining for the canonical T cell activation marker, CD69, after overnight co-culture with antigen-negative (K562 cell line) and antigen-positive (MM1S cell line) targets in the presence of increasing concentrations of 4-OHT (FIG. 7A). A unique dose-dependent T cell response was observed for each construct, with the proximity of the LBD to the cell membrane correlating to background activation (activation in the absence of ligand) and sensitivity to ligand. All constructs displayed activation levels comparable to the positive control (canonical CAR) at increasing drug concentrations.

Figure 7B:
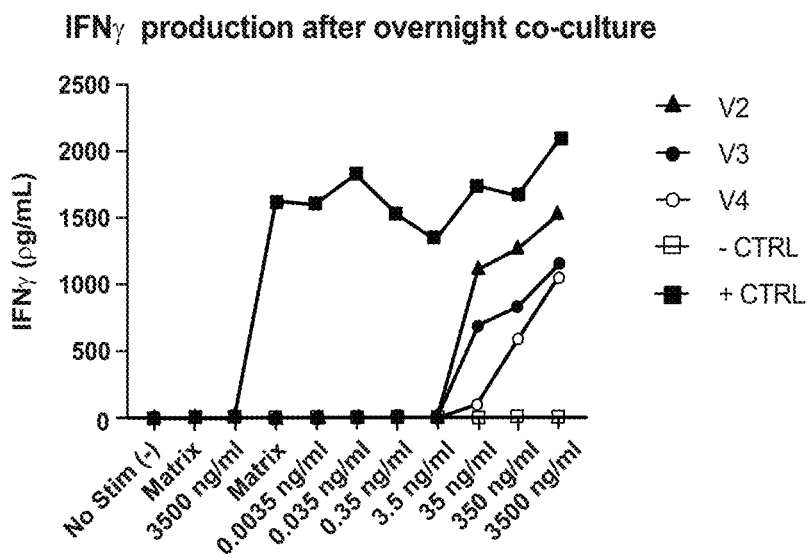
FIG. 7B is a graph showing IFN-γ production by primary human T cells transduced with lentiviral vectors encoding J6M0-ERa-LBD CAR construct after overnight co-culture with antigen-negative (K562 cell line) and antigen-positive (MM1S cell line) targets.

The ability of the J6M0-ERa-LBD CAR cells to produce inflammatory cytokines was assessed via IFN-γ ELISA on co-culture supernatants isolated from overnight co-cultures of T cells with antigen-negative (K562 cell line) and antigen-positive (MM1S cell line) targets in the presence of increasing concentrations of 4-OHT. IFN-γ production was shown to be dose-dependent, with all NHR-LBD constructs producing cytokine at increasing ligand concentrations (FIG. 7B).

Figure 8A:
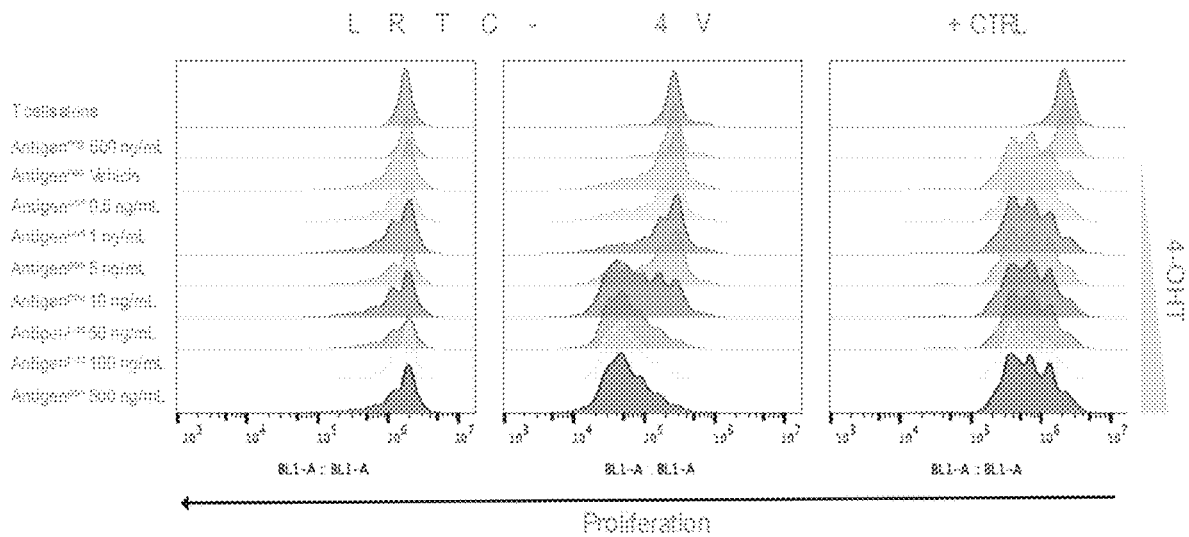
FIG. 8A is a set of flow cytometry diagrams showing proliferation of primary human CD4 T cells that were transduced with lentiviral vectors encoding V4 FMC63-ERa-LBD CAR or canonical CAR controls, co-cultured with either antigen-negative (K562 cell line) or antigen-positive (Raji cell line) targets, and with increasing concentrations of ligand 4-OHT.

Example 8—Ligand-Induced NHR-LBD CAR T Cell Proliferation and Killing are Antigen- and Ligand-Dependent Primary human CD4 T cells were transduced with lentiviral vectors encoding V4 FMC63-ERa-LBD CAR or canonical CAR controls. The cells were labeled with carboxyfluorescein succinimidyl ester ("CFSE") prior to co-culture with either antigen-negative (K562 cell line) or antigen-positive (Raji cell line) targets. The cells were also co-cultured with increasing concentrations of ligand (4-OHT). Three days after co-culture, cells were analyzed via flow cytometry and proliferation was assessed by dilution of CFSE dye on CD4+ T cells. FMC63-ERa-LBD CART cells proliferated only in the presence of antigen and ligand (FIG. 8A).

Figure 8B:
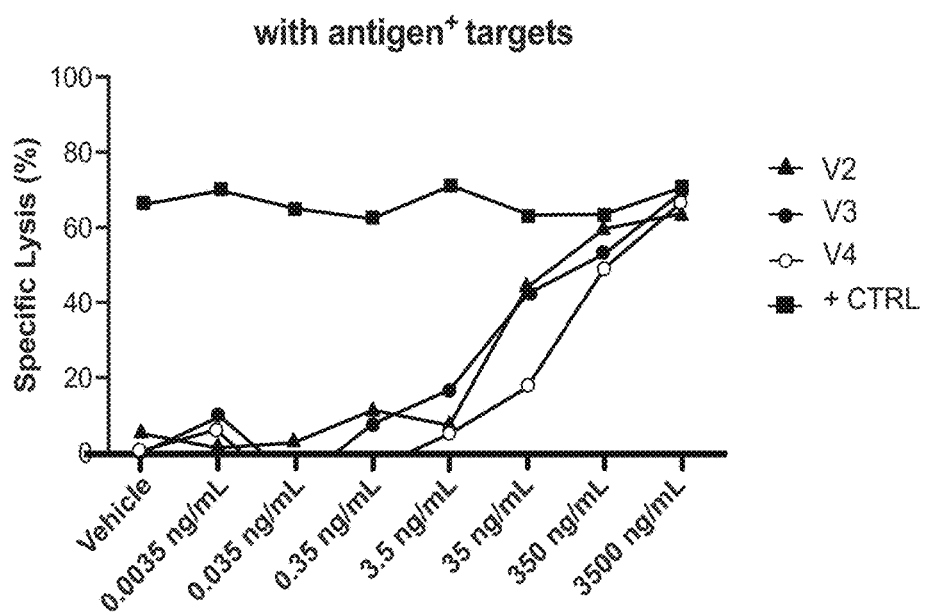
FIG. 8B is graph showing lysis of antigen-positive targets (MM1S cell line) mediated by primary human T cells transduced with lentiviral vectors encoding J6M0-ERa-LBD CAR constructs with increasing concentrations of 4-OHT.

Primary human T cells were transduced with lentiviral vectors encoding the J6M0-ERa-LBD CAR construct described in Example 7. The ability of T cells bearing the J6M0-ERa-LBD CAR construct to kill antigen-positive targets (MM1S cell line) in a drug-dependent manner was assessed via a flow cytometry-based killing assay. Target cells were labeled with CF SE prior to co-culture, and the number of cells remaining in each well after co-culture was determined via quantification of a fixed volume using the Intellicyt flow cytometer. Specific lysis was determined by comparing the number of targets remaining per experimental well to the number of targets remaining in control wells that contained both targets and non-antigen specific conventional CAR T cells (−CTRL). Specific lysis was reported as a percentage derived from the following equation: 1−(# events per experiment well/# average events−CTRL wells). Target cell killing was dependent on the dose of the ligand, with all constructs eliminating antigen-positive targets at levels comparable to the conventional CAR (+CTRL) at higher drug doses (FIG. 8B).

Figure 9:
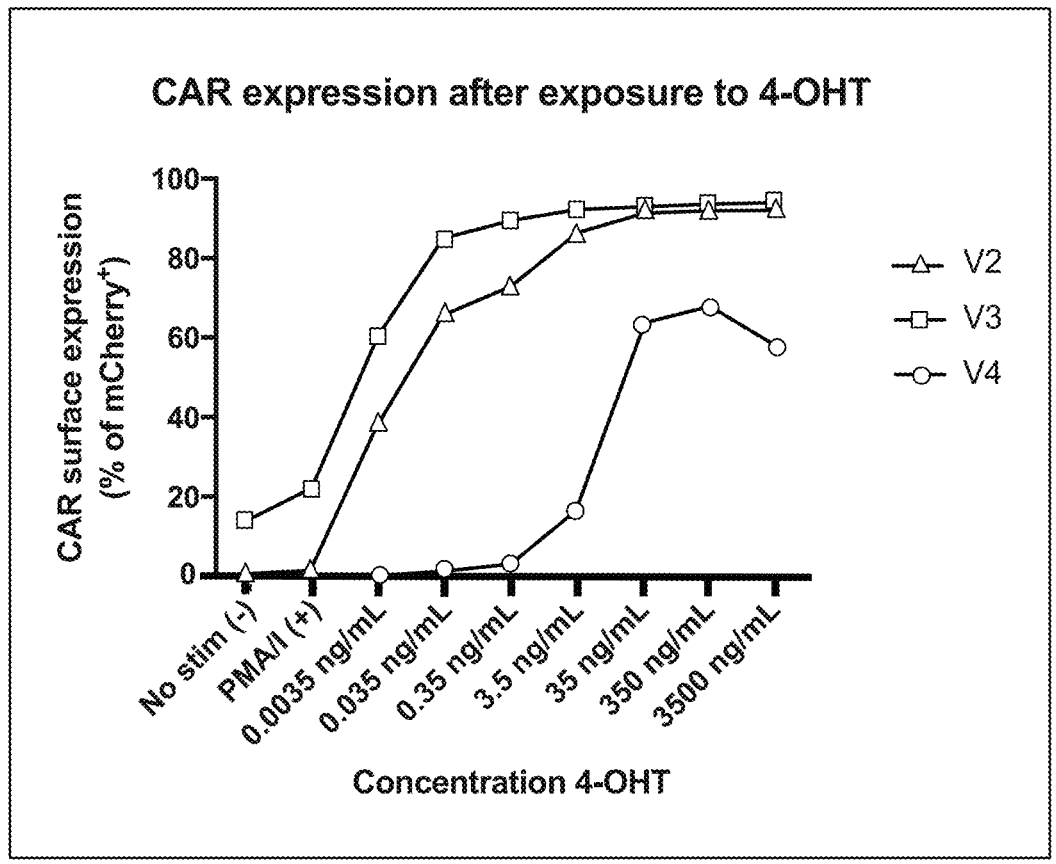
FIG. 9 is a graph showing surface expression of various CAR constructs having a LBD at different locations relative to the cell membrane at increasing concentrations of 4-OHT.

Example 9—the Location of the LBD within the CAR Polypeptide Determines Sensitivity to Ligand-Induced Surface Expression of NHR-LBD CAR The dose responsiveness of the V2, V3, and V4 constructs shown in FIG. 1 was compared in Jurkat T cells. Detection of surface expression of NHR-LBD CAR protein on Jurkat T cells was performed after incubation for one hour with 4-OHT ligand at the concentrations indicated on the x-axis of FIG. 9. Surface receptor expression was detected using an anti-cMyc antibody, and was reported as a percentage of reporter-positive cells (as determined by mCherry expression). The ligand dose at which surface expression was detected for each construct corresponded to the location of the LBD, in relation to the surface membrane, for each construct. Construct V4, which harbors the LBD immediately adjacent to the surface membrane, showed no detectable surface expression in the absence of ligand, with surface expression detected only at higher concentrations of 4-OHT. In contrast, when the LBD was located further from the membrane (see e.g., V2), a higher basal level of surface expression was detected (~20%), and enhanced sensitivity to 4-OHT was observed. Activation of Jurkat T cells with PMA/Ionomycin did not lead to ligand-independent NHR-LBD CAR surface expression, demonstrating that activation of the T cell alone (through the endogenous TCR, for example) does not result in trafficking of the receptor to the cell surface.

Figure 10A:
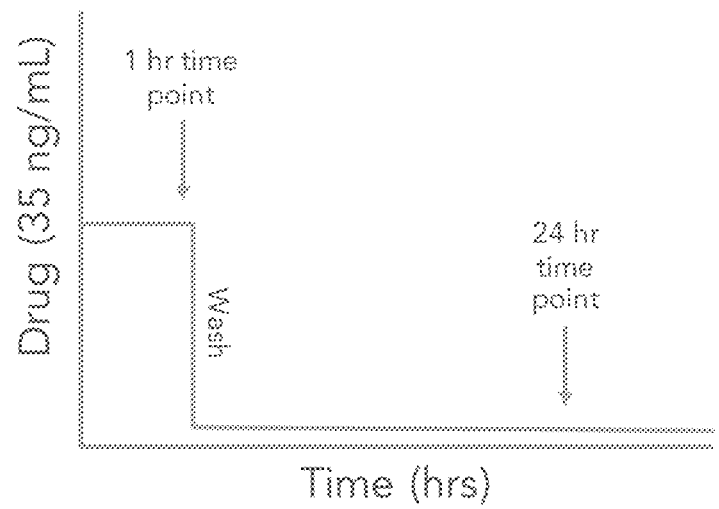
FIG. 10A is a schematic showing timeline of the experimental procedure.

Example 10—Duration of NHR-LBD CAR Surface Expression is Dependent on the Location of LBD in Polypeptide T cells were transduced with FMC63-ERa-LBD CARs and were exposed to 4-OHT at 35 ng/mL for one hour before either being stained for surface expression using an anti-cMyc antibody, or being washed and cultured overnight in the absence of drug (timeline shown in FIG. 10A).

Figure 10B:
FIG. 10B is a bar graph showing surface expression of various CAR constructs before and after co-culture with 4-OHT.

The number of cells expressing surface protein was reported as a percentage of reporter-positive cells (as determined by mCherry expression). The duration of NHR-LBD CAR expression on the cell surface for constructs V2, V3, and V4 was determined. The construct that harbored the LBD most proximal to the membrane (V4) showed the most rapid and complete return to baseline 24 hours after ligand removal (FIG. 10B, bars labeled "V4").

Figure 11A:
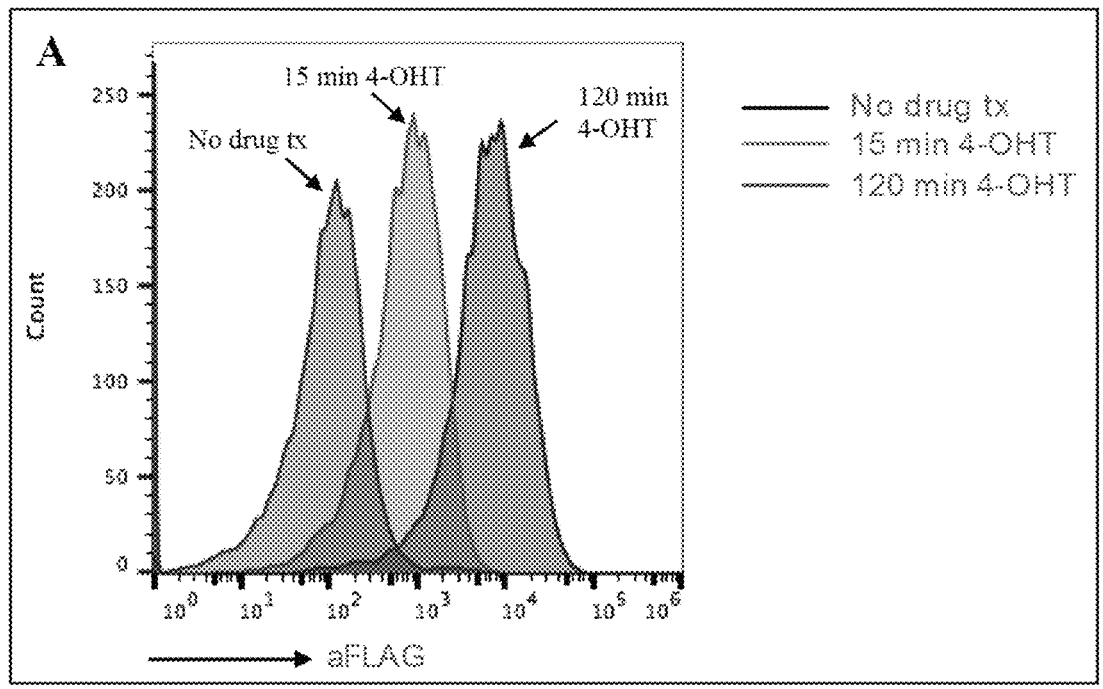
FIG. 11A is a set of flow cytometry diagrams showing Jurkat T cells that were transduced with the FLAG-ERa-LBD CAR, and left untreated or treated with 4-OHT for 15 or 120 minutes.

Example 11—Kinetics of Surface Expression in NHR-LBD-CAR Constructs after Ligand Addition Jurkat T cells were transduced with the FLAG-ERa-LBD construct used in Example 5 were left untreated or were treated with 500 ng/mL 4-OHT for 15 minutes or 120 minutes, and surface expression was detected after ligand treatment. Ligand treatment induced surface expression within 15 minutes, and further upregulation was observed over time (FIG. 11A).

Figure 11B:
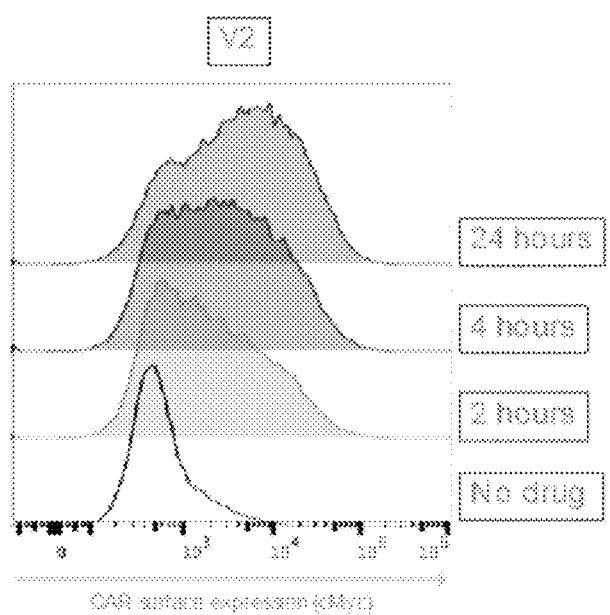
FIG. 11B is a set of flow cytometry diagrams showing human T cells that were transduced with lentiviral vector encoding the FMC63-ERa-LBD CAR, and left untreated or treated with 4-OHT for 2 hours, 4 hours, or 24 hours.

Human T cells were transduced with lentiviral vector encoding the FMC63-ERa-LBD CAR (v2 as shown in FIG. 1). The cells were treated with the ERa ligand 4-OHT for the indicated duration, and then stained for surface expression of the CAR (FIG. 11B). The data in FIG. 11B show similar kinetics for the ligand treatment induced surface expression as was observed for Jurkat T cells.

Figure 12:
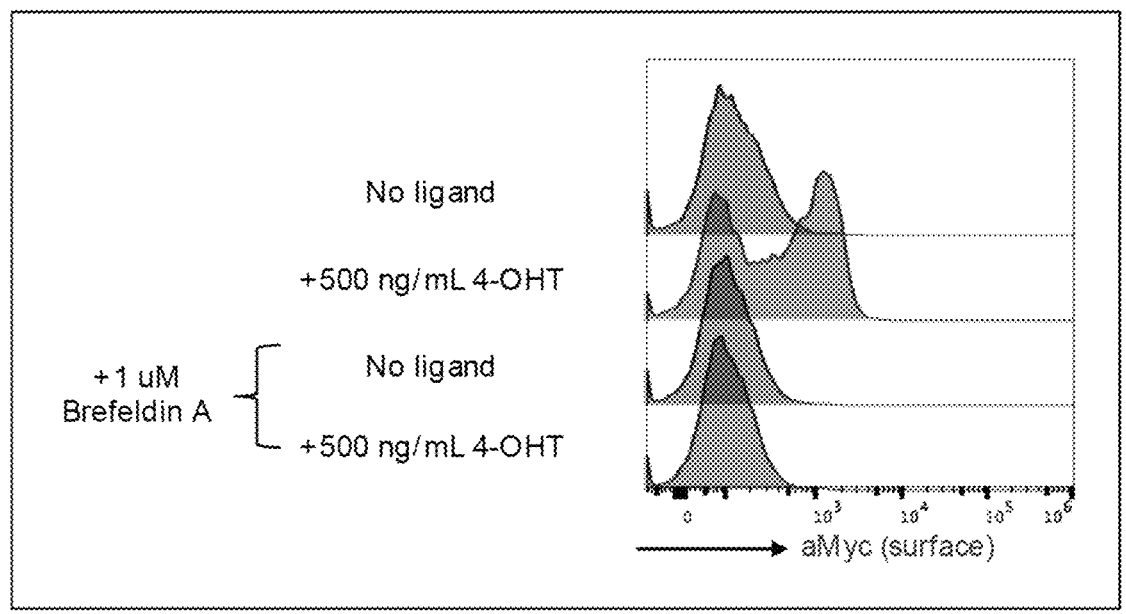
FIG. 12 is a set of flow cytometry diagrams of primary human T cells expressing FMC63-CARs having ERa LBDs. The cells were either left untreated or were treated with 500 ng/mL 4-OHT. Some samples were pretreated with 1 μM Brefeldin A.

Example 12—Brefeldin a Treatment Blocks Ligand-Induced Surface Trafficking of NHR LBD Fusions Primary human T cells expressing FMC63-CAR with ERa LBD fusion were left untreated or were treated with 500 ng/mL 4-OHT ligand for two hours to induce surface expression of the CAR. Prior to 4-OHT treatment, half the cells were pre-treated with 1 uM Brefeldin A (FIG. 12, bottom two panels) to inhibit protein export from the Golgi. Brefeldin A pre-treatment prevented 4-OHT-induced increase in surface protein expression. Without wishing to be bound by theory, these data suggest that increased surface expression arises from relocalization of a pool of polypeptides that is sequestered intracellularly in the absence of ligand.

Example 13—Generation of Constructs

Figure 13:
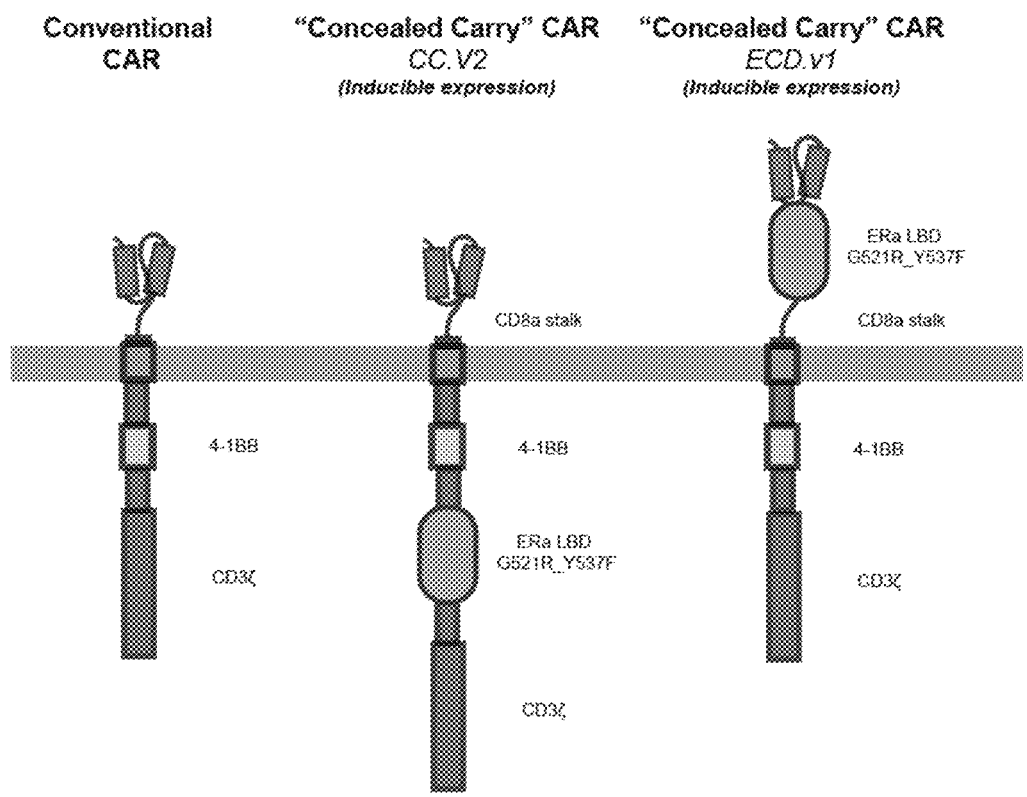
FIG. 13 is a diagram of the v2 CAR construct and ECD.v1 CAR (also called LBD-ECD CAR) construct tested. The cellular membrane is depicted as a gray box. The extracellular scFv domain, the extracellular ERa LBD, the transmembrane domain (embedded in the cellular membrane), the intracellular 4-1BB domain, and the intracellular CD3γdomain are depicted.

A conventional chimeric antigen receptor ("Conventional CAR", FIG. 13, left) was modified to include the estrogen receptor alpha ("ERa") ligand binding domain ("ERa LBD," FIG. 1, in green) either in the intracellular portion of the protein (v2 CAR as described in Example 1) or in the extracellular portion of the protein ("Concealed Carry' CAR ECD.v1" or "LBD-ECD CAR"). Point mutations were introduced into the ERa LBD domain of both v2 CAR and ECD.v1 CAR. The nucleic acid and polypeptide sequences of v2 CAR (are shown above as SEQ ID NOs: 30 and 31) and ECD.v1 (SEQ ID NOs: 97 and 98) are provided below.

(ECD v.1 CAR)

SEQ ID NO: 97 atgcttctcctggtgacaagccttctgctctgtgagttaccacacccagca ttcctcctgattcctgaacagaagctgataagtgaggaggacttggacatc cagatgacccagaccaccagcagcctgagcgccagcctgggcgatagagtg accatcagctgcagagccagccaggacatcagcaagtacctgaactggtat cagcagaaacccgacggcaccgtgaagctgctgatctaccacaccagcaga ctgcacagcggcgtgcccagcagatttctggcagcggctccggcaccgac tacagcctgaccatctccaacctggaacaggaagatatcgctacctacttc tgtcagcaaggcaacaccctgccctacaccttcggcggaggcaccaagctg gaaatcacaggcggcggaggatctggcggaggcggaagtggcggaggggga tctgaagtgaaactgcaggaaagcggccctggcctggtggcccatctcag tctctgagcgtgacctgtaccgtgtccggcgtgtccctgcctgactatggc gtgtcctggatcagacagcccccagaaagggcctggaatggctgggagtg atctggggcagcgagacaaacctactacaacagcgccctgaagtcccggctg accatcatcaaggacaactccaagagccaggtgttcctgaagatgaacagc ctgcagaccgacgacaccgccatctactactgcgccaagcactactactac ggcggcagctacgccatggactactggggccagggcacaagcgtgaccgtg tctagcggatccgatagaaggaggcggcagaatgctgaaacacaagcggcag agggacgacggggaaggcagaggcgaagtgggatctgccggcgatatgaga gccgccaacctgtggcctagcccctgatgatcaagcggagcaagaagaac tccctggccctgagcctgaccgccgaccagatggtgtctgccctgctggat gccgagccccatcctgtacagcgagtacgaccccaccagaccttcagc gaggccagcatgatgggcctgctgaccaacctggccgaccgggaactggtg cacatgatcaactgggccaagcgggtgcccggcttcgtggatctgacactg cacgaccaggtgcacctgctggaatgcgcttggctggaaatcctgatgatc ggcctcgtgtggcggagcatggaacaccctggcaagctgctgttcgccccc aacctgctgctggaccggaaccagggcaaatgcgtggaaggcatggtggaa atcttcgacatgctgctggccacctccagccggttccggatgatgaacctg cagggcgaagagtcgtgtgtctgaagtccatcatcctgctgaatagcggc gtgtacaccttcctgagcagcacctgaaaagcctggaagaaaaggaccac atccaccgggtgctggacaagatcaccgacaccctgattcacctgatggcc aaggccggactgaccctgcagcagcagcatcagagactggctcagctgctg ctgatcctgtcccacatccggcacatgagcaacaagcggatggaacatctg tacagcatgaagtgcaagaacgtggtgcctctgttcgatctgctgctggaa atgctggacgcccacaggctgcacgcccaacatccggatccaccacgacg ccagcgccgcgaccaccaacaccggcgcccaccatcgcgtcgcagccctg -continued tccctgcgcccagaggcgtgccggccagcggcgggggcgcagtgcacacg agggggctggacttcgcctgtgatatctatatctgggcgcccttggccggg acttgtgggtccttctcctgtcactggttatcaccctttactgcaaacgg ggcagaaagaaactcctgtatatattcaaacaaccatttatgagaccagta caaactactcaagaggaagatggctgtagctgccgatttccagaagaagaa gaaggaggatgtgaactgagagtgaagttcagcaggagcgcagacgccccc gcgtaccagcagggccagaaccagctctataacgagctcaatctaggacga agagaggagtacgatgttttggacaagagacgtggccgggaccctgagatg ggggaaagccgagaaggaagaaccctcaggaaggcctgtacaatgaactg cagaaagataagatggcggaggcctacagtgagattgggatgaaaggcgag cgccggaggggcaaggggcacgatggcctttaccagggtctcagtacagcc accaaggacacctacgacgccttcacatgcaggccctgccccctcgctag (ECD v.1 CAR)
SEQ ID NO: 98
MLLLVTSLLLCELPHPAFLLIPEQKLISEEDLDIQMTQTTSSLSASLGDRV
TISCRASQDISKYLNWYQQKPDGTVKLLIYHTSRLHSGVPSRFSGSGSGTD
YSLTISNLEQEDIATYFCQQGNTLPYTFGGGTKLEITGGGGSGGGGSGGGG
SEVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYYY
GGSYAMDYWGQGTSVTVSSGSDRRGGRMLKHKRQRDDGEGRGEVGSAGDMR
AANLWPSPLMIKRSKKNSLALSLTADQMVSALLDAEPPILYSEYDPTRPFS
EASMMGLLTNLADRELVHMINWAKRVPGFVDLTLHDQVHLLECAWLEILMI
GLVWRSMEHPGKLLFAPNLLLDRNQGKCVEGMVEIFDMLLATSSRFRMMNL
QGEEFVCLKSIILLNSGVYTFLSSTLKSLEEKDHIHRVLDKITDTLIHLMA
KAGLTLQQQHQRLAQLLLILSHIRHMSNKRMEHLYSMKCKNVVPLFDLLLE
MLDAHRLHAPTSGSTTTPAPRPPTPAPTIASQPLSLRPEACRPAAGGAVHT
RGLDFACDIYIWAPLAGTCGVLLLSLVITLYCKRGRKKLLYIFKQPFMRPV
QTTQEEDGCSCRFPEEEEGGCELRVKFSRSADAPAYQQGQNLYNELNLGR
REEYDVLDKRRGRDPEMGGKPRRKNPQEGLYNELQKDKMAEAYSEIGMKGE
RRRGKGHDGLYQGLSTATKDTYDALHMQALPPR The protein and nucleic acid sequence of each
domain in ECD.v1, going from the N-terminus to the
C-terminus, in ECD.v1 are shown below.
(CSF2RA signal peptide)
SEQ ID NO: 99
atgcttctcctggtgacaagccttctgctctgtgagttaccacacccagca ttcctcctgattcct (CSF2RA signal peptide)
SEQ ID NO: 100
MLLLVTSLLLCELPHPAFLLIP (cMyc tag)
SEQ ID NO: 101
gaacagaagctgataagtgaggaggacttg (cMyc tag)
SEQ ID NO: 102
EQKLISEEDL (FMC63 $V_L$)
SEQ ID NO: 103
gacatccagatgacccagaccaccagcagcctgagcgccagcctgggcgat agagtgaccatcagctgcagagccagccaggacatcagcaagtacctgaac tggtatcagcagaaacccgacggcaccgtgaagctgctgatctaccacacc agcagactgcacagcggcgtgcccagcagattttctggcagcggctccggc accgactacgcctgaccatctccaacctggaacaggaagatatcgctacc tacttctgtcagcaaggcaacaccctgccctacaccttcggcggaggcacc aagctggaaatcaca (FMC63 $V_H$)
SEQ ID NO: 104
DIQMTQTTSSLSASLGDRVTISCRASQDISKYLNWYQQKPDGTVKLLIYHT
SRLHSGVPSRFSGSGSGTDYSLTISNLEQEDIATYFCQQGNTLPYTFGGGT
KLEIT ($(G_4S)_3$ linker between $V_L$ and $V_H$)
SEQ ID NO: 105
ggcggcggaggatctggcggaggcggaagtggcggaggggggatct ($(G_4S)_3$ linker between $V_L$ and $V_H$)
SEQ ID NO: 106
GGGGSGGGGSGGGGS (FMC63 $V_H$)
SEQ ID NO: 107
gaagtgaaactgcaggaaagcggccctggcctggtggcccccatctcagtct ctgagcgtgacctgtaccgtgtccggcgtgtccctgcctgactatggcgtg tcctggatcagacagcccccagaaagggcctggaatggctgggagtgatc tggggcagcgagacaacctactacaacagcgccctgaagtcccggctgacc atcatcaaggacaactccaagagccaggtgttcctgaagatgaacagcctg cagaccgacgacaccgccatctactactgcgccaagcactactactacggc ggcagctacgccatggactactggggccagggcacaagcgtgaccgtgtct agc (FMC63 $V_H$)
SEQ ID NO: 108
EVKLQESGPGLVAPSQSLSVTCTVSGVSLPDYGVSWIRQPPRKGLEWLGVI
WGSETTYYNSALKSRLTIIKDNSKSQVFLKMNSLQTDDTAIYYCAKHYYYG
GSYAMDYWGQGTSVTVSS GS linker between $V_H$ domain and estrogen
receptor alpha ligand binding domain
ggatcc GS linker between VH domain and estrogen receptor
alpha ligand binding domain
GS (Estrogen receptor alpha ligand binding domain)
(sequence encoding hinge underlined, sequence
encoding helix 12 in bold)
SEQ ID NO: 109
<u>gatagaagaggcggcagaatgctgaaacacaagcggcagagggacgacggg</u>

<u>gaaggcagaggcgaagtgggatctgccggcgatatgagagccgccaacctg</u>

<u>tggcctagcccctgatgatcaagcggagcaagaagaactccctggccctg</u> agcctgaccgccgaccagatggtgtctgccctgctggatgccgagccccc atcctgtacagcgagtacgaccccaccagacccttcagcgaggccagcatg atgggcctgctgaccaacctggccgaccgggaactggtgcacatgatcaac -continued tgggccaagcgggtgcccggcttcgtggatctgacactgcacgaccaggtg cacctgctggaatgcgcttggctggaaatcctgatgatcggcctcgtgtgg cggagcatggaacaccctggcaagctgctgttcgccccaacctgctgctg gaccggaaccagggcaaatgcgtggaaggcatggtggaaatcttcgacatg ctgctggccacctccagccggttccggatgatgaacctgcagggcgaagag ttcgtgtgtctgaagtccatcatcctgctgaatagcggcgtgtacaccttc ctgagcagcaccctgaaaagcctggaagaaaaggaccacatccaccgggtg ctggacaagatcaccgacaccctgattcacctgatggccaaggccggactg accctgcagcagcagcatcagagactggctcagctgctgctgatcctgtcc cacatccggcacatgagcaacaagcggatggaacatctgtacagcatgaag tgcaagaacgtggtgcctctgttcgatctgctgctggaaatgctggacgcc cacaggctgcacgccccaacatcc

(Estrogen receptor alpha ligand binding domain)
(hinge underlined, helix 12 in bold)

SEQ ID NO: 110

<u>DRRGGRMLKHKRQRDDGEGRGEVGSAGDMRAANLWPSPLMIKRSKKNSLAL</u>

<u>SLTADQMVSALLDAEPPILYSEYDPTRPFSEASMMGLLTNLADRELVHMIN</u>

<u>WAKRVPGFVDLTLHDQVHLLECAWLEILMIGLVWRSMEHPGKLLFAPNLLL</u>

<u>DRNQGKCVEGMVEIFDMLLATSSRFRMMNLQGEEFVCLKSIILLNSGVYTF</u>

<u>LSSTLKSLEEKDHIHRVLDKITDTLIHLMAKAGLTLQQQHQRLAQLLLILS</u>

<u>HIRHMSNKRMEHLYSMKCKN</u>VVPLFDLLLEMLDAHRLHAPTS

GS-linker between estrogen receptor alpha ligand
binding domain and CD8 alpha hinge region
ggatcc GS-linker between estrogen receptor alpha ligand
binding domain and CD8 alpha hinge region
GS (CD8 alpha hinge)
SEQ ID NO: 111
accacgacgccagcgccgcgaccaccaacaccggcgccaccatcgcgtcg cagcccctgtccctgcgcccagaggcgtgccggccagcggcggggggcgca gtgcacacgaggggggctggacttcgcctgtgatatctacatctgggcgccc ttggccgggacttgtggggtccttctcctgtcactggttatcacccttac tgc (CD8 alpha hinge)
SEQ ID NO: 112
TTTPAPRPPTPAPTIASQPLSLRPEACRPAAGGAVHTRGLDFAC (CD8 alpha transmembrane domain)
SEQ ID NO: 113
gatatctacatctgggcgcccttggccgggacttgtggggtccttctcctg
tcactggttatcacccttactgc (CD8 alpha transmembrane domain)
SEQ ID NO: 114
DIYIWAPLAGTCGVLLLSLVITLYC (4-1BB costimulatory domain)
SEQ ID NO: 115
aaacggggcagaaagaaactcctgtatatattcaaacaaccatttatgaga ccagtacaaactactcaagaggaagatggctgtagctgccgatttccagaa gaagaagaaggaggatgtgaa -continued (4-1BB costimulatory domain)
SEQ ID NO: 116
KRGRKKLLYIFKQPFMRPVQTTQEEDGCSCRFPEEEEGGCE (CD3 zeta signaling domain)
SEQ ID NO: 117
ctgagagtgaagttcagcaggagcgcagacgcccccgcgtaccagcagggc cagaaccagctctataacgagctcaatctaggacgaagagaggagtacgat gttttggacaagagacgtggccgggaccctgagatggggggaaagccgaga aggaagaaccctcaggaaggcctgtacaatgaactgcagaaagataagatg gcggaggcctacagtgagattgggatgaaaggcgagcgccggagggggcaag gggcacgatggcctttaccagggtctcagtacagccaccaaggacacctac gacgccttcacatgcaggccctgccccctcgc (CD3 zeta signaling domain)
SEQ ID NO: 118
LRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTY

DALHMQALPPR

Figure 14:
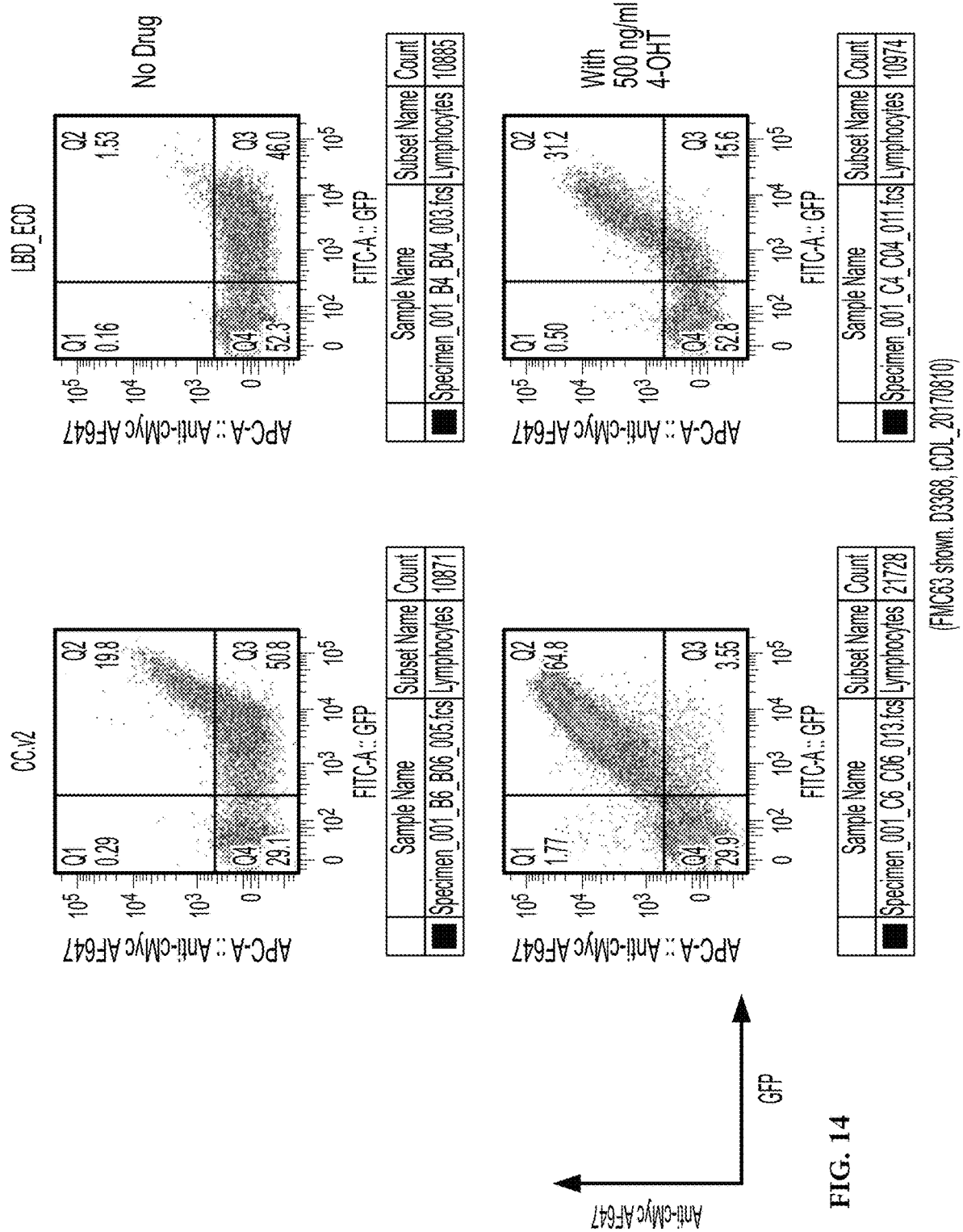
FIG. 14 depicts a set of flow cytometry dot plots for cells expressing the v2 CAR construct or LBD-ECD CAR construct. The cells were either left untreated or were treated with 500 ng/mL 4-hydroxytamoxifen ("4-OHT").

Example 14—LBD-ECD Reduces Background Localization of the CAR to the Cell Surface in the Absence of Ligand Primary human T cells were transduced with lentiviral vectors encoding the CC.v2 or LBD ECD.v1 construct as indicated. Cells were left un-treated or treated with 500 ng/mL of 4-OHT. Duration of treatment was as shown in FIG. 14. Cells were subsequently stained for surface expression of the chimeric receptor using anti-Myc AlexaFluor 647 antibody.

Placement of the LBD to the extracellular portion of the CAR reduces the background levels of CAR surface expression when the ligand has not been added, relative to when the LBD is placed in the intracellular portion of the CAR (FIG. 14). Both v2 CAR and ECD.v1 were expressed on the surface of cells when 500 ng/ml of 4-OHT was added.

Example 15—LBD-ECD CAR Kills Cells in a Drug Dependent Manner

Primary human T cells were transduced with lentiviral vectors encoding the LBD ECD.v1 or control CAR construct as indicated. T cells were allowed to rest after expansion and subsequently co-cultured with luciferase expressing Nalm6 tumor cells at an effector:target ratio shown in FIG. 15. After 24 hours of co-culture the cells were lysed and luciferase substrate added to quantify the number of surviving tumor cells.

Figure 15:
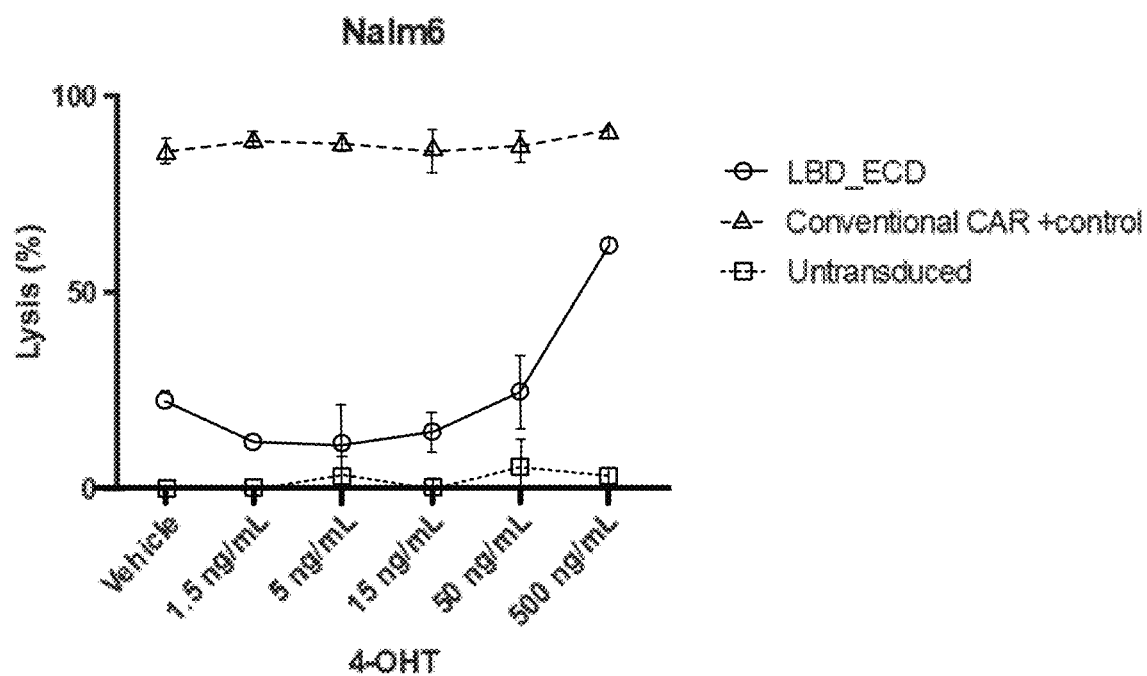
FIG. 15 is a graph showing the destruction of Nalm 6 tumor cells (% lysis) by T cells transduced with a lentiviral vector encoding LBD-ECD CAR construct (ECD.v1). Cells were treated with between 1.5 ng/mL to 500 ng/mL 4-OHT. The positive control was T cells transduced with a lentiviral vector encoding constitutive CAR. The negative control was T cells with LBD-ECD CAR that were not treated with 4-OHT.

LBD ECD.v1 CAR kills cells in a drug dependent manner. The addition of increasing amounts of 4-OHT leads to greater levels of cell lysis (approximately 50% lysis at 500 ng/mL 4-OHT) (FIG. 15).

Example 16—LBD-ECD CAR is Localized Intracellularly in Activated T Cells

Primary human T cells were transduced with lentiviral vectors encoding the LBD_ECD, CC.v2, or constitutive control CAR construct as indicated. After cells had rested, cells were re-stimulated with aCD3/aCD28 dynabeads for 48 hours. Cells were subsequently stained with anti-Myc antibody to detect surface expression of the CAR, and analyzed via flow cytometry.

CARs with an extracellular LBD (LBD ECD v1) are localized intracellularly in T cells that are activated when exposed to a CD3/CD28 beads. CARs with an intracellular LBD (v2 CAR) show some localization to the cell surface in activated T cells (FIG. 16).

Example 17—ECD.v1 CAR (LBD ECD) Produces Cytokine IL-2

Figure 16:
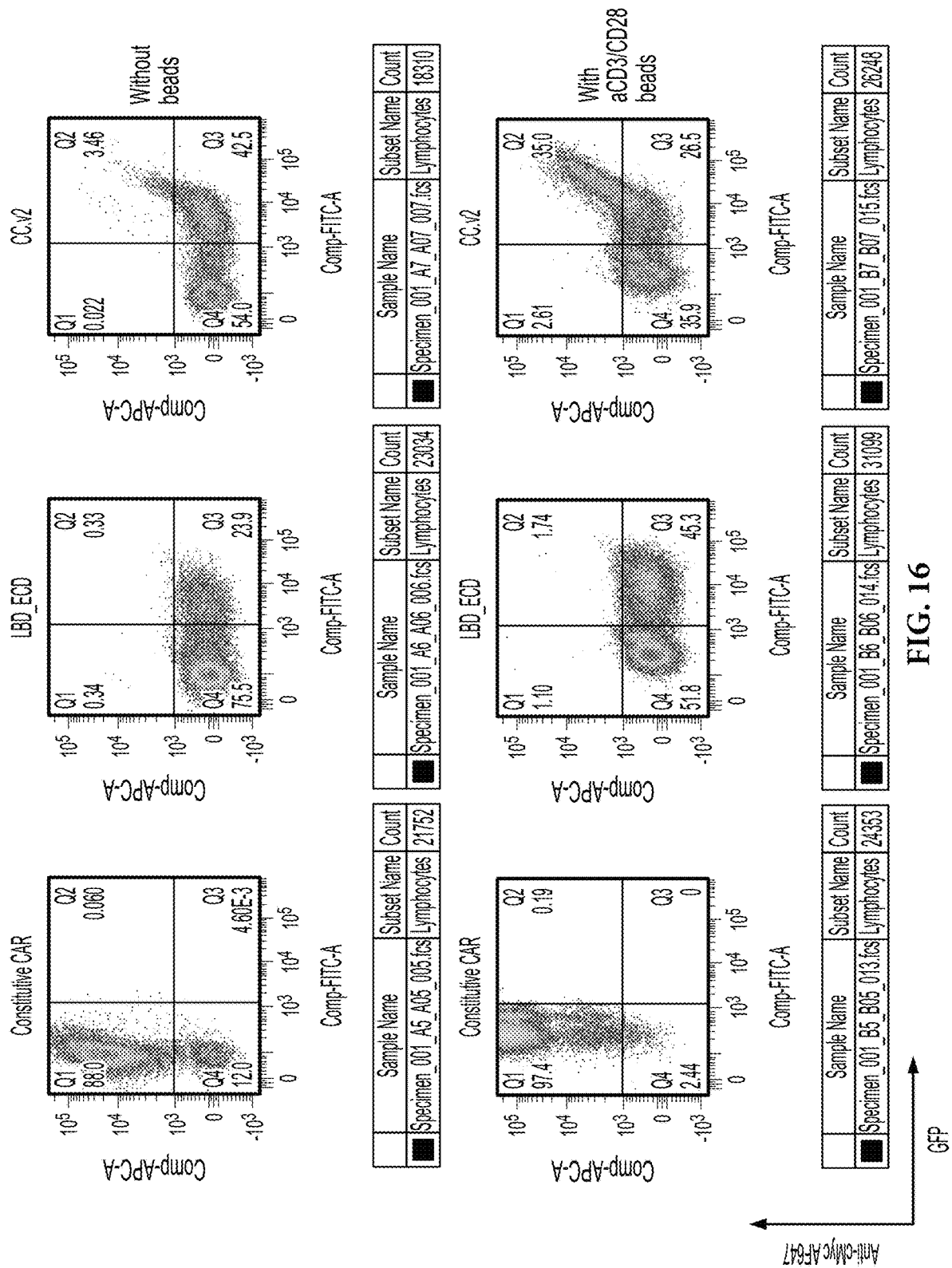
FIG. 16 depicts a set of flow cytometry dot plots for cells expressing a constitutive CAR, LBD-ECD CAR, or v2 CAR. Cells were either left untreated, or stimulated with beads containing a CD3/CD28 for 48 hours prior to flow cytometry. Beads, Dynabeads aCD3/aCD28, were from ThermoFisher. See, Trickett et al., *J. Immunol. Methods* 275:251-255, 2003. Each construct was fused to a cMyc tag.
Figure 17:
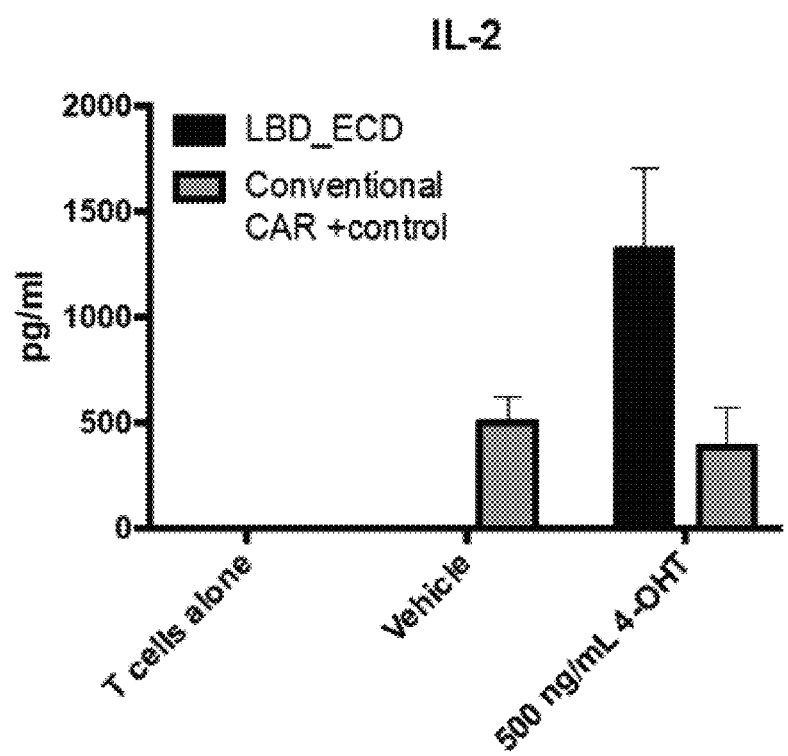
FIG. 17 is a graph showing IL-2 production from ECD.v1 CAR-T cells or conventional CAR-Tcells after overnight co-culture of the CAR-bearing T cells with NALM-6 targets in the presence (500 ng/mL) or absence of 4-hydroxytamoxifen.

IL-2 production from the ECD.v1 CAR T cells was compared to the conventional CAR+control after overnight co-culture of CAR-bearing T cells with NALM-6 targets in the presence (500 ng/mL) or absence of 4-hydroxytamoxifen (FIG. 16). IL-2 production from the ECD.v1 CAR receptor (FIG. 13) was comparable to the conventional CAR control, dependent upon 4-hydroxytamoxifen, and undetectable in the absence of drug.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing membrane localization of at least a portion of a single-chain chimeric polypeptide to an extracellular side of the membrane in a mammalian cell, the method comprising:
   contacting a mammalian cell expressing a single-chain chimeric polypeptide with an amount of amoxifen sufficient to induce localization of at least a portion of the single-chain chimeric polypeptide to an extracellular side of the membrane of the cell;
   wherein the single-chain chimeric polypeptide comprises the amino sequences of SEQ ID NO: 31, SEQ ID NO: 33 or SEQ ID NO: 35.

2. The method of claim 1, further comprising:
   introducing a nucleic acid encoding the single-chain chimeric polypeptide into a mammalian cell to generate the mammalian cell expressing the single-chain chimeric antigen receptor.

3. The method of claim 2, wherein the mammalian cell is a T cell.

4. The method of claim 3, wherein the T cell is selected from the group consisting of: a CD8+ T cell, a CD4+ T cell, a memory T cell, a Treg cell, and a natural killer T cell.

5. The method of claim 1, wherein the mammalian cell is a mammalian cell previously obtained from a subject.

6. The method of claim 5, wherein the subject has been identified or diagnosed as having a blood cancer.

7. The method of claim 1, wherein the contacting step is performed in vitro.

8. The method of claim 7, wherein the mammal has a blood cancer.

9. The method of claim 1, wherein the contacting step is performed in a mammal.

10. The method of 9, wherein the contacting step results in the treatment of the blood cancer in the mammal.

11. A method of reversibly altering membrane localization of a single-chain chimeric polypeptide in a mammalian cell, the method comprising:
  (a) contacting a mammalian cell expressing a single-chain chimeric polypeptide with an amount of amoxifen sufficient to induce localization of at least a portion of the single-chain chimeric polypeptide to an extracellular side of the plasma membrane of the cell; and
  (b) contacting the mammalian cell with a reduced amount of amoxifen that results in a decreased level of the single-chain chimeric polypeptide on an extracellular side of the membrane of the mammalian cell;
  wherein the single-chain chimeric polypeptide comprises the amino sequences of SEQ ID NO: 31, SEQ ID NO: 33 or SEQ ID NO: 35.

12. The method of claim 11, further comprising:
  (c) contacting the mammalian cell with an amount of tamoxifen that results in an increased level of at least a portion of the single-chain chimeric polypeptide to the extracellular side of the plasma membrane of the cell as compared to the level in (b).

13. A method of inducing plasma membrane localization of at least a portion of a single-chain chimeric polypeptide to an extracellular side of the plasma membrane in a mammalian cell, the method comprising:
  contacting a mammalian cell expressing a single-chain chimeric polypeptide with an amount of tamoxifen sufficient to induce localization of at least a portion of the single-chain chimeric polypeptide to an extracellular side of the plasma membrane of the cell;
  wherein the single-chain chimeric polypeptide comprises the amino acid sequence of SEQ ID NO: 31, SEQ ID NO: 33 or SEQ ID NO: 35.

14. The method of claim 13, further comprising, before step (a):
  introducing a nucleic acid encoding the single-chain chimeric polypeptide into a mammalian cell to generate the mammalian cell expressing the single-chain chimeric polypeptide.

15. The method of claim 13, wherein the mammalian cell is a T cell.

16. The method of claim 13, wherein the mammalian cell is from a subject identified or diagnosed as having blood cancer.

17. The method of claim 13, further comprising obtaining the mammalian cell from the subject.

18. The method of claim 13, wherein the contact step is performed in vitro.

* * * * *

UNITED STATES PATENT AND TRADEMARK OFFICE
CERTIFICATE OF CORRECTION

PATENT NO. : 11,993,660 B2
APPLICATION NO. : 17/402009
DATED : May 28, 2024
INVENTOR(S) : Stephen Santoro et al.

It is certified that error appears in the above-identified patent and that said Letters Patent is hereby corrected as shown below:

In the Claims

Column 325, Line 61, delete "amoxifen" and insert therefore --tamoxifen--.

Column 326, Line 58, delete "antigen receptor" and insert therefore --polypeptide--.

Column 327, Line 13, delete "amoxifen" and insert therefore --tamoxifen--; and
       Line 18, delete "amoxifen" and insert therefore --tamoxifen--.

Signed and Sealed this
Third Day of September, 2024

Katherine Kelly Vidal
*Director of the United States Patent and Trademark Office*